United States Patent
Lubos et al.

(10) Patent No.: US 11,213,575 B2
(45) Date of Patent: Jan. 4, 2022

(54) CELL-PENETRATING BACTERIAL E3-UBIQITIN-LIGASES FOR USE IN IMMUNOTHERAPY

(71) Applicant: WESTFÄLISCHE WILHELMS-UNIVERSITÄT MÜNSTER, Muenster (DE)

(72) Inventors: Marie-Luise Lubos, Muenster (DE); Alexander Schmidt, Havixbeck (DE); Christian Rueter, Muenster (DE)

(73) Assignee: WESTFÄLISCHE WILHELMS-UNIVERSITÄT MÜNSTER, Muenster (DE)

(*) Notice: Subject to any disclaimer, the term of this patent is extended or adjusted under 35 U.S.C. 154(b) by 0 days.

(21) Appl. No.: 16/537,022

(22) Filed: Aug. 9, 2019

(65) Prior Publication Data

US 2020/0038493 A1 Feb. 6, 2020

Related U.S. Application Data

(63) Continuation of application No. 15/022,827, filed as application No. PCT/EP2014/070142 on Sep. 22, 2014, now Pat. No. 10,406,215.

(30) Foreign Application Priority Data

Sep. 20, 2013 (EP) .................................. 13185412

(51) Int. Cl.
| | |
|---|---|
| A61K 38/53 | (2006.01) |
| C07K 14/25 | (2006.01) |
| C07K 14/255 | (2006.01) |
| C12N 9/00 | (2006.01) |
| A61K 38/16 | (2006.01) |

(52) U.S. Cl.
CPC ............ *A61K 38/53* (2013.01); *A61K 38/164* (2013.01); *C07K 14/25* (2013.01); *C07K 14/255* (2013.01); *C12N 9/93* (2013.01); *C07K 2319/10* (2013.01); *C07K 2319/43* (2013.01); *C07K 2319/70* (2013.01); *C07K 2319/73* (2013.01); *C12Y 603/02019* (2013.01)

(58) Field of Classification Search
None
See application file for complete search history.

(56) References Cited

U.S. PATENT DOCUMENTS

2008/0261241 A1* 10/2008 Roy .................... G01N 33/5023
435/7.8

OTHER PUBLICATIONS

"Hyperimmune Serum Reactive Antigen SEQ ID No. 1002," DATABASE Geneseq [Online], EBI Accession No. AED82666, Jan. 12, 2006.
Panthel, K., et al. (2005) *Salmonella* Pathogenicity Island and 2-Mediated Overexpression of Chimeric SspH2 Proteins for Simultaneous Induction of Antigen-Specific CD4 and CD8 T Cells, Infection and Immunity 73: 334-341.
Wang, F., et al. (2013) Shigella Flexneri T3SS Effector IpaH4.5 Modulates the Host Inflammatory Response via Interaction with NF-1<B p65 Protein, Cellular Microbiology 15:474-485.
Ruter, C., et al. (2010) A Newly Identified Bacterial Cell-Penetrating Peptide that Reduces the Transcription of Pro-Inflammatory Cytokines, Journal of Cell Science 123:2190-2198.
Miao, E.A., and Miller, S.I., et al. (2000) A Conserved Amino Acid Sequence Directing Intracellular Type III Secretion by *Salmonella typhimurium*, Proceedings of the National Academy of Sciences 97:7539-7544.
Nikolaus, T., et al. (2001) SseBCD Proteins are Secreted by the Type III Secretion System of Salmonella Pathogenicity Island 2 and Function as a Translocon, Journal of Bacteriology 183:6036-6045.
Zhu, Y., et al., (2008) Structure of a Shigella Effector Reveals a New Class of Ubiquitin Ligases, Nature Structural & Molecular Biology, 15:1302-1308.
Quezada, C.M., et al. (2009) A Family of *Salmonella* Virulence Factors Functions as a Distinct Class of Autoregulated E3 Ubiquitin Ligases, Proceedings of the National Academy of Sciences, 106:4864-4869.
Rohde, J.R., et al. (2007) Type III Secretion Effectors of the IpaH Family Are E3 Ubiquitin Ligases, Cell Host & Microbe 1 :77-83.

* cited by examiner

*Primary Examiner* — Brian Gangle
(74) *Attorney, Agent, or Firm* — Duane Morris LLP; Deborah L. Lu

(57) ABSTRACT

The present invention relates to cell-penetrating effector proteins of type III secretion system (T3SS)-containing bacteria of the genus *Salmonella* or *Shigella* and variants, fragments and immunomodulatory domains thereof, for use in immunotherapy. The present invention further relates to cell-penetrating effector proteins of type III secretion system (T3SS)-containing bacteria of the genus *Salmonella* or *Shigella* and variants, fragments and immunomodulatory domains thereof, for delivering cargo molecules into eukaryotic cells.

16 Claims, 33 Drawing Sheets

Specification includes a Sequence Listing.

FIGURE 3
SspH1-Nter
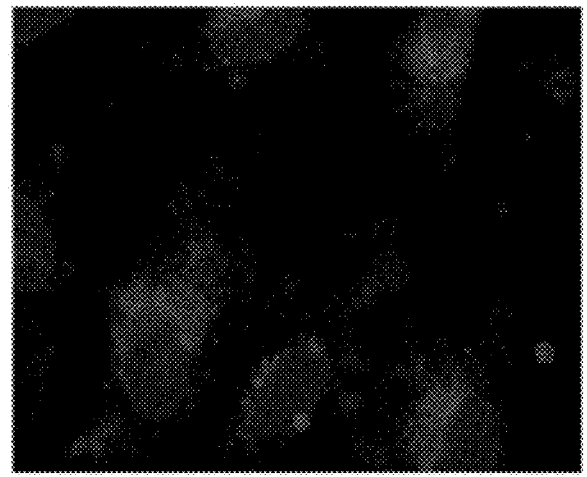
SspH1
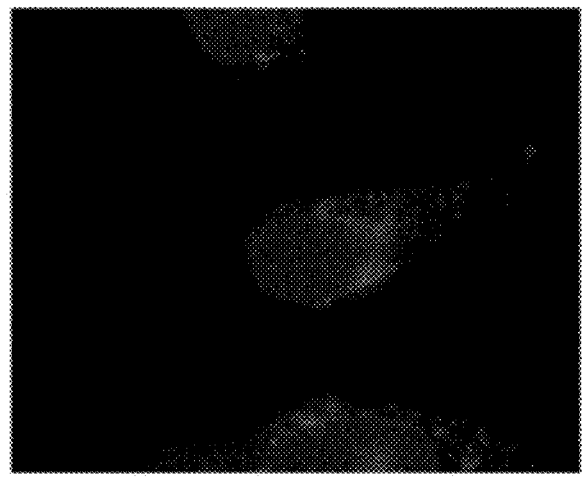

IpaH1.4

IpaH4.5

IpaH7.8

IpaH9.8

SlrP

FIGURE 14

SlrP

>gi|267992540|gb|ACY87425.1| leucine-rich repeat-containing protein [Salmonella enterica subsp. enterica serovar Typhimurium str. 14028S]

(SEQ ID NO: 1)
MFNITNIQSTARHQSISNEASTEVPLKEEIWNKISAFFSSEHQVEAQNCIAYLCHPPETASPEEIKSK
FECLRMLAFPAYADNIQYSRGGADQYCILSENSQEILSIVFNTEGYTVEGGGKSVTYTRVTESEQA
SSASGSKDAVNYELIWSEWVKEAPAKEAANREEAVQRMRDCLKNNKTELRLKILGLTTIPAYIPE
QITTLILDNNELKSLPENLQGNIKTLYANSNQLTSIPATLPDTIQEMELSINRITELPERLPSALQSLDL
FHNKISCLPENLPEELRYLSVYDNSIRTLPAHLPSEITHLNVQSNSLTALPETLPPGLKTLEAGENAL
TSLPASLPPELQVLDVSKNQITVLPETLPPTITTLDVSRNALTNLPENLPAALQIMQASRNNLVRLP
ESLPHFRGEGPQPTRIIVEYNPFSERTIQNMQRLMSSVDYQGPRVLFAMGDFSIVRVTRPLHQAV
QGWLTSLEEEDVNQWRAFEAEANAAAFSGFLDYLGDTQNTRHPDFKEQVSAWLMRLAEDSALR
ETVFIIAMNATISCEDRVTLAYHQMQEATLVHDAERGAFDSHLAE**LIMAGREIFRLEQIESLAREKV
KRLF**FIDEVEVFLGFQNQLRESLSLTTMTRDMRFYNVSGITESDLDEAEIRIKMAENRDFHKWFAL
WGPWHKVLERIAPEEWREMMAKRDECIETDEYQSRVNAELEDLRIADDSDAERTTEVQMDAERA
IGIKIMEEINQTLFTEIMENILLKKEVSSLMSAYWR

Area of LRR stretches: LRR 1-10 (AA 200-410 = SEQ ID NO: 28)
       Ubiquitin ligase domain (AA 462-765 = SEQ ID NO: 19)

Maximal protein-transduction domains:
       APAKEAANREEAVQRMRDCLKNNKTELRLKILGLTTIPA = SEQ ID NO: 37
       LPAALQIMQASRNNLVRL = SEQ ID NO: 38
       LIMAGREIFRLEQIESLAREKVKRLF = SEQ ID NO: 39

FIGURE 15

SspH1:

>gi|267993082|gb|ACY87967.1| SspH1 [Salmonella enterica subsp. enterica serovar Typhimurium str. 14028S]

(SEQ ID NO: 2)
MFNIRNTQPSVSMQAIAGAAAPEASPEEIVWEKIQVFFPQENYEEAQQCLAELCHPARGMLPDHIS
SQFARLKALTFPAWEENIQCNRDGINQFCILDAGSKEILSITLDDAGNYTVNCQGYSEAHDFIMDT
EPGEECTEFAEGASGTSLRPATTVSQKAAEYDAVWSKWERDAPAGESPGRAAVVQEMRDCLNN
GNPVLNVGASGLTTLPDRLPPHITTLVIPDNNLTSLPELPEGLRELEVSGNLQLTSLPSLPQGLQKL
WAYNNWLASLPTLPPGLGDLAVSNNQLTSLPEMPPALRELRVSGNNLTSLPALPSGL**QKLWAYN
NRLTSLPEMSPGLQELDVSHNQLTRLPQSLTGLSSAARVYLDGNPLSVRTLQALR**DIIGHSGIRIHF
DMAGPSVPREARALHLAVADWLTSAREGEAAQADRWQAFGLEDNAAAFSLVLDRLRETENFKK
DAGFKAQISSWLTQLAEDAALRAKTFAMATEATSTCEDRVTHALHQMNNVQLVHNAEKGEYDN
NLQGLVSTGREMFRLATLEQIAREKAGTLALVDDVEVYLAFQNKLKESLELTSVTSEMRFFDVSGV
TVSDLQAAELQVKTAENSGFSKWILQWGPLHSVLERKVPERFNALREKQISDYEDTYRKLYDEVL
KSSGLVDDTDAERTIGVSAMDSAKKEFLDGLRALVDEVLGSYLTARWRLN

LRR stretch: LRR 1-8 (AA 217-381 = SEQ ID NO: 29)
Ubiquitin ligase domain (AA 404-700 = SEQ ID NO: 20)

Maximal protein-transduction domains:
ARLKALTFPA = SEQ ID NO: 40
LQKLWAYNNRL = SEQ ID NO: 41
LSVRTLQALR = SEQ ID NO: 42
ALRAKTFAMAT = SEQ ID NO: 43
RFNALREKQI = SEQ ID NO: 44
LTARWRLN = SEQ ID NO: 45

FIGURE 16

SspH2:
>gi|267994325|gb|ACY89210.1| leucine-rich repeat-containing protein [Salmonella enterica subsp. enterica serovar Typhimurium str. 14028S]

(SEQ ID NO: 3)
MPFHIGSGCLPATISNRRIYRIAWSDTPPEMSSWEKMKEFFCSTHQTEALECIWTICHPPAGTTRE
DVINRFELLRTLAYAGWEESIHSGQHGENYFCILDEDSQEILSVTLDDAGNYTVNCQGYSETHRLT
LDTAQGEEGTGHAEGASGTFRTSFLPATTAPQTPAEYDAVWSAWRRAAPAEESRGRAAVVQK
MRACLNNGNAVLNVGESGLTTLPDCLPAHITTLVIPDNNLTSLPALPPELRTLEVSGNQLTSLPVLP
PGLLELSIFSNPLTHLPALPSGLCKLWIFGNQLTSLPVLPPGLQELSVSDNQLASLPALPSELCKLW
AYNNQLTSLPMLPSGLQELSVSDNQLASLPTLPSELYKLWAYNNRLTSLPALPSGLKELIVSGNRL
TSLPVLPSELKELMVSGNRLTSLPMLPSGLLSLSVYRNQLTRLPESLIHLSSETTVNLEGNPLSERT
LQALREITSAPGYSGPIIRFDMAGASAPRETRALHLAAADWLVPAREGEPAPADRWHMFGQEDN
ADAFSLFLDRLSETENFIKDAGFKAQISSWLAQLAEDEALRANTFAMATEATSSCEDRVTFFLHQM
KNVQLVHNAEKGQYDNDLAALVATGREMFRLGKLEQIAREKVRTLALVDEIEVWLAYQNKLKKS
LGLTSVTSEMRFFDVSGVTVTDLQDAELQVKAAEKSEFREWILQWGPLHRVLERKAPERVNALR
EKQISDYEETYRMLSDTELRPSGLVGNTDAERTIGARAMESAKKTFLDGLRPLVEEMLGSYLNVQ
WRRN

LRR stretch: LRR 1-12 (AA 223-466 = SEQ ID NO: 30)
Ubiquitin ligase domain (AA 492-788 = SEQ ID NO: 21)

Maximal protein-transduction domains:
ATISNRRIYRIA = SEQ ID NO: 46
AVWSAWRRAAPAEESRGRAAVVQKMRACLNN = SEQ ID NO: 47
NDLAALVATGREMFRLGKLEQIAREKVRTLALVD = SEQ ID NO: 48
VWLAYQNKLKKSLGLT = SEQ ID NO: 49
RVLERKAPERVNALREKQIS = SEQ ID NO: 50
RTIGARAMESAKKTFLDGLR = SEQ ID NO: 51

FIGURE 17

IpaH1.4

>tr|Q9AJU5|Q9AJU5_SHIFL Putative uncharacterized protein ipaH1.4 OS=Shigella flexneri GN=ipaH1.4 PE=4 SV=1

(SEQ ID NO: 4)
MIKSTNIQAIGSGIMHQINNVYSLTPLSLPMELTPSCNEFYLKTWSEWEKNGTPGEQRNIAFNRLKI
CLQNQEAELNLSELDLKTLPDLPPQITTLEIRKNLLTHLPDLPPMLKVIHAQFNQLESLPALPETLEE
LNAGDNKIKELPFLPENLTHLRVHNNRLHILPLLPPELKLLVVSGNRLDSIPPFPDKLEGLALANNFIE
QLPELPFSMNRAVLMNNNLTTLPESVLRLAQNAFVNVAGNPLSGHTMRTLQQITTGPDYSGPRIF
FSMGNSATISAPEHSLADAVTAWFPENKQSDVSQIWHAFEHEEHANTFSAFLDRLSDTVSARNTS
GFREQVAAWLEKLSASAELRQQSFAVAADATESCEDRVALTWNNLRKTLLVHQASEGLFDNDT
GALLSLGREMFRLEILEDIARDKVRTLHFVDEIEVYLAFQTMLAEKLQLSTAVKEMRFYGVSGVTAN
DLRTAEAMVRSREENEFTDWFSLWGPWHAVLKRTEADRWAQAEEQKYEMLENEYSQRVADRL
KASGLSGDADAEREAGAQVMRETEQQIYRQLTDEVLALRLSENGSNHIA ubiquitin ligase domain (AA 241- 571 = SEQ ID NO: 22)
Area of LRR stretches: (AA 92-213 = SEQ ID NO: 31)

Maximal protein-transduction domains:
DRVALTWNNLRKTLLV = SEQ ID NO: 52
SQRVADRLKASGL = SEQ ID NO: 53

FIGURE 18

IpaH2.5

>gi|12329051|emb|CAC05782.1| IpaH2.5, member of the IpaH family, probably secreted by the Mxi-Spa machinery, function unknown [Shigella flexneri 5a str. M90T]

(SEQ ID NO: 5)
MIKSTNIQVIGSGIMHQINNIHSLTLFSLPVSLSPSCNEYYLKVWSEWEKNGTPGEQRNIAFNRLKIC
LQNQEAELNLSELDLKTLPDLPPQITTLEIRKNLLTHLPDLPPMLKVIHAQFNQLESLPALPETLEEL
NAGDNKIKELPFLPENLTHLRVHNNRLHILPLLPPELKLLVVSGNRLDSIPPFPDKLEGLALANNFIE
QLPELPFSMNRAVLMNNNLTTLPESVLRLAQNAFVNVAGNPLSGHTMRTLQQITTGPDYSGPRIF
FSMGNSATISAPEHSLADAVTAWFPENKQSDVSQIWHAFEHEEHANTFSAFLDRLSDTVSARNTS
GFREQVAAWLEKLSASAELRQQSFAVAADATESCEDRVALTWNNLRKTLLVHQASEGLFDNDT
GALLSLGREMFRLEILEDIARDKVRTLHFVDEIEVYLAFQTMLAEKLQLSTAVKEMRFYGVSGVTAN
DLRTAEAMVRSREENEFTDWFSLWGPWHAVLKRTEADRWAQAEEQKYEMLENEYSQRVADRL
KASGLSGDADAEREAGAQVMRETEQQIYRQLTDEVLA ubiquitin ligase domain (AA 241-563 = SEQ ID NO: 23)
     Area of LRR stretches: (AA 92-213 = SEQ ID NO: 32)

Maximal protein-transduction domains:
    DRVALTWNNLRKTLL = SEQ ID NO: 54
    SQRVADRLKASGL = SEQ ID NO: 550

FIGURE 19

IpaH3

Shigella flexneri 5a str. M90T

>tr|I0VDT7|I0VDT7_SHIFL Invasion plasmid antigen OS=Shigella flexneri 5a str. M90T GN=ipaH_3 PE=4 SV=1

(SEQ ID NO: 6)

MLPTNNNHRLISNSFSTYSIDTSRAYENYLTHWTEWKNNRIQEEQRDIAFQRLVSCLQNQETNLDL
SELGLTTLPEIPPGIKSINISKNNLSLISPLPASLTQLNVSYNRLIELPALPQGLKLLNASHNQLITLPTL
PISLKELHVSNNQLCSLPVLPELLETLDVSCNGLAVLPPLPFSLQEISAIGNLLSELPPLPHNIHSIWAI
DNMLTDIPYLPENLRNGYFDINQISHIPESILNLRNECSIDISDNPLSSHALQSLQRLTSSPDYHGPQI
YFSMSDGQQNTLHRPLADAVTAWFPENKQSDVSQIWHAFEHEEHANTFSAFLDRLSDTVSARNT
SGFREQVAAWLEKLSASAELRQQSFAVAADATESCEDRVALTWNNLRKTLLVHQASEGLFDNDT
GALLSLGREMFRLEILEDIARDKVRTLHFVDEIEVYLAFQTMLAEKLQLSTAVKEMRFYGVSGVTAN
DLRTAEAMVRSREENEFTDWFSLWGPWHAVLKRTEADRWAQAEEQKYEMLENEY**PQRVADRL
KASGL**SGDADAEREAGAQVMRETEQQIYRQLTDEVLALRLPENGSQLHHS ubiquitin ligase domain (AA 291- 583 = SEQ ID NO: 24)
      Area of LRR stretches: (AA 92-213 = SEQ ID NO: 33)

Maximal protein-transduction domains:
DRVALTWNNLRKTLLV = SEQ ID NO: 55
PQRVADRLKASGL = SEQ ID NO: 56

FIGURE 20

IpaH4.5

>gi|12329057|emb|CAC05788.1| IpaH4.5, member of the IpaH family, probably secreted by the Mxi-Spa secretion machinery, function unknown [Shigella flexneri 5a str. M90T]

(SEQ ID NO: 7)
MKPINNHSFFRSLCGLSCISRLSVEEQCTRDYHRIWDD**WAREGTTTENRIQAVRLLKICLDTREPV
LNLSLLKLRSL**PPLPLHIRELNISNNELISLPENSPLLTELHVNGNNLNILPTLPSQLIKLNISFNRNLS
CLPSLPPYLQSLSARFNSLETLPELPSTLTILRIEGNRLTVLPELPHRLQELFVSGNRLQELPEFP**QS
LKYLKVGENQLRRLSRLPQELLALD**VSNNLLTSLPENIITLPICTNVNISGNPLSTHVLQSLQRLTSS
PDYHGPQIYFSMSDGQQNTLHRPLADAVTAWFPENKQSDVSQIWHAFEHEEHANTFSAFLDRLS
DTVSARNTSGFREQVAAWLEKLSASAELRQQSFAVAADATESCEDRVALTWNNLRKTLLVHQAS
EGLFDNDTGALLSLGREMFRLEILEDIARDKVRTLHFVDEIEVYLAFQTMLAEKLQLSTAVKEMRFY
GVSGVTANDLRTAEAMVRSREENEFTDWFSLWGPWHAVLKRTEADRWAQAEEQKYEMLENEY
SQRVADRLKASGLSGDADAEREAGAQVMRET EQQIYRQLTDEVLA

LRR stretch: LRR 1-10 (AA 63-270 = SEQ ID NO: 34)
      ubiquitin ligase domain (AA 293 – 574 = SEQ ID NO: 25)

Maximal protein-transduction domains:
WAREGTTTENRIQAVRLLKICLDTREPVLNLSLLKLRSL = SEQ ID NO: 57
QSLKYLKVGENQLRRLSRLPQELLALD = SEQ ID NO: 58
DRVALTWNNLRKTLL = SEQ ID NO: 59
QRVADRLKASGL = SEQ ID NO: 551

FIGURE 21

IpaH7.8

>gi|12329056|emb|CAC05787.1| IpaH7.8, member of the IpaH family, secreted by the Mxi-Spa secretion machinery, function unknown [Shigella flexneri 5a str. M90T]

(SEQ ID NO: 8)

MFSVNNTHSSVSCSPSINSNSTSNEHYLRILTEWEKNSSPGEERGIAFNRLSQCFQNQEAVLNLS
DLNLTSLPELPKHISALIVENNKLTSLPKLPAFLKELNADNNRLSVIPELPESLTTLSVRSNQLENLPV
LPNHLTSLFVENNRLYNLPALPEKLKFLHVYYNRLTTLPDLPDKLEILCAQRNNLVTFPQFSDRNNI
RQKEYYFHFNQITTLPESFSQLDSSYRINISGNPLSTRVLQSLQRLTSSPDYHGPQIYFSMSDGQQ
NTL**HRPLADAVTAWFPENKQSDVSQIWHAFEHEEHANTFSAFLDRLSDTVSARNTSGFREQVAA
WLEKLSASAELRQQSFAVAADATESCEDRVALTWNNLRKTLLV**HQASEGLFDNDTGALLSLGRE
MFRLEILEDIARDKVRTLHFVDEIEVYLAFQTMLAEKLQLSTAVKEMRFYGVSGVTANDLRTAEAM
VRSREENEFTDWFSLWGPWHAVLKRTEADRWAQAEEQKYEMLENEYSQRVADRLKASGLSGD
ADAEREAGAQVMRETEQQIYRQLTDEVLALRLSENGS RLHHS

LRR stretch: LRR 1-9 (AA 58-248 = SEQ ID NO: 35)
ubiquitin ligase domain (AA 271-565 = SEQ ID NO: 26)

Maximal protein-transduction domains
TRVLQSLQRLT = SEQ ID NO: 60
DRVALTWNNLRKTLLV = SEQ ID NO: 61
SQRVADRLKASGL = SEQ ID NO: 62

FIGURE 22

IpaH9.8

>gi|12329122|emb|CAC05853.1| IpaH9.8, secreted by the Mxi-Spa secretion machinery, function unknown [Shigella flexneri 5a str. M90T]

(SEQ ID NO: 9)
MLPINNNFSLPQNSFYNTISGTYADYFSAWDKWEKQALPGEERDEAVSRLKECLINNSDELRLDRL
NLSSLPDNLPAQITLLNVSYNQLTNLPELPVTLKKLYSASNKLSELPVLPPALESLQVQHNELENLP
ALPDSLLTMNISYNEIVSLPSLPQALKNLRATRNFLTELPAFSEGNNPVVREYFFDRNQISHIPESIL
NLRNECSIHISDNPLSSHALQALQRLTSSPDYHGPRIYFSMSDGQQNTLHRPLADAVTAWFPENK
QSDVSQIWHAFEHEEHANTFSAFLDRLSDTVSARNTSGFREQVAAWLEKLSASAELRQQSFAVA
ADATESCEDRVALTWNNLRKTLLVHQASEGLFDNDTGALLSLGREMFRLEILEDIARDKVRTLHF
VDEIEVYLAFQTMLAEKLQLSTAVKEMRFYGVSGVTANDLRTAEAMVRSREENEFTDWFSLWGP
WHAVLKRTEADRWAQAEEQKYEMLENEYPQRVADRLKASGLSGDADAEREAGAQVMRETEQQ
IYRQLTDEVLALRLFENGSQLHHS ubiquitin ligase domain (AA 251-545 = SEQ ID NO: 27)
Area of LRR stretches: LRR 1-8 (AA 57-228 = SEQ ID NO: 36)

Maximal protein-transduction domains:
SLPSLPQALKNLRATRNFLT = SEQ ID NO: 63
DRVALTWNNLRKTLLV = SEQ ID NO: 64
PQRVADRLKASGL = SEQ ID NO: 65

SEQUENCE LISTING

```
<160> NUMBER OF SEQ ID NOS: 556

<210> SEQ ID NO 1
<211> LENGTH: 765
<212> TYPE: PRT
<213> ORGANISM: Salmonella enterica
```

<400> SEQUENCE: 1

```
Met Phe Asn Ile Thr Asn Ile Gln Ser Thr Ala Arg His Gln Ser Ile
1               5                  10                  15

Ser Asn Glu Ala Ser Thr Glu Val Pro Leu Lys Glu Glu Ile Trp Asn
            20                  25                  30

Lys Ile Ser Ala Phe Phe Ser Glu His Gln Val Glu Ala Gln Asn
        35                  40                  45

Cys Ile Ala Tyr Leu Cys His Pro Pro Glu Thr Ala Ser Pro Glu Glu
    50                  55                  60

Ile Lys Ser Lys Phe Glu Cys Leu Arg Met Leu Ala Phe Pro Ala Tyr
65                  70                  75                  80

Ala Asp Asn Ile Gln Tyr Ser Arg Gly Gly Ala Asp Gln Tyr Cys Ile
                85                  90                  95

Leu Ser Glu Asn Ser Gln Glu Ile Leu Ser Ile Val Phe Asn Thr Glu
                100                 105                 110

Gly Tyr Thr Val Glu Gly Gly Lys Ser Val Thr Tyr Thr Arg Val
        115                 120                 125

Thr Glu Ser Glu Gln Ala Ser Ser Ala Ser Gly Ser Lys Asp Ala Val
    130                 135                 140

Asn Tyr Glu Leu Ile Trp Ser Glu Trp Val Lys Glu Ala Pro Ala Lys
145                 150                 155                 160

Glu Ala Ala Asn Arg Glu Glu Ala Val Gln Arg Met Arg Asp Cys Leu
                165                 170                 175

Lys Asn Asn Lys Thr Glu Leu Arg Leu Lys Ile Leu Gly Leu Thr Thr
            180                 185                 190

Ile Pro Ala Tyr Ile Pro Glu Gln Ile Thr Thr Leu Ile Leu Asp Asn
        195                 200                 205

Asn Glu Leu Lys Ser Leu Pro Glu Asn Leu Gln Gly Asn Ile Lys Thr
    210                 215                 220

Leu Tyr Ala Asn Ser Asn Gln Leu Thr Ser Ile Pro Ala Thr Leu Pro
225                 230                 235                 240

Asp Thr Ile Gln Glu Met Glu Leu Ser Ile Asn Arg Ile Thr Glu Leu
                245                 250                 255

Pro Glu Arg Leu Pro Ser Ala Leu Gln Ser Leu Asp Leu Phe His Asn
            260                 265                 270

Lys Ile Ser Cys Leu Pro Glu Asn Leu Pro Glu Glu Leu Arg Tyr Leu
        275                 280                 285

Ser Val Tyr Asp Asn Ser Ile Arg Thr Leu Pro Ala His Leu Pro Ser
    290                 295                 300

Glu Ile Thr His Leu Asn Val Gln Ser Asn Ser Leu Thr Ala Leu Pro
305                 310                 315                 320

Glu Thr Leu Pro Pro Gly Leu Lys Thr Leu Glu Ala Gly Glu Asn Ala
                325                 330                 335

Leu Thr Ser Leu Pro Ala Ser Leu Pro Pro Gly Leu Gln Val Leu Asp
            340                 345                 350

Val Ser Lys Asn Gln Ile Thr Val Leu Pro Glu Thr Leu Pro Pro Thr
        355                 360                 365

Ile Thr Thr Leu Asp Val Ser Arg Asn Ala Leu Thr Asn Leu Pro Glu
    370                 375                 380

Asn Leu Pro Ala Ala Leu Gln Ile Met Gln Ala Ser Arg Asn Asn Leu
385                 390                 395                 400

Val Arg Leu Pro Glu Ser Leu Pro His Phe Arg Gly Glu Gly Pro Gln
```

Pro Thr Arg Ile Ile Val Glu Tyr Asn Pro Phe Ser Glu Arg Thr Ile
        405                 410                 415

Gln Asn Met Gln Arg Leu Met Ser Ser Val Asp Tyr Gln Gly Pro Arg
    420                 425                 430

Val Leu Phe Ala Met Gly Asp Phe Ser Ile Val Arg Val Thr Arg Pro
435                 440                 445

Leu His Gln Ala Val Gln Gly Trp Leu Thr Ser Leu Glu Glu Glu Asp
450                 455                 460

Val Asn Gln Trp Arg Ala Phe Glu Ala Glu Asn Ala Ala Ala Phe
465                 470                 475                 480

Ser Gly Phe Leu Asp Tyr Leu Gly Asp Thr Gln Asn Thr Arg His Pro
    485                 490                 495

Asp Phe Lys Glu Gln Val Ser Ala Trp Leu Met Arg Leu Ala Glu Asp
    500                 505                 510

Ser Ala Leu Arg Glu Thr Val Phe Ile Ile Ala Met Asn Ala Thr Ile
    515                 520                 525

Ser Cys Glu Asp Arg Val Thr Leu Ala Tyr His Gln Met Gln Glu Ala
545                 550                 555                 560

Thr Leu Val His Asp Ala Glu Arg Gly Ala Phe Asp Ser His Leu Ala
                565                 570                 575

Glu Leu Ile Met Ala Gly Arg Glu Ile Phe Arg Leu Leu Gln Ile Glu
            580                 585                 590

Ser Leu Ala Arg Glu Lys Val Lys Arg Leu Phe Phe Ile Asp Glu Val
        595                 600                 605

Glu Val Phe Leu Gly Phe Gln Asn Gln Leu Arg Glu Ser Leu Ser Leu
    610                 615                 620

Thr Thr Met Thr Arg Asp Met Arg Phe Tyr Asn Val Ser Gly Ile Thr
625                 630                 635                 640

Glu Ser Asp Leu Asp Glu Ala Glu Ile Arg Ile Lys Met Ala Glu Asn
                645                 650                 655

Arg Asp Phe His Lys Trp Phe Ala Leu Trp Gly Pro Trp His Lys Val
            660                 665                 670

Leu Glu Arg Ile Ala Pro Glu Glu Trp Arg Glu Met Met Ala Lys Arg
        675                 680                 685

Asp Glu Cys Ile Glu Thr Asp Gly Tyr Gln Ser Arg Val Asn Ala Glu
    690                 695                 700

Leu Glu Asp Leu Arg Ile Ala Asp Asp Ser Asp Ala Glu Arg Thr Thr
705                 710                 715                 720

Glu Val Gln Met Asp Ala Glu Arg Ala Ile Gly Ile Lys Ile Met Glu
                725                 730                 735

Glu Ile Asn Gln Thr Leu Phe Thr Glu Ile Met Glu Asn Ile Leu Leu
            740                 745                 750

Lys Lys Glu Val Ser Ser Leu Met Ser Ala Tyr Trp Arg
        755                 760                 765

<210> SEQ ID NO 2
<211> LENGTH: 700
<212> TYPE: PRT
<213> ORGANISM: Salmonella enterica

<400> SEQUENCE: 2

Met Phe Asn Ile Arg Asn Thr Gln Pro Ser Val Ser Met Gln Ala Ile
1               5                   10                  15

```
Ala Gly Ala Ala Ala Pro Glu Ala Ser Pro Glu Ile Val Trp Glu
         20                  25                  30
Lys Ile Gln Val Phe Phe Pro Gln Glu Asn Tyr Glu Glu Ala Gln Gln
         35                  40                  45
Cys Leu Ala Glu Leu Cys His Pro Ala Arg Gly Met Leu Pro Asp His
         50                  55                  60
Ile Ser Ser Gln Phe Ala Arg Leu Lys Ala Leu Thr Phe Pro Ala Trp
 65                  70                  75                  80
Glu Glu Asn Ile Gln Cys Asn Arg Asp Gly Ile Asn Gln Phe Cys Ile
                 85                  90                  95
Leu Asp Ala Gly Ser Lys Glu Ile Leu Ser Ile Thr Leu Asp Asp Ala
                100                 105                 110
Gly Asn Tyr Thr Val Asn Cys Gln Gly Tyr Ser Glu Ala His Asp Phe
            115                 120                 125
Ile Met Asp Thr Glu Pro Gly Glu Cys Thr Glu Phe Ala Glu Gly
            130                 135                 140
Ala Ser Gly Thr Ser Leu Arg Pro Ala Thr Thr Val Ser Gln Lys Ala
145                 150                 155                 160
Ala Glu Tyr Asp Ala Val Trp Ser Lys Trp Glu Arg Asp Ala Pro Ala
                165                 170                 175
Gly Glu Ser Pro Gly Arg Ala Ala Val Val Gln Glu Met Arg Asp Cys
            180                 185                 190
Leu Asn Gly Asn Pro Val Leu Asn Val Gly Ala Ser Gly Leu Thr
            195                 200                 205
Thr Leu Pro Asp Arg Leu Pro Pro His Ile Thr Thr Leu Val Ile Pro
210                 215                 220
Asp Asn Asn Leu Thr Ser Leu Pro Glu Leu Pro Glu Gly Leu Arg Glu
225                 230                 235                 240
Leu Glu Val Ser Gly Asn Leu Gln Leu Thr Ser Leu Pro Ser Leu Pro
                245                 250                 255
Gln Gly Leu Gln Lys Leu Trp Ala Tyr Asn Asn Trp Leu Ala Ser Leu
            260                 265                 270
Pro Thr Leu Pro Pro Gly Leu Gly Asp Leu Ala Val Ser Asn Asn Gln
            275                 280                 285
Leu Thr Ser Leu Pro Glu Met Pro Pro Ala Leu Arg Glu Leu Arg Val
            290                 295                 300
Ser Gly Asn Asn Leu Thr Ser Leu Pro Ala Leu Pro Ser Gly Leu Gln
305                 310                 315                 320
Lys Leu Trp Ala Tyr Asn Asn Arg Leu Thr Ser Leu Pro Glu Met Ser
                325                 330                 335
Pro Gly Leu Gln Glu Leu Asp Val Ser His Asn Gln Leu Thr Arg Leu
            340                 345                 350
Pro Gln Ser Leu Thr Gly Leu Ser Ser Ala Ala Arg Val Tyr Leu Asp
            355                 360                 365
Gly Asn Pro Leu Ser Val Arg Thr Leu Gln Ala Leu Arg Asp Ile Ile
            370                 375                 380
Gly His Ser Gly Ile Arg Ile His Phe Asp Met Ala Gly Pro Ser Val
385                 390                 395                 400
Pro Arg Glu Ala Arg Ala Leu His Leu Ala Val Ala Asp Trp Leu Thr
                405                 410                 415
Ser Ala Arg Glu Gly Glu Ala Ala Gln Ala Asp Arg Trp Gln Ala Phe
            420                 425                 430
Gly Leu Glu Asp Asn Ala Ala Ala Phe Ser Leu Val Leu Asp Arg Leu
```

```
                435                 440                 445
Arg Glu Thr Glu Asn Phe Lys Lys Asp Ala Gly Phe Lys Ala Gln Ile
450                 455                 460

Ser Ser Trp Leu Thr Gln Leu Ala Glu Asp Ala Ala Leu Arg Ala Lys
465                 470                 475                 480

Thr Phe Ala Met Ala Thr Glu Ala Thr Ser Thr Cys Glu Asp Arg Val
                485                 490                 495

Thr His Ala Leu His Gln Met Asn Asn Val Gln Leu Val His Asn Ala
                500                 505                 510

Glu Lys Gly Glu Tyr Asp Asn Asn Leu Gln Gly Leu Val Ser Thr Gly
            515                 520                 525

Arg Glu Met Phe Arg Leu Ala Thr Leu Glu Gln Ile Ala Arg Glu Lys
            530                 535                 540

Ala Gly Thr Leu Ala Leu Val Asp Asp Val Glu Val Tyr Leu Ala Phe
545                 550                 555                 560

Gln Asn Lys Leu Lys Glu Ser Leu Glu Leu Thr Ser Val Thr Ser Glu
                565                 570                 575

Met Arg Phe Phe Asp Val Ser Gly Val Thr Val Ser Asp Leu Gln Ala
                580                 585                 590

Ala Glu Leu Gln Val Lys Thr Ala Glu Asn Ser Gly Phe Ser Lys Trp
            595                 600                 605

Ile Leu Gln Trp Gly Pro Leu His Ser Val Leu Glu Arg Lys Val Pro
610                 615                 620

Glu Arg Phe Asn Ala Leu Arg Glu Lys Gln Ile Ser Asp Tyr Glu Asp
625                 630                 635                 640

Thr Tyr Arg Lys Leu Tyr Asp Glu Val Leu Lys Ser Ser Gly Leu Val
                645                 650                 655

Asp Asp Thr Asp Ala Glu Arg Thr Ile Gly Val Ser Ala Met Asp Ser
                660                 665                 670

Ala Lys Lys Glu Phe Leu Asp Gly Leu Arg Ala Leu Val Asp Glu Val
            675                 680                 685

Leu Gly Ser Tyr Leu Thr Ala Arg Trp Arg Leu Asn
            690                 695                 700

<210> SEQ ID NO 3
<211> LENGTH: 788
<212> TYPE: PRT
<213> ORGANISM: Salmonella enterica

<400> SEQUENCE: 3

Met Pro Phe His Ile Gly Ser Gly Cys Leu Pro Ala Thr Ile Ser Asn
1               5                   10                  15

Arg Arg Ile Tyr Arg Ile Ala Trp Ser Asp Thr Pro Pro Glu Met Ser
            20                  25                  30

Ser Trp Glu Lys Met Lys Glu Phe Phe Cys Ser Thr His Gln Thr Glu
        35                  40                  45

Ala Leu Glu Cys Ile Trp Thr Ile Cys His Pro Pro Ala Gly Thr Thr
    50                  55                  60

Arg Glu Asp Val Ile Asn Arg Phe Glu Leu Leu Arg Thr Leu Ala Tyr
65                  70                  75                  80

Ala Gly Trp Glu Glu Ser Ile His Ser Gly Gln His Gly Glu Asn Tyr
                85                  90                  95

Phe Cys Ile Leu Asp Glu Asp Ser Gln Glu Ile Leu Ser Val Thr Leu
            100                 105                 110
```

```
Asp Asp Ala Gly Asn Tyr Thr Val Asn Cys Gln Gly Tyr Ser Glu Thr
            115                 120                 125

His Arg Leu Thr Leu Asp Thr Ala Gln Gly Glu Glu Gly Thr Gly His
    130                 135                 140

Ala Glu Gly Ala Ser Gly Thr Phe Arg Thr Ser Phe Leu Pro Ala Thr
145                 150                 155                 160

Thr Ala Pro Gln Thr Pro Ala Glu Tyr Asp Ala Val Trp Ser Ala Trp
                165                 170                 175

Arg Arg Ala Ala Pro Ala Glu Glu Ser Arg Gly Arg Ala Ala Val Val
            180                 185                 190

Gln Lys Met Arg Ala Cys Leu Asn Asn Gly Asn Ala Val Leu Asn Val
    195                 200                 205

Gly Glu Ser Gly Leu Thr Thr Leu Pro Asp Cys Leu Pro Ala His Ile
210                 215                 220

Thr Thr Leu Val Ile Pro Asp Asn Asn Leu Thr Ser Leu Pro Ala Leu
225                 230                 235                 240

Pro Pro Glu Leu Arg Thr Leu Glu Val Ser Gly Asn Gln Leu Thr Ser
                245                 250                 255

Leu Pro Val Leu Pro Pro Gly Leu Leu Glu Leu Ser Ile Phe Ser Asn
            260                 265                 270

Pro Leu Thr His Leu Pro Ala Leu Pro Ser Gly Leu Cys Lys Leu Trp
    275                 280                 285

Ile Phe Gly Asn Gln Leu Thr Ser Leu Pro Val Leu Pro Pro Gly Leu
290                 295                 300

Gln Glu Leu Ser Val Ser Asp Asn Gln Leu Ala Ser Leu Pro Ala Leu
305                 310                 315                 320

Pro Ser Glu Leu Cys Lys Leu Trp Ala Tyr Asn Asn Gln Leu Thr Ser
                325                 330                 335

Leu Pro Met Leu Pro Ser Gly Leu Gln Glu Leu Ser Val Ser Asp Asn
            340                 345                 350

Gln Leu Ala Ser Leu Pro Thr Leu Pro Ser Glu Leu Tyr Lys Leu Trp
    355                 360                 365

Ala Tyr Asn Asn Arg Leu Thr Ser Leu Pro Ala Leu Pro Ser Gly Leu
370                 375                 380

Lys Glu Leu Ile Val Ser Gly Asn Arg Leu Thr Ser Leu Pro Val Leu
385                 390                 395                 400

Pro Ser Glu Leu Lys Glu Leu Met Val Ser Gly Asn Arg Leu Thr Ser
                405                 410                 415

Leu Pro Met Leu Pro Ser Gly Leu Leu Ser Leu Ser Val Tyr Arg Asn
            420                 425                 430

Gln Leu Thr Arg Leu Pro Glu Ser Leu Ile His Leu Ser Ser Glu Thr
    435                 440                 445

Thr Val Asn Leu Glu Gly Asn Pro Leu Ser Glu Arg Thr Leu Gln Ala
450                 455                 460

Leu Arg Glu Ile Thr Ser Ala Pro Gly Tyr Ser Gly Pro Ile Ile Arg
465                 470                 475                 480

Phe Asp Met Ala Gly Ala Ser Ala Pro Arg Glu Thr Arg Ala Leu His
                485                 490                 495

Leu Ala Ala Ala Asp Trp Leu Val Pro Ala Arg Glu Gly Glu Pro Ala
            500                 505                 510

Pro Ala Asp Arg Trp His Met Phe Gly Gln Glu Asp Asn Ala Asp Ala
    515                 520                 525

Phe Ser Leu Phe Leu Asp Arg Leu Ser Glu Thr Glu Asn Phe Ile Lys
```

```
                530                 535                 540

Asp Ala Gly Phe Lys Ala Gln Ile Ser Ser Trp Leu Ala Gln Leu Ala
545                 550                 555                 560

Glu Asp Glu Ala Leu Arg Ala Asn Thr Phe Ala Met Ala Thr Glu Ala
                565                 570                 575

Thr Ser Ser Cys Glu Asp Arg Val Thr Phe Phe Leu His Gln Met Lys
                580                 585                 590

Asn Val Gln Leu Val His Asn Ala Glu Lys Gly Gln Tyr Asp Asn Asp
                595                 600                 605

Leu Ala Ala Leu Val Ala Thr Gly Arg Glu Met Phe Arg Leu Gly Lys
610                 615                 620

Leu Glu Gln Ile Ala Arg Glu Lys Val Arg Thr Leu Ala Leu Val Asp
625                 630                 635                 640

Glu Ile Glu Val Trp Leu Ala Tyr Gln Asn Lys Leu Lys Lys Ser Leu
                645                 650                 655

Gly Leu Thr Ser Val Thr Ser Glu Met Arg Phe Phe Asp Val Ser Gly
                660                 665                 670

Val Thr Val Thr Asp Leu Gln Asp Ala Glu Leu Gln Val Lys Ala Ala
                675                 680                 685

Glu Lys Ser Glu Phe Arg Glu Trp Ile Leu Gln Trp Gly Pro Leu His
690                 695                 700

Arg Val Leu Glu Arg Lys Ala Pro Glu Arg Val Asn Ala Leu Arg Glu
705                 710                 715                 720

Lys Gln Ile Ser Asp Tyr Glu Glu Thr Tyr Arg Met Leu Ser Asp Thr
                725                 730                 735

Glu Leu Arg Pro Ser Gly Leu Val Gly Asn Thr Asp Ala Glu Arg Thr
                740                 745                 750

Ile Gly Ala Arg Ala Met Glu Ser Ala Lys Lys Thr Phe Leu Asp Gly
                755                 760                 765

Leu Arg Pro Leu Val Glu Glu Met Leu Gly Ser Tyr Leu Asn Val Gln
                770                 775                 780

Trp Arg Arg Asn
785

<210> SEQ ID NO 4
<211> LENGTH: 575
<212> TYPE: PRT
<213> ORGANISM: Shigella flexneri

<400> SEQUENCE: 4

Met Ile Lys Ser Thr Asn Ile Gln Ala Ile Gly Ser Gly Ile Met His
1               5                   10                  15

Gln Ile Asn Asn Val Tyr Ser Leu Thr Pro Leu Ser Leu Pro Met Glu
                20                  25                  30

Leu Thr Pro Ser Cys Asn Glu Phe Tyr Leu Lys Thr Trp Ser Glu Trp
            35                  40                  45

Glu Lys Asn Gly Thr Pro Gly Glu Gln Arg Asn Ile Ala Phe Asn Arg
        50                  55                  60

Leu Lys Ile Cys Leu Gln Asn Gln Glu Ala Glu Leu Asn Leu Ser Glu
65              70                  75                  80

Leu Asp Leu Lys Thr Leu Pro Asp Leu Pro Gln Ile Thr Thr Leu
                85                  90                  95

Glu Ile Arg Lys Asn Leu Leu Thr His Leu Pro Asp Leu Pro Pro Met
                100                 105                 110
```

```
Leu Lys Val Ile His Ala Gln Phe Asn Gln Leu Glu Ser Leu Pro Ala
        115                 120                 125

Leu Pro Glu Thr Leu Glu Glu Leu Asn Ala Gly Asp Asn Lys Ile Lys
130                 135                 140

Glu Leu Pro Phe Leu Pro Glu Asn Leu Thr His Leu Arg Val His Asn
145                 150                 155                 160

Asn Arg Leu His Ile Leu Pro Leu Leu Pro Glu Leu Lys Leu Leu
                165                 170                 175

Val Val Ser Gly Asn Arg Leu Asp Ser Ile Pro Pro Phe Pro Asp Lys
            180                 185                 190

Leu Glu Gly Leu Ala Leu Ala Asn Asn Phe Ile Glu Gln Leu Pro Glu
        195                 200                 205

Leu Pro Phe Ser Met Asn Arg Ala Val Leu Met Asn Asn Asn Leu Thr
    210                 215                 220

Thr Leu Pro Glu Ser Val Leu Arg Leu Ala Gln Asn Ala Phe Val Asn
225                 230                 235                 240

Val Ala Gly Asn Pro Leu Ser Gly His Thr Met Arg Thr Leu Gln Gln
                245                 250                 255

Ile Thr Thr Gly Pro Asp Tyr Ser Gly Pro Arg Ile Phe Phe Ser Met
            260                 265                 270

Gly Asn Ser Ala Thr Ile Ser Ala Pro Glu His Ser Leu Ala Asp Ala
        275                 280                 285

Val Thr Ala Trp Phe Pro Glu Asn Lys Gln Ser Asp Val Ser Gln Ile
    290                 295                 300

Trp His Ala Phe Glu His Glu His Ala Asn Thr Phe Ser Ala Phe
305                 310                 315                 320

Leu Asp Arg Leu Ser Asp Thr Val Ser Ala Arg Asn Thr Ser Gly Phe
                325                 330                 335

Arg Glu Gln Val Ala Ala Trp Leu Glu Lys Leu Ser Ala Ser Ala Glu
            340                 345                 350

Leu Arg Gln Gln Ser Phe Ala Val Ala Ala Asp Ala Thr Glu Ser Cys
        355                 360                 365

Glu Asp Arg Val Ala Leu Thr Trp Asn Asn Leu Arg Lys Thr Leu Leu
370                 375                 380

Val His Gln Ala Ser Glu Gly Leu Phe Asp Asn Asp Thr Gly Ala Leu
385                 390                 395                 400

Leu Ser Leu Gly Arg Glu Met Phe Arg Leu Glu Ile Leu Glu Asp Ile
                405                 410                 415

Ala Arg Asp Lys Val Arg Thr Leu His Phe Val Asp Glu Ile Glu Val
            420                 425                 430

Tyr Leu Ala Phe Gln Thr Met Leu Ala Glu Lys Leu Gln Leu Ser Thr
        435                 440                 445

Ala Val Lys Glu Met Arg Phe Tyr Gly Val Ser Gly Val Thr Ala Asn
    450                 455                 460

Asp Leu Arg Thr Ala Glu Ala Met Val Arg Ser Arg Glu Glu Asn Glu
465                 470                 475                 480

Phe Thr Asp Trp Phe Ser Leu Trp Gly Pro Trp His Ala Val Leu Lys
                485                 490                 495

Arg Thr Glu Ala Asp Arg Trp Ala Gln Ala Glu Gln Lys Tyr Glu
            500                 505                 510

Met Leu Glu Asn Glu Tyr Ser Gln Arg Val Ala Asp Arg Leu Lys Ala
        515                 520                 525

Ser Gly Leu Ser Gly Asp Ala Asp Ala Glu Arg Glu Ala Gly Ala Gln
```

```
                530           535           540
Val Met Arg Glu Thr Glu Gln Gln Ile Tyr Arg Gln Leu Thr Asp Glu
545                 550                 555                 560

Val Leu Ala Leu Arg Leu Ser Glu Asn Gly Ser Asn His Ile Ala
                565                 570                 575

<210> SEQ ID NO 5
<211> LENGTH: 563
<212> TYPE: PRT
<213> ORGANISM: Shigella flexneri

<400> SEQUENCE: 5

Met Ile Lys Ser Thr Asn Ile Gln Val Ile Gly Ser Gly Ile Met His
1               5                   10                  15

Gln Ile Asn Asn Ile His Ser Leu Thr Leu Phe Ser Leu Pro Val Ser
                20                  25                  30

Leu Ser Pro Ser Cys Asn Glu Tyr Tyr Leu Lys Val Trp Ser Glu Trp
            35                  40                  45

Glu Lys Asn Gly Thr Pro Gly Glu Gln Arg Asn Ile Ala Phe Asn Arg
        50                  55                  60

Leu Lys Ile Cys Leu Gln Asn Gln Glu Ala Glu Leu Asn Leu Ser Glu
65                  70                  75                  80

Leu Asp Leu Lys Thr Leu Pro Asp Leu Pro Gln Ile Thr Thr Leu
                85                  90                  95

Glu Ile Arg Lys Asn Leu Leu Thr His Leu Pro Asp Leu Pro Pro Met
                100                 105                 110

Leu Lys Val Ile His Ala Gln Phe Asn Gln Leu Glu Ser Leu Pro Ala
            115                 120                 125

Leu Pro Glu Thr Leu Glu Glu Leu Asn Ala Gly Asp Asn Lys Ile Lys
        130                 135                 140

Glu Leu Pro Phe Leu Pro Glu Asn Leu Thr His Leu Arg Val His Asn
145                 150                 155                 160

Asn Arg Leu His Ile Leu Pro Leu Leu Pro Glu Leu Lys Leu Leu
                165                 170                 175

Val Val Ser Gly Asn Arg Leu Asp Ser Ile Pro Pro Phe Pro Asp Lys
            180                 185                 190

Leu Glu Gly Leu Ala Leu Ala Asn Asn Phe Ile Glu Gln Leu Pro Glu
        195                 200                 205

Leu Pro Phe Ser Met Asn Arg Ala Val Leu Met Asn Asn Asn Leu Thr
210                 215                 220

Thr Leu Pro Glu Ser Val Leu Arg Leu Ala Gln Asn Ala Phe Val Asn
225                 230                 235                 240

Val Ala Gly Asn Pro Leu Ser Gly His Thr Met Arg Thr Leu Gln Gln
                245                 250                 255

Ile Thr Thr Gly Pro Asp Tyr Ser Gly Pro Arg Ile Phe Phe Ser Met
            260                 265                 270

Gly Asn Ser Ala Thr Ile Ser Ala Pro Glu His Ser Leu Ala Asp Ala
        275                 280                 285

Val Thr Ala Trp Phe Pro Glu Asn Lys Gln Ser Asp Val Ser Gln Ile
    290                 295                 300

Trp His Ala Phe Glu His Glu His Ala Asn Thr Phe Ser Ala Phe
305                 310                 315                 320

Leu Asp Arg Leu Ser Asp Thr Val Ser Ala Arg Asn Thr Ser Gly Phe
                325                 330                 335
```

```
Arg Glu Gln Val Ala Ala Trp Leu Glu Lys Leu Ser Ala Ser Ala Glu
            340                 345                 350

Leu Arg Gln Gln Ser Phe Ala Val Ala Ala Asp Ala Thr Glu Ser Cys
        355                 360                 365

Glu Asp Arg Val Ala Leu Thr Trp Asn Asn Leu Arg Lys Thr Leu Leu
    370                 375                 380

Val His Gln Ala Ser Glu Gly Leu Phe Asp Asn Asp Thr Gly Ala Leu
385                 390                 395                 400

Leu Ser Leu Gly Arg Glu Met Phe Arg Leu Glu Ile Leu Glu Asp Ile
                405                 410                 415

Ala Arg Asp Lys Val Arg Thr Leu His Phe Val Asp Glu Ile Glu Val
            420                 425                 430

Tyr Leu Ala Phe Gln Thr Met Leu Ala Glu Lys Leu Gln Leu Ser Thr
        435                 440                 445

Ala Val Lys Glu Met Arg Phe Tyr Gly Val Ser Gly Val Thr Ala Asn
    450                 455                 460

Asp Leu Arg Thr Ala Glu Ala Met Val Arg Ser Arg Glu Glu Asn Glu
465                 470                 475                 480

Phe Thr Asp Trp Phe Ser Leu Trp Gly Pro Trp His Ala Val Leu Lys
                485                 490                 495

Arg Thr Glu Ala Asp Arg Trp Ala Gln Ala Glu Gln Lys Tyr Glu
            500                 505                 510

Met Leu Glu Asn Glu Tyr Ser Gln Arg Val Ala Asp Arg Leu Lys Ala
        515                 520                 525

Ser Gly Leu Ser Gly Asp Ala Asp Ala Glu Arg Glu Ala Gly Ala Gln
    530                 535                 540

Val Met Arg Glu Thr Glu Gln Gln Ile Tyr Arg Gln Leu Thr Asp Glu
545                 550                 555                 560

Val Leu Ala

<210> SEQ ID NO 6
<211> LENGTH: 583
<212> TYPE: PRT
<213> ORGANISM: Shigella flexneri

<400> SEQUENCE: 6

Met Leu Pro Thr Asn Asn His Arg Leu Ile Ser Asn Ser Phe Ser
1               5                   10                  15

Thr Tyr Ser Ile Asp Thr Ser Arg Ala Tyr Glu Asn Tyr Leu Thr His
            20                  25                  30

Trp Thr Glu Trp Lys Asn Asn Arg Ile Gln Glu Glu Gln Arg Asp Ile
        35                  40                  45

Ala Phe Gln Arg Leu Val Ser Cys Leu Gln Asn Gln Glu Thr Asn Leu
    50                  55                  60

Asp Leu Ser Glu Leu Gly Leu Thr Thr Leu Pro Glu Ile Pro Pro Gly
65                  70                  75                  80

Ile Lys Ser Ile Asn Ile Ser Lys Asn Asn Leu Ser Leu Ile Ser Pro
                85                  90                  95

Leu Pro Ala Ser Leu Thr Gln Leu Asn Val Ser Tyr Asn Arg Leu Ile
            100                 105                 110

Glu Leu Pro Ala Leu Pro Gln Gly Leu Lys Leu Leu Asn Ala Ser His
        115                 120                 125

Asn Gln Leu Ile Thr Leu Pro Thr Leu Pro Ile Ser Leu Lys Glu Leu
    130                 135                 140
```

```
His Val Ser Asn Asn Gln Leu Cys Ser Leu Pro Val Leu Pro Glu Leu
145                 150                 155                 160

Leu Glu Thr Leu Asp Val Ser Cys Asn Gly Leu Ala Val Leu Pro Pro
            165                 170                 175

Leu Pro Phe Ser Leu Gln Glu Ile Ser Ala Ile Gly Asn Leu Leu Ser
        180                 185                 190

Glu Leu Pro Pro Leu Pro His Asn Ile His Ser Ile Trp Ala Ile Asp
    195                 200                 205

Asn Met Leu Thr Asp Ile Pro Tyr Leu Pro Glu Asn Leu Arg Asn Gly
        210                 215                 220

Tyr Phe Asp Ile Asn Gln Ile Ser His Ile Pro Glu Ser Ile Leu Asn
225                 230                 235                 240

Leu Arg Asn Glu Cys Ser Ile Asp Ile Ser Asp Asn Pro Leu Ser Ser
                245                 250                 255

His Ala Leu Gln Ser Leu Gln Arg Leu Thr Ser Ser Pro Asp Tyr His
            260                 265                 270

Gly Pro Gln Ile Tyr Phe Ser Met Ser Asp Gly Gln Gln Asn Thr Leu
        275                 280                 285

His Arg Pro Leu Ala Asp Ala Val Thr Ala Trp Phe Pro Glu Asn Lys
    290                 295                 300

Gln Ser Asp Val Ser Gln Ile Trp His Ala Phe Glu His Glu His
305                 310                 315                 320

Ala Asn Thr Phe Ser Ala Phe Leu Asp Arg Leu Ser Asp Thr Val Ser
                325                 330                 335

Ala Arg Asn Thr Ser Gly Phe Arg Glu Gln Val Ala Ala Trp Leu Glu
            340                 345                 350

Lys Leu Ser Ala Ser Ala Glu Leu Arg Gln Gln Ser Phe Ala Val Ala
        355                 360                 365

Ala Asp Ala Thr Glu Ser Cys Glu Asp Arg Val Ala Leu Thr Trp Asn
    370                 375                 380

Asn Leu Arg Lys Thr Leu Leu Val His Gln Ala Ser Glu Gly Leu Phe
385                 390                 395                 400

Asp Asn Asp Thr Gly Ala Leu Leu Ser Leu Gly Arg Glu Met Phe Arg
                405                 410                 415

Leu Glu Ile Leu Glu Asp Ile Ala Arg Asp Lys Val Arg Thr Leu His
            420                 425                 430

Phe Val Asp Glu Ile Glu Val Tyr Leu Ala Phe Gln Thr Met Leu Ala
        435                 440                 445

Glu Lys Leu Gln Leu Ser Thr Ala Val Lys Glu Met Arg Phe Tyr Gly
    450                 455                 460

Val Ser Gly Val Thr Ala Asn Asp Leu Arg Thr Ala Glu Ala Met Val
465                 470                 475                 480

Arg Ser Arg Glu Glu Asn Glu Phe Thr Asp Trp Phe Ser Leu Trp Gly
                485                 490                 495

Pro Trp His Ala Val Leu Lys Arg Thr Glu Ala Asp Arg Trp Ala Gln
            500                 505                 510

Ala Glu Glu Gln Lys Tyr Glu Met Leu Glu Asn Glu Tyr Pro Gln Arg
        515                 520                 525

Val Ala Asp Arg Leu Lys Ala Ser Gly Leu Ser Gly Asp Ala Asp Ala
    530                 535                 540

Glu Arg Glu Ala Gly Ala Gln Val Met Arg Glu Thr Glu Gln Gln Ile
545                 550                 555                 560

Tyr Arg Gln Leu Thr Asp Glu Val Leu Ala Leu Arg Leu Pro Glu Asn
```

Gly Ser Gln Leu His His Ser
            580

<210> SEQ ID NO 7
<211> LENGTH: 574
<212> TYPE: PRT
<213> ORGANISM: Shigella flexneri

<400> SEQUENCE: 7

Met Lys Pro Ile Asn Asn His Ser Phe Phe Arg Ser Leu Cys Gly Leu
1               5                   10                  15

Ser Cys Ile Ser Arg Leu Ser Val Glu Glu Cys Thr Arg Asp Tyr
                20                  25                  30

His Arg Ile Trp Asp Asp Trp Ala Arg Glu Gly Thr Thr Thr Glu Asn
            35                  40                  45

Arg Ile Gln Ala Val Arg Leu Leu Lys Ile Cys Leu Asp Thr Arg Glu
        50                  55                  60

Pro Val Leu Asn Leu Ser Leu Lys Leu Arg Ser Leu Pro Pro Leu
65                  70                  75                  80

Pro Leu His Ile Arg Glu Leu Asn Ile Ser Asn Asn Glu Leu Ile Ser
                85                  90                  95

Leu Pro Glu Asn Ser Pro Leu Leu Thr Glu Leu His Val Asn Gly Asn
            100                 105                 110

Asn Leu Asn Ile Leu Pro Thr Leu Pro Ser Gln Leu Ile Lys Leu Asn
        115                 120                 125

Ile Ser Phe Asn Arg Asn Leu Ser Cys Leu Pro Ser Leu Pro Pro Tyr
130                 135                 140

Leu Gln Ser Leu Ser Ala Arg Phe Asn Ser Leu Glu Thr Leu Pro Glu
145                 150                 155                 160

Leu Pro Ser Thr Leu Thr Ile Leu Arg Ile Glu Gly Asn Arg Leu Thr
                165                 170                 175

Val Leu Pro Glu Leu Pro His Arg Leu Gln Glu Leu Phe Val Ser Gly
            180                 185                 190

Asn Arg Leu Gln Glu Leu Pro Glu Phe Pro Gln Ser Leu Lys Tyr Leu
        195                 200                 205

Lys Val Gly Glu Asn Gln Leu Arg Arg Leu Ser Arg Leu Pro Gln Glu
210                 215                 220

Leu Leu Ala Leu Asp Val Ser Asn Asn Leu Leu Thr Ser Leu Pro Glu
225                 230                 235                 240

Asn Ile Ile Thr Leu Pro Ile Cys Thr Asn Val Asn Ile Ser Gly Asn
                245                 250                 255

Pro Leu Ser Thr His Val Leu Gln Ser Leu Gln Arg Leu Thr Ser Ser
            260                 265                 270

Pro Asp Tyr His Gly Pro Gln Ile Tyr Phe Ser Met Ser Asp Gly Gln
        275                 280                 285

Gln Asn Thr Leu His Arg Pro Leu Ala Asp Ala Val Thr Ala Trp Phe
290                 295                 300

Pro Glu Asn Lys Gln Ser Asp Val Ser Gln Ile Trp His Ala Phe Glu
305                 310                 315                 320

His Glu Glu His Ala Asn Thr Phe Ser Ala Phe Leu Asp Arg Leu Ser
                325                 330                 335

Asp Thr Val Ser Ala Arg Asn Thr Ser Gly Phe Arg Glu Gln Val Ala
            340                 345                 350

```
Ala Trp Leu Glu Lys Leu Ser Ala Ser Ala Glu Leu Arg Gln Gln Ser
            355                 360                 365

Phe Ala Val Ala Ala Asp Ala Thr Glu Ser Cys Glu Asp Arg Val Ala
    370                 375                 380

Leu Thr Trp Asn Asn Leu Arg Lys Thr Leu Leu Val His Gln Ala Ser
385                 390                 395                 400

Glu Gly Leu Phe Asp Asn Asp Thr Gly Ala Leu Leu Ser Leu Gly Arg
                405                 410                 415

Glu Met Phe Arg Leu Glu Ile Leu Glu Asp Ile Ala Arg Asp Lys Val
            420                 425                 430

Arg Thr Leu His Phe Val Asp Glu Ile Glu Val Tyr Leu Ala Phe Gln
        435                 440                 445

Thr Met Leu Ala Glu Lys Leu Gln Leu Ser Thr Ala Val Lys Glu Met
    450                 455                 460

Arg Phe Tyr Gly Val Ser Gly Val Thr Ala Asn Asp Leu Arg Thr Ala
465                 470                 475                 480

Glu Ala Met Val Arg Ser Arg Glu Glu Asn Glu Phe Thr Asp Trp Phe
                485                 490                 495

Ser Leu Trp Gly Pro Trp His Ala Val Leu Lys Arg Thr Glu Ala Asp
            500                 505                 510

Arg Trp Ala Gln Ala Glu Gln Lys Tyr Glu Met Leu Glu Asn Glu
        515                 520                 525

Tyr Ser Gln Arg Val Ala Asp Arg Leu Lys Ala Ser Gly Leu Ser Gly
    530                 535                 540

Asp Ala Asp Ala Glu Arg Glu Ala Gly Ala Gln Val Met Arg Glu Thr
545                 550                 555                 560

Glu Gln Gln Ile Tyr Arg Gln Leu Thr Asp Glu Val Leu Ala
                565                 570

<210> SEQ ID NO 8
<211> LENGTH: 565
<212> TYPE: PRT
<213> ORGANISM: Shigella flexneri

<400> SEQUENCE: 8

Met Phe Ser Val Asn Asn Thr His Ser Ser Val Ser Cys Ser Pro Ser
1               5                   10                  15

Ile Asn Ser Asn Ser Thr Ser Asn Glu His Tyr Leu Arg Ile Leu Thr
            20                  25                  30

Glu Trp Glu Lys Asn Ser Ser Pro Gly Glu Glu Arg Gly Ile Ala Phe
        35                  40                  45

Asn Arg Leu Ser Gln Cys Phe Gln Asn Gln Glu Ala Val Leu Asn Leu
    50                  55                  60

Ser Asp Leu Asn Leu Thr Ser Leu Pro Glu Leu Pro Lys His Ile Ser
65                  70                  75                  80

Ala Leu Ile Val Glu Asn Asn Lys Leu Thr Ser Leu Pro Lys Leu Pro
                85                  90                  95

Ala Phe Leu Lys Glu Leu Asn Ala Asp Asn Asn Arg Leu Ser Val Ile
            100                 105                 110

Pro Glu Leu Pro Glu Ser Leu Thr Thr Leu Ser Val Arg Ser Asn Gln
        115                 120                 125

Leu Glu Asn Leu Pro Val Leu Pro Asn His Leu Thr Ser Leu Phe Val
    130                 135                 140

Glu Asn Asn Arg Leu Tyr Asn Leu Pro Ala Leu Pro Glu Lys Leu Lys
145                 150                 155                 160
```

```
Phe Leu His Val Tyr Tyr Asn Arg Leu Thr Thr Leu Pro Asp Leu Pro
                165                 170                 175

Asp Lys Leu Glu Ile Leu Cys Ala Gln Arg Asn Asn Leu Val Thr Phe
            180                 185                 190

Pro Gln Phe Ser Asp Arg Asn Asn Ile Arg Gln Lys Glu Tyr Tyr Phe
        195                 200                 205

His Phe Asn Gln Ile Thr Thr Leu Pro Glu Ser Phe Ser Gln Leu Asp
    210                 215                 220

Ser Ser Tyr Arg Ile Asn Ile Ser Gly Asn Pro Leu Ser Thr Arg Val
225                 230                 235                 240

Leu Gln Ser Leu Gln Arg Leu Thr Ser Ser Pro Asp Tyr His Gly Pro
                245                 250                 255

Gln Ile Tyr Phe Ser Met Ser Asp Gly Gln Gln Asn Thr Leu His Arg
            260                 265                 270

Pro Leu Ala Asp Ala Val Thr Ala Trp Phe Pro Glu Asn Lys Gln Ser
        275                 280                 285

Asp Val Ser Gln Ile Trp His Ala Phe Glu His Glu His Ala Asn
    290                 295                 300

Thr Phe Ser Ala Phe Leu Asp Arg Leu Ser Asp Thr Val Ser Ala Arg
305                 310                 315                 320

Asn Thr Ser Gly Phe Arg Glu Gln Val Ala Ala Trp Leu Glu Lys Leu
                325                 330                 335

Ser Ala Ser Ala Glu Leu Arg Gln Gln Ser Phe Ala Val Ala Ala Asp
            340                 345                 350

Ala Thr Glu Ser Cys Glu Asp Arg Val Ala Leu Thr Trp Asn Asn Leu
        355                 360                 365

Arg Lys Thr Leu Leu Val His Gln Ala Ser Glu Gly Leu Phe Asp Asn
    370                 375                 380

Asp Thr Gly Ala Leu Leu Ser Leu Gly Arg Glu Met Phe Arg Leu Glu
385                 390                 395                 400

Ile Leu Glu Asp Ile Ala Arg Asp Lys Val Arg Thr Leu His Phe Val
                405                 410                 415

Asp Glu Ile Glu Val Tyr Leu Ala Phe Gln Thr Met Leu Ala Glu Lys
            420                 425                 430

Leu Gln Leu Ser Thr Ala Val Lys Glu Met Arg Phe Tyr Gly Val Ser
        435                 440                 445

Gly Val Thr Ala Asn Asp Leu Arg Thr Ala Glu Ala Met Val Arg Ser
    450                 455                 460

Arg Glu Glu Asn Glu Phe Thr Asp Trp Phe Ser Leu Trp Gly Pro Trp
465                 470                 475                 480

His Ala Val Leu Lys Arg Thr Glu Ala Asp Arg Trp Ala Gln Ala Glu
                485                 490                 495

Glu Gln Lys Tyr Glu Met Leu Glu Asn Glu Tyr Ser Gln Arg Val Ala
            500                 505                 510

Asp Arg Leu Lys Ala Ser Gly Leu Ser Gly Asp Ala Asp Ala Glu Arg
        515                 520                 525

Glu Ala Gly Ala Gln Val Met Arg Glu Thr Glu Gln Gln Ile Tyr Arg
    530                 535                 540

Gln Leu Thr Asp Glu Val Leu Ala Leu Arg Leu Ser Glu Asn Gly Ser
545                 550                 555                 560

Arg Leu His His Ser
                565
```

```
<210> SEQ ID NO 9
<211> LENGTH: 545
<212> TYPE: PRT
<213> ORGANISM: Shigella flexneri

<400> SEQUENCE: 9
```

| | | | | | | | | | | | | | | | |
|---|---|---|---|---|---|---|---|---|---|---|---|---|---|---|---|
| Met | Leu | Pro | Ile | Asn | Asn | Asn | Phe | Ser | Leu | Pro | Gln | Asn | Ser | Phe | Tyr |
| 1 | | | | 5 | | | | | 10 | | | | | 15 | |
| Asn | Thr | Ile | Ser | Gly | Thr | Tyr | Ala | Asp | Tyr | Phe | Ser | Ala | Trp | Asp | Lys |
| | | | 20 | | | | | 25 | | | | | 30 | | |
| Trp | Glu | Lys | Gln | Ala | Leu | Pro | Gly | Glu | Glu | Arg | Asp | Glu | Ala | Val | Ser |
| | | 35 | | | | | 40 | | | | | 45 | | | |
| Arg | Leu | Lys | Glu | Cys | Leu | Ile | Asn | Asn | Ser | Asp | Glu | Leu | Arg | Leu | Asp |
| | 50 | | | | | 55 | | | | | 60 | | | | |
| Arg | Leu | Asn | Leu | Ser | Ser | Leu | Pro | Asp | Asn | Leu | Pro | Ala | Gln | Ile | Thr |
| 65 | | | | | 70 | | | | | 75 | | | | | 80 |
| Leu | Leu | Asn | Val | Ser | Tyr | Asn | Gln | Leu | Thr | Asn | Leu | Pro | Glu | Leu | Pro |
| | | | | 85 | | | | | 90 | | | | | 95 | |
| Val | Thr | Leu | Lys | Lys | Leu | Tyr | Ser | Ala | Ser | Asn | Lys | Leu | Ser | Glu | Leu |
| | | | 100 | | | | | 105 | | | | | 110 | | |
| Pro | Val | Leu | Pro | Pro | Ala | Leu | Glu | Ser | Leu | Gln | Val | Gln | His | Asn | Glu |
| | | 115 | | | | | 120 | | | | | 125 | | | |
| Leu | Glu | Asn | Leu | Pro | Ala | Leu | Pro | Asp | Ser | Leu | Leu | Thr | Met | Asn | Ile |
| | 130 | | | | | 135 | | | | | 140 | | | | |
| Ser | Tyr | Asn | Glu | Ile | Val | Ser | Leu | Pro | Ser | Leu | Pro | Gln | Ala | Leu | Lys |
| 145 | | | | | 150 | | | | | 155 | | | | | 160 |
| Asn | Leu | Arg | Ala | Thr | Arg | Asn | Phe | Leu | Thr | Glu | Leu | Pro | Ala | Phe | Ser |
| | | | | 165 | | | | | 170 | | | | | 175 | |
| Glu | Gly | Asn | Asn | Pro | Val | Val | Arg | Glu | Tyr | Phe | Phe | Asp | Arg | Asn | Gln |
| | | | 180 | | | | | 185 | | | | | 190 | | |
| Ile | Ser | His | Ile | Pro | Glu | Ser | Ile | Leu | Asn | Leu | Arg | Asn | Glu | Cys | Ser |
| | | 195 | | | | | 200 | | | | | 205 | | | |
| Ile | His | Ile | Ser | Asp | Asn | Pro | Leu | Ser | Ser | His | Ala | Leu | Gln | Ala | Leu |
| | 210 | | | | | 215 | | | | | 220 | | | | |
| Gln | Arg | Leu | Thr | Ser | Ser | Pro | Asp | Tyr | His | Gly | Pro | Arg | Ile | Tyr | Phe |
| 225 | | | | | 230 | | | | | 235 | | | | | 240 |
| Ser | Met | Ser | Asp | Gly | Gln | Gln | Asn | Thr | Leu | His | Arg | Pro | Leu | Ala | Asp |
| | | | | 245 | | | | | 250 | | | | | 255 | |
| Ala | Val | Thr | Ala | Trp | Phe | Pro | Glu | Asn | Lys | Gln | Ser | Asp | Val | Ser | Gln |
| | | | 260 | | | | | 265 | | | | | 270 | | |
| Ile | Trp | His | Ala | Phe | Glu | His | Glu | His | Ala | Asn | Thr | Phe | Ser | Ala |
| | | 275 | | | | | 280 | | | | | 285 | | | |
| Phe | Leu | Asp | Arg | Leu | Ser | Asp | Thr | Val | Ser | Ala | Arg | Asn | Thr | Ser | Gly |
| | 290 | | | | | 295 | | | | | 300 | | | | |
| Phe | Arg | Glu | Gln | Val | Ala | Ala | Trp | Leu | Glu | Lys | Leu | Ser | Ala | Ser | Ala |
| 305 | | | | | 310 | | | | | 315 | | | | | 320 |
| Glu | Leu | Arg | Gln | Gln | Ser | Phe | Ala | Val | Ala | Asp | Ala | Thr | Glu | Ser |
| | | | | 325 | | | | | 330 | | | | | 335 | |
| Cys | Glu | Asp | Arg | Val | Ala | Leu | Thr | Trp | Asn | Asn | Leu | Arg | Lys | Thr | Leu |
| | | | 340 | | | | | 345 | | | | | 350 | | |
| Leu | Val | His | Gln | Ala | Ser | Glu | Gly | Leu | Phe | Asp | Asn | Asp | Thr | Gly | Ala |
| | | 355 | | | | | 360 | | | | | 365 | | | |
| Leu | Leu | Ser | Leu | Gly | Arg | Glu | Met | Phe | Arg | Leu | Glu | Ile | Leu | Glu | Asp |
| | 370 | | | | | 375 | | | | | 380 | | | | |

```
Ile Ala Arg Asp Lys Val Arg Thr Leu His Phe Val Asp Glu Ile Glu
385                 390                 395                 400

Val Tyr Leu Ala Phe Gln Thr Met Leu Ala Glu Lys Leu Gln Leu Ser
            405                 410                 415

Thr Ala Val Lys Glu Met Arg Phe Tyr Gly Val Ser Gly Val Thr Ala
        420                 425                 430

Asn Asp Leu Arg Thr Ala Glu Ala Met Val Arg Ser Arg Glu Glu Asn
    435                 440                 445

Glu Phe Thr Asp Trp Phe Ser Leu Trp Gly Pro Trp His Ala Val Leu
450                 455                 460

Lys Arg Thr Glu Ala Asp Arg Trp Ala Gln Ala Glu Glu Gln Lys Tyr
465                 470                 475                 480

Glu Met Leu Glu Asn Glu Tyr Pro Gln Arg Val Ala Asp Arg Leu Lys
                485                 490                 495

Ala Ser Gly Leu Ser Gly Asp Ala Asp Ala Glu Arg Glu Ala Gly Ala
            500                 505                 510

Gln Val Met Arg Glu Thr Gln Gln Ile Tyr Arg Gln Leu Thr Asp
        515                 520                 525

Glu Val Leu Ala Leu Arg Leu Phe Glu Asn Gly Ser Gln Leu His His
530                 535                 540

Ser
545

<210> SEQ ID NO 10
<211> LENGTH: 2298
<212> TYPE: DNA
<213> ORGANISM: Salmonella enterica

<400> SEQUENCE: 10
atgtttaata ttactaatat acaatctacg gcaaggcatc aaagtattag caatgaggcc     60
tcaacagagg tgcctttaaa agaagagata tggaataaaa taagtgcctt tttctcttca    120
gaacatcagg ttgaagcaca aaactgcatc gcttatcttt gtcatccacc tgaaaccgcc    180
tcgccagaag agatcaaaag caagtttgaa tgtttaagga tgttagcttt cccggcgtat    240
gcggataata ttcagtatag tagaggaggg gcagaccaat actgtatttt gagtgaaaat    300
agtcaggaaa ttctgtctat agttttaat acagagggct ataccgttga gggagggga     360 aagtcagtca cctataccg tgtgacagaa agcgagcagg cgagtagcgc ttccggctcc    420
aaagatgctg tgaattatga gttaatctgg tctgagtggg taaaagaggc gccagcgaaa    480
gaggcagcaa atcgtgaaga agccgtacaa cggatgcgtg actgcctgaa aaataataag    540
acggaacttc gtctgaaaat attaggactt accactatac ctgcctatat tcctgagcag    600
ataactactc tgatactcga taacaatgaa ctgaaaagtt gccggaaaaa tttacaggga    660
aatataaaga ccctgtatgc caacagtaat cagctaacca gtatccctgc cacgttaccg    720
gataccatac aggaaatgga gctgagcatt aaccgtatta ctgaattgcc ggaacgtttg    780
ccttcagcgc ttcaatcgct ggatcttttc cataataaaa ttagttgctt acctgaaaat    840
ctacctgagg aacttcggta cctgagcgtt tatgataaca gcataaggac actgccagca    900
catcttccgt cagagattac ccatttgaat gtgcagagta attcgttaac cgctttgcct    960
gaaacattgc cgccgggcct gaagactctg gaggccggcg aaaatgcctt aaccagtctg   1020
cccgcatcgt taccaccaga attacaggtc tggatgtaa gtaaaaatca gattacggtt   1080
ctgcctgaaa cacttcctcc cacgataaca acgctggatg tttcccgtaa cgcattgact   1140
```

```
aatctaccgg aaaacctccc ggcggcatta caaataatgc aggcctctcg caataacctg   1200
gtccgtctcc cggagtcgtt accccatttt cgtggtgaag gacctcaacc tacaagaata   1260
atcgtagaat ataatccttt ttcagaacga acaatacaga atatgcagcg gctaatgtcc   1320
tctgtagatt atcagggacc ccgggtattg tttgccatgg gcgacttttc aattgttcgg   1380
gtaactcgac cactgcatca agctgtccag gggtggctaa ccagtctcga ggaggaagac   1440
gtcaaccaat ggcgggcgtt tgaggcagag gcaaacgcgg cggctttcag cggattcctg   1500
gactatcttg gtgatacgca gaatacccga cacccggatt taaggaaca agtctccgcc    1560 tggctaatgc gcctggctga agatagcgca ctaagaaaa ccgtatttat tatagcgatg     1620
aatgcaacga taagctgtga agatcgggtc acactggcat accaccaaat gcaggaagcg   1680
acgttggttc atgatgctga agaggcgcc tttgatagcc acttagcgga actgattatg      1740
gcggggcgtg aaatctttcg gctggagcaa atagaatcgc tcgccagaga aaaggtaaaa   1800
cggctgtttt ttattgacga agtcgaagta tttctggggt ttcagaatca gttacgagag   1860
tcgctgtcgc tgacaacaat gacccgggat atgcgatttt ataacgtttc gggtatcact   1920
gagtctgacc tggacgaggc ggaaataagg ataaaaatgg ctgaaaatag ggattttcac   1980
aaatggtttg cgctgtgggg gccgtggcat aaagtgctgg agcgcatagc gccagaagag   2040
tggcgtgaaa tgatggctaa aagggatgag tgtattgaaa cggatgagta tcagagccgg   2100
gtcaatgctg aactggaaga tttaagaata gcagacgact ctgacgcaga gcgtactact   2160
gaggtacaga tggatgcaga gcgtgctatt gggataaaaa taatgaaaga gatcaatcag   2220 accctctta ctgagatcat ggagaatata ttgctgaaaa aagaggtgag ctcgctcatg    2280
agcgcctact ggcgatag                                                  2298
```

<210> SEQ ID NO 11
<211> LENGTH: 2103
<212> TYPE: DNA
<213> ORGANISM: Salmonella enterica

<400> SEQUENCE: 11

```
atgtttaata tccgcaatac acaaccttct gtaagtatgc aggctattgc tggtgcagcg    60
gcaccagagg catctccgga agaaattgta tgggaaaaaa ttcaggtttt tttcccgcag   120
gaaaattacg aagaagcgca acagtgtctc gctgaacttt gccatccggc ccggggaatg   180
ttgcctgatc atatcagcag ccagtttgcg cgtttaaaag cgcttacctt ccccgcgtgg   240
gaggagaata ttcagtgtaa cagggatggt ataaatcagt tttgtattct ggatgcaggc   300
agcaaggaga tattgtcaat cactcttgat gatgccggga actataccgt gaattgtcag   360
gggtacagtg aagcacatga cttcatcatg gacacagaac cggagagga atgcacagaa   420 ttcgcggagg gggcatccgg gacatccctc cgccctgcca caacggtttc acagaaggca   480
gcagagtatg atgctgtctg gtcaaaatgg gaaagggatg caccagcagg agagtcaccc   540
ggccgcgcag cagtggtaca ggaaatgcgt gattgcctga taacggcaa tccagtgctt    600 aacgtgggag cgtcaggtct taccaccttt accagaccgtt taccaccgca tattacaaca   660
ctggttattc ctgataataa tctgaccagc ctgccggagt tgccggaagg actacgggag   720
ctggaggtct ctggtaacct acaactgacc agcctgccat cgctgccgca gggactacag   780
aagctgtggg cctataataa ttggctggcc agcctgccga cgttgccgcc aggactaggg    840
gatctggcgg tctctaataa ccagctgacc agcctgccgg agatgccgcc agcactacgg   900
```

```
gagctgaggg tctctggtaa caacctgacc agcctgccgg cgctgccgtc aggactacag    960
aagctgtggg cctataataa tcggctgacc agcctgccgg agatgtcgcc aggactacag   1020
gagctggatg tctctcataa ccagctgacc cgcctgccgc aaagcctcac gggtctgtct   1080
tcagcggcac gcgtatatct ggacgggaat ccactgtctg tacgcactct gcaggctctg   1140
cgggacatca ttggccattc aggcatcagg atacacttcg atatggcggg gccttccgtc   1200
ccccgggaag cccgggcact gcacctgcg gtcgctgact ggctgacgtc tgcacgggag   1260
ggggaagcgg cccaggcaga cagatggcag gcgttcggac tggaagataa cgccgccgcc   1320
ttcagcctgg tcctggacag actgcgtgag acggaaaact tcaaaaaaga cgcgggcttt   1380
aaggcacaga tatcatcctg gctgacacaa ctggctgaag atgctgcgct gagagcaaaa   1440
acctttgcca tggcaacaga ggcaacatca acctgcgagg accgggtcac acatgccctg   1500
caccagatga ataacgtaca actggtacat aatgcagaaa aaggggaata cgacaacaat   1560
ctccaggggc tggttttccac ggggcgtgag atgttccgcc tggcaacact ggaacagatt   1620
gcccgggaaa aagccggaac actggcttta gtcgatgacg ttgaggtcta tctggcgttc   1680
cagaataagc tgaaggaatc acttgagctg accagcgtga cgtcagaaat gcgtttcttt   1740
gacgtttccg gcgtgacggt ttcagacctt caggctgcgg agcttcaggt gaaaaccgct   1800
gaaaacagcg ggttcagtaa atggatactg cagtgggggc cgttacacag cgtgctggaa   1860
cgcaaagtgc cggaacgctt taacgcgctt cgtgaaaagc aaatatcgga ttatgaagac   1920
acgtaccgga agctgtatga cgaagtgctg aaatcgtccg ggctggtcga cgataccgat   1980
gcagaacgta ctatcggagt aagtgcgatg gatagtgcga aaaagaatt tctggatggc   2040 ctgcgcgctc ttgtggatga ggtgctgggt agctatctga cagcccggtg gcgtcttaac   2100
tga                                                                 2103

<210> SEQ ID NO 12
<211> LENGTH: 2367
<212> TYPE: DNA
<213> ORGANISM: Salmonella enterica

<400> SEQUENCE: 12
atgccctttc atattggaag cggatgtctt cccgccacca tcagtaatcg ccgcatttat     60
cgtattgcct ggtctgatac ccccctgaa atgagttcct gggaaaaaat gaaggaattt    120
ttttgctcaa cgcaccagac tgaagcgctg gagtgcatct ggacgatttg tcacccgccg    180
gccggaacga cgcgggagga tgtgatcaac agatttgaac tgctcaggac gctcgcgtat    240
gccggatggg aggaaagcat tcattccggc cagcacgggg aaaattactt ctgtattctg    300
gatgaagaca gtcaggagat attgtcagtc accccttgatg atgccgggaa ctataccgta    360
aattgccagg ggtacagtga acacatcgc ctcaccctgg acacagcaca gggtgaggag    420
ggcacaggac acgcggaagg ggcatccggg acattcagga catccttcct ccctgccaca    480
acggctccac agacgccagc agagtatgat gctgtctggt cagcgtggag aagggctgca    540
cccgcagaag agtcacgcgg ccgtgcagca gtggtacaga aaatgcgtgc ctgcctgaat    600
aatggcaatg cagtgcttaa cgtgggagaa tcaggtctta ccaccttgcc agactgttta    660
cccgcgcata ttaccacact ggttattcct gataataatc tgaccagcct gccggcgctg    720
cgccagaaac tgcggacgct ggaggtctct ggtaaccagc tgactagcct gccggtgctg    780
ccgccaggac tactggaact gtcgatcttt agtaacccgc tgacccacct gccggcgctg    840
ccgtcaggac tatgtaagct gtggatcttt ggtaatcaac tgaccagcct gccggtgttg    900
```

```
ccgccagggc tacaggagct gtcggtatct gataaccaac tggccagcct gccggcgctg    960
ccgtcagaat tatgtaagct gtgggcctat aataaccagc tgaccagcct gccgatgttg   1020
ccgtcagggc tacaggagct gtcggtatct gataaccaac tggccagcct gccgacgctg   1080
ccgtcagaat tatataagct gtgggcctat aataatcggc tgaccagcct gccggcgttg   1140
ccgtcaggac tgaaggagct gattgtatct ggtaaccggc tgaccagtct gccggtgctg   1200
ccgtcagaac tgaaggagct gatggtatct ggtaaccggc tgaccagcct gccgatgctg   1260
ccgtcaggac tactgtcgct gtcggtctat cgtaaccagc tgacccgcct gccggaaagt   1320
ctcattcatc tgtcttcaga gacaaccgta aatctggaag gaacccact  gtctgaacgt   1380 actttgcagg cgctgcggga gatcaccagc gcgcctggct attcaggccc cataatacga   1440
ttcgatatgg cgggagcctc cgccccccgg gaaactcggg cactgcacct ggcggccgct   1500
gactggctgg tgcctgcccg ggaggggaa  ccggctcctg cagacagatg gcatatgttc   1560
ggacaggaag ataacgccga cgcattcagc ctcttcctgg acagactgag tgagacggaa   1620
aacttcataa aggacgcggg gtttaaggca cagatatcgt cctggctggc acaactggct   1680
gaagatgagg cgttaagagc aaacaccttt gctatggcaa cagaggcaac ctcaagctgc   1740
gaggaccggg tcacattttt tttgcaccag atgaagaacg tacagctggt acataatgca   1800
gaaaaagggc aatacgataa cgatctcgcg gcgctggttg ccacggggcg tgagatgttc   1860
cgtctgggaa aactggaaca gattgcccgg gaaaaggtca gaacgctggc tctcgttgat   1920
gaaattgagg tctggctggc gtatcagaat aagctgaaga aatcactcgg gctgaccagc   1980
gtgacgtcag aaatgcgttt ctttgacgta tccggcgtga cggttacaga ccttcaggac   2040
gcggagcttc aggtgaaagc cgctgaaaaa agcgagttca gggagtggat actgcagtgg   2100
gggccgttac acagagtgct ggagcgcaaa gcgccggaac gcgttaacgc gcttcgtgaa   2160
aagcaaatat cggattatga ggaaacgtac cggatgctgt ctgacacaga gctgagaccg   2220
tctgggctgg tcggtaatac cgatgcagag cgcactatcg gagcaagagc gatggagagc   2280
gcgaaaaaga cattttttgga tggcctgcga cctcttgtgg aggagatgct ggggagctat   2340
ctgaacgttc agtggcgtcg taactga                                       2367
```

<210> SEQ ID NO 13
<211> LENGTH: 1728
<212> TYPE: DNA
<213> ORGANISM: Shigella flexneri

<400> SEQUENCE: 13

```
atgattaaat caaccaatat acaggcaatc ggttctggca ttatgcatca aataaacaat     60
gtatactcgt taactccatt atctttacct atggaactga ctccatcttg taatgaattt    120
tatttaaaaa cctggagcga atgggaaaag aacggtaccc aggcgagcca acgcaatatc    180
gccttcaata ggctgaaaat atgtttacaa atcaagagg  cagaattaaa tttatctgag    240
ttagatttaa aaacattacc agatttaccg cctcagataa caacactgga ataagaaaa     300 aacctattaa cacatctccc tgatttacca ccaatgctta aggtaataca tgctcaattt    360
aatcaactgg aaagcttacc tgccttaccc gagacgttag aagagcttaa tgcgggtgat    420
aacaagataa agaattacc  atttcttcct gaaaatctaa ctcatttacg ggttcataat    480
aaccgattgc atattctgcc actattgcca ccggaactaa aattactggt agtttctgga    540
aacagattag acagcattcc cccctttcca gataagcttg aagggctggc tctggctaat    600
```

```
aattttatag aacaactacc ggaattacct tttagtatga acagggctgt gctaatgaat        660
aataatctga caacacttcc ggaaagtgtc ctgagattag ctcagaatgc cttcgtaaat        720
gttgcaggta atccattgtc tggccatacc atgcgtacac tacaacaaat aaccaccgga        780
ccagattatt ctggtcctcg aatatttttc tctatgggaa attctgccac aatttccgct        840
ccagaacact ccctggctga tgccgtgaca gcatggttcc cggaaaacaa acaatctgat        900
gtatcacaga tatggcatgc ttttgaacat gaagagcatg ccaacacctt ttccgcgttc        960
cttgaccgcc tttccgatac cgtctctgca cgcaatacct ccggattccg tgaacaggtc       1020
gctgcatggc tggaaaaact cagtgcctct gcggagcttc gacagcagtc tttcgctgtt       1080
gctgctgatg ccactgagag ctgtgaggac cgtgtcgcgc tcacatggaa caatctccgg       1140
aaaaccctcc tggtccatca ggcatcagaa ggccttttcg ataatgatac cggcgctctg       1200
ctctccctgg gcagggaaat gttccgcctc gaaattctgg aggacattgc ccgggataaa       1260
gtcagaactc tccattttgt ggatgagata aagtctacc tggccttcca gaccatgctc       1320
gcagagaaac ttcagctctc cactgccgtg aaggaaatgc gtttctatgg cgtgtcggga       1380
gtgacagcaa atgacctccg cactgccgaa gctatggtca aagccgtga agagaatgaa       1440 tttacggact ggttctccct ctggggacca tggcatgctg tactgaagcg tacgaaagct       1500
gaccgctggg cgcaggcaga agagcagaag tatgagatgc tggagaatga gtactctcag       1560
agggtggctg accggctgaa agcatcaggt ctgagcggtg atgcggatgc ggagagggaa       1620
gccggtgcac aggtgatgcg tgagactgaa cagcagattt accgtcagtt gactgacgag       1680
gtactggccc tgcgattgtc tgaaaacggc tcaaatcata tcgcataa                    1728

<210> SEQ ID NO 14
<211> LENGTH: 1692
<212> TYPE: DNA
<213> ORGANISM: Shigella flexneri

<400> SEQUENCE: 14
atgattaaat caacaaatat acaggtaatc ggttctggta ttatgcatca aataaacaac         60
atacactcgt taactctatt ttctttgcct gtgagtttga gtccatcttg taatgaatat        120
tatttaaaag tctggagtga atgggaaaag aacggtaccc caggcgagca acgcaatatc        180
gccttcaata ggctgaaaat atgttttacaa aatcaagagg cagaattaaa tttatctgag        240
ttagatttaa aaacattacc agatttaccg cctcagataa caacactgga aataagaaaa        300
aacctattaa cacatctccc tgattttacca ccaatgctta aggtaataca tgctcaattt        360
aatcaactgg aaagcttacc tgccttaccc gagacgttag aagagcttaa tgcgggtgat        420
aacaagataa aagaattacc atttcttcct gaaaatctaa ctcatttacg ggttcataat        480
aaccgattgc atattctgcc actattgcca ccggaactaa aattactggt agtttctgga        540
aacagattag acagcattcc ccccttttcca gataagcttg aagggctggc tctggctaat        600
aattttatag aacaactacc ggaattacct tttagtatga acagggctgt gctaatgaat        660
aataatctga caacacttcc ggaaagtgtc ctgagattag ctcagaatgc cttcgtaaat        720
gttgcaggta atccattgtc tggccatacc atgcgtacac tacaacaaat aaccaccgga        780
ccagattatt ctggtcctcg aatatttttc tctatgggaa attctgccac aatttccgct        840
ccagaacact ccctggctga tgccgtgaca gcatggttcc cggaaaacaa acaatctgat        900
gtatcacaga tatggcatgc ttttgaacat gaagagcatg ccaacacctt ttccgcgttc        960
cttgaccgcc tttccgatac cgtctctgca cgcaatacct ccggattccg tgaacaggtc       1020
```

```
gctgcatggc tggaaaaact cagtgcctct gcggagcttc gacagcagtc tttcgctgtt    1080
gctgctgatg ccactgagag ctgtgaggac cgtgtcgcgc tcacatggaa caatctccgg    1140
aaaaccctcc tggtccatca ggcatcagaa ggccttttcg ataatgatac cggcgctctg    1200
ctctccctgg gcagggaaat gttccgcctc gaaattctgg aggatattgc ccgggataaa    1260
gtcagaactc tccattttgt ggatgagata gaagtctacc tggccttcca gaccatgctc    1320
gcagagaaac ttcagctctc tactgccgtg aaggaaatgc gtttctatgg cgtgtcggga    1380
gtgacagcaa atgacctccg cactgccgaa gccatggtca aagccgtga agagaatgaa    1440 tttacggact ggttctccct ctggggacca tggcatgctg tactgaagcg tacgaagct    1500 gaccgctggg cgcaggcaga agagcagaag tatgagatgc tggagaatga gtactctcag    1560
agggtggctg accggctgaa agcatcaggt ctgagcggtg atgcggatgc ggagagggaa    1620
gccggtgcac aggtgatgcg tgagactgaa cagcagattt accgtcagtt gactgacgag    1680
gtactggcct ga                                                        1692

<210> SEQ ID NO 15
<211> LENGTH: 1752
<212> TYPE: DNA
<213> ORGANISM: Shigella flexneri

<400> SEQUENCE: 15
atgctcccga caaataacaa tcacagatta atttcaaatt cgttctccac ttattcaatc      60
gacactagcc gcgcatatga aaattatcta acccattgga ctgaatggaa aaataaccgc     120
atacaagaag aacaacgaga catcgctttt cagcgactag tatcatgtct acaaaaccaa     180
gagacgaacc tggacttgtc tgaattaggc ctgacaacat acctgaaat ccccccggga     240 attaaatcaa ttaatataag taaaaataat ttaagcttaa tctccccatt gcctgcgtcc     300
cttacacaac ttaatgtcag ctataacaga cttattgaac tgcctgcttt gcctcaagga     360
cttaaattat tgaatgcgtc ccacaatcaa ctaatcacac tacccacact ccccatatct     420
ttgaaggagc ttcatgtctc aaataatcaa ttatgttctc ttcctgtttt accagaacta     480
ctggaaacat tagatgtatc atgtaatggg ctggcagttt taccaccttt accatttct     540 ttacaagaga ttagcgcaat agggaatctt cttagtgaac tcccccctct acctcacaac     600
attcactcca tatgggcaat cgacaatatg ttaaccgata ttccataccct gccggaaaat     660 ttaaggaacg gttattttga cataaatcag ataagtcata tcccggaaag cattcttaat     720
ctgaggaatg aatgttcaat agatattagt gataacccat tgtcatccca tgctctgcaa     780
tccctgcaaa gattaacatc ttcgccggac taccacggcc cgcagattta cttctccatg     840
agtgacggac aacagaatac actccatcgc cccctggctg atgccgtgac agcatggttc     900
ccggaaaaca aacaatctga tgtatcacag atatggcatg cttttgaaca tgaagagcac     960
gccaacacct tttccgcgtt ccttgaccgc ctttccgata ccgtctctgc acgcaatacc    1020
tccggattcc gtgaacaggt cgctgcatgg ctggaaaaac tcagtgcctc tgcggagctt    1080
cgacagcagt ctttcgctgt tgctgctgat gccactgaaa gctgtgagga ccgtgtcgcg    1140
ctcacatgga acaatctccg gaaaaccctc tggtccatca ggcatctga aggccttttc    1200 gataatgata ccggcgctct gctctccctg gcagggaaa tgttccgcct cgaaattctg    1260
gaggacattg cccgggataa agtcagaact ctccattttg tggatgagat agaagtctac    1320
ctggccttcc agaccatgct cgcagagaaa cttcagctct ccactgccgt gaaggaaatg    1380
```

-continued

| | |
|---|---|
| cgtttctatg gcgtgtcggg agtgacagca aatgacctcc gcactgccga agccatggtc | 1440 |
| agaagccgtg aagagaatga atttacggac tggttctccc tctggggacc atggcatgct | 1500 |
| gtactgaagc gtacggaagc tgaccgctgg gcgcaggcag aagagcagaa gtatgagatg | 1560 |
| ctggagaatg agtaccctca gagggtggct gaccggctga agcatcagg tctgagcggt | 1620 |
| gatgcggatg cggagaggga agccggtgca caggtgatgc gtgagactga acagcagatt | 1680 |
| taccgtcagc tgactgacga ggtactggcc ctgcgattgc ctgaaaacgg ctcacaactg | 1740 |
| caccattcat aa | 1752 |

<210> SEQ ID NO 16
<211> LENGTH: 1725
<212> TYPE: DNA
<213> ORGANISM: Shigella flexneri

<400> SEQUENCE: 16

| | |
|---|---|
| atgaaaccga tcaacaatca ttcttttttt cgttcccttt gtggcttatc atgtatatct | 60 |
| cgtttatcgg tagaagaaca gtgtaccaga gattaccacc gcatctggga tgactgggct | 120 |
| agggaaggaa caacaacaga aaatcgcatc caggcggttc gattattgaa aatatgtctg | 180 |
| gatacccggg agcctgttct caatttaagc ttactgaaac tacgttcttt accaccactc | 240 |
| cctttgcata tacgtgaact taatatttcc aacaatgagt taatctccct acctgaaaat | 300 |
| tctccgcttt tgacagaact tcatgtaaat ggtaacaact tgaatatact cccgacactt | 360 |
| ccatctcaac tgattaagct taatatttca ttcaatcgaa atttgtcatg tctgccatca | 420 |
| ttaccaccat atttacaatc actctcggca cgttttaata gtctggagac gttaccagag | 480 |
| cttccatcaa cgctaacaat attacgtatt gaaggtaatc gccttactgt cttgcctgaa | 540 |
| ttgcctcata gactacaaga actctttgtt tccggcaaca gactacagga actaccagaa | 600 |
| tttcctcaga gcttaaaata tttgaaggta ggtgaaaatc aactacgcag attatccaga | 660 |
| ttaccgcaag aactattggc actggatgtt tccaataacc tactaacttc attacccgaa | 720 |
| aatataatca cattgcccat ttgtacgaat gttaacattt cagggaatcc attgtcgact | 780 |
| cacgttctgc aatccctgca aagattaacc tcttcgccgg actaccacgg cccgcagatt | 840 |
| tacttctcca tgagtgacgg acaacagaat acactccatc gccccctggc tgatgccgtg | 900 |
| acagcatggt tcccggaaaa caaacaatct gatgtatcac agatatggca tgcttttgaa | 960 |
| catgaagagc atgccaacac cttttccgcg ttccttgacc gcctttccga taccgtctct | 1020 |
| gcacgcaata cctccggatt ccgtgaacag gtcgctgcat ggctggaaaa actcagtgcc | 1080 |
| tctgcggagc ttcgacagca gtctttcgct gttgctgctg atgccactga gagctgtgag | 1140 |
| gaccgtgtcg cgctcacatg gaacaatctc cggaaaaccc tcctggtcca tcaggcatca | 1200 |
| gaaggccttt tcgataatga taccggcgct ctgctctccc tgggcaggga aatgttccgc | 1260 |
| ctcgaaattc tggaggatat tgcccgggat aaagtcagaa ctctccattt tgtggatgag | 1320 |
| atagaagtct acctggcctt ccagaccatg ctcgcagaga aacttcagct ctccactgcc | 1380 |
| gtgaaggaaa tgcgtttcta tggcgtgtcg ggagtgacag caaatgacct ccgcactgcc | 1440 |
| gaagctatgg tcagaagccg tgaagagaat gaatttacgg actggttctc cctctgggga | 1500 |
| ccatggcatg ctgtactgaa gcgtacggaa gctgaccgct gggcgcaggc agaagagcag | 1560 |
| aagtatgaga tgctggagaa tgagtactct cagagggtgg ctgaccggct gaaagcatca | 1620 |
| ggtctgagcg gtgatgcgga tgcggagagg gaagccggtg cacaggtgat gcgtgagact | 1680 |
| gaacagcaga tttaccgtca gttgactgac gaggtactgg cctga | 1725 |

<210> SEQ ID NO 17
<211> LENGTH: 1698
<212> TYPE: DNA
<213> ORGANISM: Shigella flexneri

<400> SEQUENCE: 17

| | | | | | |
|---|---|---|---|---|---|
| atgttctctg | taaataatac | acactcatca | gtttcttgct | cccctctat | taactcaaac | 60 |
| tcaaccagta | atgaacatta | tctgagaatc | ctgactgaat | gggaaaagaa | ctcttctccc | 120 |
| ggggaagagc | gaggcattgc | ttttaacaga | ctctcccagt | gctttcagaa | tcaagaagca | 180 |
| gtattaaatt | tatcagacct | aaatttgacg | tctcttcccg | aattaccaaa | gcatatttct | 240 |
| gctttgattg | tagaaaataa | taaattaaca | tcattgccaa | agctgcctgc | atttcttaaa | 300 |
| gaacttaatg | ctgataataa | caggctttct | gtgataccag | aacttcctga | gtcattaaca | 360 |
| actttaagtg | ttcgttctaa | tcaactggaa | aaccttcctg | ttttgccaaa | ccatttaaca | 420 |
| tcattatttg | ttgaaaataa | caggctatat | aacttaccgg | ctcttcccga | aaaattgaaa | 480 |
| tttttacatg | tttattataa | caggctgaca | acattacccg | acttaccgga | taaactggaa | 540 |
| attctctgtg | ctcagcgcaa | taatctggtt | acttttcctc | aattttctga | tagaaacaat | 600 |
| atcagacaaa | aggaatatta | ttttcatttt | aatcagataa | ccactcttcc | ggagagtttt | 660 |
| tcacaattag | attcaagtta | caggattaat | atttcaggga | atccattgtc | gactcgcgtt | 720 |
| ctgcaatccc | tgcaaagatt | aacctcttcg | ccggactacc | acggcccgca | gatttacttc | 780 |
| tccatgagtg | acggacaaca | gaatacactc | catcgccccc | tggctgatgc | cgtgacagca | 840 |
| tggttcccgg | aaaacaaaca | atctgatgta | tcacagatat | ggcatgcttt | tgaacatgaa | 900 |
| gagcatgcca | acacctttc | cgcgttcctt | gaccgccttt | ccgataccgt | ctctgcacgc | 960 |
| aatacctccg | gattccgtga | acaggtcgct | gcatggctgg | aaaaactcag | tgcctctgcg | 1020 |
| gagcttcgac | agcagtcttt | cgctgttgct | gctgatgcca | ctgagagctg | tgaggaccgt | 1080 |
| gtcgcgctca | catggaacaa | tctccggaaa | accctcctgg | tccatcaggc | atcagaaggc | 1140 |
| cttttcgata | atgataccgg | cgctctgctc | tccctgggca | gggaaatgtt | ccgcctcgaa | 1200 |
| attctggagg | acattgcccg | ggataaagtc | agaactctcc | attttgtgga | tgagatagaa | 1260 |
| gtctacctgg | ccttccagac | catgctcgca | gagaaacttc | agctctccac | tgccgtgaag | 1320 |
| gaaatgcgtt | tctatggcgt | gtcgggagtg | acagcaaatg | acctccgcac | tgccgaagct | 1380 |
| atggtcagaa | gccgtgaaga | gaatgaattt | acggactggt | tctccctctg | gggaccatgg | 1440 |
| catgctgtac | tgaagcgtac | ggaagctgac | cgctgggcgc | aggcagaaga | gcagaagtat | 1500 |
| gagatgctgg | agaatgagta | ctctcagagg | gtggctgacc | ggctgaaagc | atcaggtctg | 1560 |
| agcggtgatg | cggatgcgga | gagggaagcc | ggtgcacagg | tgatgcgtga | gactgaacag | 1620 |
| cagatttacc | gtcagctgac | tgacgaggta | ctggccctgc | gattgtctga | aaacggctca | 1680 |
| cgactgcacc | attcataa | | | | | 1698 |

<210> SEQ ID NO 18
<211> LENGTH: 1638
<212> TYPE: DNA
<213> ORGANISM: Shigella flexneri

<400> SEQUENCE: 18

| | | | | | |
|---|---|---|---|---|---|
| atgttaccga | taataataa | cttttcattg | ccccaaaatt | cttttataa | cactatttcc | 60 |
| ggtacatatg | ctgattactt | ttcagcatgg | gataaatggg | aaaaacaagc | gctccccggt | 120 |

```
gaagagcgtg atgaggctgt ctcccgactt aaagaatgtc ttatcaataa ttccgatgaa    180
cttcgactgg accgtttaaa tctgtcctcg ctacctgaca acttaccagc tcagataacg    240
ctgctcaatg tatcatataa tcaattaact aacctacctg aactgcctgt tacgctaaaa    300
aaattatatt ccgccagcaa taaattatca gaattgcccg tgctacctcc tgcgctggag    360
tcacttcagg tacaacacaa tgagctggaa aacctgccag ctttacccga ttcgttattg    420
actatgaata tcagctataa cgaaatagtc tccttaccat cgctcccaca ggctcttaaa    480
aatctcagag cgacccgtaa tttcctcact gagctaccag cattttctga gggaaataat    540
cccgttgtca gagagtattt ttttgataga aatcagataa gtcatatccc ggaaaagcatt   600 cttaatctga ggaatgaatg ttcaatacat attagtgata acccattatc atcccatgct    660
ctgcaagccc tgcaaagatt aacctcttcg ccggactacc acggcccacg gatttacttc    720
tccatgagtg acggacaaca gaatacactc catcgccccc tggctgatgc cgtgacagca    780
tggttcccgg aaaacaaaca atctgatgta tcacagatat ggcatgcttt tgaacatgaa    840
gagcatgcca acacctttt cgcgttcctt gaccgccttt ccgataccgt ctctgcacgc    900 aataccctccg gattccgtga acaggtcgct gcatggctgg aaaaactcag tgcctctgcg   960
gagcttcgac agcagtcttt cgctgttgct gctgatgcca ctgagagctg tgaggaccgt   1020
gtcgcgctca catggaacaa tctccggaaa accctcctgg tccatcaggc atcagaaggc   1080
cttttcgata tgataccgg cgctctgctc tccctgggca gggaaatgtt ccgcctcgaa    1140
attctggagg atattgcccg ggataaagtc agaactctcc attttgtgga tgagatagaa   1200
gtctacctgg ccttccagac catgctcgca gagaaacttc agctctccac tgccgtgaag   1260
gaaatgcgtt tctatggcgt gtcgggagtg acagcaaatg acctccgcac tgccgaagcc   1320
atggtcagaa gccgtgaaga gaatgaattt acggactggt tctccctctg ggaccatgg    1380 catgctgtac tgaagcgtac ggaagctgac cgctgggcgc aggcagaaga gcagaaatat   1440
gagatgctgg agaatgagta ccctcagagg gtggctgacc ggctgaaagc atcaggtctg   1500
agcggtgatg cggatgcgga gagggaagcc ggtgcacagg tgatgcgtga gactgaacag   1560
cagatttacc gtcagctgac tgacgaggta ctggccctgc gattgtttga aaacggctca   1620
caactgcacc attcataa                                                 1638
```

<210> SEQ ID NO 19
<211> LENGTH: 304
<212> TYPE: PRT
<213> ORGANISM: Salmonella enterica

<400> SEQUENCE: 19

Thr Arg Pro Leu His Gln Ala Val Gln Gly Trp Leu Thr Ser Leu Glu
1               5                   10                  15

Glu Glu Asp Val Asn Gln Trp Arg Ala Phe Glu Ala Glu Ala Asn Ala
            20                  25                  30

Ala Ala Phe Ser Gly Phe Leu Asp Tyr Leu Gly Asp Thr Gln Asn Thr
        35                  40                  45

Arg His Pro Asp Phe Lys Glu Gln Val Ser Ala Trp Leu Met Arg Leu
    50                  55                  60

Ala Glu Asp Ser Ala Leu Arg Glu Thr Val Phe Ile Ile Ala Met Asn
65                  70                  75                  80

Ala Thr Ile Ser Cys Glu Asp Arg Val Thr Leu Ala Tyr His Gln Met
                85                  90                  95

Gln Glu Ala Thr Leu Val His Asp Ala Glu Arg Gly Ala Phe Asp Ser

```
                100             105             110
His Leu Ala Glu Leu Ile Met Ala Gly Arg Glu Ile Phe Arg Leu Glu
            115                 120                 125

Gln Ile Glu Ser Leu Ala Arg Glu Lys Val Lys Arg Leu Phe Phe Ile
        130                 135                 140

Asp Glu Val Glu Val Phe Leu Gly Phe Gln Asn Gln Leu Arg Glu Ser
145                 150                 155                 160

Leu Ser Leu Thr Thr Met Thr Arg Asp Met Arg Phe Tyr Asn Val Ser
                165                 170                 175

Gly Ile Thr Glu Ser Asp Leu Asp Glu Ala Glu Ile Arg Ile Lys Met
            180                 185                 190

Ala Glu Asn Arg Asp Phe His Lys Trp Phe Ala Leu Trp Gly Pro Trp
        195                 200                 205

His Lys Val Leu Glu Arg Ile Ala Pro Glu Glu Trp Arg Glu Met Met
    210                 215                 220

Ala Lys Arg Asp Glu Cys Ile Glu Thr Asp Glu Tyr Gln Ser Arg Val
225                 230                 235                 240

Asn Ala Glu Leu Glu Asp Leu Arg Ile Ala Asp Asp Ser Asp Ala Glu
                245                 250                 255

Arg Thr Thr Glu Val Gln Met Asp Ala Glu Arg Ala Ile Gly Ile Lys
            260                 265                 270

Ile Met Glu Glu Ile Asn Gln Thr Leu Phe Thr Glu Ile Met Glu Asn
        275                 280                 285

Ile Leu Leu Lys Lys Glu Val Ser Ser Leu Met Ser Ala Tyr Trp Arg
    290                 295                 300
```

<210> SEQ ID NO 20
<211> LENGTH: 297
<212> TYPE: PRT
<213> ORGANISM: Salmonella enterica

<400> SEQUENCE: 20

```
Ala Arg Ala Leu His Leu Ala Val Ala Asp Trp Leu Thr Ser Ala Arg
1               5                   10                  15

Glu Gly Glu Ala Ala Gln Ala Asp Arg Trp Gln Ala Phe Gly Leu Glu
            20                  25                  30

Asp Asn Ala Ala Ala Phe Ser Leu Val Leu Asp Arg Leu Arg Glu Thr
        35                  40                  45

Glu Asn Phe Lys Lys Asp Ala Gly Phe Lys Ala Gln Ile Ser Ser Trp
    50                  55                  60

Leu Thr Gln Leu Ala Glu Asp Ala Ala Leu Arg Ala Lys Thr Phe Ala
65                  70                  75                  80

Met Ala Thr Glu Ala Thr Ser Thr Cys Glu Asp Arg Val Thr His Ala
                85                  90                  95

Leu His Gln Met Asn Asn Val Gln Leu Val His Asn Ala Glu Lys Gly
            100                 105                 110

Glu Tyr Asp Asn Asn Leu Gln Gly Leu Val Ser Thr Gly Arg Glu Met
        115                 120                 125

Phe Arg Leu Ala Thr Leu Glu Gln Ile Ala Arg Glu Lys Ala Gly Thr
    130                 135                 140

Leu Ala Leu Val Asp Asp Val Glu Val Tyr Leu Ala Phe Gln Asn Lys
145                 150                 155                 160

Leu Lys Glu Ser Leu Glu Leu Thr Ser Val Thr Ser Glu Met Arg Phe
                165                 170                 175
```

```
Phe Asp Val Ser Gly Val Thr Val Ser Asp Leu Gln Ala Ala Glu Leu
            180                 185                 190

Gln Val Lys Thr Ala Glu Asn Ser Gly Phe Ser Lys Trp Ile Leu Gln
        195                 200                 205

Trp Gly Pro Leu His Ser Val Leu Glu Arg Lys Val Pro Glu Arg Phe
    210                 215                 220

Asn Ala Leu Arg Glu Lys Gln Ile Ser Asp Tyr Glu Asp Thr Tyr Arg
225                 230                 235                 240

Lys Leu Tyr Asp Glu Val Leu Lys Ser Ser Gly Leu Val Asp Asp Thr
                245                 250                 255

Asp Ala Glu Arg Thr Ile Gly Val Ser Ala Met Asp Ser Ala Lys Lys
            260                 265                 270

Glu Phe Leu Asp Gly Leu Arg Ala Leu Val Asp Glu Val Leu Gly Ser
        275                 280                 285

Tyr Leu Thr Ala Arg Trp Arg Leu Asn
    290                 295

<210> SEQ ID NO 21
<211> LENGTH: 297
<212> TYPE: PRT
<213> ORGANISM: Salmonella enterica

<400> SEQUENCE: 21

Thr Arg Ala Leu His Leu Ala Ala Asp Trp Leu Val Pro Ala Arg
1               5                   10                  15

Glu Gly Glu Pro Ala Pro Ala Asp Arg Trp His Met Phe Gly Gln Glu
                20                  25                  30

Asp Asn Ala Asp Ala Phe Ser Leu Phe Leu Asp Arg Leu Ser Glu Thr
            35                  40                  45

Glu Asn Phe Ile Lys Asp Ala Gly Phe Lys Ala Gln Ile Ser Ser Trp
        50                  55                  60

Leu Ala Gln Leu Ala Glu Asp Glu Ala Leu Arg Ala Asn Thr Phe Ala
65                  70                  75                  80

Met Ala Thr Glu Ala Thr Ser Ser Cys Glu Asp Arg Val Thr Phe Phe
                85                  90                  95

Leu His Gln Met Lys Asn Val Gln Leu Val His Asn Ala Glu Lys Gly
            100                 105                 110

Gln Tyr Asp Asn Asp Leu Ala Ala Leu Val Ala Thr Gly Arg Glu Met
        115                 120                 125

Phe Arg Leu Gly Lys Leu Glu Gln Ile Ala Arg Glu Lys Val Arg Thr
    130                 135                 140

Leu Ala Leu Val Asp Glu Ile Glu Val Trp Leu Ala Tyr Gln Asn Lys
145                 150                 155                 160

Leu Lys Lys Ser Leu Gly Leu Thr Ser Val Thr Ser Glu Met Arg Phe
                165                 170                 175

Phe Asp Val Ser Gly Val Thr Val Thr Asp Leu Gln Asp Ala Glu Leu
            180                 185                 190

Gln Val Lys Ala Ala Glu Lys Ser Glu Phe Arg Glu Trp Ile Leu Gln
        195                 200                 205

Trp Gly Pro Leu His Arg Val Leu Glu Arg Lys Ala Pro Glu Arg Val
    210                 215                 220

Asn Ala Leu Arg Glu Lys Gln Ile Ser Asp Tyr Glu Glu Thr Tyr Arg
225                 230                 235                 240

Met Leu Ser Asp Thr Glu Leu Arg Pro Ser Gly Leu Val Gly Asn Thr
                245                 250                 255
```

```
Asp Ala Glu Arg Thr Ile Gly Ala Arg Ala Met Glu Ser Ala Lys Lys
            260                 265                 270

Thr Phe Leu Asp Gly Leu Arg Pro Leu Val Glu Met Leu Gly Ser
    275                 280                 285

Tyr Leu Asn Val Gln Trp Arg Arg Asn
    290                 295

<210> SEQ ID NO 22
<211> LENGTH: 331
<212> TYPE: PRT
<213> ORGANISM: Shigella flexneri

<400> SEQUENCE: 22

Val Ala Gly Asn Pro Leu Ser Gly His Thr Met Arg Thr Leu Gln Gln
1               5                   10                  15

Ile Thr Thr Gly Pro Asp Tyr Ser Gly Pro Arg Ile Phe Phe Ser Met
                20                  25                  30

Gly Asn Ser Ala Thr Ile Ser Ala Pro Glu His Ser Leu Ala Asp Ala
            35                  40                  45

Val Thr Ala Trp Phe Pro Glu Asn Lys Gln Ser Asp Val Ser Gln Ile
    50                  55                  60

Trp His Ala Phe Glu His Glu His Ala Asn Thr Phe Ser Ala Phe
65                  70                  75                  80

Leu Asp Arg Leu Ser Asp Thr Val Ser Ala Arg Asn Thr Ser Gly Phe
                85                  90                  95

Arg Glu Gln Val Ala Ala Trp Leu Glu Lys Leu Ser Ala Ser Ala Glu
            100                 105                 110

Leu Arg Gln Gln Ser Phe Ala Val Ala Ala Asp Ala Thr Glu Ser Cys
    115                 120                 125

Glu Asp Arg Val Ala Leu Thr Trp Asn Asn Leu Arg Lys Thr Leu Leu
130                 135                 140

Val His Gln Ala Ser Glu Gly Leu Phe Asp Asn Asp Thr Gly Ala Leu
145                 150                 155                 160

Leu Ser Leu Gly Arg Glu Met Phe Arg Leu Glu Ile Leu Glu Asp Ile
                165                 170                 175

Ala Arg Asp Lys Val Arg Thr Leu His Phe Val Asp Glu Ile Glu Val
            180                 185                 190

Tyr Leu Ala Phe Gln Thr Met Leu Ala Glu Lys Leu Gln Leu Ser Thr
    195                 200                 205

Ala Val Lys Glu Met Arg Phe Tyr Gly Val Ser Gly Val Thr Ala Asn
    210                 215                 220

Asp Leu Arg Thr Ala Glu Ala Met Val Arg Ser Arg Glu Glu Asn Glu
225                 230                 235                 240

Phe Thr Asp Trp Phe Ser Leu Trp Gly Pro Trp His Ala Val Leu Lys
                245                 250                 255

Arg Thr Glu Ala Asp Arg Trp Ala Gln Ala Glu Gln Lys Tyr Glu
            260                 265                 270

Met Leu Glu Asn Glu Tyr Ser Gln Arg Val Ala Asp Arg Leu Lys Ala
    275                 280                 285

Ser Gly Leu Ser Gly Asp Ala Asp Ala Glu Arg Glu Gly Ala Gln
    290                 295                 300

Val Met Arg Glu Thr Glu Gln Gln Ile Tyr Arg Gln Leu Thr Asp Glu
305                 310                 315                 320

Val Leu Ala Leu Arg Leu Ser Glu Asn Gly Ser
```

<210> SEQ ID NO 23
<211> LENGTH: 323
<212> TYPE: PRT
<213> ORGANISM: Shigella flexneri

<400> SEQUENCE: 23

| | | | | | | | | | | | | | | |
|---|---|---|---|---|---|---|---|---|---|---|---|---|---|---|
| Val | Ala | Gly | Asn | Pro | Leu | Ser | Gly | His | Thr | Met | Arg | Thr | Leu | Gln | Gln |
| 1 | | | | 5 | | | | | 10 | | | | | 15 | |
| Ile | Thr | Thr | Gly | Pro | Asp | Tyr | Ser | Gly | Pro | Arg | Ile | Phe | Phe | Ser | Met |
| | | | 20 | | | | | 25 | | | | | 30 | | |
| Gly | Asn | Ser | Ala | Thr | Ile | Ser | Ala | Pro | Glu | His | Ser | Leu | Ala | Asp | Ala |
| | | | 35 | | | | 40 | | | | | 45 | | | |
| Val | Thr | Ala | Trp | Phe | Pro | Glu | Asn | Lys | Gln | Ser | Asp | Val | Ser | Gln | Ile |
| | 50 | | | | | 55 | | | | | 60 | | | | |
| Trp | His | Ala | Phe | Glu | His | Glu | His | Ala | Asn | Thr | Phe | Ser | Ala | Phe |
| 65 | | | | | 70 | | | | | 75 | | | | | 80 |
| Leu | Asp | Arg | Leu | Ser | Asp | Thr | Val | Ser | Ala | Arg | Asn | Thr | Ser | Gly | Phe |
| | | | | 85 | | | | | 90 | | | | | 95 | |
| Arg | Glu | Gln | Val | Ala | Ala | Trp | Leu | Glu | Lys | Leu | Ser | Ala | Ser | Ala | Glu |
| | | | 100 | | | | | 105 | | | | | 110 | | |
| Leu | Arg | Gln | Gln | Ser | Phe | Ala | Val | Ala | Ala | Asp | Ala | Thr | Glu | Ser | Cys |
| | | | 115 | | | | | 120 | | | | | 125 | | |
| Glu | Asp | Arg | Val | Ala | Leu | Thr | Trp | Asn | Asn | Leu | Arg | Lys | Thr | Leu | Leu |
| 130 | | | | | 135 | | | | | 140 | | | | | |
| Val | His | Gln | Ala | Ser | Glu | Gly | Leu | Phe | Asp | Asn | Asp | Thr | Gly | Ala | Leu |
| 145 | | | | | 150 | | | | | 155 | | | | | 160 |
| Leu | Ser | Leu | Gly | Arg | Glu | Met | Phe | Arg | Leu | Glu | Ile | Leu | Glu | Asp | Ile |
| | | | | 165 | | | | | 170 | | | | | 175 | |
| Ala | Arg | Asp | Lys | Val | Arg | Thr | Leu | His | Phe | Val | Asp | Glu | Ile | Glu | Val |
| | | | 180 | | | | | 185 | | | | | 190 | | |
| Tyr | Leu | Ala | Phe | Gln | Thr | Met | Leu | Ala | Glu | Lys | Leu | Gln | Leu | Ser | Thr |
| | | | 195 | | | | | 200 | | | | | 205 | | |
| Ala | Val | Lys | Glu | Met | Arg | Phe | Tyr | Gly | Val | Ser | Gly | Val | Thr | Ala | Asn |
| 210 | | | | | 215 | | | | | 220 | | | | | |
| Asp | Leu | Arg | Thr | Ala | Glu | Ala | Met | Val | Arg | Ser | Arg | Glu | Glu | Asn | Glu |
| 225 | | | | | 230 | | | | | 235 | | | | | 240 |
| Phe | Thr | Asp | Trp | Phe | Ser | Leu | Trp | Gly | Pro | Trp | His | Ala | Val | Leu | Lys |
| | | | | 245 | | | | | 250 | | | | | 255 | |
| Arg | Thr | Glu | Ala | Asp | Arg | Trp | Ala | Gln | Ala | Glu | Gln | Lys | Tyr | Glu |
| | | | 260 | | | | | 265 | | | | | 270 | | |
| Met | Leu | Glu | Asn | Glu | Tyr | Ser | Gln | Arg | Val | Ala | Asp | Arg | Leu | Lys | Ala |
| | | | 275 | | | | | 280 | | | | | 285 | | |
| Ser | Gly | Leu | Ser | Gly | Asp | Ala | Asp | Ala | Glu | Arg | Glu | Ala | Gly | Ala | Gln |
| | | | 290 | | | | | 295 | | | | | 300 | | |
| Val | Met | Arg | Glu | Thr | Glu | Gln | Gln | Ile | Tyr | Arg | Gln | Leu | Thr | Asp | Glu |
| 305 | | | | | 310 | | | | | 315 | | | | | 320 |
| Val | Leu | Ala | | | | | | | | | | | | | |

<210> SEQ ID NO 24
<211> LENGTH: 293
<212> TYPE: PRT
<213> ORGANISM: Shigella flexneri

<400> SEQUENCE: 24

```
Pro Leu Ala Asp Ala Val Thr Ala Trp Phe Pro Glu Asn Lys Gln Ser
1               5                   10                  15

Asp Val Ser Gln Ile Trp His Ala Phe Glu His Glu His Ala Asn
            20                  25                  30

Thr Phe Ser Ala Phe Leu Asp Arg Leu Ser Asp Thr Val Ser Ala Arg
        35                  40                  45

Asn Thr Ser Gly Phe Arg Glu Gln Val Ala Ala Trp Leu Glu Lys Leu
50                  55                  60

Ser Ala Ser Ala Glu Leu Arg Gln Gln Ser Phe Ala Val Ala Ala Asp
65                  70                  75                  80

Ala Thr Glu Ser Cys Glu Asp Arg Val Ala Leu Thr Trp Asn Asn Leu
                85                  90                  95

Arg Lys Thr Leu Leu Val His Gln Ala Ser Glu Gly Leu Phe Asp Asn
                100                 105                 110

Asp Thr Gly Ala Leu Leu Ser Leu Gly Arg Glu Met Phe Arg Leu Glu
            115                 120                 125

Ile Leu Glu Asp Ile Ala Arg Asp Lys Val Arg Thr Leu His Phe Val
130                 135                 140

Asp Glu Ile Glu Val Tyr Leu Ala Phe Gln Thr Met Leu Ala Glu Lys
145                 150                 155                 160

Leu Gln Leu Ser Thr Ala Val Lys Glu Met Arg Phe Tyr Gly Val Ser
                165                 170                 175

Gly Val Thr Ala Asn Asp Leu Arg Thr Ala Glu Ala Met Val Arg Ser
                180                 185                 190

Arg Glu Glu Asn Glu Phe Thr Asp Trp Phe Ser Leu Trp Gly Pro Trp
                195                 200                 205

His Ala Val Leu Lys Arg Thr Glu Ala Asp Arg Trp Ala Gln Ala Glu
            210                 215                 220

Glu Gln Lys Tyr Glu Met Leu Glu Asn Glu Tyr Pro Gln Arg Val Ala
225                 230                 235                 240

Asp Arg Leu Lys Ala Ser Gly Leu Ser Gly Asp Ala Asp Ala Glu Arg
                245                 250                 255

Glu Ala Gly Ala Gln Val Met Arg Glu Thr Gln Gln Ile Tyr Arg
                260                 265                 270

Gln Leu Thr Asp Glu Val Leu Ala Leu Arg Leu Pro Glu Asn Gly Ser
            275                 280                 285

Gln Leu His His Ser
    290

<210> SEQ ID NO 25
<211> LENGTH: 282
<212> TYPE: PRT
<213> ORGANISM: Shigella flexneri

<400> SEQUENCE: 25

His Arg Pro Leu Ala Asp Ala Val Thr Ala Trp Phe Pro Glu Asn Lys
1               5                   10                  15

Gln Ser Asp Val Ser Gln Ile Trp His Ala Phe Glu His Glu His
            20                  25                  30

Ala Asn Thr Phe Ser Ala Phe Leu Asp Arg Leu Ser Asp Thr Val Ser
        35                  40                  45

Ala Arg Asn Thr Ser Gly Phe Arg Glu Gln Val Ala Ala Trp Leu Glu
50                  55                  60

Lys Leu Ser Ala Ser Ala Glu Leu Arg Gln Gln Ser Phe Ala Val Ala
```

```
             65                  70                  75                  80
Ala Asp Ala Thr Glu Ser Cys Glu Asp Arg Val Ala Leu Thr Trp Asn
                 85                  90                  95

Asn Leu Arg Lys Thr Leu Leu Val His Gln Ala Ser Glu Gly Leu Phe
            100                 105                 110

Asp Asn Asp Thr Gly Ala Leu Leu Ser Leu Gly Arg Glu Met Phe Arg
            115                 120                 125

Leu Glu Ile Leu Glu Asp Ile Ala Arg Asp Lys Val Arg Thr Leu His
            130                 135                 140

Phe Val Asp Glu Ile Glu Val Tyr Leu Ala Phe Gln Thr Met Leu Ala
145                 150                 155                 160

Glu Lys Leu Gln Leu Ser Thr Ala Val Lys Glu Met Arg Phe Tyr Gly
                165                 170                 175

Val Ser Gly Val Thr Ala Asn Asp Leu Arg Thr Ala Glu Ala Met Val
            180                 185                 190

Arg Ser Arg Glu Glu Asn Glu Phe Thr Asp Trp Phe Ser Leu Trp Gly
            195                 200                 205

Pro Trp His Ala Val Leu Lys Arg Thr Glu Ala Asp Arg Trp Ala Gln
            210                 215                 220

Ala Glu Glu Gln Lys Tyr Glu Met Leu Glu Asn Glu Tyr Ser Gln Arg
225                 230                 235                 240

Val Ala Asp Arg Leu Lys Ala Ser Gly Leu Ser Gly Asp Ala Asp Ala
                245                 250                 255

Glu Arg Glu Ala Gly Ala Gln Val Met Arg Glu Thr Glu Gln Gln Ile
            260                 265                 270

Tyr Arg Gln Leu Thr Asp Glu Val Leu Ala
            275                 280

<210> SEQ ID NO 26
<211> LENGTH: 295
<212> TYPE: PRT
<213> ORGANISM: Shigella flexneri

<400> SEQUENCE: 26

His Arg Pro Leu Ala Asp Ala Val Thr Ala Trp Phe Pro Glu Asn Lys
1               5                   10                  15

Gln Ser Asp Val Ser Gln Ile Trp His Ala Phe Glu His Glu Glu His
                20                  25                  30

Ala Asn Thr Phe Ser Ala Phe Leu Asp Arg Leu Ser Asp Thr Val Ser
            35                  40                  45

Ala Arg Asn Thr Ser Gly Phe Arg Glu Gln Val Ala Ala Trp Leu Glu
        50                  55                  60

Lys Leu Ser Ala Ser Ala Glu Leu Arg Gln Gln Ser Phe Ala Val Ala
65                  70                  75                  80

Ala Asp Ala Thr Glu Ser Cys Glu Asp Arg Val Ala Leu Thr Trp Asn
                85                  90                  95

Asn Leu Arg Lys Thr Leu Leu Val His Gln Ala Ser Glu Gly Leu Phe
            100                 105                 110

Asp Asn Asp Thr Gly Ala Leu Leu Ser Leu Gly Arg Glu Met Phe Arg
            115                 120                 125

Leu Glu Ile Leu Glu Asp Ile Ala Arg Asp Lys Val Arg Thr Leu His
            130                 135                 140

Phe Val Asp Glu Ile Glu Val Tyr Leu Ala Phe Gln Thr Met Leu Ala
145                 150                 155                 160
```

```
Glu Lys Leu Gln Leu Ser Thr Ala Val Lys Glu Met Arg Phe Tyr Gly
            165                 170                 175

Val Ser Gly Val Thr Ala Asn Asp Leu Arg Thr Ala Glu Ala Met Val
        180                 185                 190

Arg Ser Arg Glu Glu Asn Glu Phe Thr Asp Trp Phe Ser Leu Trp Gly
        195                 200                 205

Pro Trp His Ala Val Leu Lys Arg Thr Glu Ala Asp Arg Trp Ala Gln
        210                 215                 220

Ala Glu Glu Gln Lys Tyr Glu Met Leu Glu Asn Glu Tyr Ser Gln Arg
225                 230                 235                 240

Val Ala Asp Arg Leu Lys Ala Ser Gly Leu Ser Gly Asp Ala Asp Ala
                245                 250                 255

Glu Arg Glu Ala Gly Ala Gln Val Met Arg Glu Thr Glu Gln Gln Ile
            260                 265                 270

Tyr Arg Gln Leu Thr Asp Glu Val Leu Ala Leu Arg Leu Ser Glu Asn
        275                 280                 285

Gly Ser Arg Leu His His Ser
        290                 295

<210> SEQ ID NO 27
<211> LENGTH: 295
<212> TYPE: PRT
<213> ORGANISM: Shigella flexneri

<400> SEQUENCE: 27

His Arg Pro Leu Ala Asp Ala Val Thr Ala Trp Phe Pro Glu Asn Lys
1               5                   10                  15

Gln Ser Asp Val Ser Gln Ile Trp His Ala Phe Glu His Glu Glu His
                20                  25                  30

Ala Asn Thr Phe Ser Ala Phe Leu Asp Arg Leu Ser Asp Thr Val Ser
            35                  40                  45

Ala Arg Asn Thr Ser Gly Phe Arg Glu Gln Val Ala Ala Trp Leu Glu
        50                  55                  60

Lys Leu Ser Ala Ser Ala Glu Leu Arg Gln Gln Ser Phe Ala Val Ala
65                  70                  75                  80

Ala Asp Ala Thr Glu Ser Cys Glu Asp Arg Val Ala Leu Thr Trp Asn
                85                  90                  95

Asn Leu Arg Lys Thr Leu Leu Val His Gln Ala Ser Glu Gly Leu Phe
            100                 105                 110

Asp Asn Asp Thr Gly Ala Leu Leu Ser Leu Gly Arg Glu Met Phe Arg
        115                 120                 125

Leu Glu Ile Leu Glu Asp Ile Ala Arg Asp Lys Val Arg Thr Leu His
130                 135                 140

Phe Val Asp Glu Ile Glu Val Tyr Leu Ala Phe Gln Thr Met Leu Ala
145                 150                 155                 160

Glu Lys Leu Gln Leu Ser Thr Ala Val Lys Glu Met Arg Phe Tyr Gly
            165                 170                 175

Val Ser Gly Val Thr Ala Asn Asp Leu Arg Thr Ala Glu Ala Met Val
        180                 185                 190

Arg Ser Arg Glu Glu Asn Glu Phe Thr Asp Trp Phe Ser Leu Trp Gly
        195                 200                 205

Pro Trp His Ala Val Leu Lys Arg Thr Glu Ala Asp Arg Trp Ala Gln
        210                 215                 220

Ala Glu Glu Gln Lys Tyr Glu Met Leu Glu Asn Glu Tyr Pro Gln Arg
225                 230                 235                 240
```

```
Val Ala Asp Arg Leu Lys Ala Ser Gly Leu Ser Gly Asp Ala Asp Ala
            245                 250                 255

Glu Arg Glu Ala Gly Ala Gln Val Met Arg Glu Thr Glu Gln Gln Ile
        260                 265                 270

Tyr Arg Gln Leu Thr Asp Glu Val Leu Ala Leu Arg Leu Phe Glu Asn
        275                 280                 285

Gly Ser Gln Leu His His Ser
        290                 295

<210> SEQ ID NO 28
<211> LENGTH: 211
<212> TYPE: PRT
<213> ORGANISM: Salmonella enterica

<400> SEQUENCE: 28

Gln Ile Thr Thr Leu Ile Leu Asp Asn Asn Glu Leu Lys Ser Leu Pro
1               5                   10                  15

Glu Asn Leu Gln Gly Asn Ile Lys Thr Leu Tyr Ala Asn Ser Asn Gln
            20                  25                  30

Leu Thr Ser Ile Pro Ala Thr Leu Pro Asp Thr Ile Gln Glu Met Glu
        35                  40                  45

Leu Ser Ile Asn Arg Ile Thr Glu Leu Pro Glu Arg Leu Pro Ser Ala
50                  55                  60

Leu Gln Ser Leu Asp Leu Phe His Asn Lys Ile Ser Cys Leu Pro Glu
65                  70                  75                  80

Asn Leu Pro Glu Glu Leu Arg Tyr Leu Ser Val Tyr Asp Asn Ser Ile
                85                  90                  95

Arg Thr Leu Pro Ala His Leu Pro Ser Glu Ile Thr His Leu Asn Val
            100                 105                 110

Gln Ser Asn Ser Leu Thr Ala Leu Pro Glu Thr Leu Pro Pro Gly Leu
        115                 120                 125

Lys Thr Leu Glu Ala Gly Glu Asn Ala Leu Thr Ser Leu Pro Ala Ser
    130                 135                 140

Leu Pro Pro Glu Leu Gln Val Leu Asp Val Ser Lys Asn Gln Ile Thr
145                 150                 155                 160

Val Leu Pro Glu Thr Leu Pro Pro Thr Ile Thr Thr Leu Asp Val Ser
                165                 170                 175

Arg Asn Ala Leu Thr Asn Leu Pro Glu Asn Leu Pro Ala Ala Leu Gln
            180                 185                 190

Ile Met Gln Ala Ser Arg Asn Asn Leu Val Arg Leu Pro Glu Ser Leu
        195                 200                 205

Pro His Phe
    210

<210> SEQ ID NO 29
<211> LENGTH: 165
<212> TYPE: PRT
<213> ORGANISM: Salmonella enterica

<400> SEQUENCE: 29

His Ile Thr Thr Leu Val Ile Pro Asp Asn Asn Leu Thr Ser Leu Pro
1               5                   10                  15

Glu Leu Pro Glu Gly Leu Arg Glu Leu Glu Val Ser Gly Asn Leu Gln
            20                  25                  30

Leu Thr Ser Leu Pro Ser Leu Pro Gln Gly Leu Gln Lys Leu Trp Ala
        35                  40                  45
```

Tyr Asn Asn Trp Leu Ala Ser Leu Pro Thr Leu Pro Pro Gly Leu Gly
            50                  55                  60

Asp Leu Ala Val Ser Asn Gln Leu Thr Ser Leu Pro Glu Met Pro
 65                  70                  75                  80

Pro Ala Leu Arg Glu Leu Arg Val Ser Gly Asn Asn Leu Thr Ser Leu
                85                  90                  95

Pro Ala Leu Pro Ser Gly Leu Gln Lys Leu Trp Ala Tyr Asn Asn Arg
                100                 105                 110

Leu Thr Ser Leu Pro Glu Met Ser Pro Gly Leu Gln Glu Leu Asp Val
            115                 120                 125

Ser His Asn Gln Leu Thr Arg Leu Pro Gln Ser Leu Thr Gly Leu Ser
            130                 135                 140

Ser Ala Ala Arg Val Tyr Leu Asp Gly Asn Pro Leu Ser Val Arg Thr
145                 150                 155                 160

Leu Gln Ala Leu Arg
                165

<210> SEQ ID NO 30
<211> LENGTH: 244
<212> TYPE: PRT
<213> ORGANISM: Salmonella enterica

<400> SEQUENCE: 30

His Ile Thr Thr Leu Val Ile Pro Asp Asn Asn Leu Thr Ser Leu Pro
 1               5                  10                  15

Ala Leu Pro Pro Glu Leu Arg Thr Leu Glu Val Ser Gly Asn Gln Leu
                20                  25                  30

Thr Ser Leu Pro Val Leu Pro Pro Gly Leu Leu Glu Leu Ser Ile Phe
            35                  40                  45

Ser Asn Pro Leu Thr His Leu Pro Ala Leu Pro Ser Gly Leu Cys Lys
 50                 55                  60

Leu Trp Ile Phe Gly Asn Gln Leu Thr Ser Leu Pro Val Leu Pro Pro
 65                 70                  75                  80

Gly Leu Gln Glu Leu Ser Val Ser Asp Asn Gln Leu Ala Ser Leu Pro
                85                  90                  95

Ala Leu Pro Ser Glu Leu Cys Lys Leu Trp Ala Tyr Asn Asn Gln Leu
                100                 105                 110

Thr Ser Leu Pro Met Leu Pro Ser Gly Leu Gln Glu Leu Ser Val Ser
            115                 120                 125

Asp Asn Gln Leu Ala Ser Leu Pro Thr Leu Pro Ser Glu Leu Tyr Lys
            130                 135                 140

Leu Trp Ala Tyr Asn Asn Arg Leu Thr Ser Leu Pro Ala Leu Pro Ser
145                 150                 155                 160

Gly Leu Lys Glu Leu Ile Val Ser Gly Asn Arg Leu Thr Ser Leu Pro
                165                 170                 175

Val Leu Pro Ser Glu Leu Lys Glu Leu Met Val Ser Gly Asn Arg Leu
                180                 185                 190

Thr Ser Leu Pro Met Leu Pro Ser Gly Leu Leu Ser Leu Ser Val Tyr
            195                 200                 205

Arg Asn Gln Leu Thr Arg Leu Pro Glu Ser Leu Ile His Leu Ser Ser
            210                 215                 220

Glu Thr Thr Val Asn Leu Glu Gly Asn Pro Leu Ser Glu Arg Thr Leu
225                 230                 235                 240

Gln Ala Leu Arg

<210> SEQ ID NO 31
<211> LENGTH: 122
<212> TYPE: PRT
<213> ORGANISM: Shigella flexneri

<400> SEQUENCE: 31

Gln Ile Thr Thr Leu Glu Ile Arg Lys Asn Leu Leu Thr His Leu Pro
1               5                   10                  15

Asp Leu Pro Pro Met Leu Lys Val Ile His Ala Gln Phe Asn Gln Leu
            20                  25                  30

Glu Ser Leu Pro Ala Leu Pro Glu Thr Leu Glu Glu Leu Asn Ala Gly
        35                  40                  45

Asp Asn Lys Ile Lys Glu Leu Pro Phe Leu Pro Glu Asn Leu Thr His
    50                  55                  60

Leu Arg Val His Asn Asn Arg Leu His Ile Leu Pro Leu Leu Pro Pro
65                  70                  75                  80

Glu Leu Lys Leu Leu Val Val Ser Gly Asn Arg Leu Asp Ser Ile Pro
                85                  90                  95

Pro Phe Pro Asp Lys Leu Glu Gly Leu Ala Leu Ala Asn Asn Phe Ile
            100                 105                 110

Glu Gln Leu Pro Glu Leu Pro Phe Ser Met
        115                 120

<210> SEQ ID NO 32
<211> LENGTH: 122
<212> TYPE: PRT
<213> ORGANISM: Shigella flexneri

<400> SEQUENCE: 32

Gln Ile Thr Thr Leu Glu Ile Arg Lys Asn Leu Leu Thr His Leu Pro
1               5                   10                  15

Asp Leu Pro Pro Met Leu Lys Val Ile His Ala Gln Phe Asn Gln Leu
            20                  25                  30

Glu Ser Leu Pro Ala Leu Pro Glu Thr Leu Glu Glu Leu Asn Ala Gly
        35                  40                  45

Asp Asn Lys Ile Lys Glu Leu Pro Phe Leu Pro Glu Asn Leu Thr His
    50                  55                  60

Leu Arg Val His Asn Asn Arg Leu His Ile Leu Pro Leu Leu Pro Pro
65                  70                  75                  80

Glu Leu Lys Leu Leu Val Val Ser Gly Asn Arg Leu Asp Ser Ile Pro
                85                  90                  95

Pro Phe Pro Asp Lys Leu Glu Gly Leu Ala Leu Ala Asn Asn Phe Ile
            100                 105                 110

Glu Gln Leu Pro Glu Leu Pro Phe Ser Met
        115                 120

<210> SEQ ID NO 33
<211> LENGTH: 162
<212> TYPE: PRT
<213> ORGANISM: Shigella flexneri

<400> SEQUENCE: 33

Gly Ile Lys Ser Ile Asn Ile Ser Lys Asn Leu Ser Leu Ile Ser
1               5                   10                  15

Pro Leu Pro Ala Ser Leu Thr Gln Leu Asn Val Ser Tyr Asn Arg Leu
            20                  25                  30

```
Ile Glu Leu Pro Ala Leu Pro Gln Gly Leu Lys Leu Asn Ala Ser
         35                  40                  45

His Asn Gln Leu Ile Thr Leu Pro Thr Leu Pro Ile Ser Leu Lys Glu
 50                  55                  60

Leu His Val Ser Asn Asn Gln Leu Cys Ser Leu Pro Val Leu Pro Glu
 65                  70                  75                  80

Leu Leu Glu Thr Leu Asp Val Ser Cys Asn Gly Leu Ala Val Leu Pro
                 85                  90                  95

Pro Leu Pro Phe Ser Leu Gln Glu Ile Ser Ala Ile Gly Asn Leu Leu
            100                 105                 110

Ser Glu Leu Pro Pro Leu Pro His Asn Ile His Ser Ile Trp Ala Ile
            115                 120                 125

Asp Asn Met Leu Thr Asp Ile Pro Tyr Leu Pro Glu Asn Leu Arg Asn
130                 135                 140

Gly Tyr Phe Asp Ile Asn Gln Ile Ser His Ile Pro Glu Ser Ile Leu
145                 150                 155                 160

Asn Leu

<210> SEQ ID NO 34
<211> LENGTH: 232
<212> TYPE: PRT
<213> ORGANISM: Shigella flexneri

<400> SEQUENCE: 34

Trp Ala Arg Glu Gly Thr Thr Thr Glu Asn Arg Ile Gln Ala Val Arg
 1               5                  10                  15

Leu Leu Lys Ile Cys Leu Asp Thr Arg Glu Pro Val Leu Asn Leu Ser
             20                  25                  30

Leu Leu Lys Leu Arg Ser Leu Pro Pro Leu Pro Leu His Ile Arg Glu
         35                  40                  45

Leu Asn Ile Ser Asn Asn Glu Leu Ile Ser Leu Pro Glu Asn Ser Pro
 50                  55                  60

Leu Leu Thr Glu Leu His Val Asn Gly Asn Asn Leu Asn Ile Leu Pro
 65                  70                  75                  80

Thr Leu Pro Ser Gln Leu Ile Lys Leu Asn Ile Ser Phe Asn Arg Asn
                 85                  90                  95

Leu Ser Cys Leu Pro Ser Leu Pro Pro Tyr Leu Gln Ser Leu Ser Ala
            100                 105                 110

Arg Phe Asn Ser Leu Glu Thr Leu Pro Glu Leu Pro Ser Thr Leu Thr
            115                 120                 125

Ile Leu Arg Ile Glu Gly Asn Arg Leu Thr Val Leu Pro Glu Leu Pro
130                 135                 140

His Arg Leu Gln Glu Leu Phe Val Ser Gly Asn Arg Leu Gln Glu Leu
145                 150                 155                 160

Pro Glu Phe Pro Gln Ser Leu Lys Tyr Leu Lys Val Gly Glu Asn Gln
                165                 170                 175

Leu Arg Arg Leu Ser Arg Leu Pro Gln Glu Leu Leu Ala Leu Asp Val
            180                 185                 190

Ser Asn Asn Leu Leu Thr Ser Leu Pro Glu Asn Ile Ile Thr Leu Pro
            195                 200                 205

Ile Cys Thr Asn Val Asn Ile Ser Gly Asn Pro Leu Ser Thr His Val
210                 215                 220

Leu Gln Ser Leu Gln Arg Leu Thr
225                 230
```

```
<210> SEQ ID NO 35
<211> LENGTH: 248
<212> TYPE: PRT
<213> ORGANISM: Shigella flexneri

<400> SEQUENCE: 35

Met Phe Ser Val Asn Asn Thr His Ser Ser Val Ser Cys Ser Pro Ser
1               5                   10                  15

Ile Asn Ser Asn Ser Thr Ser Asn Glu His Tyr Leu Arg Ile Leu Thr
            20                  25                  30

Glu Trp Glu Lys Asn Ser Ser Pro Gly Glu Glu Arg Gly Ile Ala Phe
        35                  40                  45

Asn Arg Leu Ser Gln Cys Phe Gln Asn Gln Glu Ala Val Leu Asn Leu
    50                  55                  60

Ser Asp Leu Asn Leu Thr Ser Leu Pro Gly Leu Pro Lys His Ile Ser
65                  70                  75                  80

Ala Leu Ile Val Glu Asn Asn Lys Leu Thr Ser Leu Pro Lys Leu Pro
                85                  90                  95

Ala Phe Leu Lys Glu Leu Asn Ala Asp Asn Asn Arg Leu Ser Val Ile
            100                 105                 110

Pro Glu Leu Pro Glu Ser Leu Thr Thr Leu Ser Val Arg Ser Asn Gln
        115                 120                 125

Leu Glu Asn Leu Pro Val Leu Pro Asn His Leu Thr Ser Leu Phe Val
    130                 135                 140

Glu Asn Asn Arg Leu Tyr Asn Leu Pro Ala Leu Pro Glu Lys Leu Lys
145                 150                 155                 160

Phe Leu His Val Tyr Tyr Asn Arg Leu Thr Thr Leu Pro Asp Leu Pro
                165                 170                 175

Asp Lys Leu Glu Ile Leu Cys Ala Gln Arg Asn Asn Leu Val Thr Phe
            180                 185                 190

Pro Gln Phe Ser Asp Arg Asn Asn Ile Arg Gln Lys Glu Tyr Tyr Phe
        195                 200                 205

His Phe Asn Gln Ile Thr Thr Leu Pro Glu Ser Phe Ser Gln Leu Asp
    210                 215                 220

Ser Ser Tyr Arg Ile Asn Ile Ser Gly Asn Pro Leu Ser Thr Arg Val
225                 230                 235                 240

Leu Gln Ser Leu Gln Arg Leu Thr
                245

<210> SEQ ID NO 36
<211> LENGTH: 172
<212> TYPE: PRT
<213> ORGANISM: Shigella flexneri

<400> SEQUENCE: 36

Asn Ser Asp Glu Leu Arg Leu Asp Arg Leu Asn Leu Ser Ser Leu Pro
1               5                   10                  15

Asp Asn Leu Pro Ala Gln Ile Thr Leu Leu Asn Val Ser Tyr Asn Gln
            20                  25                  30

Leu Thr Asn Leu Pro Glu Leu Pro Val Thr Leu Lys Lys Leu Tyr Ser
        35                  40                  45

Ala Ser Asn Lys Leu Ser Glu Leu Pro Val Leu Pro Pro Ala Leu Glu
    50                  55                  60

Ser Leu Gln Val Gln His Asn Glu Leu Glu Asn Leu Pro Ala Leu Pro
65                  70                  75                  80
```

```
Asp Ser Leu Leu Thr Met Asn Ile Ser Tyr Asn Glu Ile Val Ser Leu
                85                  90                  95

Pro Ser Leu Pro Gln Ala Leu Lys Asn Leu Arg Ala Thr Arg Asn Phe
            100                 105                 110

Leu Thr Glu Leu Pro Ala Phe Ser Glu Gly Asn Asn Pro Val Val Arg
        115                 120                 125

Glu Tyr Phe Phe Asp Arg Asn Gln Ile Ser His Ile Pro Glu Ser Ile
    130                 135                 140

Leu Asn Leu Arg Asn Glu Cys Ser Ile His Ile Ser Asp Asn Pro Leu
145                 150                 155                 160

Ser Ser His Ala Leu Gln Ala Leu Gln Arg Leu Thr
                165                 170
```

```
<210> SEQ ID NO 37
<211> LENGTH: 39
<212> TYPE: PRT
<213> ORGANISM: Salmonella enterica

<400> SEQUENCE: 37

Ala Pro Ala Lys Glu Ala Ala Asn Arg Glu Glu Ala Val Gln Arg Met
1               5                   10                  15

Arg Asp Cys Leu Lys Asn Asn Lys Thr Glu Leu Arg Leu Lys Ile Leu
            20                  25                  30

Gly Leu Thr Thr Ile Pro Ala
        35
```

```
<210> SEQ ID NO 38
<211> LENGTH: 18
<212> TYPE: PRT
<213> ORGANISM: Salmonella enterica

<400> SEQUENCE: 38

Leu Pro Ala Ala Leu Gln Ile Met Gln Ala Ser Arg Asn Asn Leu Val
1               5                   10                  15

Arg Leu
```

```
<210> SEQ ID NO 39
<211> LENGTH: 26
<212> TYPE: PRT
<213> ORGANISM: Salmonella enterica

<400> SEQUENCE: 39

Leu Ile Met Ala Gly Arg Glu Ile Phe Arg Leu Glu Gln Ile Glu Ser
1               5                   10                  15

Leu Ala Arg Glu Lys Val Lys Arg Leu Phe
            20                  25
```

```
<210> SEQ ID NO 40
<211> LENGTH: 10
<212> TYPE: PRT
<213> ORGANISM: Salmonella enterica

<400> SEQUENCE: 40

Ala Arg Leu Lys Ala Leu Thr Phe Pro Ala
1               5                   10
```

```
<210> SEQ ID NO 41
<211> LENGTH: 11
<212> TYPE: PRT
<213> ORGANISM: Salmonella enterica
```

<400> SEQUENCE: 41

Leu Gln Lys Leu Trp Ala Tyr Asn Asn Arg Leu
1               5                   10

<210> SEQ ID NO 42
<211> LENGTH: 10
<212> TYPE: PRT
<213> ORGANISM: Salmonella enterica

<400> SEQUENCE: 42

Leu Ser Val Arg Thr Leu Gln Ala Leu Arg
1               5                   10

<210> SEQ ID NO 43
<211> LENGTH: 11
<212> TYPE: PRT
<213> ORGANISM: Salmonella enterica

<400> SEQUENCE: 43

Ala Leu Arg Ala Lys Thr Phe Ala Met Ala Thr
1               5                   10

<210> SEQ ID NO 44
<211> LENGTH: 10
<212> TYPE: PRT
<213> ORGANISM: Salmonella enterica

<400> SEQUENCE: 44

Arg Phe Asn Ala Leu Arg Glu Lys Gln Ile
1               5                   10

<210> SEQ ID NO 45
<211> LENGTH: 8
<212> TYPE: PRT
<213> ORGANISM: Salmonella enterica

<400> SEQUENCE: 45

Leu Thr Ala Arg Trp Arg Leu Asn
1               5

<210> SEQ ID NO 46
<211> LENGTH: 12
<212> TYPE: PRT
<213> ORGANISM: Salmonella enterica

<400> SEQUENCE: 46

Ala Thr Ile Ser Asn Arg Arg Ile Tyr Arg Ile Ala
1               5                   10

<210> SEQ ID NO 47
<211> LENGTH: 31
<212> TYPE: PRT
<213> ORGANISM: Salmonella enterica

<400> SEQUENCE: 47

Ala Val Trp Ser Ala Trp Arg Arg Ala Ala Pro Ala Glu Glu Ser Arg
1               5                   10                  15

Gly Arg Ala Ala Val Val Gln Lys Met Arg Ala Cys Leu Asn Asn
            20                  25                  30

<210> SEQ ID NO 48
<211> LENGTH: 34
<212> TYPE: PRT
<213> ORGANISM: Salmonella enterica

<400> SEQUENCE: 48

Asn Asp Leu Ala Ala Leu Val Ala Thr Gly Arg Glu Met Phe Arg Leu
1               5                   10                  15

Gly Lys Leu Glu Gln Ile Ala Arg Glu Lys Val Arg Thr Leu Ala Leu
            20                  25                  30

Val Asp

<210> SEQ ID NO 49
<211> LENGTH: 16
<212> TYPE: PRT
<213> ORGANISM: Salmonella enterica

<400> SEQUENCE: 49

Val Trp Leu Ala Tyr Gln Asn Lys Leu Lys Lys Ser Leu Gly Leu Thr
1               5                   10                  15

<210> SEQ ID NO 50
<211> LENGTH: 20
<212> TYPE: PRT
<213> ORGANISM: Salmonella enterica

<400> SEQUENCE: 50

Arg Val Leu Glu Arg Lys Ala Pro Glu Arg Val Asn Ala Leu Arg Glu
1               5                   10                  15

Lys Gln Ile Ser
            20

<210> SEQ ID NO 51
<211> LENGTH: 20
<212> TYPE: PRT
<213> ORGANISM: Salmonella enterica

<400> SEQUENCE: 51

Arg Thr Ile Gly Ala Arg Ala Met Glu Ser Ala Lys Lys Thr Phe Leu
1               5                   10                  15

Asp Gly Leu Arg
            20

<210> SEQ ID NO 52
<211> LENGTH: 16
<212> TYPE: PRT
<213> ORGANISM: Shigella flexneri

<400> SEQUENCE: 52

Asp Arg Val Ala Leu Thr Trp Asn Asn Leu Arg Lys Thr Leu Leu Val
1               5                   10                  15

<210> SEQ ID NO 53
<211> LENGTH: 13
<212> TYPE: PRT
<213> ORGANISM: Shigella flexneri

<400> SEQUENCE: 53

Ser Gln Arg Val Ala Asp Arg Leu Lys Ala Ser Gly Leu
1               5                   10

<210> SEQ ID NO 54
<211> LENGTH: 15
<212> TYPE: PRT
<213> ORGANISM: Shigella flexneri

<400> SEQUENCE: 54

Asp Arg Val Ala Leu Thr Trp Asn Asn Leu Arg Lys Thr Leu Leu
1               5                   10                  15

<210> SEQ ID NO 55
<211> LENGTH: 16
<212> TYPE: PRT
<213> ORGANISM: Shigella flexneri

<400> SEQUENCE: 55

Asp Arg Val Ala Leu Thr Trp Asn Asn Leu Arg Lys Thr Leu Leu Val
1               5                   10                  15

<210> SEQ ID NO 56
<211> LENGTH: 13
<212> TYPE: PRT
<213> ORGANISM: Shigella flexneri

<400> SEQUENCE: 56

Pro Gln Arg Val Ala Asp Arg Leu Lys Ala Ser Gly Leu
1               5                   10

<210> SEQ ID NO 57
<211> LENGTH: 39
<212> TYPE: PRT
<213> ORGANISM: Shigella flexneri

<400> SEQUENCE: 57

Trp Ala Arg Glu Gly Thr Thr Thr Glu Asn Arg Ile Gln Ala Val Arg
1               5                   10                  15

Leu Leu Lys Ile Cys Leu Asp Thr Arg Glu Pro Val Leu Asn Leu Ser
            20                  25                  30

Leu Leu Lys Leu Arg Ser Leu
        35

<210> SEQ ID NO 58
<211> LENGTH: 27
<212> TYPE: PRT
<213> ORGANISM: Shigella flexneri

<400> SEQUENCE: 58

Gln Ser Leu Lys Tyr Leu Lys Val Gly Glu Asn Gln Leu Arg Arg Leu
1               5                   10                  15

Ser Arg Leu Pro Gln Glu Leu Leu Ala Leu Asp
            20                  25

<210> SEQ ID NO 59
<211> LENGTH: 15
<212> TYPE: PRT
<213> ORGANISM: Shigella flexneri

<400> SEQUENCE: 59

Asp Arg Val Ala Leu Thr Trp Asn Asn Leu Arg Lys Thr Leu Leu
1               5                   10                  15

<210> SEQ ID NO 60
<211> LENGTH: 11
<212> TYPE: PRT
<213> ORGANISM: Shigella flexneri

<400> SEQUENCE: 60

Thr Arg Val Leu Gln Ser Leu Gln Arg Leu Thr
1               5                   10

```
<210> SEQ ID NO 61
<211> LENGTH: 16
<212> TYPE: PRT
<213> ORGANISM: Shigella flexneri

<400> SEQUENCE: 61

Asp Arg Val Ala Leu Thr Trp Asn Asn Leu Arg Lys Thr Leu Leu Val
1               5                   10                  15

<210> SEQ ID NO 62
<211> LENGTH: 13
<212> TYPE: PRT
<213> ORGANISM: Shigella flexneri

<400> SEQUENCE: 62

Ser Gln Arg Val Ala Asp Arg Leu Lys Ala Ser Gly Leu
1               5                   10

<210> SEQ ID NO 63
<211> LENGTH: 20
<212> TYPE: PRT
<213> ORGANISM: Shigella flexneri

<400> SEQUENCE: 63

Ser Leu Pro Ser Leu Pro Gln Ala Leu Lys Asn Leu Arg Ala Thr Arg
1               5                   10                  15

Asn Phe Leu Thr
            20

<210> SEQ ID NO 64
<211> LENGTH: 16
<212> TYPE: PRT
<213> ORGANISM: Shigella flexneri

<400> SEQUENCE: 64

Asp Arg Val Ala Leu Thr Trp Asn Asn Leu Arg Lys Thr Leu Leu Val
1               5                   10                  15

<210> SEQ ID NO 65
<211> LENGTH: 13
<212> TYPE: PRT
<213> ORGANISM: Shigella flexneri

<400> SEQUENCE: 65

Pro Gln Arg Val Ala Asp Arg Leu Lys Ala Ser Gly Leu
1               5                   10

<210> SEQ ID NO 66
<211> LENGTH: 10
<212> TYPE: PRT
<213> ORGANISM: Salmonella enterica

<400> SEQUENCE: 66

Ser Leu Ala Arg Glu Lys Val Lys Arg Leu
1               5                   10

<210> SEQ ID NO 67
<211> LENGTH: 13
<212> TYPE: PRT
<213> ORGANISM: Salmonella enterica

<400> SEQUENCE: 67

Cys Leu Lys Asn Asn Lys Thr Glu Leu Arg Leu Lys Ile
1               5                   10
```

```
<210> SEQ ID NO 68
<211> LENGTH: 13
<212> TYPE: PRT
<213> ORGANISM: Salmonella enterica

<400> SEQUENCE: 68

Leu Lys Asn Asn Lys Thr Glu Leu Arg Leu Lys Ile Leu
1               5                   10

<210> SEQ ID NO 69
<211> LENGTH: 13
<212> TYPE: PRT
<213> ORGANISM: Salmonella enterica

<400> SEQUENCE: 69

Lys Asn Asn Lys Thr Glu Leu Arg Leu Lys Ile Leu Gly
1               5                   10

<210> SEQ ID NO 70
<211> LENGTH: 14
<212> TYPE: PRT
<213> ORGANISM: Salmonella enterica

<400> SEQUENCE: 70

Cys Leu Lys Asn Asn Lys Thr Glu Leu Arg Leu Lys Ile Leu
1               5                   10

<210> SEQ ID NO 71
<211> LENGTH: 14
<212> TYPE: PRT
<213> ORGANISM: Salmonella enterica

<400> SEQUENCE: 71

Leu Lys Asn Asn Lys Thr Glu Leu Arg Leu Lys Ile Leu Gly
1               5                   10

<210> SEQ ID NO 72
<211> LENGTH: 14
<212> TYPE: PRT
<213> ORGANISM: Salmonella enterica

<400> SEQUENCE: 72

Lys Asn Asn Lys Thr Glu Leu Arg Leu Lys Ile Leu Gly Leu
1               5                   10

<210> SEQ ID NO 73
<211> LENGTH: 14
<212> TYPE: PRT
<213> ORGANISM: Salmonella enterica

<400> SEQUENCE: 73

Ala Leu Gln Ile Met Gln Ala Ser Arg Asn Asn Leu Val Arg
1               5                   10

<210> SEQ ID NO 74
<211> LENGTH: 15
<212> TYPE: PRT
<213> ORGANISM: Salmonella enterica

<400> SEQUENCE: 74

Ala Ala Leu Gln Ile Met Gln Ala Ser Arg Asn Asn Leu Val Arg
1               5                   10                  15
```

-continued

```
<210> SEQ ID NO 75
<211> LENGTH: 15
<212> TYPE: PRT
<213> ORGANISM: Salmonella enterica

<400> SEQUENCE: 75

Ala Leu Gln Ile Met Gln Ala Ser Arg Asn Asn Leu Val Arg Leu
1               5                   10                  15

<210> SEQ ID NO 76
<211> LENGTH: 16
<212> TYPE: PRT
<213> ORGANISM: Salmonella enterica

<400> SEQUENCE: 76

Cys Leu Lys Asn Asn Lys Thr Glu Leu Arg Leu Lys Ile Leu Gly Leu
1               5                   10                  15

<210> SEQ ID NO 77
<211> LENGTH: 16
<212> TYPE: PRT
<213> ORGANISM: Salmonella enterica

<400> SEQUENCE: 77

Leu Lys Asn Asn Lys Thr Glu Leu Arg Leu Lys Ile Leu Gly Leu Thr
1               5                   10                  15

<210> SEQ ID NO 78
<211> LENGTH: 16
<212> TYPE: PRT
<213> ORGANISM: Salmonella enterica

<400> SEQUENCE: 78

Ala Ala Leu Gln Ile Met Gln Ala Ser Arg Asn Asn Leu Val Arg Leu
1               5                   10                  15

<210> SEQ ID NO 79
<211> LENGTH: 16
<212> TYPE: PRT
<213> ORGANISM: Salmonella enterica

<400> SEQUENCE: 79

Arg Leu Glu Gln Ile Glu Ser Leu Ala Arg Glu Lys Val Lys Arg Leu
1               5                   10                  15

<210> SEQ ID NO 80
<211> LENGTH: 21
<212> TYPE: PRT
<213> ORGANISM: Salmonella enterica

<400> SEQUENCE: 80

Ala Gly Arg Glu Ile Phe Arg Leu Glu Gln Ile Glu Ser Leu Ala Arg
1               5                   10                  15

Glu Lys Val Lys Arg
            20

<210> SEQ ID NO 81
<211> LENGTH: 21
<212> TYPE: PRT
<213> ORGANISM: Salmonella enterica

<400> SEQUENCE: 81

Gly Arg Glu Ile Phe Arg Leu Glu Gln Ile Glu Ser Leu Ala Arg Glu
1               5                   10                  15
```

Lys Val Lys Arg Leu
        20

<210> SEQ ID NO 82
<211> LENGTH: 22
<212> TYPE: PRT
<213> ORGANISM: Salmonella enterica

<400> SEQUENCE: 82

Glu Ala Val Gln Arg Met Arg Asp Cys Leu Lys Asn Asn Lys Thr Glu
1               5                   10                  15

Leu Arg Leu Lys Ile Leu
        20

<210> SEQ ID NO 83
<211> LENGTH: 22
<212> TYPE: PRT
<213> ORGANISM: Salmonella enterica

<400> SEQUENCE: 83

Ala Val Gln Arg Met Arg Asp Cys Leu Lys Asn Asn Lys Thr Glu Leu
1               5                   10                  15

Arg Leu Lys Ile Leu Gly
        20

<210> SEQ ID NO 84
<211> LENGTH: 22
<212> TYPE: PRT
<213> ORGANISM: Salmonella enterica

<400> SEQUENCE: 84

Val Gln Arg Met Arg Asp Cys Leu Lys Asn Asn Lys Thr Glu Leu Arg
1               5                   10                  15

Leu Lys Ile Leu Gly Leu
        20

<210> SEQ ID NO 85
<211> LENGTH: 22
<212> TYPE: PRT
<213> ORGANISM: Salmonella enterica

<400> SEQUENCE: 85

Gln Arg Met Arg Asp Cys Leu Lys Asn Asn Lys Thr Glu Leu Arg Leu
1               5                   10                  15

Lys Ile Leu Gly Leu Thr
        20

<210> SEQ ID NO 86
<211> LENGTH: 22
<212> TYPE: PRT
<213> ORGANISM: Salmonella enterica

<400> SEQUENCE: 86

Arg Met Arg Asp Cys Leu Lys Asn Asn Lys Thr Glu Leu Arg Leu Lys
1               5                   10                  15

Ile Leu Gly Leu Thr Thr
        20

<210> SEQ ID NO 87
<211> LENGTH: 22
<212> TYPE: PRT
<213> ORGANISM: Salmonella enterica -continued

```
<400> SEQUENCE: 87

Met Ala Gly Arg Glu Ile Phe Arg Leu Glu Gln Ile Glu Ser Leu Ala
1               5                   10                  15
Arg Glu Lys Val Lys Arg
            20

<210> SEQ ID NO 88
<211> LENGTH: 22
<212> TYPE: PRT
<213> ORGANISM: Salmonella enterica

<400> SEQUENCE: 88

Ala Gly Arg Glu Ile Phe Arg Leu Glu Gln Ile Glu Ser Leu Ala Arg
1               5                   10                  15
Glu Lys Val Lys Arg Leu
            20

<210> SEQ ID NO 89
<211> LENGTH: 24
<212> TYPE: PRT
<213> ORGANISM: Salmonella enterica

<400> SEQUENCE: 89

Glu Ala Val Gln Arg Met Arg Asp Cys Leu Lys Asn Asn Lys Thr Glu
1               5                   10                  15
Leu Arg Leu Lys Ile Leu Gly Leu
            20

<210> SEQ ID NO 90
<211> LENGTH: 24
<212> TYPE: PRT
<213> ORGANISM: Salmonella enterica

<400> SEQUENCE: 90

Ala Val Gln Arg Met Arg Asp Cys Leu Lys Asn Asn Lys Thr Glu Leu
1               5                   10                  15
Arg Leu Lys Ile Leu Gly Leu Thr
            20

<210> SEQ ID NO 91
<211> LENGTH: 24
<212> TYPE: PRT
<213> ORGANISM: Salmonella enterica

<400> SEQUENCE: 91

Gln Arg Met Arg Asp Cys Leu Lys Asn Asn Lys Thr Glu Leu Arg Leu
1               5                   10                  15
Lys Ile Leu Gly Leu Thr Thr Ile
            20

<210> SEQ ID NO 92
<211> LENGTH: 24
<212> TYPE: PRT
<213> ORGANISM: Salmonella enterica

<400> SEQUENCE: 92

Leu Ile Met Ala Gly Arg Glu Ile Phe Arg Leu Glu Gln Ile Glu Ser
1               5                   10                  15
Leu Ala Arg Glu Lys Val Lys Arg
            20
```

```
<210> SEQ ID NO 93
<211> LENGTH: 24
<212> TYPE: PRT
<213> ORGANISM: Salmonella enterica

<400> SEQUENCE: 93

Ile Met Ala Gly Arg Glu Ile Phe Arg Leu Glu Gln Ile Glu Ser Leu
1               5                   10                  15

Ala Arg Glu Lys Val Lys Arg Leu
            20

<210> SEQ ID NO 94
<211> LENGTH: 25
<212> TYPE: PRT
<213> ORGANISM: Salmonella enterica

<400> SEQUENCE: 94

Leu Ile Met Ala Gly Arg Glu Ile Phe Arg Leu Glu Gln Ile Glu Ser
1               5                   10                  15

Leu Ala Arg Glu Lys Val Lys Arg Leu
            20                  25

<210> SEQ ID NO 95
<211> LENGTH: 26
<212> TYPE: PRT
<213> ORGANISM: Salmonella enterica

<400> SEQUENCE: 95

Asn Arg Glu Glu Ala Val Gln Arg Met Arg Asp Cys Leu Lys Asn Asn
1               5                   10                  15

Lys Thr Glu Leu Arg Leu Lys Ile Leu Gly
            20                  25

<210> SEQ ID NO 96
<211> LENGTH: 26
<212> TYPE: PRT
<213> ORGANISM: Salmonella enterica

<400> SEQUENCE: 96

Arg Glu Glu Ala Val Gln Arg Met Arg Asp Cys Leu Lys Asn Asn Lys
1               5                   10                  15

Thr Glu Leu Arg Leu Lys Ile Leu Gly Leu
            20                  25

<210> SEQ ID NO 97
<211> LENGTH: 26
<212> TYPE: PRT
<213> ORGANISM: Salmonella enterica

<400> SEQUENCE: 97

Ala Val Gln Arg Met Arg Asp Cys Leu Lys Asn Asn Lys Thr Glu Leu
1               5                   10                  15

Arg Leu Lys Ile Leu Gly Leu Thr Thr Ile
            20                  25

<210> SEQ ID NO 98
<211> LENGTH: 28
<212> TYPE: PRT
<213> ORGANISM: Salmonella enterica

<400> SEQUENCE: 98

Glu Ala Ala Asn Arg Glu Glu Ala Val Gln Arg Met Arg Asp Cys Leu
1               5                   10                  15
```

```
<210> SEQ ID NO 99
<211> LENGTH: 28
<212> TYPE: PRT
<213> ORGANISM: Salmonella enterica

<400> SEQUENCE: 99

Ala Ala Asn Arg Glu Glu Ala Val Gln Arg Met Arg Asp Cys Leu Lys
1               5                   10                  15

Asn Asn Lys Thr Glu Leu Arg Leu Lys Ile Leu Gly
            20                  25

<210> SEQ ID NO 100
<211> LENGTH: 28
<212> TYPE: PRT
<213> ORGANISM: Salmonella enterica

<400> SEQUENCE: 100

Ala Asn Arg Glu Glu Ala Val Gln Arg Met Arg Asp Cys Leu Lys Asn
1               5                   10                  15

Asn Lys Thr Glu Leu Arg Leu Lys Ile Leu Gly Leu
            20                  25

<210> SEQ ID NO 101
<211> LENGTH: 28
<212> TYPE: PRT
<213> ORGANISM: Salmonella enterica

<400> SEQUENCE: 101

Asn Arg Glu Glu Ala Val Gln Arg Met Arg Asp Cys Leu Lys Asn Asn
1               5                   10                  15

Lys Thr Glu Leu Arg Leu Lys Ile Leu Gly Leu Thr
            20                  25

<210> SEQ ID NO 102
<211> LENGTH: 28
<212> TYPE: PRT
<213> ORGANISM: Salmonella enterica

<400> SEQUENCE: 102

Arg Glu Glu Ala Val Gln Arg Met Arg Asp Cys Leu Lys Asn Asn Lys
1               5                   10                  15

Thr Glu Leu Arg Leu Lys Ile Leu Gly Leu Thr Thr
            20                  25

<210> SEQ ID NO 103
<211> LENGTH: 28
<212> TYPE: PRT
<213> ORGANISM: Salmonella enterica

<400> SEQUENCE: 103

Ala Val Gln Arg Met Arg Asp Cys Leu Lys Asn Asn Lys Thr Glu Leu
1               5                   10                  15

Arg Leu Lys Ile Leu Gly Leu Thr Thr Ile Pro Ala
            20                  25

<210> SEQ ID NO 104
<211> LENGTH: 29
<212> TYPE: PRT
<213> ORGANISM: Salmonella enterica
```

```
<400> SEQUENCE: 104

Ala Pro Ala Lys Glu Ala Ala Asn Arg Glu Glu Ala Val Gln Arg Met
1               5                   10                  15

Arg Asp Cys Leu Lys Asn Asn Lys Thr Glu Leu Arg Leu
            20                  25

<210> SEQ ID NO 105
<211> LENGTH: 29
<212> TYPE: PRT
<213> ORGANISM: Salmonella enterica

<400> SEQUENCE: 105

Ala Lys Glu Ala Ala Asn Arg Glu Glu Ala Val Gln Arg Met Arg Asp
1               5                   10                  15

Cys Leu Lys Asn Asn Lys Thr Glu Leu Arg Leu Lys Ile
            20                  25

<210> SEQ ID NO 106
<211> LENGTH: 29
<212> TYPE: PRT
<213> ORGANISM: Salmonella enterica

<400> SEQUENCE: 106

Glu Ala Ala Asn Arg Glu Glu Ala Val Gln Arg Met Arg Asp Cys Leu
1               5                   10                  15

Lys Asn Asn Lys Thr Glu Leu Arg Leu Lys Ile Leu Gly
            20                  25

<210> SEQ ID NO 107
<211> LENGTH: 29
<212> TYPE: PRT
<213> ORGANISM: Salmonella enterica

<400> SEQUENCE: 107

Ala Ala Asn Arg Glu Glu Ala Val Gln Arg Met Arg Asp Cys Leu Lys
1               5                   10                  15

Asn Asn Lys Thr Glu Leu Arg Leu Lys Ile Leu Gly Leu
            20                  25

<210> SEQ ID NO 108
<211> LENGTH: 29
<212> TYPE: PRT
<213> ORGANISM: Salmonella enterica

<400> SEQUENCE: 108

Ala Asn Arg Glu Glu Ala Val Gln Arg Met Arg Asp Cys Leu Lys Asn
1               5                   10                  15

Asn Lys Thr Glu Leu Arg Leu Lys Ile Leu Gly Leu Thr
            20                  25

<210> SEQ ID NO 109
<211> LENGTH: 29
<212> TYPE: PRT
<213> ORGANISM: Salmonella enterica

<400> SEQUENCE: 109

Arg Glu Glu Ala Val Gln Arg Met Arg Asp Cys Leu Lys Asn Asn Lys
1               5                   10                  15

Thr Glu Leu Arg Leu Lys Ile Leu Gly Leu Thr Thr Ile
            20                  25
```

<210> SEQ ID NO 110
<211> LENGTH: 17
<212> TYPE: PRT
<213> ORGANISM: Salmonella enterica

<400> SEQUENCE: 110

Arg Asp Cys Leu Lys Asn Asn Lys Thr Glu Leu Arg Leu Lys Ile Leu
1               5                   10                  15

Gly

<210> SEQ ID NO 111
<211> LENGTH: 17
<212> TYPE: PRT
<213> ORGANISM: Salmonella enterica

<400> SEQUENCE: 111

Cys Leu Lys Asn Asn Lys Thr Glu Leu Arg Leu Lys Ile Leu Gly Leu
1               5                   10                  15

Thr

<210> SEQ ID NO 112
<211> LENGTH: 18
<212> TYPE: PRT
<213> ORGANISM: Salmonella enterica

<400> SEQUENCE: 112

Met Arg Asp Cys Leu Lys Asn Asn Lys Thr Glu Leu Arg Leu Lys Ile
1               5                   10                  15

Leu Gly

<210> SEQ ID NO 113
<211> LENGTH: 18
<212> TYPE: PRT
<213> ORGANISM: Salmonella enterica

<400> SEQUENCE: 113

Arg Asp Cys Leu Lys Asn Asn Lys Thr Glu Leu Arg Leu Lys Ile Leu
1               5                   10                  15

Gly Leu

<210> SEQ ID NO 114
<211> LENGTH: 18
<212> TYPE: PRT
<213> ORGANISM: Salmonella enterica

<400> SEQUENCE: 114

Leu Pro Ala Ala Leu Gln Ile Met Gln Ala Ser Arg Asn Asn Leu Val
1               5                   10                  15

Arg Leu

<210> SEQ ID NO 115
<211> LENGTH: 18
<212> TYPE: PRT
<213> ORGANISM: Salmonella enterica

<400> SEQUENCE: 115

Ile Phe Arg Leu Glu Gln Ile Glu Ser Leu Ala Arg Glu Lys Val Lys
1               5                   10                  15

Arg Leu

```
<210> SEQ ID NO 116
<211> LENGTH: 19
<212> TYPE: PRT
<213> ORGANISM: Salmonella enterica

<400> SEQUENCE: 116

Arg Met Arg Asp Cys Leu Lys Asn Asn Lys Thr Glu Leu Arg Leu Lys
1               5                   10                  15

Ile Leu Gly

<210> SEQ ID NO 117
<211> LENGTH: 19
<212> TYPE: PRT
<213> ORGANISM: Salmonella enterica

<400> SEQUENCE: 117

Met Arg Asp Cys Leu Lys Asn Asn Lys Thr Glu Leu Arg Leu Lys Ile
1               5                   10                  15

Leu Gly Leu

<210> SEQ ID NO 118
<211> LENGTH: 19
<212> TYPE: PRT
<213> ORGANISM: Salmonella enterica

<400> SEQUENCE: 118

Arg Asp Cys Leu Lys Asn Asn Lys Thr Glu Leu Arg Leu Lys Ile Leu
1               5                   10                  15

Gly Leu Thr

<210> SEQ ID NO 119
<211> LENGTH: 20
<212> TYPE: PRT
<213> ORGANISM: Salmonella enterica

<400> SEQUENCE: 119

Arg Met Arg Asp Cys Leu Lys Asn Asn Lys Thr Glu Leu Arg Leu Lys
1               5                   10                  15

Ile Leu Gly Leu
            20

<210> SEQ ID NO 120
<211> LENGTH: 20
<212> TYPE: PRT
<213> ORGANISM: Salmonella enterica

<400> SEQUENCE: 120

Met Arg Asp Cys Leu Lys Asn Asn Lys Thr Glu Leu Arg Leu Lys Ile
1               5                   10                  15

Leu Gly Leu Thr
            20

<210> SEQ ID NO 121
<211> LENGTH: 20
<212> TYPE: PRT
<213> ORGANISM: Salmonella enterica

<400> SEQUENCE: 121

Arg Asp Cys Leu Lys Asn Asn Lys Thr Glu Leu Arg Leu Lys Ile Leu
1               5                   10                  15

Gly Leu Thr Thr
            20
```

<210> SEQ ID NO 122
<211> LENGTH: 21
<212> TYPE: PRT
<213> ORGANISM: Salmonella enterica

<400> SEQUENCE: 122

Ala Val Gln Arg Met Arg Asp Cys Leu Lys Asn Asn Lys Thr Glu Leu
1               5                   10                  15

Arg Leu Lys Ile Leu
            20

<210> SEQ ID NO 123
<211> LENGTH: 21
<212> TYPE: PRT
<213> ORGANISM: Salmonella enterica

<400> SEQUENCE: 123

Val Gln Arg Met Arg Asp Cys Leu Lys Asn Asn Lys Thr Glu Leu Arg
1               5                   10                  15

Leu Lys Ile Leu Gly
            20

<210> SEQ ID NO 124
<211> LENGTH: 21
<212> TYPE: PRT
<213> ORGANISM: Salmonella enterica

<400> SEQUENCE: 124

Gln Arg Met Arg Asp Cys Leu Lys Asn Asn Lys Thr Glu Leu Arg Leu
1               5                   10                  15

Lys Ile Leu Gly Leu
            20

<210> SEQ ID NO 125
<211> LENGTH: 21
<212> TYPE: PRT
<213> ORGANISM: Salmonella enterica

<400> SEQUENCE: 125

Arg Met Arg Asp Cys Leu Lys Asn Asn Lys Thr Glu Leu Arg Leu Lys
1               5                   10                  15

Ile Leu Gly Leu Thr
            20

<210> SEQ ID NO 126
<211> LENGTH: 21
<212> TYPE: PRT
<213> ORGANISM: Salmonella enterica

<400> SEQUENCE: 126

Arg Asp Cys Leu Lys Asn Asn Lys Thr Glu Leu Arg Leu Lys Ile Leu
1               5                   10                  15

Gly Leu Thr Thr Ile
            20

<210> SEQ ID NO 127
<211> LENGTH: 23
<212> TYPE: PRT
<213> ORGANISM: Salmonella enterica

<400> SEQUENCE: 127

-continued

Glu Ala Val Gln Arg Met Arg Asp Cys Leu Lys Asn Asn Lys Thr Glu
1               5                   10                  15

Leu Arg Leu Lys Ile Leu Gly
            20

<210> SEQ ID NO 128
<211> LENGTH: 23
<212> TYPE: PRT
<213> ORGANISM: Salmonella enterica

<400> SEQUENCE: 128

Ala Val Gln Arg Met Arg Asp Cys Leu Lys Asn Asn Lys Thr Glu Leu
1               5                   10                  15

Arg Leu Lys Ile Leu Gly Leu
            20

<210> SEQ ID NO 129
<211> LENGTH: 23
<212> TYPE: PRT
<213> ORGANISM: Salmonella enterica

<400> SEQUENCE: 129

Val Gln Arg Met Arg Asp Cys Leu Lys Asn Asn Lys Thr Glu Leu Arg
1               5                   10                  15

Leu Lys Ile Leu Gly Leu Thr
            20

<210> SEQ ID NO 130
<211> LENGTH: 23
<212> TYPE: PRT
<213> ORGANISM: Salmonella enterica

<400> SEQUENCE: 130

Gln Arg Met Arg Asp Cys Leu Lys Asn Asn Lys Thr Glu Leu Arg Leu
1               5                   10                  15

Lys Ile Leu Gly Leu Thr Thr
            20

<210> SEQ ID NO 131
<211> LENGTH: 23
<212> TYPE: PRT
<213> ORGANISM: Salmonella enterica

<400> SEQUENCE: 131

Arg Met Arg Asp Cys Leu Lys Asn Asn Lys Thr Glu Leu Arg Leu Lys
1               5                   10                  15

Ile Leu Gly Leu Thr Thr Ile
            20

<210> SEQ ID NO 132
<211> LENGTH: 23
<212> TYPE: PRT
<213> ORGANISM: Salmonella enterica

<400> SEQUENCE: 132

Ile Met Ala Gly Arg Glu Ile Phe Arg Leu Glu Gln Ile Glu Ser Leu
1               5                   10                  15

Ala Arg Glu Lys Val Lys Arg
            20

<210> SEQ ID NO 133
<211> LENGTH: 23

```
<212> TYPE: PRT
<213> ORGANISM: Salmonella enterica

<400> SEQUENCE: 133

Met Ala Gly Arg Glu Ile Phe Arg Leu Glu Gln Ile Glu Ser Leu Ala
1               5                   10                  15

Arg Glu Lys Val Lys Arg Leu
            20

<210> SEQ ID NO 134
<211> LENGTH: 23
<212> TYPE: PRT
<213> ORGANISM: Salmonella enterica

<400> SEQUENCE: 134

Ala Gly Arg Glu Ile Phe Arg Leu Glu Gln Ile Glu Ser Leu Ala Arg
1               5                   10                  15

Glu Lys Val Lys Arg Leu Phe
            20

<210> SEQ ID NO 135
<211> LENGTH: 24
<212> TYPE: PRT
<213> ORGANISM: Salmonella enterica

<400> SEQUENCE: 135

Glu Ala Val Gln Arg Met Arg Asp Cys Leu Lys Asn Asn Lys Thr Glu
1               5                   10                  15

Leu Arg Leu Lys Ile Leu Gly Leu
            20

<210> SEQ ID NO 136
<211> LENGTH: 24
<212> TYPE: PRT
<213> ORGANISM: Salmonella enterica

<400> SEQUENCE: 136

Ala Val Gln Arg Met Arg Asp Cys Leu Lys Asn Asn Lys Thr Glu Leu
1               5                   10                  15

Arg Leu Lys Ile Leu Gly Leu Thr
            20

<210> SEQ ID NO 137
<211> LENGTH: 25
<212> TYPE: PRT
<213> ORGANISM: Salmonella enterica

<400> SEQUENCE: 137

Arg Glu Glu Ala Val Gln Arg Met Arg Asp Cys Leu Lys Asn Asn Lys
1               5                   10                  15

Thr Glu Leu Arg Leu Lys Ile Leu Gly
            20                  25

<210> SEQ ID NO 138
<211> LENGTH: 25
<212> TYPE: PRT
<213> ORGANISM: Salmonella enterica

<400> SEQUENCE: 138

Glu Ala Val Gln Arg Met Arg Asp Cys Leu Lys Asn Asn Lys Thr Glu
1               5                   10                  15

Leu Arg Leu Lys Ile Leu Gly Leu Thr
```

```
                        20                  25

<210> SEQ ID NO 139
<211> LENGTH: 25
<212> TYPE: PRT
<213> ORGANISM: Salmonella enterica

<400> SEQUENCE: 139

Ala Val Gln Arg Met Arg Asp Cys Leu Lys Asn Asn Lys Thr Glu Leu
1               5                   10                  15

Arg Leu Lys Ile Leu Gly Leu Thr Thr
            20                  25

<210> SEQ ID NO 140
<211> LENGTH: 25
<212> TYPE: PRT
<213> ORGANISM: Salmonella enterica

<400> SEQUENCE: 140

Arg Met Arg Asp Cys Leu Lys Asn Asn Lys Thr Glu Leu Arg Leu Lys
1               5                   10                  15

Ile Leu Gly Leu Thr Thr Ile Pro Ala
            20                  25

<210> SEQ ID NO 141
<211> LENGTH: 27
<212> TYPE: PRT
<213> ORGANISM: Salmonella enterica

<400> SEQUENCE: 141

Ala Ala Asn Arg Glu Glu Ala Val Gln Arg Met Arg Asp Cys Leu Lys
1               5                   10                  15

Asn Asn Lys Thr Glu Leu Arg Leu Lys Ile Leu
            20                  25

<210> SEQ ID NO 142
<211> LENGTH: 27
<212> TYPE: PRT
<213> ORGANISM: Salmonella enterica

<400> SEQUENCE: 142

Ala Asn Arg Glu Glu Ala Val Gln Arg Met Arg Asp Cys Leu Lys Asn
1               5                   10                  15

Asn Lys Thr Glu Leu Arg Leu Lys Ile Leu Gly
            20                  25

<210> SEQ ID NO 143
<211> LENGTH: 27
<212> TYPE: PRT
<213> ORGANISM: Salmonella enterica

<400> SEQUENCE: 143

Asn Arg Glu Glu Ala Val Gln Arg Met Arg Asp Cys Leu Lys Asn Asn
1               5                   10                  15

Lys Thr Glu Leu Arg Leu Lys Ile Leu Gly Leu
            20                  25

<210> SEQ ID NO 144
<211> LENGTH: 27
<212> TYPE: PRT
<213> ORGANISM: Salmonella enterica

<400> SEQUENCE: 144
```

```
Arg Glu Glu Ala Val Gln Arg Met Arg Asp Cys Leu Lys Asn Asn Lys
1               5                   10                  15

Thr Glu Leu Arg Leu Lys Ile Leu Gly Leu Thr
            20                  25
```

<210> SEQ ID NO 145
<211> LENGTH: 30
<212> TYPE: PRT
<213> ORGANISM: Salmonella enterica

<400> SEQUENCE: 145

```
Ala Pro Ala Lys Glu Ala Ala Asn Arg Glu Glu Ala Val Gln Arg Met
1               5                   10                  15

Arg Asp Cys Leu Lys Asn Asn Lys Thr Glu Leu Arg Leu Lys
            20                  25                  30
```

<210> SEQ ID NO 146
<211> LENGTH: 30
<212> TYPE: PRT
<213> ORGANISM: Salmonella enterica

<400> SEQUENCE: 146

```
Pro Ala Lys Glu Ala Ala Asn Arg Glu Glu Ala Val Gln Arg Met Arg
1               5                   10                  15

Asp Cys Leu Lys Asn Asn Lys Thr Glu Leu Arg Leu Lys Ile
            20                  25                  30
```

<210> SEQ ID NO 147
<211> LENGTH: 30
<212> TYPE: PRT
<213> ORGANISM: Salmonella enterica

<400> SEQUENCE: 147

```
Ala Lys Glu Ala Ala Asn Arg Glu Glu Ala Val Gln Arg Met Arg Asp
1               5                   10                  15

Cys Leu Lys Asn Asn Lys Thr Glu Leu Arg Leu Lys Ile Leu
            20                  25                  30
```

<210> SEQ ID NO 148
<211> LENGTH: 30
<212> TYPE: PRT
<213> ORGANISM: Salmonella enterica

<400> SEQUENCE: 148

```
Lys Glu Ala Ala Asn Arg Glu Glu Ala Val Gln Arg Met Arg Asp Cys
1               5                   10                  15

Leu Lys Asn Asn Lys Thr Glu Leu Arg Leu Lys Ile Leu Gly
            20                  25                  30
```

<210> SEQ ID NO 149
<211> LENGTH: 30
<212> TYPE: PRT
<213> ORGANISM: Salmonella enterica

<400> SEQUENCE: 149

```
Glu Ala Ala Asn Arg Glu Glu Ala Val Gln Arg Met Arg Asp Cys Leu
1               5                   10                  15

Lys Asn Asn Lys Thr Glu Leu Arg Leu Lys Ile Leu Gly Leu
            20                  25                  30
```

<210> SEQ ID NO 150

```
<211> LENGTH: 30
<212> TYPE: PRT
<213> ORGANISM: Salmonella enterica

<400> SEQUENCE: 150

Ala Ala Asn Arg Glu Glu Ala Val Gln Arg Met Arg Asp Cys Leu Lys
1               5                   10                  15

Asn Asn Lys Thr Glu Leu Arg Leu Lys Ile Leu Gly Leu Thr
            20                  25                  30

<210> SEQ ID NO 151
<211> LENGTH: 30
<212> TYPE: PRT
<213> ORGANISM: Salmonella enterica

<400> SEQUENCE: 151

Ala Asn Arg Glu Glu Ala Val Gln Arg Met Arg Asp Cys Leu Lys Asn
1               5                   10                  15

Asn Lys Thr Glu Leu Arg Leu Lys Ile Leu Gly Leu Thr Thr
            20                  25                  30

<210> SEQ ID NO 152
<211> LENGTH: 10
<212> TYPE: PRT
<213> ORGANISM: Salmonella enterica

<400> SEQUENCE: 152

Leu Ser Val Arg Thr Leu Gln Ala Leu Arg
1               5                   10

<210> SEQ ID NO 153
<211> LENGTH: 10
<212> TYPE: PRT
<213> ORGANISM: Salmonella enterica

<400> SEQUENCE: 153

Ala Arg Leu Lys Ala Leu Thr Phe Pro Ala
1               5                   10

<210> SEQ ID NO 154
<211> LENGTH: 10
<212> TYPE: PRT
<213> ORGANISM: Salmonella enterica

<400> SEQUENCE: 154

Arg Phe Asn Ala Leu Arg Glu Lys Gln Ile
1               5                   10

<210> SEQ ID NO 155
<211> LENGTH: 8
<212> TYPE: PRT
<213> ORGANISM: Salmonella enterica

<400> SEQUENCE: 155

Leu Thr Ala Arg Trp Arg Leu Asn
1               5

<210> SEQ ID NO 156
<211> LENGTH: 11
<212> TYPE: PRT
<213> ORGANISM: Salmonella enterica

<400> SEQUENCE: 156

Leu Gln Lys Leu Trp Ala Tyr Asn Asn Arg Leu
```

```
1               5                   10
```

<210> SEQ ID NO 157
<211> LENGTH: 11
<212> TYPE: PRT
<213> ORGANISM: Salmonella enterica

<400> SEQUENCE: 157

```
Ala Leu Arg Ala Lys Thr Phe Ala Met Ala Thr
1               5                   10
```

<210> SEQ ID NO 158
<211> LENGTH: 10
<212> TYPE: PRT
<213> ORGANISM: Salmonella enterica

<400> SEQUENCE: 158

```
Ser Arg Gly Arg Ala Ala Val Val Gln Lys
1               5                   10
```

<210> SEQ ID NO 159
<211> LENGTH: 10
<212> TYPE: PRT
<213> ORGANISM: Salmonella enterica

<400> SEQUENCE: 159

```
Arg Gly Arg Ala Ala Val Val Gln Lys Met
1               5                   10
```

<210> SEQ ID NO 160
<211> LENGTH: 10
<212> TYPE: PRT
<213> ORGANISM: Salmonella enterica

<400> SEQUENCE: 160

```
Gly Arg Ala Ala Val Val Gln Lys Met Arg
1               5                   10
```

<210> SEQ ID NO 161
<211> LENGTH: 10
<212> TYPE: PRT
<213> ORGANISM: Salmonella enterica

<400> SEQUENCE: 161

```
Arg Ala Ala Val Val Gln Lys Met Arg Ala
1               5                   10
```

<210> SEQ ID NO 162
<211> LENGTH: 11
<212> TYPE: PRT
<213> ORGANISM: Salmonella enterica

<400> SEQUENCE: 162

```
Gly Arg Ala Ala Val Val Gln Lys Met Arg Ala
1               5                   10
```

<210> SEQ ID NO 163
<211> LENGTH: 11
<212> TYPE: PRT
<213> ORGANISM: Salmonella enterica

<400> SEQUENCE: 163

```
Arg Ala Ala Val Val Gln Lys Met Arg Ala Cys
1               5                   10
```

<210> SEQ ID NO 164
<211> LENGTH: 11
<212> TYPE: PRT
<213> ORGANISM: Salmonella enterica

<400> SEQUENCE: 164

Phe Arg Leu Gly Lys Leu Glu Gln Ile Ala Arg
1               5                   10

<210> SEQ ID NO 165
<211> LENGTH: 11
<212> TYPE: PRT
<213> ORGANISM: Salmonella enterica

<400> SEQUENCE: 165

Lys Leu Glu Gln Ile Ala Arg Glu Lys Val Arg
1               5                   10

<210> SEQ ID NO 166
<211> LENGTH: 11
<212> TYPE: PRT
<213> ORGANISM: Salmonella enterica

<400> SEQUENCE: 166

Gln Ile Ala Arg Glu Lys Val Arg Thr Leu Ala
1               5                   10

<210> SEQ ID NO 167
<211> LENGTH: 11
<212> TYPE: PRT
<213> ORGANISM: Salmonella enterica

<400> SEQUENCE: 167

Ile Ala Arg Glu Lys Val Arg Thr Leu Ala Leu
1               5                   10

<210> SEQ ID NO 168
<211> LENGTH: 11
<212> TYPE: PRT
<213> ORGANISM: Salmonella enterica

<400> SEQUENCE: 168

Ala Arg Glu Lys Val Arg Thr Leu Ala Leu Val
1               5                   10

<210> SEQ ID NO 169
<211> LENGTH: 12
<212> TYPE: PRT
<213> ORGANISM: Salmonella enterica

<400> SEQUENCE: 169

Ser Arg Gly Arg Ala Ala Val Val Gln Lys Met Arg
1               5                   10

<210> SEQ ID NO 170
<211> LENGTH: 12
<212> TYPE: PRT
<213> ORGANISM: Salmonella enterica

<400> SEQUENCE: 170

Arg Gly Arg Ala Ala Val Val Gln Lys Met Arg Ala
1               5                   10

<210> SEQ ID NO 171

```
<211> LENGTH: 12
<212> TYPE: PRT
<213> ORGANISM: Salmonella enterica

<400> SEQUENCE: 171

Arg Ala Ala Val Val Gln Lys Met Arg Ala Cys Leu
1               5                   10

<210> SEQ ID NO 172
<211> LENGTH: 13
<212> TYPE: PRT
<213> ORGANISM: Salmonella enterica

<400> SEQUENCE: 172

Arg Arg Ala Ala Pro Ala Glu Glu Ser Arg Gly Arg Ala
1               5                   10

<210> SEQ ID NO 173
<211> LENGTH: 13
<212> TYPE: PRT
<213> ORGANISM: Salmonella enterica

<400> SEQUENCE: 173

Ser Arg Gly Arg Ala Ala Val Val Gln Lys Met Arg Ala
1               5                   10

<210> SEQ ID NO 174
<211> LENGTH: 13
<212> TYPE: PRT
<213> ORGANISM: Salmonella enterica

<400> SEQUENCE: 174

Arg Gly Arg Ala Ala Val Val Gln Lys Met Arg Ala Cys
1               5                   10

<210> SEQ ID NO 175
<211> LENGTH: 13
<212> TYPE: PRT
<213> ORGANISM: Salmonella enterica

<400> SEQUENCE: 175

Arg Ala Ala Val Val Gln Lys Met Arg Ala Cys Leu Asn
1               5                   10

<210> SEQ ID NO 176
<211> LENGTH: 13
<212> TYPE: PRT
<213> ORGANISM: Salmonella enterica

<400> SEQUENCE: 176

Phe Arg Leu Gly Lys Leu Glu Gln Ile Ala Arg Glu Lys
1               5                   10

<210> SEQ ID NO 177
<211> LENGTH: 13
<212> TYPE: PRT
<213> ORGANISM: Salmonella enterica

<400> SEQUENCE: 177

Arg Leu Gly Lys Leu Glu Gln Ile Ala Arg Glu Lys Val
1               5                   10

<210> SEQ ID NO 178
<211> LENGTH: 13
<212> TYPE: PRT
```

-continued

<213> ORGANISM: Salmonella enterica

<400> SEQUENCE: 178

Leu Gly Lys Leu Glu Gln Ile Ala Arg Glu Lys Val Arg
1               5                   10

<210> SEQ ID NO 179
<211> LENGTH: 13
<212> TYPE: PRT
<213> ORGANISM: Salmonella enterica

<400> SEQUENCE: 179

Gln Ile Ala Arg Glu Lys Val Arg Thr Leu Ala Leu Val
1               5                   10

<210> SEQ ID NO 180
<211> LENGTH: 13
<212> TYPE: PRT
<213> ORGANISM: Salmonella enterica

<400> SEQUENCE: 180

Trp Leu Ala Tyr Gln Asn Lys Leu Lys Lys Ser Leu Gly
1               5                   10

<210> SEQ ID NO 181
<211> LENGTH: 13
<212> TYPE: PRT
<213> ORGANISM: Salmonella enterica

<400> SEQUENCE: 181

Leu Ala Tyr Gln Asn Lys Leu Lys Lys Ser Leu Gly Leu
1               5                   10

<210> SEQ ID NO 182
<211> LENGTH: 14
<212> TYPE: PRT
<213> ORGANISM: Salmonella enterica

<400> SEQUENCE: 182

Arg Val Leu Glu Arg Lys Ala Pro Glu Arg Val Asn Ala Leu
1               5                   10

<210> SEQ ID NO 183
<211> LENGTH: 14
<212> TYPE: PRT
<213> ORGANISM: Salmonella enterica

<400> SEQUENCE: 183

Val Leu Glu Arg Lys Ala Pro Glu Arg Val Asn Ala Leu Arg
1               5                   10

<210> SEQ ID NO 184
<211> LENGTH: 14
<212> TYPE: PRT
<213> ORGANISM: Salmonella enterica

<400> SEQUENCE: 184

Lys Ala Pro Glu Arg Val Asn Ala Leu Arg Glu Lys Gln Ile
1               5                   10

<210> SEQ ID NO 185
<211> LENGTH: 14
<212> TYPE: PRT
<213> ORGANISM: Salmonella enterica

```
<400> SEQUENCE: 185

Arg Thr Ile Gly Ala Arg Ala Met Glu Ser Ala Lys Lys Thr
1               5                   10

<210> SEQ ID NO 186
<211> LENGTH: 15
<212> TYPE: PRT
<213> ORGANISM: Salmonella enterica

<400> SEQUENCE: 186

Gly Arg Glu Met Phe Arg Leu Gly Lys Leu Glu Gln Ile Ala Arg
1               5                   10                  15

<210> SEQ ID NO 187
<211> LENGTH: 15
<212> TYPE: PRT
<213> ORGANISM: Salmonella enterica

<400> SEQUENCE: 187

Met Phe Arg Leu Gly Lys Leu Glu Gln Ile Ala Arg Glu Lys Val
1               5                   10                  15

<210> SEQ ID NO 188
<211> LENGTH: 15
<212> TYPE: PRT
<213> ORGANISM: Salmonella enterica

<400> SEQUENCE: 188

Phe Arg Leu Gly Lys Leu Glu Gln Ile Ala Arg Glu Lys Val Arg
1               5                   10                  15

<210> SEQ ID NO 189
<211> LENGTH: 15
<212> TYPE: PRT
<213> ORGANISM: Salmonella enterica

<400> SEQUENCE: 189

Arg Thr Ile Gly Ala Arg Ala Met Glu Ser Ala Lys Lys Thr Phe
1               5                   10                  15

<210> SEQ ID NO 190
<211> LENGTH: 15
<212> TYPE: PRT
<213> ORGANISM: Salmonella enterica

<400> SEQUENCE: 190

Arg Leu Gly Lys Leu Glu Gln Ile Ala Arg Glu Lys Val Arg Thr
1               5                   10                  15

<210> SEQ ID NO 191
<211> LENGTH: 15
<212> TYPE: PRT
<213> ORGANISM: Salmonella enterica

<400> SEQUENCE: 191

Val Trp Leu Ala Tyr Gln Asn Lys Leu Lys Lys Ser Leu Gly Leu
1               5                   10                  15

<210> SEQ ID NO 192
<211> LENGTH: 15
<212> TYPE: PRT
<213> ORGANISM: Salmonella enterica

<400> SEQUENCE: 192
```

```
Trp Leu Ala Tyr Gln Asn Lys Leu Lys Lys Ser Leu Gly Leu Thr
1               5                   10                  15
```

<210> SEQ ID NO 193
<211> LENGTH: 16
<212> TYPE: PRT
<213> ORGANISM: Salmonella enterica

<400> SEQUENCE: 193

```
Val Leu Glu Arg Lys Ala Pro Glu Arg Val Asn Ala Leu Arg Glu Lys
1               5                   10                  15
```

<210> SEQ ID NO 194
<211> LENGTH: 16
<212> TYPE: PRT
<213> ORGANISM: Salmonella enterica

<400> SEQUENCE: 194

```
Arg Thr Ile Gly Ala Arg Ala Met Glu Ser Ala Lys Lys Thr Phe Leu
1               5                   10                  15
```

<210> SEQ ID NO 195
<211> LENGTH: 17
<212> TYPE: PRT
<213> ORGANISM: Salmonella enterica

<400> SEQUENCE: 195

```
Trp Arg Arg Ala Ala Pro Ala Glu Glu Ser Arg Gly Arg Ala Ala Val
1               5                   10                  15

Val
```

<210> SEQ ID NO 196
<211> LENGTH: 17
<212> TYPE: PRT
<213> ORGANISM: Salmonella enterica

<400> SEQUENCE: 196

```
Arg Arg Ala Ala Pro Ala Glu Glu Ser Arg Gly Arg Ala Ala Val Val
1               5                   10                  15

Gln
```

<210> SEQ ID NO 197
<211> LENGTH: 17
<212> TYPE: PRT
<213> ORGANISM: Salmonella enterica

<400> SEQUENCE: 197

```
Arg Ala Ala Pro Ala Glu Glu Ser Arg Gly Arg Ala Ala Val Val Gln
1               5                   10                  15

Lys
```

<210> SEQ ID NO 198
<211> LENGTH: 17
<212> TYPE: PRT
<213> ORGANISM: Salmonella enterica

<400> SEQUENCE: 198

```
Val Leu Glu Arg Lys Ala Pro Glu Arg Val Asn Ala Leu Arg Glu Lys
1               5                   10                  15

Gln
```

<210> SEQ ID NO 199

```
<211> LENGTH: 18
<212> TYPE: PRT
<213> ORGANISM: Salmonella enterica

<400> SEQUENCE: 199

Trp Arg Arg Ala Ala Pro Ala Glu Glu Ser Arg Gly Arg Ala Ala Val
1               5                   10                  15

Val Gln

<210> SEQ ID NO 200
<211> LENGTH: 18
<212> TYPE: PRT
<213> ORGANISM: Salmonella enterica

<400> SEQUENCE: 200

Arg Arg Ala Ala Pro Ala Glu Glu Ser Arg Gly Arg Ala Ala Val Val
1               5                   10                  15

Gln Lys

<210> SEQ ID NO 201
<211> LENGTH: 18
<212> TYPE: PRT
<213> ORGANISM: Salmonella enterica

<400> SEQUENCE: 201

Thr Gly Arg Glu Met Phe Arg Leu Gly Lys Leu Glu Gln Ile Ala Arg
1               5                   10                  15

Glu Lys

<210> SEQ ID NO 202
<211> LENGTH: 18
<212> TYPE: PRT
<213> ORGANISM: Salmonella enterica

<400> SEQUENCE: 202

Met Phe Arg Leu Gly Lys Leu Glu Gln Ile Ala Arg Glu Lys Val Arg
1               5                   10                  15

Thr Leu

<210> SEQ ID NO 203
<211> LENGTH: 18
<212> TYPE: PRT
<213> ORGANISM: Salmonella enterica

<400> SEQUENCE: 203

Phe Arg Leu Gly Lys Leu Glu Gln Ile Ala Arg Glu Lys Val Arg Thr
1               5                   10                  15

Leu Ala

<210> SEQ ID NO 204
<211> LENGTH: 18
<212> TYPE: PRT
<213> ORGANISM: Salmonella enterica

<400> SEQUENCE: 204

Arg Leu Gly Lys Leu Glu Gln Ile Ala Arg Glu Lys Val Arg Thr Leu
1               5                   10                  15

Ala Leu

<210> SEQ ID NO 205
<211> LENGTH: 19
```

```
<212> TYPE: PRT
<213> ORGANISM: Salmonella enterica

<400> SEQUENCE: 205

Ala Trp Arg Arg Ala Ala Pro Ala Glu Glu Ser Arg Gly Arg Ala Ala
1               5                   10                  15

Val Val Gln

<210> SEQ ID NO 206
<211> LENGTH: 19
<212> TYPE: PRT
<213> ORGANISM: Salmonella enterica

<400> SEQUENCE: 206

Trp Arg Arg Ala Ala Pro Ala Glu Glu Ser Arg Gly Arg Ala Ala Val
1               5                   10                  15

Val Gln Lys

<210> SEQ ID NO 207
<211> LENGTH: 19
<212> TYPE: PRT
<213> ORGANISM: Salmonella enterica

<400> SEQUENCE: 207

Arg Arg Ala Ala Pro Ala Glu Glu Ser Arg Gly Arg Ala Ala Val Val
1               5                   10                  15

Gln Lys Met

<210> SEQ ID NO 208
<211> LENGTH: 19
<212> TYPE: PRT
<213> ORGANISM: Salmonella enterica

<400> SEQUENCE: 208

Arg Ala Ala Pro Ala Glu Glu Ser Arg Gly Arg Ala Ala Val Val Gln
1               5                   10                  15

Lys Met Arg

<210> SEQ ID NO 209
<211> LENGTH: 20
<212> TYPE: PRT
<213> ORGANISM: Salmonella enterica

<400> SEQUENCE: 209

Ala Trp Arg Arg Ala Ala Pro Ala Glu Glu Ser Arg Gly Arg Ala Ala
1               5                   10                  15

Val Val Gln Lys
                20

<210> SEQ ID NO 210
<211> LENGTH: 20
<212> TYPE: PRT
<213> ORGANISM: Salmonella enterica

<400> SEQUENCE: 210

Trp Arg Arg Ala Ala Pro Ala Glu Glu Ser Arg Gly Arg Ala Ala Val
1               5                   10                  15

Val Gln Lys Met
                20

<210> SEQ ID NO 211
```

```
<211> LENGTH: 20
<212> TYPE: PRT
<213> ORGANISM: Salmonella enterica

<400> SEQUENCE: 211

Arg Arg Ala Ala Pro Ala Glu Glu Ser Arg Gly Arg Ala Ala Val Val
1               5                   10                  15

Gln Lys Met Arg
            20

<210> SEQ ID NO 212
<211> LENGTH: 20
<212> TYPE: PRT
<213> ORGANISM: Salmonella enterica

<400> SEQUENCE: 212

Arg Ala Ala Pro Ala Glu Glu Ser Arg Gly Arg Ala Ala Val Val Gln
1               5                   10                  15

Lys Met Arg Ala
            20

<210> SEQ ID NO 213
<211> LENGTH: 20
<212> TYPE: PRT
<213> ORGANISM: Salmonella enterica

<400> SEQUENCE: 213

Arg Val Leu Glu Arg Lys Ala Pro Glu Arg Val Asn Ala Leu Arg Glu
1               5                   10                  15

Lys Gln Ile Ser
            20

<210> SEQ ID NO 214
<211> LENGTH: 20
<212> TYPE: PRT
<213> ORGANISM: Salmonella enterica

<400> SEQUENCE: 214

Arg Thr Ile Gly Ala Arg Ala Met Glu Ser Ala Lys Lys Thr Phe Leu
1               5                   10                  15

Asp Gly Leu Arg
            20

<210> SEQ ID NO 215
<211> LENGTH: 21
<212> TYPE: PRT
<213> ORGANISM: Salmonella enterica

<400> SEQUENCE: 215

Ser Ala Trp Arg Arg Ala Ala Pro Ala Glu Glu Ser Arg Gly Arg Ala
1               5                   10                  15

Ala Val Val Gln Lys
            20

<210> SEQ ID NO 216
<211> LENGTH: 21
<212> TYPE: PRT
<213> ORGANISM: Salmonella enterica

<400> SEQUENCE: 216

Ala Trp Arg Arg Ala Ala Pro Ala Glu Glu Ser Arg Gly Arg Ala Ala
1               5                   10                  15
```

Val Val Gln Lys Met
            20

<210> SEQ ID NO 217
<211> LENGTH: 21
<212> TYPE: PRT
<213> ORGANISM: Salmonella enterica

<400> SEQUENCE: 217

Trp Arg Arg Ala Ala Pro Ala Glu Glu Ser Arg Gly Arg Ala Ala Val
1               5                   10                  15

Val Gln Lys Met Arg
            20

<210> SEQ ID NO 218
<211> LENGTH: 21
<212> TYPE: PRT
<213> ORGANISM: Salmonella enterica

<400> SEQUENCE: 218

Arg Arg Ala Ala Pro Ala Glu Glu Ser Arg Gly Arg Ala Ala Val Val
1               5                   10                  15

Gln Lys Met Arg Ala
            20

<210> SEQ ID NO 219
<211> LENGTH: 21
<212> TYPE: PRT
<213> ORGANISM: Salmonella enterica

<400> SEQUENCE: 219

Ala Ala Leu Val Ala Thr Gly Arg Glu Met Phe Arg Leu Gly Lys Leu
1               5                   10                  15

Glu Gln Ile Ala Arg
            20

<210> SEQ ID NO 220
<211> LENGTH: 21
<212> TYPE: PRT
<213> ORGANISM: Salmonella enterica

<400> SEQUENCE: 220

Leu Val Ala Thr Gly Arg Glu Met Phe Arg Leu Gly Lys Leu Glu Gln
1               5                   10                  15

Ile Ala Arg Glu Lys
            20

<210> SEQ ID NO 221
<211> LENGTH: 21
<212> TYPE: PRT
<213> ORGANISM: Salmonella enterica

<400> SEQUENCE: 221

Ala Thr Gly Arg Glu Met Phe Arg Leu Gly Lys Leu Glu Gln Ile Ala
1               5                   10                  15

Arg Glu Lys Val Arg
            20

<210> SEQ ID NO 222
<211> LENGTH: 21
<212> TYPE: PRT
<213> ORGANISM: Salmonella enterica

```
<400> SEQUENCE: 222

Gly Arg Glu Met Phe Arg Leu Gly Lys Leu Glu Gln Ile Ala Arg Glu
1               5                   10                  15

Lys Val Arg Thr Leu
            20

<210> SEQ ID NO 223
<211> LENGTH: 21
<212> TYPE: PRT
<213> ORGANISM: Salmonella enterica

<400> SEQUENCE: 223

Arg Glu Met Phe Arg Leu Gly Lys Leu Glu Gln Ile Ala Arg Glu Lys
1               5                   10                  15

Val Arg Thr Leu Ala
            20

<210> SEQ ID NO 224
<211> LENGTH: 21
<212> TYPE: PRT
<213> ORGANISM: Salmonella enterica

<400> SEQUENCE: 224

Glu Met Phe Arg Leu Gly Lys Leu Glu Gln Ile Ala Arg Glu Lys Val
1               5                   10                  15

Arg Thr Leu Ala Leu
            20

<210> SEQ ID NO 225
<211> LENGTH: 21
<212> TYPE: PRT
<213> ORGANISM: Salmonella enterica

<400> SEQUENCE: 225

Met Phe Arg Leu Gly Lys Leu Glu Gln Ile Ala Arg Glu Lys Val Arg
1               5                   10                  15

Thr Leu Ala Leu Val
            20

<210> SEQ ID NO 226
<211> LENGTH: 21
<212> TYPE: PRT
<213> ORGANISM: Salmonella enterica

<400> SEQUENCE: 226

Phe Arg Leu Gly Lys Leu Glu Gln Ile Ala Arg Glu Lys Val Arg Thr
1               5                   10                  15

Leu Ala Leu Val Asp
            20

<210> SEQ ID NO 227
<211> LENGTH: 20
<212> TYPE: PRT
<213> ORGANISM: Salmonella enterica

<400> SEQUENCE: 227

Arg Leu Gly Lys Leu Glu Gln Ile Ala Arg Glu Lys Val Arg Thr Leu
1               5                   10                  15

Ala Leu Val Asp
            20
```

```
<210> SEQ ID NO 228
<211> LENGTH: 22
<212> TYPE: PRT
<213> ORGANISM: Salmonella enterica

<400> SEQUENCE: 228

Ala Trp Arg Arg Ala Ala Pro Ala Glu Glu Ser Arg Gly Arg Ala Ala
1               5                   10                  15

Val Val Gln Lys Met Arg
            20

<210> SEQ ID NO 229
<211> LENGTH: 22
<212> TYPE: PRT
<213> ORGANISM: Salmonella enterica

<400> SEQUENCE: 229

Trp Arg Arg Ala Ala Pro Ala Glu Glu Ser Arg Gly Arg Ala Ala Val
1               5                   10                  15

Val Gln Lys Met Arg Ala
            20

<210> SEQ ID NO 230
<211> LENGTH: 22
<212> TYPE: PRT
<213> ORGANISM: Salmonella enterica

<400> SEQUENCE: 230

Arg Arg Ala Ala Pro Ala Glu Glu Ser Arg Gly Arg Ala Ala Val Val
1               5                   10                  15

Gln Lys Met Arg Ala Cys
            20

<210> SEQ ID NO 231
<211> LENGTH: 22
<212> TYPE: PRT
<213> ORGANISM: Salmonella enterica

<400> SEQUENCE: 231

Leu Ala Ala Leu Val Ala Thr Gly Arg Glu Met Phe Arg Leu Gly Lys
1               5                   10                  15

Leu Glu Gln Ile Ala Arg
            20

<210> SEQ ID NO 232
<211> LENGTH: 22
<212> TYPE: PRT
<213> ORGANISM: Salmonella enterica

<400> SEQUENCE: 232

Ala Leu Val Ala Thr Gly Arg Glu Met Phe Arg Leu Gly Lys Leu Glu
1               5                   10                  15

Gln Ile Ala Arg Glu Lys
            20

<210> SEQ ID NO 233
<211> LENGTH: 22
<212> TYPE: PRT
<213> ORGANISM: Salmonella enterica

<400> SEQUENCE: 233

Ala Thr Gly Arg Glu Met Phe Arg Leu Gly Lys Leu Glu Gln Ile Ala
1               5                   10                  15
```

```
Arg Glu Lys Val Arg Thr
        20

<210> SEQ ID NO 234
<211> LENGTH: 22
<212> TYPE: PRT
<213> ORGANISM: Salmonella enterica

<400> SEQUENCE: 234

Thr Gly Arg Glu Met Phe Arg Leu Gly Lys Leu Glu Gln Ile Ala Arg
1               5                   10                  15

Glu Lys Val Arg Thr Leu
        20

<210> SEQ ID NO 235
<211> LENGTH: 22
<212> TYPE: PRT
<213> ORGANISM: Salmonella enterica

<400> SEQUENCE: 235

Gly Arg Glu Met Phe Arg Leu Gly Lys Leu Glu Gln Ile Ala Arg Glu
1               5                   10                  15

Lys Val Arg Thr Leu Ala
        20

<210> SEQ ID NO 236
<211> LENGTH: 22
<212> TYPE: PRT
<213> ORGANISM: Salmonella enterica

<400> SEQUENCE: 236

Arg Glu Met Phe Arg Leu Gly Lys Leu Glu Gln Ile Ala Arg Glu Lys
1               5                   10                  15

Val Arg Thr Leu Ala Leu
        20

<210> SEQ ID NO 237
<211> LENGTH: 22
<212> TYPE: PRT
<213> ORGANISM: Salmonella enterica

<400> SEQUENCE: 237

Glu Met Phe Arg Leu Gly Lys Leu Glu Gln Ile Ala Arg Glu Lys Val
1               5                   10                  15

Arg Thr Leu Ala Leu Val
        20

<210> SEQ ID NO 238
<211> LENGTH: 22
<212> TYPE: PRT
<213> ORGANISM: Salmonella enterica

<400> SEQUENCE: 238

Met Phe Arg Leu Gly Lys Leu Glu Gln Ile Ala Arg Glu Lys Val Arg
1               5                   10                  15

Thr Leu Ala Leu Val Asp
        20

<210> SEQ ID NO 239
<211> LENGTH: 24
<212> TYPE: PRT
<213> ORGANISM: Salmonella enterica
```

<400> SEQUENCE: 239

Trp Ser Ala Trp Arg Arg Ala Ala Pro Ala Glu Glu Ser Arg Gly Arg
1               5                   10                  15

Ala Ala Val Val Gln Lys Met Arg
            20

<210> SEQ ID NO 240
<211> LENGTH: 24
<212> TYPE: PRT
<213> ORGANISM: Salmonella enterica

<400> SEQUENCE: 240

Ser Ala Trp Arg Arg Ala Ala Pro Ala Glu Glu Ser Arg Gly Arg Ala
1               5                   10                  15

Ala Val Val Gln Lys Met Arg Ala
            20

<210> SEQ ID NO 241
<211> LENGTH: 24
<212> TYPE: PRT
<213> ORGANISM: Salmonella enterica

<400> SEQUENCE: 241

Trp Arg Arg Ala Ala Pro Ala Glu Glu Ser Arg Gly Arg Ala Ala Val
1               5                   10                  15

Val Gln Lys Met Arg Ala Cys Leu
            20

<210> SEQ ID NO 242
<211> LENGTH: 24
<212> TYPE: PRT
<213> ORGANISM: Salmonella enterica

<400> SEQUENCE: 242

Arg Arg Ala Ala Pro Ala Glu Glu Ser Arg Gly Arg Ala Ala Val Val
1               5                   10                  15

Gln Lys Met Arg Ala Cys Leu Asn
            20

<210> SEQ ID NO 243
<211> LENGTH: 24
<212> TYPE: PRT
<213> ORGANISM: Salmonella enterica

<400> SEQUENCE: 243

Leu Ala Ala Leu Val Ala Thr Gly Arg Glu Met Phe Arg Leu Gly Lys
1               5                   10                  15

Leu Glu Gln Ile Ala Arg Glu Lys
            20

<210> SEQ ID NO 244
<211> LENGTH: 24
<212> TYPE: PRT
<213> ORGANISM: Salmonella enterica

<400> SEQUENCE: 244

Ala Ala Leu Val Ala Thr Gly Arg Glu Met Phe Arg Leu Gly Lys Leu
1               5                   10                  15

Glu Gln Ile Ala Arg Glu Lys Val
            20

<210> SEQ ID NO 245
<211> LENGTH: 24
<212> TYPE: PRT
<213> ORGANISM: Salmonella enterica

<400> SEQUENCE: 245

Ala Leu Val Ala Thr Gly Arg Glu Met Phe Arg Leu Gly Lys Leu Glu
1               5                   10                  15

Gln Ile Ala Arg Glu Lys Val Arg
            20

<210> SEQ ID NO 246
<211> LENGTH: 24
<212> TYPE: PRT
<213> ORGANISM: Salmonella enterica

<400> SEQUENCE: 246

Ala Thr Gly Arg Glu Met Phe Arg Leu Gly Lys Leu Glu Gln Ile Ala
1               5                   10                  15

Arg Glu Lys Val Arg Thr Leu Ala
            20

<210> SEQ ID NO 247
<211> LENGTH: 24
<212> TYPE: PRT
<213> ORGANISM: Salmonella enterica

<400> SEQUENCE: 247

Thr Gly Arg Glu Met Phe Arg Leu Gly Lys Leu Glu Gln Ile Ala Arg
1               5                   10                  15

Glu Lys Val Arg Thr Leu Ala Leu
            20

<210> SEQ ID NO 248
<211> LENGTH: 24
<212> TYPE: PRT
<213> ORGANISM: Salmonella enterica

<400> SEQUENCE: 248

Gly Arg Glu Met Phe Arg Leu Gly Lys Leu Glu Gln Ile Ala Arg Glu
1               5                   10                  15

Lys Val Arg Thr Leu Ala Leu Val
            20

<210> SEQ ID NO 249
<211> LENGTH: 24
<212> TYPE: PRT
<213> ORGANISM: Salmonella enterica

<400> SEQUENCE: 249

Arg Glu Met Phe Arg Leu Gly Lys Leu Glu Gln Ile Ala Arg Glu Lys
1               5                   10                  15

Val Arg Thr Leu Ala Leu Val Asp
            20

<210> SEQ ID NO 250
<211> LENGTH: 27
<212> TYPE: PRT
<213> ORGANISM: Salmonella enterica

<400> SEQUENCE: 250

Asp Leu Ala Ala Leu Val Ala Thr Gly Arg Glu Met Phe Arg Leu Gly

```
                1               5                  10                  15
Lys Leu Glu Gln Ile Ala Arg Glu Lys Val Arg
                20                  25

<210> SEQ ID NO 251
<211> LENGTH: 27
<212> TYPE: PRT
<213> ORGANISM: Salmonella enterica

<400> SEQUENCE: 251

Leu Ala Ala Leu Val Ala Thr Gly Arg Glu Met Phe Arg Leu Gly Lys
1               5                   10                  15

Leu Glu Gln Ile Ala Arg Glu Lys Val Arg Thr
                20                  25

<210> SEQ ID NO 252
<211> LENGTH: 27
<212> TYPE: PRT
<213> ORGANISM: Salmonella enterica

<400> SEQUENCE: 252

Ala Ala Leu Val Ala Thr Gly Arg Glu Met Phe Arg Leu Gly Lys Leu
1               5                   10                  15

Glu Gln Ile Ala Arg Glu Lys Val Arg Thr Leu
                20                  25

<210> SEQ ID NO 253
<211> LENGTH: 27
<212> TYPE: PRT
<213> ORGANISM: Salmonella enterica

<400> SEQUENCE: 253

Ala Leu Val Ala Thr Gly Arg Glu Met Phe Arg Leu Gly Lys Leu Glu
1               5                   10                  15

Gln Ile Ala Arg Glu Lys Val Arg Thr Leu Ala
                20                  25

<210> SEQ ID NO 254
<211> LENGTH: 27
<212> TYPE: PRT
<213> ORGANISM: Salmonella enterica

<400> SEQUENCE: 254

Leu Val Ala Thr Gly Arg Glu Met Phe Arg Leu Gly Lys Leu Glu Gln
1               5                   10                  15

Ile Ala Arg Glu Lys Val Arg Thr Leu Ala Leu
                20                  25

<210> SEQ ID NO 255
<211> LENGTH: 27
<212> TYPE: PRT
<213> ORGANISM: Salmonella enterica

<400> SEQUENCE: 255

Ala Thr Gly Arg Glu Met Phe Arg Leu Gly Lys Leu Glu Gln Ile Ala
1               5                   10                  15

Arg Glu Lys Val Arg Thr Leu Ala Leu Val Asp
                20                  25

<210> SEQ ID NO 256
<211> LENGTH: 30
<212> TYPE: PRT
```

<213> ORGANISM: Salmonella enterica

<400> SEQUENCE: 256

Asn Asp Leu Ala Ala Leu Val Ala Thr Gly Arg Glu Met Phe Arg Leu
1               5                   10                  15
Gly Lys Leu Glu Gln Ile Ala Arg Glu Lys Val Arg Thr Leu
            20                  25                  30

<210> SEQ ID NO 257
<211> LENGTH: 30
<212> TYPE: PRT
<213> ORGANISM: Salmonella enterica

<400> SEQUENCE: 257

Asp Leu Ala Ala Leu Val Ala Thr Gly Arg Glu Met Phe Arg Leu Gly
1               5                   10                  15
Lys Leu Glu Gln Ile Ala Arg Glu Lys Val Arg Thr Leu Ala
            20                  25                  30

<210> SEQ ID NO 258
<211> LENGTH: 30
<212> TYPE: PRT
<213> ORGANISM: Salmonella enterica

<400> SEQUENCE: 258

Leu Ala Ala Leu Val Ala Thr Gly Arg Glu Met Phe Arg Leu Gly Lys
1               5                   10                  15
Leu Glu Gln Ile Ala Arg Glu Lys Val Arg Thr Leu Ala Leu
            20                  25                  30

<210> SEQ ID NO 259
<211> LENGTH: 30
<212> TYPE: PRT
<213> ORGANISM: Salmonella enterica

<400> SEQUENCE: 259

Ala Ala Leu Val Ala Thr Gly Arg Glu Met Phe Arg Leu Gly Lys Leu
1               5                   10                  15
Glu Gln Ile Ala Arg Glu Lys Val Arg Thr Leu Ala Leu Val
            20                  25                  30

<210> SEQ ID NO 260
<211> LENGTH: 10
<212> TYPE: PRT
<213> ORGANISM: Salmonella enterica

<400> SEQUENCE: 260

Gln Ile Ala Arg Glu Lys Val Arg Thr Leu
1               5                   10

<210> SEQ ID NO 261
<211> LENGTH: 10
<212> TYPE: PRT
<213> ORGANISM: Salmonella enterica

<400> SEQUENCE: 261

Ile Ala Arg Glu Lys Val Arg Thr Leu Ala
1               5                   10

<210> SEQ ID NO 262
<211> LENGTH: 10
<212> TYPE: PRT
<213> ORGANISM: Salmonella enterica

```
<400> SEQUENCE: 262

Ala Arg Glu Lys Val Arg Thr Leu Ala Leu
1               5                   10

<210> SEQ ID NO 263
<211> LENGTH: 10
<212> TYPE: PRT
<213> ORGANISM: Salmonella enterica

<400> SEQUENCE: 263

Arg Glu Lys Val Arg Thr Leu Ala Leu Val
1               5                   10

<210> SEQ ID NO 264
<211> LENGTH: 10
<212> TYPE: PRT
<213> ORGANISM: Salmonella enterica

<400> SEQUENCE: 264

Tyr Gln Asn Lys Leu Lys Lys Ser Leu Gly
1               5                   10

<210> SEQ ID NO 265
<211> LENGTH: 10
<212> TYPE: PRT
<213> ORGANISM: Salmonella enterica

<400> SEQUENCE: 265

Gln Asn Lys Leu Lys Lys Ser Leu Gly Leu
1               5                   10

<210> SEQ ID NO 266
<211> LENGTH: 10
<212> TYPE: PRT
<213> ORGANISM: Salmonella enterica

<400> SEQUENCE: 266

Arg Lys Ala Pro Glu Arg Val Asn Ala Leu
1               5                   10

<210> SEQ ID NO 267
<211> LENGTH: 10
<212> TYPE: PRT
<213> ORGANISM: Salmonella enterica

<400> SEQUENCE: 267

Lys Ala Pro Glu Arg Val Asn Ala Leu Arg
1               5                   10

<210> SEQ ID NO 268
<211> LENGTH: 11
<212> TYPE: PRT
<213> ORGANISM: Salmonella enterica

<400> SEQUENCE: 268

Leu Ala Tyr Gln Asn Lys Leu Lys Lys Ser Leu
1               5                   10

<210> SEQ ID NO 269
<211> LENGTH: 11
<212> TYPE: PRT
<213> ORGANISM: Salmonella enterica

<400> SEQUENCE: 269
```

Ala Tyr Gln Asn Lys Leu Lys Lys Ser Leu Gly
1               5                   10

<210> SEQ ID NO 270
<211> LENGTH: 11
<212> TYPE: PRT
<213> ORGANISM: Salmonella enterica

<400> SEQUENCE: 270

Arg Val Asn Ala Leu Arg Glu Lys Gln Ile Ser
1               5                   10

<210> SEQ ID NO 271
<211> LENGTH: 12
<212> TYPE: PRT
<213> ORGANISM: Salmonella enterica

<400> SEQUENCE: 271

Ala Thr Ile Ser Asn Arg Arg Ile Tyr Arg Ile Ala
1               5                   10

<210> SEQ ID NO 272
<211> LENGTH: 12
<212> TYPE: PRT
<213> ORGANISM: Salmonella enterica

<400> SEQUENCE: 272

Met Phe Arg Leu Gly Lys Leu Glu Gln Ile Ala Arg
1               5                   10

<210> SEQ ID NO 273
<211> LENGTH: 12
<212> TYPE: PRT
<213> ORGANISM: Salmonella enterica

<400> SEQUENCE: 273

Arg Leu Gly Lys Leu Glu Gln Ile Ala Arg Glu Lys
1               5                   10

<210> SEQ ID NO 274
<211> LENGTH: 12
<212> TYPE: PRT
<213> ORGANISM: Salmonella enterica

<400> SEQUENCE: 274

Gly Lys Leu Glu Gln Ile Ala Arg Glu Lys Val Arg
1               5                   10

<210> SEQ ID NO 275
<211> LENGTH: 12
<212> TYPE: PRT
<213> ORGANISM: Salmonella enterica

<400> SEQUENCE: 275

Gln Ile Ala Arg Glu Lys Val Arg Thr Leu Ala Leu
1               5                   10

<210> SEQ ID NO 276
<211> LENGTH: 12
<212> TYPE: PRT
<213> ORGANISM: Salmonella enterica

<400> SEQUENCE: 276

Ile Ala Arg Glu Lys Val Arg Thr Leu Ala Leu Val

```
<210> SEQ ID NO 277
<211> LENGTH: 12
<212> TYPE: PRT
<213> ORGANISM: Salmonella enterica

<400> SEQUENCE: 277

Leu Ala Tyr Gln Asn Lys Leu Lys Lys Ser Leu Gly
1               5                   10

<210> SEQ ID NO 278
<211> LENGTH: 12
<212> TYPE: PRT
<213> ORGANISM: Salmonella enterica

<400> SEQUENCE: 278

Ala Tyr Gln Asn Lys Leu Lys Lys Ser Leu Gly Leu
1               5                   10

<210> SEQ ID NO 279
<211> LENGTH: 13
<212> TYPE: PRT
<213> ORGANISM: Salmonella enterica

<400> SEQUENCE: 279

Arg Thr Ile Gly Ala Arg Ala Met Glu Ser Ala Lys Lys
1               5                   10

<210> SEQ ID NO 280
<211> LENGTH: 14
<212> TYPE: PRT
<213> ORGANISM: Salmonella enterica

<400> SEQUENCE: 280

Arg Arg Ala Ala Pro Ala Glu Glu Ser Arg Gly Arg Ala Ala
1               5                   10

<210> SEQ ID NO 281
<211> LENGTH: 14
<212> TYPE: PRT
<213> ORGANISM: Salmonella enterica

<400> SEQUENCE: 281

Glu Ser Arg Gly Arg Ala Ala Val Val Gln Lys Met Arg Ala
1               5                   10

<210> SEQ ID NO 282
<211> LENGTH: 14
<212> TYPE: PRT
<213> ORGANISM: Salmonella enterica

<400> SEQUENCE: 282

Arg Gly Arg Ala Ala Val Val Gln Lys Met Arg Ala Cys Leu
1               5                   10

<210> SEQ ID NO 283
<211> LENGTH: 14
<212> TYPE: PRT
<213> ORGANISM: Salmonella enterica

<400> SEQUENCE: 283

Met Phe Arg Leu Gly Lys Leu Glu Gln Ile Ala Arg Glu Lys
1               5                   10
```

<210> SEQ ID NO 284
<211> LENGTH: 14
<212> TYPE: PRT
<213> ORGANISM: Salmonella enterica

<400> SEQUENCE: 284

Phe Arg Leu Gly Lys Leu Glu Gln Ile Ala Arg Glu Lys Val
1               5                   10

<210> SEQ ID NO 285
<211> LENGTH: 14
<212> TYPE: PRT
<213> ORGANISM: Salmonella enterica

<400> SEQUENCE: 285

Arg Leu Gly Lys Leu Glu Gln Ile Ala Arg Glu Lys Val Arg
1               5                   10

<210> SEQ ID NO 286
<211> LENGTH: 14
<212> TYPE: PRT
<213> ORGANISM: Salmonella enterica

<400> SEQUENCE: 286

Val Trp Leu Ala Tyr Gln Asn Lys Leu Lys Lys Ser Leu Gly
1               5                   10

<210> SEQ ID NO 287
<211> LENGTH: 14
<212> TYPE: PRT
<213> ORGANISM: Salmonella enterica

<400> SEQUENCE: 287

Trp Leu Ala Tyr Gln Asn Lys Leu Lys Lys Ser Leu Gly Leu
1               5                   10

<210> SEQ ID NO 288
<211> LENGTH: 15
<212> TYPE: PRT
<213> ORGANISM: Salmonella enterica

<400> SEQUENCE: 288

Arg Arg Ala Ala Pro Ala Glu Glu Ser Arg Gly Arg Ala Ala Val
1               5                   10                  15

<210> SEQ ID NO 289
<211> LENGTH: 15
<212> TYPE: PRT
<213> ORGANISM: Salmonella enterica

<400> SEQUENCE: 289

Ser Arg Gly Arg Ala Ala Val Val Gln Lys Met Arg Ala Cys Leu
1               5                   10                  15

<210> SEQ ID NO 290
<211> LENGTH: 15
<212> TYPE: PRT
<213> ORGANISM: Salmonella enterica

<400> SEQUENCE: 290

Arg Gly Arg Ala Ala Val Val Gln Lys Met Arg Ala Cys Leu Asn
1               5                   10                  15

<210> SEQ ID NO 291

```
<211> LENGTH: 16
<212> TYPE: PRT
<213> ORGANISM: Salmonella enterica

<400> SEQUENCE: 291

Trp Arg Arg Ala Ala Pro Ala Glu Glu Ser Arg Gly Arg Ala Ala Val
1               5                   10                  15

<210> SEQ ID NO 292
<211> LENGTH: 16
<212> TYPE: PRT
<213> ORGANISM: Salmonella enterica

<400> SEQUENCE: 292

Arg Arg Ala Ala Pro Ala Glu Glu Ser Arg Gly Arg Ala Ala Val Val
1               5                   10                  15

<210> SEQ ID NO 293
<211> LENGTH: 16
<212> TYPE: PRT
<213> ORGANISM: Salmonella enterica

<400> SEQUENCE: 293

Ala Glu Glu Ser Arg Gly Arg Ala Ala Val Val Gln Lys Met Arg Ala
1               5                   10                  15

<210> SEQ ID NO 294
<211> LENGTH: 16
<212> TYPE: PRT
<213> ORGANISM: Salmonella enterica

<400> SEQUENCE: 294

Arg Gly Arg Ala Ala Val Val Gln Lys Met Arg Ala Cys Leu Asn Asn
1               5                   10                  15

<210> SEQ ID NO 295
<211> LENGTH: 16
<212> TYPE: PRT
<213> ORGANISM: Salmonella enterica

<400> SEQUENCE: 295

Met Phe Arg Leu Gly Lys Leu Glu Gln Ile Ala Arg Glu Lys Val Arg
1               5                   10                  15

<210> SEQ ID NO 296
<211> LENGTH: 16
<212> TYPE: PRT
<213> ORGANISM: Salmonella enterica

<400> SEQUENCE: 296

Phe Arg Leu Gly Lys Leu Glu Gln Ile Ala Arg Glu Lys Val Arg Thr
1               5                   10                  15

<210> SEQ ID NO 297
<211> LENGTH: 16
<212> TYPE: PRT
<213> ORGANISM: Salmonella enterica

<400> SEQUENCE: 297

Arg Leu Gly Lys Leu Glu Gln Ile Ala Arg Glu Lys Val Arg Thr Leu
1               5                   10                  15

<210> SEQ ID NO 298
<211> LENGTH: 17
<212> TYPE: PRT
```

<213> ORGANISM: Salmonella enterica

<400> SEQUENCE: 298

Leu Ala Ala Leu Val Ala Thr Gly Arg Glu Met Phe Arg Leu Gly Lys
1               5                   10                  15

Leu

<210> SEQ ID NO 299
<211> LENGTH: 17
<212> TYPE: PRT
<213> ORGANISM: Salmonella enterica

<400> SEQUENCE: 299

Ala Thr Gly Arg Glu Met Phe Arg Leu Gly Lys Leu Glu Gln Ile Ala
1               5                   10                  15

Arg

<210> SEQ ID NO 300
<211> LENGTH: 17
<212> TYPE: PRT
<213> ORGANISM: Salmonella enterica

<400> SEQUENCE: 300

Gly Arg Glu Met Phe Arg Leu Gly Lys Leu Glu Gln Ile Ala Arg Glu
1               5                   10                  15

Lys

<210> SEQ ID NO 301
<211> LENGTH: 17
<212> TYPE: PRT
<213> ORGANISM: Salmonella enterica

<400> SEQUENCE: 301

Arg Glu Met Phe Arg Leu Gly Lys Leu Glu Gln Ile Ala Arg Glu Lys
1               5                   10                  15

Val

<210> SEQ ID NO 302
<211> LENGTH: 17
<212> TYPE: PRT
<213> ORGANISM: Salmonella enterica

<400> SEQUENCE: 302

Glu Met Phe Arg Leu Gly Lys Leu Glu Gln Ile Ala Arg Glu Lys Val
1               5                   10                  15

Arg

<210> SEQ ID NO 303
<211> LENGTH: 17
<212> TYPE: PRT
<213> ORGANISM: Salmonella enterica

<400> SEQUENCE: 303

Met Phe Arg Leu Gly Lys Leu Glu Gln Ile Ala Arg Glu Lys Val Arg
1               5                   10                  15

Thr

<210> SEQ ID NO 304
<211> LENGTH: 17
<212> TYPE: PRT
<213> ORGANISM: Salmonella enterica

<400> SEQUENCE: 304

Phe Arg Leu Gly Lys Leu Glu Gln Ile Ala Arg Glu Lys Val Arg Thr
1               5                   10                  15
Leu

<210> SEQ ID NO 305
<211> LENGTH: 17
<212> TYPE: PRT
<213> ORGANISM: Salmonella enterica

<400> SEQUENCE: 305

Arg Leu Gly Lys Leu Glu Gln Ile Ala Arg Glu Lys Val Arg Thr Leu
1               5                   10                  15
Ala

<210> SEQ ID NO 306
<211> LENGTH: 18
<212> TYPE: PRT
<213> ORGANISM: Salmonella enterica

<400> SEQUENCE: 306

Val Leu Glu Arg Lys Ala Pro Glu Arg Val Asn Ala Leu Arg Glu Lys
1               5                   10                  15
Gln Ile

<210> SEQ ID NO 307
<211> LENGTH: 18
<212> TYPE: PRT
<213> ORGANISM: Salmonella enterica

<400> SEQUENCE: 307

Leu Glu Arg Lys Ala Pro Glu Arg Val Asn Ala Leu Arg Glu Lys Gln
1               5                   10                  15
Ile Ser

<210> SEQ ID NO 308
<211> LENGTH: 19
<212> TYPE: PRT
<213> ORGANISM: Salmonella enterica

<400> SEQUENCE: 308

Arg Glu Met Phe Arg Leu Gly Lys Leu Glu Gln Ile Ala Arg Glu Lys
1               5                   10                  15
Val Arg Thr

<210> SEQ ID NO 309
<211> LENGTH: 19
<212> TYPE: PRT
<213> ORGANISM: Salmonella enterica

<400> SEQUENCE: 309

Glu Met Phe Arg Leu Gly Lys Leu Glu Gln Ile Ala Arg Glu Lys Val
1               5                   10                  15
Arg Thr Leu

<210> SEQ ID NO 310
<211> LENGTH: 19
<212> TYPE: PRT
<213> ORGANISM: Salmonella enterica

```
<400> SEQUENCE: 310

Met Phe Arg Leu Gly Lys Leu Glu Gln Ile Ala Arg Glu Lys Val Arg
1               5                   10                  15

Thr Leu Ala

<210> SEQ ID NO 311
<211> LENGTH: 19
<212> TYPE: PRT
<213> ORGANISM: Salmonella enterica

<400> SEQUENCE: 311

Phe Arg Leu Gly Lys Leu Glu Gln Ile Ala Arg Glu Lys Val Arg Thr
1               5                   10                  15

Leu Ala Leu

<210> SEQ ID NO 312
<211> LENGTH: 19
<212> TYPE: PRT
<213> ORGANISM: Salmonella enterica

<400> SEQUENCE: 312

Arg Leu Gly Lys Leu Glu Gln Ile Ala Arg Glu Lys Val Arg Thr Leu
1               5                   10                  15

Ala Leu Val

<210> SEQ ID NO 313
<211> LENGTH: 20
<212> TYPE: PRT
<213> ORGANISM: Salmonella enterica

<400> SEQUENCE: 313

Ala Leu Val Ala Thr Gly Arg Glu Met Phe Arg Leu Gly Lys Leu Glu
1               5                   10                  15

Gln Ile Ala Arg
            20

<210> SEQ ID NO 314
<211> LENGTH: 20
<212> TYPE: PRT
<213> ORGANISM: Salmonella enterica

<400> SEQUENCE: 314

Thr Gly Arg Glu Met Phe Arg Leu Gly Lys Leu Glu Gln Ile Ala Arg
1               5                   10                  15

Glu Lys Val Arg
            20

<210> SEQ ID NO 315
<211> LENGTH: 20
<212> TYPE: PRT
<213> ORGANISM: Salmonella enterica

<400> SEQUENCE: 315

Gly Arg Glu Met Phe Arg Leu Gly Lys Leu Glu Gln Ile Ala Arg Glu
1               5                   10                  15

Lys Val Arg Thr
            20

<210> SEQ ID NO 316
<211> LENGTH: 20
<212> TYPE: PRT
```

<213> ORGANISM: Salmonella enterica

<400> SEQUENCE: 316

Arg Glu Met Phe Arg Leu Gly Lys Leu Glu Gln Ile Ala Arg Glu Lys
1               5                   10                  15

Val Arg Thr Leu
            20

<210> SEQ ID NO 317
<211> LENGTH: 20
<212> TYPE: PRT
<213> ORGANISM: Salmonella enterica

<400> SEQUENCE: 317

Glu Met Phe Arg Leu Gly Lys Leu Glu Gln Ile Ala Arg Glu Lys Val
1               5                   10                  15

Arg Thr Leu Ala
            20

<210> SEQ ID NO 318
<211> LENGTH: 20
<212> TYPE: PRT
<213> ORGANISM: Salmonella enterica

<400> SEQUENCE: 318

Met Phe Arg Leu Gly Lys Leu Glu Gln Ile Ala Arg Glu Lys Val Arg
1               5                   10                  15

Thr Leu Ala Leu
            20

<210> SEQ ID NO 319
<211> LENGTH: 20
<212> TYPE: PRT
<213> ORGANISM: Salmonella enterica

<400> SEQUENCE: 319

Phe Arg Leu Gly Lys Leu Glu Gln Ile Ala Arg Glu Lys Val Arg Thr
1               5                   10                  15

Leu Ala Leu Val
            20

<210> SEQ ID NO 320
<211> LENGTH: 20
<212> TYPE: PRT
<213> ORGANISM: Salmonella enterica

<400> SEQUENCE: 320

Arg Leu Gly Lys Leu Glu Gln Ile Ala Arg Glu Lys Val Arg Thr Leu
1               5                   10                  15

Ala Leu Val Asp
            20

<210> SEQ ID NO 321
<211> LENGTH: 20
<212> TYPE: PRT
<213> ORGANISM: Salmonella enterica

<400> SEQUENCE: 321

Arg Val Leu Glu Arg Lys Ala Pro Glu Arg Val Asn Ala Leu Arg Glu
1               5                   10                  15

Lys Gln Ile Ser
            20

<210> SEQ ID NO 322
<211> LENGTH: 20
<212> TYPE: PRT
<213> ORGANISM: Salmonella enterica

<400> SEQUENCE: 322

Arg Thr Ile Gly Ala Arg Ala Met Glu Ser Ala Lys Lys Thr Phe Leu
1               5                   10                  15

Asp Gly Leu Arg
            20

<210> SEQ ID NO 323
<211> LENGTH: 21
<212> TYPE: PRT
<213> ORGANISM: Salmonella enterica

<400> SEQUENCE: 323

Ser Ala Trp Arg Arg Ala Ala Pro Ala Glu Glu Ser Arg Gly Arg Ala
1               5                   10                  15

Ala Val Val Gln Lys
            20

<210> SEQ ID NO 324
<211> LENGTH: 21
<212> TYPE: PRT
<213> ORGANISM: Salmonella enterica

<400> SEQUENCE: 324

Ala Trp Arg Arg Ala Ala Pro Ala Glu Glu Ser Arg Gly Arg Ala Ala
1               5                   10                  15

Val Val Gln Lys Met
            20

<210> SEQ ID NO 325
<211> LENGTH: 21
<212> TYPE: PRT
<213> ORGANISM: Salmonella enterica

<400> SEQUENCE: 325

Trp Arg Arg Ala Ala Pro Ala Glu Glu Ser Arg Gly Arg Ala Ala Val
1               5                   10                  15

Val Gln Lys Met Arg
            20

<210> SEQ ID NO 326
<211> LENGTH: 21
<212> TYPE: PRT
<213> ORGANISM: Salmonella enterica

<400> SEQUENCE: 326

Arg Arg Ala Ala Pro Ala Glu Glu Ser Arg Gly Arg Ala Ala Val Val
1               5                   10                  15

Gln Lys Met Arg Ala
            20

<210> SEQ ID NO 327
<211> LENGTH: 21
<212> TYPE: PRT
<213> ORGANISM: Salmonella enterica

<400> SEQUENCE: 327

```
Ala Ala Leu Val Ala Thr Gly Arg Glu Met Phe Arg Leu Gly Lys Leu
1               5                   10                  15

Glu Gln Ile Ala Arg
            20
```

<210> SEQ ID NO 328
<211> LENGTH: 21
<212> TYPE: PRT
<213> ORGANISM: Salmonella enterica

<400> SEQUENCE: 328

```
Leu Val Ala Thr Gly Arg Glu Met Phe Arg Leu Gly Lys Leu Glu Gln
1               5                   10                  15

Ile Ala Arg Glu Lys
            20
```

<210> SEQ ID NO 329
<211> LENGTH: 21
<212> TYPE: PRT
<213> ORGANISM: Salmonella enterica

<400> SEQUENCE: 329

```
Ala Thr Gly Arg Glu Met Phe Arg Leu Gly Lys Leu Glu Gln Ile Ala
1               5                   10                  15

Arg Glu Lys Val Arg
            20
```

<210> SEQ ID NO 330
<211> LENGTH: 21
<212> TYPE: PRT
<213> ORGANISM: Salmonella enterica

<400> SEQUENCE: 330

```
Ala Thr Gly Arg Glu Met Phe Arg Leu Gly Lys Leu Glu Gln Ile Ala
1               5                   10                  15

Arg Glu Lys Val Arg
            20
```

<210> SEQ ID NO 331
<211> LENGTH: 21
<212> TYPE: PRT
<213> ORGANISM: Salmonella enterica

<400> SEQUENCE: 331

```
Gly Arg Glu Met Phe Arg Leu Gly Lys Leu Glu Gln Ile Ala Arg Glu
1               5                   10                  15

Lys Val Arg Thr Leu
            20
```

<210> SEQ ID NO 332
<211> LENGTH: 21
<212> TYPE: PRT
<213> ORGANISM: Salmonella enterica

<400> SEQUENCE: 332

```
Arg Glu Met Phe Arg Leu Gly Lys Leu Glu Gln Ile Ala Arg Glu Lys
1               5                   10                  15

Val Arg Thr Leu Ala
            20
```

<210> SEQ ID NO 333
<211> LENGTH: 21

```
<212> TYPE: PRT
<213> ORGANISM: Salmonella enterica

<400> SEQUENCE: 333

Glu Met Phe Arg Leu Gly Lys Leu Glu Gln Ile Ala Arg Glu Lys Val
1               5                   10                  15

Arg Thr Leu Ala Leu
            20

<210> SEQ ID NO 334
<211> LENGTH: 21
<212> TYPE: PRT
<213> ORGANISM: Salmonella enterica

<400> SEQUENCE: 334

Met Phe Arg Leu Gly Lys Leu Glu Gln Ile Ala Arg Glu Lys Val Arg
1               5                   10                  15

Thr Leu Ala Leu Val
            20

<210> SEQ ID NO 335
<211> LENGTH: 21
<212> TYPE: PRT
<213> ORGANISM: Salmonella enterica

<400> SEQUENCE: 335

Phe Arg Leu Gly Lys Leu Glu Gln Ile Ala Arg Glu Lys Val Arg Thr
1               5                   10                  15

Leu Ala Leu Val Asp
            20

<210> SEQ ID NO 336
<211> LENGTH: 23
<212> TYPE: PRT
<213> ORGANISM: Salmonella enterica

<400> SEQUENCE: 336

Val Trp Ser Ala Trp Arg Arg Ala Ala Pro Ala Glu Glu Ser Arg Gly
1               5                   10                  15

Arg Ala Ala Val Val Gln Lys
            20

<210> SEQ ID NO 337
<211> LENGTH: 23
<212> TYPE: PRT
<213> ORGANISM: Salmonella enterica

<400> SEQUENCE: 337

Ser Ala Trp Arg Arg Ala Ala Pro Ala Glu Glu Ser Arg Gly Arg Ala
1               5                   10                  15

Ala Val Val Gln Lys Met Arg
            20

<210> SEQ ID NO 338
<211> LENGTH: 23
<212> TYPE: PRT
<213> ORGANISM: Salmonella enterica

<400> SEQUENCE: 338

Ala Trp Arg Arg Ala Ala Pro Ala Glu Glu Ser Arg Gly Arg Ala Ala
1               5                   10                  15

Val Val Gln Lys Met Arg Ala
```

<210> SEQ ID NO 339
<211> LENGTH: 23
<212> TYPE: PRT
<213> ORGANISM: Salmonella enterica

<400> SEQUENCE: 339

Trp Arg Arg Ala Ala Pro Ala Glu Glu Ser Arg Gly Arg Ala Ala Val
1               5                   10                  15

Val Gln Lys Met Arg Ala Cys
            20

<210> SEQ ID NO 340
<211> LENGTH: 23
<212> TYPE: PRT
<213> ORGANISM: Salmonella enterica

<400> SEQUENCE: 340

Arg Arg Ala Ala Pro Ala Glu Glu Ser Arg Gly Arg Ala Ala Val Val
1               5                   10                  15

Gln Lys Met Arg Ala Cys Leu
            20

<210> SEQ ID NO 341
<211> LENGTH: 23
<212> TYPE: PRT
<213> ORGANISM: Salmonella enterica

<400> SEQUENCE: 341

Ala Ala Leu Val Ala Thr Gly Arg Glu Met Phe Arg Leu Gly Lys Leu
1               5                   10                  15

Glu Gln Ile Ala Arg Glu Lys
            20

<210> SEQ ID NO 342
<211> LENGTH: 23
<212> TYPE: PRT
<213> ORGANISM: Salmonella enterica

<400> SEQUENCE: 342

Leu Val Ala Thr Gly Arg Glu Met Phe Arg Leu Gly Lys Leu Glu Gln
1               5                   10                  15

Ile Ala Arg Glu Lys Val Arg
            20

<210> SEQ ID NO 343
<211> LENGTH: 23
<212> TYPE: PRT
<213> ORGANISM: Salmonella enterica

<400> SEQUENCE: 343

Ala Thr Gly Arg Glu Met Phe Arg Leu Gly Lys Leu Glu Gln Ile Ala
1               5                   10                  15

Arg Glu Lys Val Arg Thr Leu
            20

<210> SEQ ID NO 344
<211> LENGTH: 23
<212> TYPE: PRT
<213> ORGANISM: Salmonella enterica

<400> SEQUENCE: 344

Thr Gly Arg Glu Met Phe Arg Leu Gly Lys Leu Glu Gln Ile Ala Arg
1               5                   10                  15

Glu Lys Val Arg Thr Leu Ala
            20

<210> SEQ ID NO 345
<211> LENGTH: 23
<212> TYPE: PRT
<213> ORGANISM: Salmonella enterica

<400> SEQUENCE: 345

Gly Arg Glu Met Phe Arg Leu Gly Lys Leu Glu Gln Ile Ala Arg Glu
1               5                   10                  15

Lys Val Arg Thr Leu Ala Leu
            20

<210> SEQ ID NO 346
<211> LENGTH: 23
<212> TYPE: PRT
<213> ORGANISM: Salmonella enterica

<400> SEQUENCE: 346

Arg Glu Met Phe Arg Leu Gly Lys Leu Glu Gln Ile Ala Arg Glu Lys
1               5                   10                  15

Val Arg Thr Leu Ala Leu Val
            20

<210> SEQ ID NO 347
<211> LENGTH: 26
<212> TYPE: PRT
<213> ORGANISM: Salmonella enterica

<400> SEQUENCE: 347

Ala Val Trp Ser Ala Trp Arg Arg Ala Ala Pro Ala Glu Glu Ser Arg
1               5                   10                  15

Gly Arg Ala Ala Val Val Gln Lys Met Arg
            20                  25

<210> SEQ ID NO 348
<211> LENGTH: 26
<212> TYPE: PRT
<213> ORGANISM: Salmonella enterica

<400> SEQUENCE: 348

Val Trp Ser Ala Trp Arg Arg Ala Ala Pro Glu Glu Ser Arg Gly
1               5                   10                  15

Arg Ala Ala Val Val Gln Lys Met Arg Ala
            20                  25

<210> SEQ ID NO 349
<211> LENGTH: 26
<212> TYPE: PRT
<213> ORGANISM: Salmonella enterica

<400> SEQUENCE: 349

Leu Ala Ala Leu Val Ala Thr Gly Arg Glu Met Phe Arg Leu Gly Lys
1               5                   10                  15

Leu Glu Gln Ile Ala Arg Glu Lys Val Arg
            20                  25

<210> SEQ ID NO 350

```
<211> LENGTH: 26
<212> TYPE: PRT
<213> ORGANISM: Salmonella enterica

<400> SEQUENCE: 350

Ala Ala Leu Val Ala Thr Gly Arg Glu Met Phe Arg Leu Gly Lys Leu
1               5                   10                  15

Glu Gln Ile Ala Arg Glu Lys Val Arg Thr
            20                  25

<210> SEQ ID NO 351
<211> LENGTH: 26
<212> TYPE: PRT
<213> ORGANISM: Salmonella enterica

<400> SEQUENCE: 351

Ala Leu Val Ala Thr Gly Arg Glu Met Phe Arg Leu Gly Lys Leu Glu
1               5                   10                  15

Gln Ile Ala Arg Glu Lys Val Arg Thr Leu
            20                  25

<210> SEQ ID NO 352
<211> LENGTH: 26
<212> TYPE: PRT
<213> ORGANISM: Salmonella enterica

<400> SEQUENCE: 352

Leu Val Ala Thr Gly Arg Glu Met Phe Arg Leu Gly Lys Leu Glu Gln
1               5                   10                  15

Ile Ala Arg Glu Lys Val Arg Thr Leu Ala
            20                  25

<210> SEQ ID NO 353
<211> LENGTH: 26
<212> TYPE: PRT
<213> ORGANISM: Salmonella enterica

<400> SEQUENCE: 353

Val Ala Thr Gly Arg Glu Met Phe Arg Leu Gly Lys Leu Glu Gln Ile
1               5                   10                  15

Ala Arg Glu Lys Val Arg Thr Leu Ala Leu
            20                  25

<210> SEQ ID NO 354
<211> LENGTH: 26
<212> TYPE: PRT
<213> ORGANISM: Salmonella enterica

<400> SEQUENCE: 354

Ala Thr Gly Arg Glu Met Phe Arg Leu Gly Lys Leu Glu Gln Ile Ala
1               5                   10                  15

Arg Glu Lys Val Arg Thr Leu Ala Leu Val
            20                  25

<210> SEQ ID NO 355
<211> LENGTH: 27
<212> TYPE: PRT
<213> ORGANISM: Salmonella enterica

<400> SEQUENCE: 355

Ala Val Trp Ser Ala Trp Arg Arg Ala Ala Pro Ala Glu Glu Ser Arg
1               5                   10                  15
```

Gly Arg Ala Ala Val Val Gln Lys Met Arg Ala
            20                  25

<210> SEQ ID NO 356
<211> LENGTH: 28
<212> TYPE: PRT
<213> ORGANISM: Salmonella enterica

<400> SEQUENCE: 356

Asn Asp Leu Ala Ala Leu Val Ala Thr Gly Arg Glu Met Phe Arg Leu
1               5                   10                  15

Gly Lys Leu Glu Gln Ile Ala Arg Glu Lys Val Arg
            20                  25

<210> SEQ ID NO 357
<211> LENGTH: 28
<212> TYPE: PRT
<213> ORGANISM: Salmonella enterica

<400> SEQUENCE: 357

Asp Leu Ala Ala Leu Val Ala Thr Gly Arg Glu Met Phe Arg Leu Gly
1               5                   10                  15

Lys Leu Glu Gln Ile Ala Arg Glu Lys Val Arg Thr
            20                  25

<210> SEQ ID NO 358
<211> LENGTH: 28
<212> TYPE: PRT
<213> ORGANISM: Salmonella enterica

<400> SEQUENCE: 358

Leu Ala Ala Leu Val Ala Thr Gly Arg Glu Met Phe Arg Leu Gly Lys
1               5                   10                  15

Leu Glu Gln Ile Ala Arg Glu Lys Val Arg Thr Leu
            20                  25

<210> SEQ ID NO 359
<211> LENGTH: 28
<212> TYPE: PRT
<213> ORGANISM: Salmonella enterica

<400> SEQUENCE: 359

Ala Ala Leu Val Ala Thr Gly Arg Glu Met Phe Arg Leu Gly Lys Leu
1               5                   10                  15

Glu Gln Ile Ala Arg Glu Lys Val Arg Thr Leu Ala
            20                  25

<210> SEQ ID NO 360
<211> LENGTH: 28
<212> TYPE: PRT
<213> ORGANISM: Salmonella enterica

<400> SEQUENCE: 360

Ala Leu Val Ala Thr Gly Arg Glu Met Phe Arg Leu Gly Lys Leu Glu
1               5                   10                  15

Gln Ile Ala Arg Glu Lys Val Arg Thr Leu Ala Leu
            20                  25

<210> SEQ ID NO 361
<211> LENGTH: 10
<212> TYPE: PRT
<213> ORGANISM: Shigella flexneri

```
<400> SEQUENCE: 361

Ser Gln Arg Val Ala Asp Arg Leu Lys Ala
1               5                   10

<210> SEQ ID NO 362
<211> LENGTH: 10
<212> TYPE: PRT
<213> ORGANISM: Shigella flexneri

<400> SEQUENCE: 362

Gln Arg Val Ala Asp Arg Leu Lys Ala Ser
1               5                   10

<210> SEQ ID NO 363
<211> LENGTH: 10
<212> TYPE: PRT
<213> ORGANISM: Shigella flexneri

<400> SEQUENCE: 363

Arg Val Ala Asp Arg Leu Lys Ala Ser Gly
1               5                   10

<210> SEQ ID NO 364
<211> LENGTH: 11
<212> TYPE: PRT
<213> ORGANISM: Shigella flexneri

<400> SEQUENCE: 364

Gln Arg Val Ala Asp Arg Leu Lys Ala Ser Gly
1               5                   10

<210> SEQ ID NO 365
<211> LENGTH: 11
<212> TYPE: PRT
<213> ORGANISM: Shigella flexneri

<400> SEQUENCE: 365

Arg Val Ala Asp Arg Leu Lys Ala Ser Gly Leu
1               5                   10

<210> SEQ ID NO 366
<211> LENGTH: 12
<212> TYPE: PRT
<213> ORGANISM: Shigella flexneri

<400> SEQUENCE: 366

Gln Arg Val Ala Asp Arg Leu Lys Ala Ser Gly Leu
1               5                   10

<210> SEQ ID NO 367
<211> LENGTH: 13
<212> TYPE: PRT
<213> ORGANISM: Shigella flexneri

<400> SEQUENCE: 367

Arg Val Ala Leu Thr Trp Asn Asn Leu Arg Lys Thr Leu
1               5                   10

<210> SEQ ID NO 368
<211> LENGTH: 14
<212> TYPE: PRT
<213> ORGANISM: Shigella flexneri

<400> SEQUENCE: 368
```

Arg Val Ala Leu Thr Trp Asn Asn Leu Arg Lys Thr Leu Leu
1               5                   10

<210> SEQ ID NO 369
<211> LENGTH: 15
<212> TYPE: PRT
<213> ORGANISM: Shigella flexneri

<400> SEQUENCE: 369

Asp Arg Val Ala Leu Thr Trp Asn Asn Leu Arg Lys Thr Leu Leu
1               5                   10                  15

<210> SEQ ID NO 370
<211> LENGTH: 15
<212> TYPE: PRT
<213> ORGANISM: Shigella flexneri

<400> SEQUENCE: 370

Arg Val Ala Leu Thr Trp Asn Asn Leu Arg Lys Thr Leu Leu Val
1               5                   10                  15

<210> SEQ ID NO 371
<211> LENGTH: 10
<212> TYPE: PRT
<213> ORGANISM: Shigella flexneri

<400> SEQUENCE: 371

Ser Gln Arg Val Ala Asp Arg Leu Lys Ala
1               5                   10

<210> SEQ ID NO 372
<211> LENGTH: 10
<212> TYPE: PRT
<213> ORGANISM: Shigella flexneri

<400> SEQUENCE: 372

Gln Arg Val Ala Asp Arg Leu Lys Ala Ser
1               5                   10

<210> SEQ ID NO 373
<211> LENGTH: 10
<212> TYPE: PRT
<213> ORGANISM: Shigella flexneri

<400> SEQUENCE: 373

Arg Val Ala Asp Arg Leu Lys Ala Ser Gly
1               5                   10

<210> SEQ ID NO 374
<211> LENGTH: 11
<212> TYPE: PRT
<213> ORGANISM: Shigella flexneri

<400> SEQUENCE: 374

Gln Arg Val Ala Asp Arg Leu Lys Ala Ser Gly
1               5                   10

<210> SEQ ID NO 375
<211> LENGTH: 11
<212> TYPE: PRT
<213> ORGANISM: Shigella flexneri

<400> SEQUENCE: 375

Arg Val Ala Asp Arg Leu Lys Ala Ser Gly Leu
1               5                   10

```
<210> SEQ ID NO 376
<211> LENGTH: 12
<212> TYPE: PRT
<213> ORGANISM: Shigella flexneri

<400> SEQUENCE: 376

Gln Arg Val Ala Asp Arg Leu Lys Ala Ser Gly Leu
1               5                   10

<210> SEQ ID NO 377
<211> LENGTH: 13
<212> TYPE: PRT
<213> ORGANISM: Shigella flexneri

<400> SEQUENCE: 377

Arg Val Ala Leu Thr Trp Asn Asn Leu Arg Lys Thr Leu
1               5                   10

<210> SEQ ID NO 378
<211> LENGTH: 14
<212> TYPE: PRT
<213> ORGANISM: Shigella flexneri

<400> SEQUENCE: 378

Arg Val Ala Leu Thr Trp Asn Asn Leu Arg Lys Thr Leu Leu
1               5                   10

<210> SEQ ID NO 379
<211> LENGTH: 15
<212> TYPE: PRT
<213> ORGANISM: Shigella flexneri

<400> SEQUENCE: 379

Asp Arg Val Ala Leu Thr Trp Asn Asn Leu Arg Lys Thr Leu Leu
1               5                   10                  15

<210> SEQ ID NO 380
<211> LENGTH: 15
<212> TYPE: PRT
<213> ORGANISM: Shigella flexneri

<400> SEQUENCE: 380

Arg Val Ala Leu Thr Trp Asn Asn Leu Arg Lys Thr Leu Leu Val
1               5                   10                  15

<210> SEQ ID NO 381
<211> LENGTH: 10
<212> TYPE: PRT
<213> ORGANISM: Shigella flexneri

<400> SEQUENCE: 381

Pro Gln Arg Val Ala Asp Arg Leu Lys Ala
1               5                   10

<210> SEQ ID NO 382
<211> LENGTH: 10
<212> TYPE: PRT
<213> ORGANISM: Shigella flexneri

<400> SEQUENCE: 382

Gln Arg Val Ala Asp Arg Leu Lys Ala Ser
1               5                   10
```

```
<210> SEQ ID NO 383
<211> LENGTH: 10
<212> TYPE: PRT
<213> ORGANISM: Shigella flexneri

<400> SEQUENCE: 383

Arg Val Ala Asp Arg Leu Lys Ala Ser Gly
1               5                   10

<210> SEQ ID NO 384
<211> LENGTH: 11
<212> TYPE: PRT
<213> ORGANISM: Shigella flexneri

<400> SEQUENCE: 384

Pro Gln Arg Val Ala Asp Arg Leu Lys Ala Ser
1               5                   10

<210> SEQ ID NO 385
<211> LENGTH: 11
<212> TYPE: PRT
<213> ORGANISM: Shigella flexneri

<400> SEQUENCE: 385

Gln Arg Val Ala Asp Arg Leu Lys Ala Ser Gly
1               5                   10

<210> SEQ ID NO 386
<211> LENGTH: 11
<212> TYPE: PRT
<213> ORGANISM: Shigella flexneri

<400> SEQUENCE: 386

Arg Val Ala Asp Arg Leu Lys Ala Ser Gly Leu
1               5                   10

<210> SEQ ID NO 387
<211> LENGTH: 13
<212> TYPE: PRT
<213> ORGANISM: Shigella flexneri

<400> SEQUENCE: 387

Arg Val Ala Leu Thr Trp Asn Asn Leu Arg Lys Thr Leu
1               5                   10

<210> SEQ ID NO 388
<211> LENGTH: 13
<212> TYPE: PRT
<213> ORGANISM: Shigella flexneri

<400> SEQUENCE: 388

Pro Gln Arg Val Ala Asp Arg Leu Lys Ala Ser Gly Leu
1               5                   10

<210> SEQ ID NO 389
<211> LENGTH: 14
<212> TYPE: PRT
<213> ORGANISM: Shigella flexneri

<400> SEQUENCE: 389

Arg Val Ala Leu Thr Trp Asn Asn Leu Arg Lys Thr Leu Leu
1               5                   10

<210> SEQ ID NO 390
<211> LENGTH: 15
```

<212> TYPE: PRT
<213> ORGANISM: Shigella flexneri

<400> SEQUENCE: 390

Asp Arg Val Ala Leu Thr Trp Asn Asn Leu Arg Lys Thr Leu Leu
1               5                   10                  15

<210> SEQ ID NO 391
<211> LENGTH: 15
<212> TYPE: PRT
<213> ORGANISM: Shigella flexneri

<400> SEQUENCE: 391

Arg Val Ala Leu Thr Trp Asn Asn Leu Arg Lys Thr Leu Leu Val
1               5                   10                  15

<210> SEQ ID NO 392
<211> LENGTH: 10
<212> TYPE: PRT
<213> ORGANISM: Shigella flexneri

<400> SEQUENCE: 392

Asn Arg Ile Gln Ala Val Arg Leu Leu Lys
1               5                   10

<210> SEQ ID NO 393
<211> LENGTH: 10
<212> TYPE: PRT
<213> ORGANISM: Shigella flexneri

<400> SEQUENCE: 393

Arg Ile Gln Ala Val Arg Leu Leu Lys Ile
1               5                   10

<210> SEQ ID NO 394
<211> LENGTH: 10
<212> TYPE: PRT
<213> ORGANISM: Shigella flexneri

<400> SEQUENCE: 394

Ile Gln Ala Val Arg Leu Leu Lys Ile Cys
1               5                   10

<210> SEQ ID NO 395
<211> LENGTH: 10
<212> TYPE: PRT
<213> ORGANISM: Shigella flexneri

<400> SEQUENCE: 395

Gln Ala Val Arg Leu Leu Lys Ile Cys Leu
1               5                   10

<210> SEQ ID NO 396
<211> LENGTH: 10
<212> TYPE: PRT
<213> ORGANISM: Shigella flexneri

<400> SEQUENCE: 396

Arg Leu Leu Lys Ile Cys Leu Asp Thr Arg
1               5                   10

<210> SEQ ID NO 397
<211> LENGTH: 10
<212> TYPE: PRT
<213> ORGANISM: Shigella flexneri

```
<400> SEQUENCE: 397

Leu Lys Val Gly Glu Asn Gln Leu Arg Arg
1               5                   10

<210> SEQ ID NO 398
<211> LENGTH: 10
<212> TYPE: PRT
<213> ORGANISM: Shigella flexneri

<400> SEQUENCE: 398

Lys Val Gly Glu Asn Gln Leu Arg Arg Leu
1               5                   10

<210> SEQ ID NO 399
<211> LENGTH: 10
<212> TYPE: PRT
<213> ORGANISM: Shigella flexneri

<400> SEQUENCE: 399

Ser Gln Arg Val Ala Asp Arg Leu Lys Ala
1               5                   10

<210> SEQ ID NO 400
<211> LENGTH: 10
<212> TYPE: PRT
<213> ORGANISM: Shigella flexneri

<400> SEQUENCE: 400

Gln Arg Val Ala Asp Arg Leu Lys Ala Ser
1               5                   10

<210> SEQ ID NO 401
<211> LENGTH: 10
<212> TYPE: PRT
<213> ORGANISM: Shigella flexneri

<400> SEQUENCE: 401

Arg Val Ala Asp Arg Leu Lys Ala Ser Gly
1               5                   10

<210> SEQ ID NO 402
<211> LENGTH: 11
<212> TYPE: PRT
<213> ORGANISM: Shigella flexneri

<400> SEQUENCE: 402

Glu Asn Arg Ile Gln Ala Val Arg Leu Leu Lys
1               5                   10

<210> SEQ ID NO 403
<211> LENGTH: 11
<212> TYPE: PRT
<213> ORGANISM: Shigella flexneri

<400> SEQUENCE: 403

Asn Arg Ile Gln Ala Val Arg Leu Leu Lys Ile
1               5                   10

<210> SEQ ID NO 404
<211> LENGTH: 11
<212> TYPE: PRT
<213> ORGANISM: Shigella flexneri

<400> SEQUENCE: 404
```

```
Arg Ile Gln Ala Val Arg Leu Leu Lys Ile Cys
1               5                   10

<210> SEQ ID NO 405
<211> LENGTH: 11
<212> TYPE: PRT
<213> ORGANISM: Shigella flexneri

<400> SEQUENCE: 405

Leu Lys Val Gly Glu Asn Gln Leu Arg Arg Leu
1               5                   10

<210> SEQ ID NO 406
<211> LENGTH: 11
<212> TYPE: PRT
<213> ORGANISM: Shigella flexneri

<400> SEQUENCE: 406

Gln Arg Val Ala Asp Arg Leu Lys Ala Ser Gly
1               5                   10

<210> SEQ ID NO 407
<211> LENGTH: 11
<212> TYPE: PRT
<213> ORGANISM: Shigella flexneri

<400> SEQUENCE: 407

Arg Val Ala Asp Arg Leu Lys Ala Ser Gly Leu
1               5                   10

<210> SEQ ID NO 408
<211> LENGTH: 12
<212> TYPE: PRT
<213> ORGANISM: Shigella flexneri

<400> SEQUENCE: 408

Thr Glu Asn Arg Ile Gln Ala Val Arg Leu Leu Lys
1               5                   10

<210> SEQ ID NO 409
<211> LENGTH: 12
<212> TYPE: PRT
<213> ORGANISM: Shigella flexneri

<400> SEQUENCE: 409

Glu Asn Arg Ile Gln Ala Val Arg Leu Leu Lys Ile
1               5                   10

<210> SEQ ID NO 410
<211> LENGTH: 12
<212> TYPE: PRT
<213> ORGANISM: Shigella flexneri

<400> SEQUENCE: 410

Asn Arg Ile Gln Ala Val Arg Leu Leu Lys Ile Cys
1               5                   10

<210> SEQ ID NO 411
<211> LENGTH: 12
<212> TYPE: PRT
<213> ORGANISM: Shigella flexneri

<400> SEQUENCE: 411

Arg Ile Gln Ala Val Arg Leu Leu Lys Ile Cys Leu
```

```
<210> SEQ ID NO 412
<211> LENGTH: 12
<212> TYPE: PRT
<213> ORGANISM: Shigella flexneri

<400> SEQUENCE: 412

Ala Val Arg Leu Leu Lys Ile Cys Leu Asp Thr Arg
1               5                   10

<210> SEQ ID NO 413
<211> LENGTH: 12
<212> TYPE: PRT
<213> ORGANISM: Shigella flexneri

<400> SEQUENCE: 413

Arg Arg Leu Ser Arg Leu Pro Gln Glu Leu Leu Ala
1               5                   10

<210> SEQ ID NO 414
<211> LENGTH: 12
<212> TYPE: PRT
<213> ORGANISM: Shigella flexneri

<400> SEQUENCE: 414

Gln Arg Val Ala Asp Arg Leu Lys Ala Ser Gly Leu
1               5                   10

<210> SEQ ID NO 415
<211> LENGTH: 13
<212> TYPE: PRT
<213> ORGANISM: Shigella flexneri

<400> SEQUENCE: 415

Thr Glu Asn Arg Ile Gln Ala Val Arg Leu Leu Lys Ile
1               5                   10

<210> SEQ ID NO 416
<211> LENGTH: 13
<212> TYPE: PRT
<213> ORGANISM: Shigella flexneri

<400> SEQUENCE: 416

Glu Asn Arg Ile Gln Ala Val Arg Leu Leu Lys Ile Cys
1               5                   10

<210> SEQ ID NO 417
<211> LENGTH: 13
<212> TYPE: PRT
<213> ORGANISM: Shigella flexneri

<400> SEQUENCE: 417

Asn Arg Ile Gln Ala Val Arg Leu Leu Lys Ile Cys Leu
1               5                   10

<210> SEQ ID NO 418
<211> LENGTH: 13
<212> TYPE: PRT
<213> ORGANISM: Shigella flexneri

<400> SEQUENCE: 418

Arg Ile Gln Ala Val Arg Leu Leu Lys Ile Cys Leu Asp
1               5                   10
```

<210> SEQ ID NO 419
<211> LENGTH: 26
<212> TYPE: PRT
<213> ORGANISM: Shigella flexneri

<400> SEQUENCE: 419

Gln Ala Val Arg Leu Leu Lys Ile Cys Leu Asp Thr Arg Gln Ala Val
1               5                   10                  15

Arg Leu Leu Lys Ile Cys Leu Asp Thr Arg
            20                  25

<210> SEQ ID NO 420
<211> LENGTH: 13
<212> TYPE: PRT
<213> ORGANISM: Shigella flexneri

<400> SEQUENCE: 420

Leu Lys Val Gly Glu Asn Gln Leu Arg Arg Leu Ser Arg
1               5                   10

<210> SEQ ID NO 421
<211> LENGTH: 13
<212> TYPE: PRT
<213> ORGANISM: Shigella flexneri

<400> SEQUENCE: 421

Lys Val Gly Glu Asn Gln Leu Arg Arg Leu Ser Arg Leu
1               5                   10

<210> SEQ ID NO 422
<211> LENGTH: 13
<212> TYPE: PRT
<213> ORGANISM: Shigella flexneri

<400> SEQUENCE: 422

Leu Arg Arg Leu Ser Arg Leu Pro Gln Glu Leu Leu Ala
1               5                   10

<210> SEQ ID NO 423
<211> LENGTH: 13
<212> TYPE: PRT
<213> ORGANISM: Shigella flexneri

<400> SEQUENCE: 423

Arg Arg Leu Ser Arg Leu Pro Gln Glu Leu Leu Ala Leu
1               5                   10

<210> SEQ ID NO 424
<211> LENGTH: 13
<212> TYPE: PRT
<213> ORGANISM: Shigella flexneri

<400> SEQUENCE: 424

Arg Val Ala Leu Thr Trp Asn Asn Leu Arg Lys Thr Leu
1               5                   10

<210> SEQ ID NO 425
<211> LENGTH: 14
<212> TYPE: PRT
<213> ORGANISM: Shigella flexneri

<400> SEQUENCE: 425

Glu Asn Arg Ile Gln Ala Val Arg Leu Leu Lys Ile Cys Leu
1               5                   10

<210> SEQ ID NO 426
<211> LENGTH: 14
<212> TYPE: PRT
<213> ORGANISM: Shigella flexneri

<400> SEQUENCE: 426

Asn Arg Ile Gln Ala Val Arg Leu Leu Lys Ile Cys Leu Asp
1               5                   10

<210> SEQ ID NO 427
<211> LENGTH: 14
<212> TYPE: PRT
<213> ORGANISM: Shigella flexneri

<400> SEQUENCE: 427

Arg Ile Gln Ala Val Arg Leu Leu Lys Ile Cys Leu Asp Thr
1               5                   10

<210> SEQ ID NO 428
<211> LENGTH: 14
<212> TYPE: PRT
<213> ORGANISM: Shigella flexneri

<400> SEQUENCE: 428

Ile Gln Ala Val Arg Leu Leu Lys Ile Cys Leu Asp Thr Arg
1               5                   10

<210> SEQ ID NO 429
<211> LENGTH: 14
<212> TYPE: PRT
<213> ORGANISM: Shigella flexneri

<400> SEQUENCE: 429

Leu Lys Tyr Leu Lys Val Gly Glu Asn Gln Leu Arg Arg Leu
1               5                   10

<210> SEQ ID NO 430
<211> LENGTH: 14
<212> TYPE: PRT
<213> ORGANISM: Shigella flexneri

<400> SEQUENCE: 430

Leu Lys Val Gly Glu Asn Gln Leu Arg Arg Leu Ser Arg Leu
1               5                   10

<210> SEQ ID NO 431
<211> LENGTH: 14
<212> TYPE: PRT
<213> ORGANISM: Shigella flexneri

<400> SEQUENCE: 431

Gln Leu Arg Arg Leu Ser Arg Leu Pro Gln Glu Leu Leu Ala
1               5                   10

<210> SEQ ID NO 432
<211> LENGTH: 14
<212> TYPE: PRT
<213> ORGANISM: Shigella flexneri

<400> SEQUENCE: 432

Leu Arg Arg Leu Ser Arg Leu Pro Gln Glu Leu Leu Ala Leu
1               5                   10

<210> SEQ ID NO 433
<211> LENGTH: 14
<212> TYPE: PRT
<213> ORGANISM: Shigella flexneri

<400> SEQUENCE: 433

Arg Val Ala Leu Thr Trp Asn Asn Leu Arg Lys Thr Leu Leu
1               5                   10

<210> SEQ ID NO 434
<211> LENGTH: 15
<212> TYPE: PRT
<213> ORGANISM: Shigella flexneri

<400> SEQUENCE: 434

Thr Glu Asn Arg Ile Gln Ala Val Arg Leu Leu Lys Ile Cys Leu
1               5                   10                  15

<210> SEQ ID NO 435
<211> LENGTH: 15
<212> TYPE: PRT
<213> ORGANISM: Shigella flexneri

<400> SEQUENCE: 435

Asn Arg Ile Gln Ala Val Arg Leu Leu Lys Ile Cys Leu Asp Thr
1               5                   10                  15

<210> SEQ ID NO 436
<211> LENGTH: 15
<212> TYPE: PRT
<213> ORGANISM: Shigella flexneri

<400> SEQUENCE: 436

Arg Ile Gln Ala Val Arg Leu Leu Lys Ile Cys Leu Asp Thr Arg
1               5                   10                  15

<210> SEQ ID NO 437
<211> LENGTH: 15
<212> TYPE: PRT
<213> ORGANISM: Shigella flexneri

<400> SEQUENCE: 437

Ser Leu Lys Tyr Leu Lys Val Gly Glu Asn Gln Leu Arg Arg Leu
1               5                   10                  15

<210> SEQ ID NO 438
<211> LENGTH: 15
<212> TYPE: PRT
<213> ORGANISM: Shigella flexneri

<400> SEQUENCE: 438

Leu Lys Tyr Leu Lys Val Gly Glu Asn Gln Leu Arg Arg Leu Ser
1               5                   10                  15

<210> SEQ ID NO 439
<211> LENGTH: 15
<212> TYPE: PRT
<213> ORGANISM: Shigella flexneri

<400> SEQUENCE: 439

Leu Lys Val Gly Glu Asn Gln Leu Arg Arg Leu Ser Arg Leu Pro
1               5                   10                  15

<210> SEQ ID NO 440
<211> LENGTH: 15

```
<212> TYPE: PRT
<213> ORGANISM: Shigella flexneri

<400> SEQUENCE: 440

Ser Leu Lys Tyr Leu Lys Val Gly Glu Asn Gln Leu Arg Arg Leu
1               5                   10                  15

<210> SEQ ID NO 441
<211> LENGTH: 15
<212> TYPE: PRT
<213> ORGANISM: Shigella flexneri

<400> SEQUENCE: 447

Arg Ile Gln Ala Val Arg Leu Leu Lys Ile Cys Leu Asp Thr Arg Glu
1               5                   10                  15

<210> SEQ ID NO 448
<211> LENGTH: 16
<212> TYPE: PRT
<213> ORGANISM: Shigella flexneri

<400> SEQUENCE: 448

Gln Ser Leu Lys Tyr Leu Lys Val Gly Glu Asn Gln Leu Arg Arg Leu
1               5                   10                  15

<210> SEQ ID NO 449
<211> LENGTH: 16
<212> TYPE: PRT
<213> ORGANISM: Shigella flexneri

<400> SEQUENCE: 449

Leu Lys Val Gly Glu Asn Gln Leu Arg Arg Leu Ser Arg Leu Pro Gln
1               5                   10                  15

<210> SEQ ID NO 450
<211> LENGTH: 16
<212> TYPE: PRT
<213> ORGANISM: Shigella flexneri

<400> SEQUENCE: 450

Asn Gln Leu Arg Arg Leu Ser Arg Leu Pro Gln Glu Leu Leu Ala Leu
1               5                   10                  15

<210> SEQ ID NO 451
<211> LENGTH: 17
<212> TYPE: PRT
<213> ORGANISM: Shigella flexneri

<400> SEQUENCE: 451

Glu Asn Arg Ile Gln Ala Val Arg Leu Leu Lys Ile Cys Leu Asp Thr
1               5                   10                  15

Arg

<210> SEQ ID NO 452
<211> LENGTH: 17
<212> TYPE: PRT
<213> ORGANISM: Shigella flexneri

<400> SEQUENCE: 452

Asn Arg Ile Gln Ala Val Arg Leu Leu Lys Ile Cys Leu Asp Thr Arg
1               5                   10                  15

Glu

<210> SEQ ID NO 453
<211> LENGTH: 17
<212> TYPE: PRT
<213> ORGANISM: Shigella flexneri

<400> SEQUENCE: 453

Leu Lys Tyr Leu Lys Val Gly Glu Asn Gln Leu Arg Arg Leu Ser Arg
1               5                   10                  15

Leu

<210> SEQ ID NO 454
<211> LENGTH: 18
<212> TYPE: PRT
<213> ORGANISM: Shigella flexneri

<400> SEQUENCE: 454

Ser Leu Lys Tyr Leu Lys Val Gly Glu Asn Gln Leu Arg Arg Leu Ser
1               5                   10                  15

Arg Leu

<210> SEQ ID NO 455
<211> LENGTH: 19
<212> TYPE: PRT
<213> ORGANISM: Shigella flexneri

<400> SEQUENCE: 455

Trp Ala Arg Glu Gly Thr Thr Thr Glu Asn Arg Ile Gln Ala Val Arg
1               5                   10                  15

Leu Leu Lys

<210> SEQ ID NO 456
<211> LENGTH: 19
<212> TYPE: PRT
<213> ORGANISM: Shigella flexneri

<400> SEQUENCE: 456

Gln Ser Leu Lys Tyr Leu Lys Val Gly Glu Asn Gln Leu Arg Arg Leu
1               5                   10                  15

Ser Arg Leu

<210> SEQ ID NO 457
<211> LENGTH: 19
<212> TYPE: PRT
<213> ORGANISM: Shigella flexneri

<400> SEQUENCE: 457

Leu Lys Val Gly Glu Asn Gln Leu Arg Arg Leu Ser Arg Leu Pro Gln
1               5                   10                  15

Glu Leu Leu

<210> SEQ ID NO 458
<211> LENGTH: 19
<212> TYPE: PRT
<213> ORGANISM: Shigella flexneri

<400> SEQUENCE: 458

Lys Val Gly Glu Asn Gln Leu Arg Arg Leu Ser Arg Leu Pro Gln Glu
1               5                   10                  15

Leu Leu Ala

<210> SEQ ID NO 459
<211> LENGTH: 20
<212> TYPE: PRT
<213> ORGANISM: Shigella flexneri

<400> SEQUENCE: 459

Trp Ala Arg Glu Gly Thr Thr Thr Glu Asn Arg Ile Gln Ala Val Arg
1               5                   10                  15

Leu Leu Lys Ile
            20

```
<210> SEQ ID NO 460
<211> LENGTH: 20
<212> TYPE: PRT
<213> ORGANISM: Shigella flexneri

<400> SEQUENCE: 460

Leu Lys Val Gly Glu Asn Gln Leu Arg Arg Leu Ser Arg Leu Pro Gln
1               5                   10                  15

Glu Leu Leu Ala
            20

<210> SEQ ID NO 461
<211> LENGTH: 20
<212> TYPE: PRT
<213> ORGANISM: Shigella flexneri

<400> SEQUENCE: 461

Lys Val Gly Glu Asn Gln Leu Arg Arg Leu Ser Arg Leu Pro Gln Glu
1               5                   10                  15

Leu Leu Ala Leu
            20

<210> SEQ ID NO 462
<211> LENGTH: 21
<212> TYPE: PRT
<213> ORGANISM: Shigella flexneri

<400> SEQUENCE: 462

Leu Lys Tyr Leu Lys Val Gly Glu Asn Gln Leu Arg Arg Leu Ser Arg
1               5                   10                  15

Leu Pro Gln Glu Leu
            20

<210> SEQ ID NO 463
<211> LENGTH: 21
<212> TYPE: PRT
<213> ORGANISM: Shigella flexneri

<400> SEQUENCE: 463

Lys Tyr Leu Lys Val Gly Glu Asn Gln Leu Arg Arg Leu Ser Arg Leu
1               5                   10                  15

Pro Gln Glu Leu Leu
            20

<210> SEQ ID NO 464
<211> LENGTH: 21
<212> TYPE: PRT
<213> ORGANISM: Shigella flexneri

<400> SEQUENCE: 464

Leu Lys Val Gly Glu Asn Gln Leu Arg Arg Leu Ser Arg Leu Pro Gln
1               5                   10                  15

Glu Leu Leu Ala Leu
            20

<210> SEQ ID NO 465
<211> LENGTH: 22
<212> TYPE: PRT
<213> ORGANISM: Shigella flexneri

<400> SEQUENCE: 465

Arg Leu Leu Lys Ile Cys Leu Asp Thr Arg Glu Pro Val Leu Asn Leu
1               5                   10                  15
```

```
Ser Leu Leu Lys Leu Arg
            20

<210> SEQ ID NO 466
<211> LENGTH: 22
<212> TYPE: PRT
<213> ORGANISM: Shigella flexneri

<400> SEQUENCE: 466

Leu Lys Tyr Leu Lys Val Gly Glu Asn Gln Leu Arg Arg Leu Ser Arg
1               5                   10                  15

Leu Pro Gln Glu Leu Leu
            20

<210> SEQ ID NO 467
<211> LENGTH: 22
<212> TYPE: PRT
<213> ORGANISM: Shigella flexneri

<400> SEQUENCE: 467

Lys Tyr Leu Lys Val Gly Glu Asn Gln Leu Arg Arg Leu Ser Arg Leu
1               5                   10                  15

Pro Gln Glu Leu Leu Ala
            20

<210> SEQ ID NO 468
<211> LENGTH: 22
<212> TYPE: PRT
<213> ORGANISM: Shigella flexneri

<400> SEQUENCE: 468

Tyr Leu Lys Val Gly Glu Asn Gln Leu Arg Arg Leu Ser Arg Leu Pro
1               5                   10                  15

Gln Glu Leu Leu Ala Leu
            20

<210> SEQ ID NO 469
<211> LENGTH: 23
<212> TYPE: PRT
<213> ORGANISM: Shigella flexneri

<400> SEQUENCE: 469

Leu Lys Tyr Leu Lys Val Gly Glu Asn Gln Leu Arg Arg Leu Ser Arg
1               5                   10                  15

Leu Pro Gln Glu Leu Leu Ala
            20

<210> SEQ ID NO 470
<211> LENGTH: 23
<212> TYPE: PRT
<213> ORGANISM: Shigella flexneri

<400> SEQUENCE: 470

Lys Tyr Leu Lys Val Gly Glu Asn Gln Leu Arg Arg Leu Ser Arg Leu
1               5                   10                  15

Pro Gln Glu Leu Leu Ala Leu
            20

<210> SEQ ID NO 471
<211> LENGTH: 24
<212> TYPE: PRT
<213> ORGANISM: Shigella flexneri
```

<400> SEQUENCE: 471

Ser Leu Lys Tyr Leu Lys Val Gly Glu Asn Gln Leu Arg Arg Leu Ser
1               5                   10                  15

Arg Leu Pro Gln Glu Leu Leu Ala
            20

<210> SEQ ID NO 472
<211> LENGTH: 24
<212> TYPE: PRT
<213> ORGANISM: Shigella flexneri

<400> SEQUENCE: 472

Leu Lys Tyr Leu Lys Val Gly Glu Asn Gln Leu Arg Arg Leu Ser Arg
1               5                   10                  15

Leu Pro Gln Glu Leu Leu Ala Leu
            20

<210> SEQ ID NO 473
<211> LENGTH: 24
<212> TYPE: PRT
<213> ORGANISM: Shigella flexneri

<400> SEQUENCE: 473

Lys Tyr Leu Lys Val Gly Glu Asn Gln Leu Arg Arg Leu Ser Arg Leu
1               5                   10                  15

Pro Gln Glu Leu Leu Ala Leu Asp
            20

<210> SEQ ID NO 474
<211> LENGTH: 25
<212> TYPE: PRT
<213> ORGANISM: Shigella flexneri

<400> SEQUENCE: 474

Gln Ala Val Arg Leu Leu Lys Ile Cys Leu Asp Thr Arg Glu Pro Val
1               5                   10                  15

Leu Asn Leu Ser Leu Leu Lys Leu Arg
            20                  25

<210> SEQ ID NO 475
<211> LENGTH: 25
<212> TYPE: PRT
<213> ORGANISM: Shigella flexneri

<400> SEQUENCE: 475

Gln Ser Leu Lys Tyr Leu Lys Val Gly Glu Asn Gln Leu Arg Arg Leu
1               5                   10                  15

Ser Arg Leu Pro Gln Glu Leu Leu Ala
            20                  25

<210> SEQ ID NO 476
<211> LENGTH: 25
<212> TYPE: PRT
<213> ORGANISM: Shigella flexneri

<400> SEQUENCE: 476

Ser Leu Lys Tyr Leu Lys Val Gly Glu Asn Gln Leu Arg Arg Leu Ser
1               5                   10                  15

Arg Leu Pro Gln Glu Leu Leu Ala Leu
            20                  25

<210> SEQ ID NO 477
<211> LENGTH: 25
<212> TYPE: PRT
<213> ORGANISM: Shigella flexneri

<400> SEQUENCE: 477

Leu Lys Tyr Leu Lys Val Gly Glu Asn Gln Leu Arg Arg Leu Ser Arg
1               5                   10                  15

Leu Pro Gln Glu Leu Leu Ala Leu Asp
            20                  25

<210> SEQ ID NO 478
<211> LENGTH: 26
<212> TYPE: PRT
<213> ORGANISM: Shigella flexneri

<400> SEQUENCE: 478

Arg Ile Gln Ala Val Arg Leu Leu Lys Ile Cys Leu Asp Thr Arg Glu
1               5                   10                  15

Pro Val Leu Asn Leu Ser Leu Leu Lys Leu
            20                  25

<210> SEQ ID NO 479
<211> LENGTH: 26
<212> TYPE: PRT
<213> ORGANISM: Shigella flexneri

<400> SEQUENCE: 479

Ile Gln Ala Val Arg Leu Leu Lys Ile Cys Leu Asp Thr Arg Glu Pro
1               5                   10                  15

Val Leu Asn Leu Ser Leu Leu Lys Leu Arg
            20                  25

<210> SEQ ID NO 480
<211> LENGTH: 26
<212> TYPE: PRT
<213> ORGANISM: Shigella flexneri

<400> SEQUENCE: 480

Gln Ser Leu Lys Tyr Leu Lys Val Gly Glu Asn Gln Leu Arg Arg Leu
1               5                   10                  15

Ser Arg Leu Pro Gln Glu Leu Leu Ala Leu
            20                  25

<210> SEQ ID NO 481
<211> LENGTH: 27
<212> TYPE: PRT
<213> ORGANISM: Shigella flexneri

<400> SEQUENCE: 481

Arg Ile Gln Ala Val Arg Leu Leu Lys Ile Cys Leu Asp Thr Arg Glu
1               5                   10                  15

Pro Val Leu Asn Leu Ser Leu Leu Lys Leu Arg
            20                  25

<210> SEQ ID NO 482
<211> LENGTH: 28
<212> TYPE: PRT
<213> ORGANISM: Shigella flexneri

<400> SEQUENCE: 482

Asn Arg Ile Gln Ala Val Arg Leu Leu Lys Ile Cys Leu Asp Thr Arg

```
                1               5                   10                  15

Glu Pro Val Leu Asn Leu Ser Leu Leu Lys Leu Arg
            20                  25

<210> SEQ ID NO 483
<211> LENGTH: 28
<212> TYPE: PRT
<213> ORGANISM: Shigella flexneri

<400> SEQUENCE: 483

Arg Ile Gln Ala Val Arg Leu Leu Lys Ile Cys Leu Asp Thr Arg Glu
1               5                   10                  15

Pro Val Leu Asn Leu Ser Leu Leu Lys Leu Arg Ser
            20                  25

<210> SEQ ID NO 484
<211> LENGTH: 29
<212> TYPE: PRT
<213> ORGANISM: Shigella flexneri

<400> SEQUENCE: 484

Glu Asn Arg Ile Gln Ala Val Arg Leu Leu Lys Ile Cys Leu Asp Thr
1               5                   10                  15

Arg Glu Pro Val Leu Asn Leu Ser Leu Leu Lys Leu Arg
            20                  25

<210> SEQ ID NO 485
<211> LENGTH: 29
<212> TYPE: PRT
<213> ORGANISM: Shigella flexneri

<400> SEQUENCE: 485

Arg Ile Gln Ala Val Arg Leu Leu Lys Ile Cys Leu Asp Thr Arg Glu
1               5                   10                  15

Pro Val Leu Asn Leu Ser Leu Leu Lys Leu Arg Ser Leu
            20                  25

<210> SEQ ID NO 486
<211> LENGTH: 30
<212> TYPE: PRT
<213> ORGANISM: Shigella flexneri

<400> SEQUENCE: 486

Asn Arg Ile Gln Ala Val Arg Leu Leu Lys Ile Cys Leu Asp Thr Arg
1               5                   10                  15

Glu Pro Val Leu Asn Leu Ser Leu Leu Lys Leu Arg Ser Leu
            20                  25                  30

<210> SEQ ID NO 487
<211> LENGTH: 10
<212> TYPE: PRT
<213> ORGANISM: Shigella flexneri

<400> SEQUENCE: 487

Thr Arg Val Leu Gln Ser Leu Gln Arg Leu
1               5                   10

<210> SEQ ID NO 488
<211> LENGTH: 10
<212> TYPE: PRT
<213> ORGANISM: Shigella flexneri

<400> SEQUENCE: 488
```

Arg Val Leu Gln Ser Leu Gln Arg Leu Thr
1               5                   10

<210> SEQ ID NO 489
<211> LENGTH: 10
<212> TYPE: PRT
<213> ORGANISM: Shigella flexneri

<400> SEQUENCE: 489

Ser Gln Arg Val Ala Asp Arg Leu Lys Ala
1               5                   10

<210> SEQ ID NO 490
<211> LENGTH: 10
<212> TYPE: PRT
<213> ORGANISM: Shigella flexneri

<400> SEQUENCE: 490

Gln Arg Val Ala Asp Arg Leu Lys Ala Ser
1               5                   10

<210> SEQ ID NO 491
<211> LENGTH: 10
<212> TYPE: PRT
<213> ORGANISM: Shigella flexneri

<400> SEQUENCE: 491

Arg Val Ala Asp Arg Leu Lys Ala Ser Gly
1               5                   10

<210> SEQ ID NO 492
<211> LENGTH: 11
<212> TYPE: PRT
<213> ORGANISM: Shigella flexneri

<400> SEQUENCE: 492

Gln Arg Val Ala Asp Arg Leu Lys Ala Ser Gly
1               5                   10

<210> SEQ ID NO 493
<211> LENGTH: 11
<212> TYPE: PRT
<213> ORGANISM: Shigella flexneri

<400> SEQUENCE: 493

Arg Val Ala Asp Arg Leu Lys Ala Ser Gly Leu
1               5                   10

<210> SEQ ID NO 494
<211> LENGTH: 12
<212> TYPE: PRT
<213> ORGANISM: Shigella flexneri

<400> SEQUENCE: 494

Gln Arg Val Ala Asp Arg Leu Lys Ala Ser Gly Leu
1               5                   10

<210> SEQ ID NO 495
<211> LENGTH: 13
<212> TYPE: PRT
<213> ORGANISM: Shigella flexneri

<400> SEQUENCE: 495

Arg Val Ala Leu Thr Trp Asn Asn Leu Arg Lys Thr Leu

```
1               5                   10

<210> SEQ ID NO 496
<211> LENGTH: 14
<212> TYPE: PRT
<213> ORGANISM: Shigella flexneri

<400> SEQUENCE: 496

Arg Val Ala Leu Thr Trp Asn Asn Leu Arg Lys Thr Leu Leu
1               5                   10

<210> SEQ ID NO 497
<211> LENGTH: 15
<212> TYPE: PRT
<213> ORGANISM: Shigella flexneri

<400> SEQUENCE: 497

Asp Arg Val Ala Leu Thr Trp Asn Asn Leu Arg Lys Thr Leu Leu
1               5                   10                  15

<210> SEQ ID NO 498
<211> LENGTH: 15
<212> TYPE: PRT
<213> ORGANISM: Shigella flexneri

<400> SEQUENCE: 498

Arg Val Ala Leu Thr Trp Asn Asn Leu Arg Lys Thr Leu Leu Val
1               5                   10                  15

<210> SEQ ID NO 499
<211> LENGTH: 10
<212> TYPE: PRT
<213> ORGANISM: Shigella flexneri

<400> SEQUENCE: 499

Leu Pro Gln Ala Leu Lys Asn Leu Arg Ala
1               5                   10

<210> SEQ ID NO 500
<211> LENGTH: 10
<212> TYPE: PRT
<213> ORGANISM: Shigella flexneri

<400> SEQUENCE: 500

Gln Ala Leu Lys Asn Leu Arg Ala Thr Arg
1               5                   10

<210> SEQ ID NO 501
<211> LENGTH: 10
<212> TYPE: PRT
<213> ORGANISM: Shigella flexneri

<400> SEQUENCE: 501

Ala Leu Lys Asn Leu Arg Ala Thr Arg Asn
1               5                   10

<210> SEQ ID NO 502
<211> LENGTH: 10
<212> TYPE: PRT
<213> ORGANISM: Shigella flexneri

<400> SEQUENCE: 502

Pro Gln Arg Val Ala Asp Arg Leu Lys Ala
1               5                   10
```

<210> SEQ ID NO 503
<211> LENGTH: 10
<212> TYPE: PRT
<213> ORGANISM: Shigella flexneri

<400> SEQUENCE: 503

Gln Arg Val Ala Asp Arg Leu Lys Ala Ser
1               5                   10

<210> SEQ ID NO 504
<211> LENGTH: 10
<212> TYPE: PRT
<213> ORGANISM: Shigella flexneri

<400> SEQUENCE: 504

Arg Val Ala Asp Arg Leu Lys Ala Ser Gly
1               5                   10

<210> SEQ ID NO 505
<211> LENGTH: 11
<212> TYPE: PRT
<213> ORGANISM: Shigella flexneri

<400> SEQUENCE: 505

Pro Gln Ala Leu Lys Asn Leu Arg Ala Thr Arg
1               5                   10

<210> SEQ ID NO 506
<211> LENGTH: 11
<212> TYPE: PRT
<213> ORGANISM: Shigella flexneri

<400> SEQUENCE: 506

Pro Gln Arg Val Ala Asp Arg Leu Lys Ala Ser
1               5                   10

<210> SEQ ID NO 507
<211> LENGTH: 11
<212> TYPE: PRT
<213> ORGANISM: Shigella flexneri

<400> SEQUENCE: 507

Gln Arg Val Ala Asp Arg Leu Lys Ala Ser Gly
1               5                   10

<210> SEQ ID NO 508
<211> LENGTH: 11
<212> TYPE: PRT
<213> ORGANISM: Shigella flexneri

<400> SEQUENCE: 508

Arg Val Ala Asp Arg Leu Lys Ala Ser Gly Leu
1               5                   10

<210> SEQ ID NO 509
<211> LENGTH: 12
<212> TYPE: PRT
<213> ORGANISM: Shigella flexneri

<400> SEQUENCE: 509

Leu Pro Gln Ala Leu Lys Asn Leu Arg Ala Thr Arg
1               5                   10

<210> SEQ ID NO 510

-continued

<210> SEQ ID NO 510
<211> LENGTH: 12
<212> TYPE: PRT
<213> ORGANISM: Shigella flexneri

<400> SEQUENCE: 510

Gln Arg Val Ala Asp Arg Leu Lys Ala Ser Gly Leu
1               5                   10

<210> SEQ ID NO 511
<211> LENGTH: 16
<212> TYPE: PRT
<213> ORGANISM: Shigella flexneri

<400> SEQUENCE: 511

Ser Leu Pro Ser Leu Pro Gln Ala Leu Lys Asn Leu Arg Ala Thr Arg
1               5                   10                  15

<210> SEQ ID NO 512
<211> LENGTH: 16
<212> TYPE: PRT
<213> ORGANISM: Shigella flexneri

<400> SEQUENCE: 512

Leu Pro Ser Leu Pro Gln Ala Leu Lys Asn Leu Arg Ala Thr Arg Asn
1               5                   10                  15

<210> SEQ ID NO 513
<211> LENGTH: 16
<212> TYPE: PRT
<213> ORGANISM: Shigella flexneri

<400> SEQUENCE: 513

Ser Leu Pro Gln Ala Leu Lys Asn Leu Arg Ala Thr Arg Asn Phe Leu
1               5                   10                  15

<210> SEQ ID NO 514
<211> LENGTH: 16
<212> TYPE: PRT
<213> ORGANISM: Shigella flexneri

<400> SEQUENCE: 514

Leu Pro Gln Ala Leu Lys Asn Leu Arg Ala Thr Arg Asn Phe Leu Thr
1               5                   10                  15

<210> SEQ ID NO 515
<211> LENGTH: 13
<212> TYPE: PRT
<213> ORGANISM: Shigella flexneri

<400> SEQUENCE: 515

Ser Leu Pro Gln Ala Leu Lys Asn Leu Arg Ala Thr Arg
1               5                   10

<210> SEQ ID NO 516
<211> LENGTH: 13
<212> TYPE: PRT
<213> ORGANISM: Shigella flexneri

<400> SEQUENCE: 516

Leu Pro Gln Ala Leu Lys Asn Leu Arg Ala Thr Arg Asn
1               5                   10

<210> SEQ ID NO 517
<211> LENGTH: 13
<212> TYPE: PRT

<213> ORGANISM: Shigella flexneri

<400> SEQUENCE: 517

Ala Leu Lys Asn Leu Arg Ala Thr Arg Asn Phe Leu Thr
1               5                   10

<210> SEQ ID NO 518
<211> LENGTH: 13
<212> TYPE: PRT
<213> ORGANISM: Shigella flexneri

<400> SEQUENCE: 518

Arg Val Ala Leu Thr Trp Asn Asn Leu Arg Lys Thr Leu
1               5                   10

<210> SEQ ID NO 519
<211> LENGTH: 13
<212> TYPE: PRT
<213> ORGANISM: Shigella flexneri

<400> SEQUENCE: 519

Pro Gln Arg Val Ala Asp Arg Leu Lys Ala Ser Gly Leu
1               5                   10

<210> SEQ ID NO 520
<211> LENGTH: 14
<212> TYPE: PRT
<213> ORGANISM: Shigella flexneri

<400> SEQUENCE: 520

Pro Ser Leu Pro Gln Ala Leu Lys Asn Leu Arg Ala Thr Arg
1               5                   10

<210> SEQ ID NO 521
<211> LENGTH: 14
<212> TYPE: PRT
<213> ORGANISM: Shigella flexneri

<400> SEQUENCE: 521

Ser Leu Pro Gln Ala Leu Lys Asn Leu Arg Ala Thr Arg Asn
1               5                   10

<210> SEQ ID NO 522
<211> LENGTH: 14
<212> TYPE: PRT
<213> ORGANISM: Shigella flexneri

<400> SEQUENCE: 522

Gln Ala Leu Lys Asn Leu Arg Ala Thr Arg Asn Phe Leu Thr
1               5                   10

<210> SEQ ID NO 523
<211> LENGTH: 14
<212> TYPE: PRT
<213> ORGANISM: Shigella flexneri

<400> SEQUENCE: 523

Arg Val Ala Leu Thr Trp Asn Asn Leu Arg Lys Thr Leu Leu
1               5                   10

<210> SEQ ID NO 524
<211> LENGTH: 15
<212> TYPE: PRT
<213> ORGANISM: Shigella flexneri -continued

<400> SEQUENCE: 524

Leu Pro Ser Leu Pro Gln Ala Leu Lys Asn Leu Arg Ala Thr Arg
1               5                   10                  15

<210> SEQ ID NO 525
<211> LENGTH: 15
<212> TYPE: PRT
<213> ORGANISM: Shigella flexneri

<400> SEQUENCE: 525

Pro Ser Leu Pro Gln Ala Leu Lys Asn Leu Arg Ala Thr Arg Asn
1               5                   10                  15

<210> SEQ ID NO 526
<211> LENGTH: 15
<212> TYPE: PRT
<213> ORGANISM: Shigella flexneri

<400> SEQUENCE: 526

Leu Pro Gln Ala Leu Lys Asn Leu Arg Ala Thr Arg Asn Phe Leu
1               5                   10                  15

<210> SEQ ID NO 527
<211> LENGTH: 15
<212> TYPE: PRT
<213> ORGANISM: Shigella flexneri

<400> SEQUENCE: 527

Pro Gln Ala Leu Lys Asn Leu Arg Ala Thr Arg Asn Phe Leu Thr
1               5                   10                  15

<210> SEQ ID NO 528
<211> LENGTH: 15
<212> TYPE: PRT
<213> ORGANISM: Shigella flexneri

<400> SEQUENCE: 528

Asp Arg Val Ala Leu Thr Trp Asn Asn Leu Arg Lys Thr Leu Leu
1               5                   10                  15

<210> SEQ ID NO 529
<211> LENGTH: 15
<212> TYPE: PRT
<213> ORGANISM: Shigella flexneri

<400> SEQUENCE: 529

Arg Val Ala Leu Thr Trp Asn Asn Leu Arg Lys Thr Leu Leu Val
1               5                   10                  15

<210> SEQ ID NO 530
<211> LENGTH: 30
<212> TYPE: DNA
<213> ORGANISM: artificial
<220> FEATURE:
<223> OTHER INFORMATION: Oligo F-SspHI (NheI)

<400> SEQUENCE: 530
ctagctagcg ttaccgataa ataataactt                                30

<210> SEQ ID NO 531
<211> LENGTH: 30
<212> TYPE: DNA
<213> ORGANISM: artificial
<220> FEATURE:
<223> OTHER INFORMATION: Oligo R-SspHI (XhoI)

```
<400> SEQUENCE: 531
cgcctcgagt gaatggtgca gttgtgagcc                              30

<210> SEQ ID NO 532
<211> LENGTH: 30
<212> TYPE: DNA
<213> ORGANISM: artificial
<220> FEATURE:
<223> OTHER INFORMATION: Oligo R-SspHI-Nter (XhoI)

<400> SEQUENCE: 532
ccgctcgagc cgtgggccgt ggtagtccgg                              30

<210> SEQ ID NO 533
<211> LENGTH: 53
<212> TYPE: DNA
<213> ORGANISM: artificial
<220> FEATURE:
<223> OTHER INFORMATION: Oligo F-Tat (NdeI)

<400> SEQUENCE: 533
tatgatgtgc ggccgtaaga aacgtcgcca gcgtcgccgt ccgccgcaat gcg    53

<210> SEQ ID NO 534
<211> LENGTH: 55
<212> TYPE: DNA
<213> ORGANISM: artificial
<220> FEATURE:
<223> OTHER INFORMATION: Oligo R-Tat (NheI)

<400> SEQUENCE: 534
ctagcgcatt gcggcggacg gcgacgctgg cgacgtttct tacggccgca cagca  55

<210> SEQ ID NO 535
<211> LENGTH: 51
<212> TYPE: DNA
<213> ORGANISM: artificial
<220> FEATURE:
<223> OTHER INFORMATION: Oligo F-IpaH1.4

<400> SEQUENCE: 535
gtttaacttt aagaaggaga tatacatatg attaaatcaa ccaatataca g      51

<210> SEQ ID NO 536
<211> LENGTH: 60
<212> TYPE: DNA
<213> ORGANISM: artificial
<220> FEATURE:
<223> OTHER INFORMATION: Oligo R-IpaH1.4

<400> SEQUENCE: 536
cttatcgtcg tcatccttgt aatcgctagc tgcgatatga tttgagccgt tttcagacaa   60

<210> SEQ ID NO 537
<211> LENGTH: 60
<212> TYPE: DNA
<213> ORGANISM: artificial
<220> FEATURE:
<223> OTHER INFORMATION: Oligo F-IpaH2.5/IpaH4.5

<400> SEQUENCE: 537
gtttaacttt aagaaggaga tatacatatg attaaatcaa caaatataca ggtaatcggt   60

<210> SEQ ID NO 538
```

-continued

```
<211> LENGTH: 60
<212> TYPE: DNA
<213> ORGANISM: artificial
<220> FEATURE:
<223> OTHER INFORMATION: Oligo R-IpaH2.5

<400> SEQUENCE: 538
cttatcgtcg tcatccttgt aatcgctagc ggccagtacc tcgtcagtca actgacggta    60

<210> SEQ ID NO 539
<211> LENGTH: 60
<212> TYPE: DNA
<213> ORGANISM: artificial
<220> FEATURE:
<223> OTHER INFORMATION: Oligo F-IpaH3

<400> SEQUENCE: 539
gtttaacttt aagaaggaga tatacatatg ttaccgataa ataataactt ttcattgtcc    60

<210> SEQ ID NO 540
<211> LENGTH: 60
<212> TYPE: DNA
<213> ORGANISM: artificial
<220> FEATURE:
<223> OTHER INFORMATION: Oligo R-IpaH3

<400> SEQUENCE: 540
cttatcgtcg tcatccttgt aatcgctagc gtcagctgac ggtaaatctg ctgttacagt    60

<210> SEQ ID NO 541
<211> LENGTH: 60
<212> TYPE: DNA
<213> ORGANISM: artificial
<220> FEATURE:
<223> OTHER INFORMATION: Oligo F-IpaH4.5

<400> SEQUENCE: 541
gtttaacttt aagaaggaga tatacatatg aaaccgatca acaatcattc ttttttcgt    60

<210> SEQ ID NO 542
<211> LENGTH: 60
<212> TYPE: DNA
<213> ORGANISM: artificial
<220> FEATURE:
<223> OTHER INFORMATION: Oligo F-IpaH7.8

<400> SEQUENCE: 542
gtttaacttt aagaaggaga tatacatatg ttctctgtaa ataatacaca ctcatcagtt    60

<210> SEQ ID NO 543
<211> LENGTH: 60
<212> TYPE: DNA
<213> ORGANISM: artificial
<220> FEATURE:
<223> OTHER INFORMATION: Oligo R-IpaH7.8

<400> SEQUENCE: 543
cttatcgtcg tcatccttgt aatcgctagc tgaatggtgc agtcgtgagc cgttttcaga    60

<210> SEQ ID NO 544
<211> LENGTH: 60
<212> TYPE: DNA
<213> ORGANISM: artificial
<220> FEATURE:
<223> OTHER INFORMATION: Oligo F-IpaH9.8

<400> SEQUENCE: 544
```

```
gtttaacttt aagaaggaga tatacatatg ttaccgataa ataataactt ttcattgccc    60
```

<210> SEQ ID NO 545
<211> LENGTH: 60
<212> TYPE: DNA
<213> ORGANISM: artificial
<220> FEATURE:
<223> OTHER INFORMATION: Oligo R-IpaH9.8

<400> SEQUENCE: 545

```
cttatcgtcg tcatccttgt aatcgctagc tgaatggtgc agttgtgagc cgttttcaaa    60
```

<210> SEQ ID NO 546
<211> LENGTH: 60
<212> TYPE: DNA
<213> ORGANISM: artificial
<220> FEATURE:
<223> OTHER INFORMATION: Oligo F-SspH2

<400> SEQUENCE: 546

```
gtttaacttt aagaaggaga tatacatatg ccctttcata ttggaagcgg atgtcttccc    60
```

<210> SEQ ID NO 547
<211> LENGTH: 60
<212> TYPE: DNA
<213> ORGANISM: artificial
<220> FEATURE:
<223> OTHER INFORMATION: Oligo R-SspH2

<400> SEQUENCE: 547

```
cttatcgtcg tcatccttgt aatcgctagc gttacgacgc cactgaacgt tcagatagct    60
```

<210> SEQ ID NO 548
<211> LENGTH: 60
<212> TYPE: DNA
<213> ORGANISM: artificial
<220> FEATURE:
<223> OTHER INFORMATION: Oligo F-SlrP

<400> SEQUENCE: 548

```
gtttaacttt aagaaggaga tatacatatg tttaatatta ctaatataca atctacggca    60
```

<210> SEQ ID NO 549
<211> LENGTH: 60
<212> TYPE: DNA
<213> ORGANISM: artificial
<220> FEATURE:
<223> OTHER INFORMATION: Oligo R-SlrP

<400> SEQUENCE: 549

```
cttatcgtcg tcatccttgt aatcgctagc tcgccagtag gcgctcatga gcgagctcac    60
```

<210> SEQ ID NO 550
<211> LENGTH: 13
<212> TYPE: PRT
<213> ORGANISM: Shigella flexneri

<400> SEQUENCE: 550

Ser Gln Arg Val Ala Asp Arg Leu Lys Ala Ser Gly Leu
1               5                   10

<210> SEQ ID NO 551
<211> LENGTH: 12
<212> TYPE: PRT
<213> ORGANISM: Shigella flexneri

<400> SEQUENCE: 551

Gln Arg Val Ala Asp Arg Leu Lys Ala Ser Gly Leu
1               5                   10

<210> SEQ ID NO 552
<211> LENGTH: 20
<212> TYPE: PRT
<213> ORGANISM: artificial
<220> FEATURE:
<223> OTHER INFORMATION: consensus sequence LRX repeat
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid
<220> FEATURE:
<221> NAME/KEY: misc_feature
<222> LOCATION: (15)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid

<400> SEQUENCE: 552

Leu Thr Ser Leu Pro Xaa Leu Pro Xaa Xaa Leu Xaa Xaa Leu Xaa Xaa
1               5                   10                  15

Xaa Xaa Asn Xaa
            20

<210> SEQ ID NO 553
<211> LENGTH: 21
<212> TYPE: PRT
<213> ORGANISM: artificial
<220> FEATURE:
<223> OTHER INFORMATION: consensus Leucine-rich repeat
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (16)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid

<400> SEQUENCE: 553

Leu Xaa Xaa Leu Pro Xaa Xaa Leu Pro Xaa Xaa Leu Xaa Xaa Leu Xaa
1               5                   10                  15

Xaa Xaa Xaa Asn Xaa
            20

<210> SEQ ID NO 554
<211> LENGTH: 40
<212> TYPE: PRT
<213> ORGANISM: artificial
<220> FEATURE:
<223> OTHER INFORMATION: consensus sequence leucine repeat
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid

<400> SEQUENCE: 554

Leu Xaa Ala Ala Xaa Ala Ala Xaa Ala Ala Xaa Ala Ala Xaa Ala Ala
1               5                   10                  15

Xaa Ala Ala Leu Xaa Ala Ala Xaa Ala Ala Xaa Ala Ala Pro Xaa Ala
            20                  25                  30

Ala Xaa Ala Ala Xaa Ala Ala Pro
        35                  40

<210> SEQ ID NO 555
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

```
<400> SEQUENCE: 555

His His His His His His
1               5

<210> SEQ ID NO 556
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 556

Asp Tyr Lys Asp Asp Asp Asp Lys
1               5
```

CELL-PENETRATING BACTERIAL E3-UBIQITIN-LIGASES FOR USE IN IMMUNOTHERAPY

This application is a continuation application of U.S. patent application Ser. No. 15/022,827, filed on Mar. 17, 2016, which claims benefit from International Application No. PCT/EP2014/070142, which was filed on Sep. 22, 2014 which in turn claims priority to European Patent Application No. 13185412.7 filed on Sep. 20, 2013, wherein the entireties of said patent applications are incorporated herein by reference. Also, the entire contents of the ASCII text file entitled "G6113-00010 SL.txt" having a size of 233,937 bytes, and created on Jul. 20, 2018, is incorporated herein by reference.

SEQUENCE STATEMENT

The instant application contains a Sequence Listing which has been submitted electronically and is hereby incorporated by reference in its entirety. Said ASCII copy is name G6113_00010SL.text and is 63 bytes in size.

FIELD OF THE INVENTION

The present invention relates to isolated recombinant effector proteins of type III secretion system (T3SS)-containing bacteria of the genus *Salmonella* or *Shigella* or variants, fragments or immunomodulatory domains thereof, for use in immunotherapy.

Immunotherapy is the treatment of disease by inducing, enhancing, or suppressing an immune response. The active agents of immunotherapy are called immunomodulators. The present invention relates to the use of cell-penetrating bacterial E3 ubiqitin ligases from bacteria of the genus *Salmonella* or *Shigella* as immunomodulators. Agents that inhibit or prevent activity of the immune system are called immunosuppressives. Optionally the present invention relates to the use of cell-penetrating bacterial E3 ubiqtin ligases from bacteria of the genus *Salmonella* or *Shigella* as immunosuppressives.

In particular the present invention relates to cell-penetrating recombinant effector proteins of type III secretion system (T3SS)-containing bacteria of the genus *Salmonella* or *Shigella* that modulate cytokines and/or cytokine receptors of eukaryotic cells and/or eukaryotic genes which respond to cytokines, after said effector proteins have autonomously penetrated into said eukaryotic cells. Alternatively the present invention relates to of cell-penetrating variants, fragments or immunomodulatory domains of cell-penetrating effector proteins of type III secretion system (T3SS)-containing bacteria of the genus *Salmonella* or *Shigella*, wherein said variants, fragments or immunomodulatory domains modulate cytokines and/or cytokine receptors of eukaryotic cells and/or eukaryotic genes which respond to cytokines, after said variants, fragments or immunomodulatory domains have autonomously penetrated into said eukaryotic cells.

In one aspect the present invention relates to the use of isolated recombinant effector proteins of type III secretion system (T3SS)-containing bacteria of the genus *Salmonella* or *Shigella*, wherein said effector proteins are characterized in that they are recombinantly produced or chemically synthesized, comprise an E3 ubiquitin ligase domain, preferably an Novel E3 ubiquitin ligase, optionally comprise at least one leucine-rich repeat and are cell-penetrating proteins, which translocate into eukaryotic cells without the requirement of a bacterial T3SS, or variants, fragments or immunomodulatory domains of said effector proteins, for the preparation of a pharmaceutical composition for regulating inflammatory reactions of the immune system, treating diseases caused by autoimmunity, treating acute inflammation or chronic inflammation, treating of inflammatory disorders, and/or suppressing the immune system.

Moreover the present invention relates to a pharmaceutical composition, comprising an isolated effector protein of a type III secretion system (T3SS)-containing bacterium of the genus *Salmonella* or *Shigella*, wherein the effector protein is characterized in that it is recombinantly produced or chemically synthesized, comprises an E3 ubiquitin ligase domain, optionally comprises at least one leucine-rich repeat, and is a cell-penetrating protein, which translocates into eukaryotic cells without the requirement of a bacterial T3SS.

The present invention further relates to the use of cell-penetrating effector proteins of type III secretion system (T3SS)-containing bacteria of the genus *Salmonella* or *Shigella* or variants, fragments and immunomodulatory domains of said effector proteins, for delivering cargo molecules into eukaryotic cells. Preferably the present invention relates to the use of cell-penetrating effector proteins of type III secretion system (T3SS)-containing bacteria of the genus *Salmonella* or *Shigella* or variants, fragments and immunomodulatory domains of said effector proteins, for the preparation of pharmaceutical compositions for delivering linked cargo molecules into eukaryotic cells. Preferably said effector proteins, or variants, fragments and immunomodulatory domains thereof, that are linked to said cargo molecules modulate cytokines and/or cytokine receptors of eukaryotic cells and/or eukaryotic genes which respond to cytokines, after said variants, fragments or immunomodulatory domains have autonomously penetrated into said eukaryotic cells.

Furthermore the present invention relates to the use of an isolated effector protein of a type III secretion system (T3SS)-containing bacterium of the genus *Salmonella* or *Shigella*, wherein the effector protein is characterized in that it is recombinantly produced or chemically synthesized, comprises an E3 ubiquitin ligase domain, preferably a Novel E3 ubiquitin ligase, optionally comprises at least one—leucine-rich repeat, is a cell-penetrating protein, which translocates into eukaryotic cells without the requirement of a bacterial T3SS, or the use of a variant or fragment of said effector protein for delivering at least one cargo molecule across the membrane of a eukaryotic cell, wherein the fusion construct of cargo molecule and said effector protein or variant or fragment thereof is a cell-penetrating construct, which translocates into eukaryotic cells without the requirement of a bacterial T3SS.

Hence the present invention provides pharmaceutical compositions comprising an isolated effector protein of a type III secretion system (T3SS)-containing bacterium of the genus *Salmonella* or *Shigella*, wherein the effector protein is characterized in that it is recombinantly produced or chemically synthesized, comprises an E3 ubiquitin ligase domain, preferably a Novel E3 ubiquitin ligase, optionally comprises at least one leucine-rich repeat, is a cell-penetrating protein, which translocates into eukaryotic cells without the requirement of a bacterial T3SS, or the use of a variant or fragment of said effector protein for delivering at least one cargo molecule across the membrane of a eukaryotic cell, wherein the fusion construct of cargo molecule and said effector protein or variant or fragment thereof is a cell-penetrating construct, which translocates into eukaryotic cells without the requirement of a bacterial T3SS.

BACKGROUND OF THE INVENTION

Immunosuppression involves reactions that reduce the activation or efficiency of the immune system. Immunosuppressive reactions are either due to intentional medical actions or derivable from a natural background and are, thus, largely pathogenic for the body.

In the first case of intentional medical actions, immunosuppressive activity of compounds is used for the modulation, in particular the controlled and purposeful inhibition or prevention of the activity of the immune system. The corresponding compounds are generally summarized as immunosuppressants or immuno-suppressive drugs. Immunosuppressive drugs are a heterogenic collection including the following groups: glucocorticoids, cytostatics, antibodies, drugs acting on immunophilins, TNF-binding proteins and interferons. Immunosuppressives are used, for example, to prevent the rejection of transplanted organs and tissues (e.g., bone marrow, heart, kidney, liver), treat autoimmune diseases or diseases that are most likely of autoimmune origin (e.g., rheumatoid arthritis, multiple sclerosis, myasthenia gravis, systemic lupus erythematosus, sarcoidosis, focal segmental glomerulosclerosis, Crohn's disease, Behcet's Disease, pemphigus, and ulcerative colitis) or treat non-autoimmune inflammatory diseases (e.g., long term allergic asthma control).

In the second case of natural background, immunosuppression can occur, for example, in malnutrition, aging, many types of cancer (such as leukemia, lymphoma, multiple myeloma), and certain chronic infections such as acquired immunodeficiency syndrome (AIDS). The unwanted effect of this immunosuppression is immunodeficiency that results in increased susceptibility to pathogens such as bacteria and virus. Moreover many microbial pathogens have evolved, in order to successfully infect a host organism, intriguing mechanisms to subvert host defenses (Sansonetti, 2004). These microbes circumvent and undermine innate and specific host defenses.

One of the most fascinating and widespread pathogenicity modules of Gram-negative pathogens is the type III secretion system (T3SS) that targets essential cytoplasmic processes of the host cell by directly injecting so-called effector proteins into the cytoplasm via a molecular injection machine ('molecular syringe') (Cornelis, 2002a; Cornelis, 2002b; Cornelis & Wolf-Watz, 1997). Bacterial effector proteins interfere with signaling mechanisms of the host cells, including those triggering immune responses. Especially pathogenic bacteria of the genus Yersinia, Shigella, or Salmonella harbor a wide range of effector proteins that target signaling mechanisms such as MAPK signaling cascades or pathways leading to repression of NF-κB activation (Matsumoto & Young, 2009). Moreover numerous effector proteins of pathogenic bacteria, which utilize type III or IV secretion systems to deliver effector proteins into host cells, usurp the host ubiquitin pathways (Hicks and Galan, 2010; Angot, 2007).

Ubiquitinylation results in the covalent attachment of ubiquitin to a lysine residue on a target protein. Following the initial conjugation, subsequent ubiquitin molecules can be ligated to one of seven lysines in the previously attached ubiquitin molecule, resulting in polyubiquitinylation of various linkages. Therefore, a substrate can be monoubiquitinylated at a single lysine residue, multi-ubiquitinylated at multiple lysine residues, or polyubiquitinylated at one or more lysine residues. The type of ubiquitinylation and the topology of the ubiquitin chains formed direct substrate fate. Ubiquitinylation can signal for proteasome-dependent degradation or function as non-proteolytic signals important for DNA repair, signal transduction and vesicular trafficking.

Ubiquitinylation involves an enzymatic cascade resulting in the formation of an isopeptide bond between ubiquitin and internal lysine residues of a substrate protein. This process involves an ubiquitin-activating enzyme (E1), which forms a thioester bond between a catalytic cysteine and the carboxy terminal glycine residue of ubiquitin. The ubiquitin is then transferred to an ubiquitin-conjugating enzyme (E2). Finally, an ubiquitin ligase (E3) facilitates the covalent conjugation of ubiquitin from an ubiquitin-loaded E2 to one or more lysine residues in the substrate. Therefore, E3 ubiquitin ligases confer specificity to the reaction through substrate binding. E3 ubiquitin ligases are defined by their ability to facilitate the transfer of ubiquitin from a cognate E2 to a specific substrate. There are two major known types of E3 ubiquitin ligases in eukaryotes, which possess distinct structural and mechanistic properties: the RING (really interesting new gene)/U-box domain and the HECT (homologous to E6-associated protein C terminus) domain. Bacterial effector proteins belonging to these ubiquitin ligase families are e.g. NleG2-3 from *Escherichia coli* ssp., LubX from *Legionella* spp. or SopA from *Salmonella* ssp (Hicks and Galan, 2010; Angot, 2007). In addition to that, another family of E3 ubiquitin ligases has been described that possesses a structural domain (termed NEL-domain for Novel E3 Ligase), which is distinct from either the RING or HECT domains (see e.g. Hicks and Galan, 2010). NEL E3 ligases comprise a large family of a bacterial effector proteins encoded by pathogenic bacteria, including *Shigella* ssp., *Salmonella* ssp., *Yersinia* spp., *Pseudomonas* spp., and *Escherichia coli* ssp. Examples of bacterial NEL E3 Ubiquitin ligases are IpaH1, IpaH1.4, IpaH2, IpaH2.5, IpaH3, IpaH4, IpaH4.5, IpaH5, IpaH6, IpaH7, IpaH7.8, IpaH9.8 (from *Shigella* spp.); Slrp, SspH1, SspH2 (from *Salmonella* spp.); YPA_3361, YPA_3364 (from *Yersinia* spp.); PflO1_4099, PflO1_4565, PP_2212, PP_2394, PSPTO_1492, PSPTO_4093 (from *Pseudomonas* spp.); EcoI5_01000486, EcoI5_01001536, EcoI5_01001967, EcoI5_01003958, EcoI5_01004202, EcoI5_01004539, EcoI5_01004764, EcoI5_01004830, and EcoI5_01004885 (from *Escherichia coli* spp.) (Hicks and Galan, 2010). Several of these bacterial NEL E3 ligases comprise an N-terminal leucine-rich repeat (LRR) domain and are therefore also classified as leucine-rich repeat (LRR) proteins. If said LRR is a LRR of the LPX-subtype, the proteins are called effector proteins of the LPX-subtype or effector proteins of LPX-family (Miao et al, 1999). Examples of effector proteins which comprise a NEL-domain and belong to the LPX-subtype are SspH1, SspH2, SlrP, IpaH4.5, IpaH7.8, and IpaH9.8.

For T3SS-dependent translocation of effector proteins, bacterial attachment to target cells is essential. Only cells that are contacted directly are infected via the T3SS injection machine. Surprisingly, it was recently shown that the *Yersinia* protein YopM, a secreted effector protein, is able to translocate into eukaryotic cells independently of the T3SS. Besides a T3SS-dependent translocation, YopM is able to autonomously penetrate the eukaryotic cell membrane and integrate into the cell cytosol (Rüter et al, 2010; Scharnert et al, 2013). It was suggested that the N-terminal α-helices of YopM mediate autonomous cell-penetration. Moreover it was shown that YopM can thereby deliver heterologous cargos into eukaryotic cells. Furthermore it was shown that YopM down-regulates the transcription of pro-inflammatory cytokines (e. g. TNFα, IL-12, IL-15, and IL-18) after autonomous penetration into host cells (Rüter et al, 2010).

Cell-penetrating peptides (cell-penetrating proteins, cell-permeable protein, CPPs) are proteins that are able to cross the cell membrane on their own. CPPs such as the trans-activator of transcription (Tat) protein encoded by the human immunodeficiency virus type I (HIV-1) are usually relatively short proteins or peptides (5-40 amino acids) with the ability to enter cells by different mechanisms (Frankel & Pabo, 1988) (Green & Loewenstein, 1988). Since the early studies on CPPs, numerous natural and synthetic peptides have been described to penetrate eukaryotic plasma membranes and deliver heterogeneous cargos into the host cell (Langel, 2011). The uptake mechanisms of most CPPs are poorly understood. Various uptake mechanisms of CPPs are discussed in the literature. It appears that different mechanisms can be involved in uptake of the diverse CPPs rather than a general mechanism. Initial binding of CPP to the plasma membrane seems to depend on electrostatic interactions of positively charged amino acids with negatively charged plasma membrane components. Two different models are currently discussed describing potential uptake mechanisms that follow the initial binding of the CPP to the plasma membrane. CPP uptake might be mediated by different endocytic uptake mechanisms including macropinocytosis, Clathrin-dependent and independent endocytosis, and Caveolae-dependent endocytosis, wherein after uptake, CPP need to escape from endosomal compartments during intra-cellular transport. Moreover internalization of the CPPs might occur by direct membrane penetration mechanisms, including inverted micelle and pore formation (Trabulo et al, 2010). CPPs have the ability to cross cellular membranes, either alone or in association with cargo molecules.

YopM was the first identified bacterial CPP and opened the class of bacteria-derived CPPs within the heterogeneous group of CPPs (Rüter et al, 2010). YopM shares the ability of known CPPs to translocate across eukaryotic plasma membranes and it has the capacity to deliver molecular cargos such as GFP intracellularly. However, YopM does not show sequence homologies to known CPPs, indicating unique features that promote the uptake of YopM.

Crossing the plasma membrane is a prerequisite for intracellular targeted drug and/or compound delivery (for example in gene therapy where the gene/nucleic acid has to be delivered to an intracellular compartment). Cell penetrating peptides (CPPs) are known to transport cargo molecules attached to them into cells primarily by endocytosis. Nevertheless, there is an ongoing need in the art to provide compounds, which are able to cross the plasma membrane of higher cells. Especially in the field of immunotherapy, there is a great need for improved strategies for delivering immunomodulatory agents into cells. Moreover, self-delivering immunomodulatory agents would greatly improve the current immunotherapeutic strategies.

Although the above-mentioned immunosuppressive drugs are valuable medical tools, they are not without side effects and risks. Because the majority of them act non-selectively, the immune system is less able to resist infections and the spread of malignant cells. Furthermore, the production of the majority of immunomodulatory drugs is time-consuming and expensive. Therefore, there is a need for the provision of new, effective, cell-specific, selectively acting, and inexpensive immunomodulators, particularly immunosuppressants, preferably with lower side effects and risks.

The solution to the above-indicated technical problem is achieved by providing the embodiments as characterized herein and summarized below.

SUMMARY OF THE INVENTION

In a first aspect, the present invention provides a pharmaceutical composition A, comprising an isolated effector protein of a type III secretion system (T3SS)-containing bacterium of the genus *Salmonella* or *Shigella*, wherein the effector protein is characterized in that it a) is recombinantly produced or chemically synthesized, b) comprises an E3 ubiquitin ligase repeat, c) optionally comprises at least one leucine-rich repeat, and d) is a cell-penetrating protein, which translocates into eukaryotic cells without the requirement of a bacterial T3SS.

Alternatively, the present invention provides a pharmaceutical composition B, comprising a variant, fragment, or immunomodulatory domain of an effector protein as defined in the in the previous paragraph.

Optionally the pharmaceutical composition B can be characterized in that said variant, fragment, or immunomodulatory domain is a cell-penetrating protein, which translocates into eukaryotic cells without the requirement of a bacterial T3SS.

The pharmaceutical composition B can be characterized in that optionally said variant, fragment, or immunomodulatory domain comprises an E3 ubiquitin ligase domain and optionally at least one leucine-rich repeat.

Optionally, the pharmaceutical composition B can be characterized in that said variant, fragment, or immunomodulatory domain comprises an E3 ubiquitin ligase domain and optionally at least one leucine-rich repeat.

The pharmaceutical composition A or B as described above can be further characterized in that said type III secretion system (T3SS)-containing bacterium is classified as *Salmonella bongori, Salmonella enterica, Salmonella subterranean, Salmonella typhi, Salmonella typhimurium, Salmonella enterica* serovar *typhimurium, Salmonella enteritidis, Salmonella pullorum, Salmonella dublin, Salmonella arizonae, Salmonella choleraesius, Shigella flexneri, Shigella dysenteriae, Shigella sonnei*, or *Shigella boydii.*

Optionally the pharmaceutical composition A or B can be characterized in that the E3 ubiquitin ligase domain is classified as Novel E3 Ligase.

Optionally the pharmaceutical composition A or B can be characterized in that the E3 ubiquitin ligase domain is closer to the C-terminus of said effector protein than to the N-terminus of said effector protein.

Optionally the pharmaceutical composition A or B can be characterized in that the leucine-rich repeat(s) is/are a leucine-rich repeat of the LPX-subtype.

Optionally the pharmaceutical composition A can be characterized in that the leucine-rich repeat(s) is/are closer to the N-terminus of said effector protein than to the C-terminus of said effector protein.

Optionally the pharmaceutical composition A or B can be characterized in that said effector protein is a bacterial effector protein of the LPX-Subtype.

Optionally the pharmaceutical composition A or B can be characterized in that said effector protein is SlrP, SspH1, SspH2, IpaH1.4, IpaH2.5, IpaH3, IpaH4.5, IpaH7.8, and IpaH9.8.

Optionally the pharmaceutical composition A or B can be characterized in that said effector protein has an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 9.

Optionally the pharmaceutical composition A or B can be characterized in that said effector protein is encoded by a polynucleotide selected from the group consisting of SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 18.

Optionally the pharmaceutical composition A or B can be characterized in that said effector protein, variant, fragment or immunomodulatory domain comprises an amino acid sequence selected from the group consisting of SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, or SEQ ID NO: 27.

Optionally the pharmaceutical composition A or B can be characterized in that said effector protein, variant, fragment or immunomodulatory domain comprises at least one Leucine-rich repeat, preferably at least one Leucine-rich repeat that is comprised in an amino acid sequence selected from the group consisting of SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, or SEQ ID NO: 36.

Optionally the pharmaceutical composition A or B can be characterized in that said effector protein, variant, fragment or immunomodulatory domain comprises at least one amino acid sequence selected from the group consisting of SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65 or SEQ ID NO: 550, and/or at least one amino acid sequence that corresponds to a C-terminally or N-terminally truncated fragment of an amino acid sequence selected from the group consisting of SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, or SEQ ID NO: 550.

Optionally the pharmaceutical composition A or B can be characterized in that the composition comprises no auxiliary agent which can cause the penetration of said effector protein into a eukaryotic cell.

Optionally the pharmaceutical composition A or B can be characterized in that the composition comprises no auxiliary agent selected from the group consisting of T3SS-containing bacterium, bacterium of the genus *Salmonella* or *Shigella*, and cell-penetrating molecule, wherein "cell-penetrating molecule" includes CPPs that are different from an effector protein as defined above and cell-penetrating nanoparticles.

Optionally the pharmaceutical composition A or B can be characterized in that said effector protein or variant, fragment or immunomodulatory domain thereof is linked to a cell-specific targeting agent.

Optionally the pharmaceutical composition A or B can be characterized in that said effector protein or variant, fragment or immunomodulatory domain thereof is linked to a cargo molecule, wherein optionally said cargo molecule displays a therapeutical and/or diagnostic activity and/or wherein optionally said cargo molecule comprises at least one compound selected from the group consisting of nucleic acids, polypeptides, organic molecules, small organic molecules, metals, nanoparticles, viruses, modified viruses, viral vectors, antibodies and/or plasmids.

Optionally the pharmaceutical composition A or B can be characterized in that said effector protein or variant, fragment or immunomodulatory domain thereof ubiquitinates itself and/or eukaryotic proteins after said effector protein or variant, fragment or immunomodulatory domain has autonomously penetrated into a eukaryotic cell.

Optionally the pharmaceutical composition A or B can be characterized in that said effector protein or variant, fragment or immunomodulatory domain thereof modulates cellular pathway(s) of the innate immune system of eukaryotic cells after it has autonomously penetrated into said eukaryotic cells.

Optionally the pharmaceutical composition A or B can be characterized in that said effector protein or variant, fragment or immunomodulatory domain thereof modulates cytokines and/or cytokine receptors of eukaryotic cells and/or eukaryotic genes which respond to cytokines of eukaryotic cells after said effector protein or variant, fragment or immunomodulatory domain has autonomously penetrated into said eukaryotic cells.

Optionally the pharmaceutical composition A or B can be characterized in that said effector protein or variant, fragment or immunomodulatory domain thereof downregulates the expression of cytokines and/or cytokine receptors after said effector protein or variant, fragment or immunomodulatory domain has autonomously penetrated into said eukaryotic cells.

Preferably the pharmaceutical composition A or B can be used in immunomodulatory therapy of animals or humans.

Optionally the pharmaceutical composition A or B can be used in immunosuppressive therapy of animals or humans.

Preferably the pharmaceutical composition A or B can be used in the regulation of inflammatory reactions of the immune system, treatment of diseases caused by autoimmunity, acute inflammation or chronic inflammation, treatment of inflammatory disorders, and/or for suppressing the immune system.

Furthermore, the pharmaceutical composition A or B may be for use in delivering cargo molecules across the cell membrane of a eukaryotic cell.

In one embodiment the present invention provides a method of treatment of a disease or of diseases caused by autoimmunity, treatment of acute inflammation, chronic inflammation, inflammatory disorders, pathogenic inflammatory reactions of the immune system, and/or a method of suppressing the immune system in a subject, comprising administering a in a therapeutically effective amount of a pharmaceutical composition A or B as defined above to said subject.

In another embodiment the present invention provides a kit comprising the pharmaceutical composition A or B as defined above.

In a further aspect the present invention relates to the use of an isolated effector protein of a type III secretion system (T3SS)-containing bacterium of the genus *Salmonella* or *Shigella*, wherein the effector protein is characterized in that it
 a) is recombinantly produced or chemically synthesized
 b) comprises an E3 ubiquitin ligase domain, preferably an Novel E3 ubiquitin ligase
 c) optionally comprises at least one leucine-rich domain;

d) is a cell-penetrating protein, which translocates into eukaryotic cells without the requirement of a bacterial T3SS;

or to the use of a variant, fragment or immunomodulatory domain of said effector protein, for the preparation of a pharmaceutical composition for regulating inflammatory reactions of the immune system, treating diseases caused by autoimmunity, treating acute inflammation or chronic inflammation, treating of inflammatory disorders, and/or suppressing the immune system.

In another aspect the present invention relates to the use of an isolated effector protein of a type III secretion system (T3SS)-containing bacterium of the genus *Salmonella* or *Shigella*, wherein the effector protein is characterized in that it a) is recombinantly produced or chemically synthesized
b) comprises an E3 ubiquitin ligase domain, preferably an Novel E3 ubiquitin ligase
c) optionally comprises at least one leucine-rich domain;
d) is a cell-penetrating protein, which translocates into eukaryotic cells without the requirement of a bacterial T3SS;

or to the use of a variant, fragment of said effector protein for the preparation of a pharmaceutical composition for delivering at least one cargo molecule across the membrane of a eukaryotic cell, wherein the fusion construct of cargo molecule and said effector protein or variant or fragment thereof is a cell-penetrating construct, which translocates into eukaryotic cells without the requirement of a bacterial T3SS. Additionally, the effector protein can be e) linked to the at least one cargo molecule.

Preferably said delivered cargo molecule comprises at least one compound selected from the group consisting of nucleic acids, polypeptides, organic molecules, small organic molecules, metals, dye, nano-particles, viruses, modified viruses, viral vectors, antibodies and/or plasmids.

Finally, the present invention provides isolated effector proteins of type III secretion system (T3SS)-containing bacteria of the genus *Salmonella* or *Shigella* or variants, fragments or immunomodulatory domains thereof linked to a cargo molecule and/or cell-specific targeting agent. These effector proteins can be used in immunotherapy.

DETAILED DESCRIPTION OF THE INVENTION

The present inventors identified several effector proteins of T3SS-containing bacteria of the genus *Salmonella* and *Shigella* as cell-penetrating proteins. Doing so, the present inventors identified a new subclass of bacteria-derived CPPs, all being effector proteins that comprise a C-terminal Novel E3 ubiquitin ligase domain. The present inventors first identified SspH1, SspH2, IpaH1.4, IpaH2.5, IpaH3, IpaH4.5, IpaH7.8, IpaH9.8 and SlrP as bacterial cell-penetrating proteins. Moreover the inventors succeeded in predicting protein transduction domains (PTDs) within said effector proteins and thereby identified several potential cell-penetration mediating domains within these proteins. The structural similarities of SspH1, SspH2, IpaH1.4, IpaH2.5, IpaH3, IpaH4.5, IpaH7.8, IpaH9.8 and SlrP indicate a general concept of T3SS-independent translocation. Interestingly the inventor demonstrated that cell-penetration of recombinant SspH2 affects membrane integrity of HeLa cells with no effects on cell viability, suggesting a potential direct uptake mechanism, e.g. by the formation of a transient membrane pore.

On the one, the present invention discloses SspH1, SspH2, IpaH1.4, IpaH2.5, IpaH3, IpaH4.5, IpaH7.8, IpaH9.8 and SlrP as novel cell-penetrating effector proteins and provides the use these effector proteins as novel CPPs to deliver cargo molecules into eukaryotic cells.

As mentioned above, SspH1, SspH2, IpaH1.4, IpaH 2.5, IpaH3, IpaH4.5, IpaH7.8, IpaH9.8 and SlrP all comprise a C-terminal Novel E3 ligase (NEL) domain and, apart from IpaH2.5 and IpaH1.4, they belong to effector proteins of the LPX-subtype. Effector proteins of the LPX-subtype share the presence of a Leucine-rich repeat (LRR) motif and an N-terminal α-helical structure (Miao et al, 1999).

Several bacterial effector proteins, which comprise an E3 ubiquitin ligase domain are known to interfere with the host immune response after being injected into host cells by the T3SS (Angot, 2007; Hicks and Galan, 2010). Surprisingly the present inventors found out that SspH1, an effector protein and E3-ubiquitin ligase of *Salmonella enterica* serovar *typhimurium*, is able to modulate the eukaryotic immune response when contacted with eukaryotic cells in an isolated, recombinantly expressed form. As depicted in the examples the inventors showed that recombinant SspH1 is able to autonomously penetrate into eukaryotic cells without the requirement of the *Salmonella* T3SS. Following translocation recombinant SspH1 localises to the cytoplasm as well as to the nucleus of the eukaryotic cell and surprisingly acts as functional E3 ubiquitin ligase that is able to self-ubiquitinate and form polyubiquitin chains within the eukaryotic host cell. Furthermore, the inventors found out that recombinant SspH1 binds and ubiquitinates the host kinase PKN1 and downregulates the expression of IL-8 in eukaryotic cells after it has autonomously penetrated into said eukaryotic cells.

Accordingly the present inventors not only identified SspH1, SspH2, IpaH1.4, IpaH2.5, IpaH3, IpaH4.5, IpaH7.8, IpaH9.8 and SlrP as novel cell-penetrating proteins, they also found out that these effector proteins are promising self-delivering immunotherapeutic agents.

In sum, the inventors revealed that bacterial E3 ubiquitin ligases are able to modulate the immune response of eukaryotic cells in the absence of the pathogenic bacteria from which they derive. The inventors demonstrated that isolated recombinant NEL effector proteins are able to interfere with pathways of the innate immune system of eukaryotic cells after having autonomously penetrating into said eukaryotic cells.

Hence, on the other, the present invention discloses the use of isolated recombinantly expressed or chemically synthesized bacterial cell-penetrating effector proteins, which comprise an immunomodulatory E3-ubiquitin-ligase domain, as immune therapeutic agents.

As summarized above the present invention provides the use of cell-penetrating bacterial E3 ubiqitin ligases from bacteria of the genus *Salmonella* or *Shigella* as immunomodulators.

In particular embodiments the present invention provides cell-penetrating recombinant effector proteins of type III secretion system (T3SS)-containing bacteria of the genus *Salmonella* or *Shigella* that modulate cytokines and/or cytokine receptors of eukaryotic cells and/or eukaryotic genes which respond to cytokines, after said effector proteins have autonomously penetrated into said eukaryotic cells. Alternatively the present invention provides cell-penetrating variants, fragments or immunomodulatory domains of cell-penetrating effector proteins of type III secretion system (T3SS)-containing bacteria of the genus *Salmonella* or *Shigella*, wherein said variants, fragments or immunomodulatory domains modulate cytokines and/or cytokine receptors of eukaryotic cells and/or eukaryotic genes which respond to cytokines, after said variants, fragments or immunomodulatory domains have autonomously penetrated into said eukaryotic cells.

In further embodiments the present invention provides the use of isolated recombinant effector proteins of type III secretion system (T3SS)-containing bacteria of the genus *Salmonella* or *Shigella*, wherein said effector proteins are characterized in that they are recombinantly produced or chemically synthesized, comprise an E3 ubiquitin ligase domain, preferably an Novel E3 ubiquitin ligase, optionally comprise at least one leucine-rich repeat and are cell-penetrating proteins, which translocate into eukaryotic cells without the requirement of a bacterial T3SS, or variants, fragments or immunomodulatory domains of said effector proteins, for the preparation of a pharmaceutical composition for regulating inflammatory reactions of the immune system, treating diseases caused by autoimmunity, treating acute inflammation or chronic inflammation, treating of inflammatory disorders, and/or suppressing the immune system.

Moreover the present invention provides a pharmaceutical composition, comprising an isolated effector protein of a type III secretion system (T3SS)-containing bacterium of the genus *Salmonella* or *Shigella*, wherein the effector protein is characterized in that it is recombinantly produced or chemically synthesized, comprises an E3 ubiquitin ligase domain, optionally comprises at least one leucine-rich repeat, and is a cell-penetrating protein, which translocates into eukaryotic cells without the requirement of a bacterial T3SS.

In other embodiments the present invention further provides the use of cell-penetrating effector proteins of type III secretion system (T3SS)-containing bacteria of the genus *Salmonella* or *Shigella* or variants, fragments and immunomodulatory domains of said effector proteins, for delivering cargo molecules into eukaryotic cells. Preferably the present invention relates to the use of cell-penetrating effector proteins of type III secretion system (T3SS)-containing bacteria of the genus *Salmonella* or *Shigella* or variants, fragments and immunomodulatory domains of said effector proteins, for the preparation of pharmaceutical compositions for delivering linked cargo molecules into eukaryotic cells. Preferably said effector proteins, or variants, fragments and immunomodulatory domains thereof, that are linked to said cargo molecules modulate cytokines and/or cytokine receptors of eukaryotic cells and/or eukaryotic genes which respond to cytokines, after said variants, fragments or immunomodulatory domains have autonomously penetrated into said eukaryotic cells.

Further embodiments of the present invention provide the use of an isolated effector protein of a type III secretion system (T3SS)-containing bacterium of the genus *Salmonella* or *Shigella*, wherein the effector protein is characterized in that it is recombinantly produced or chemically synthesized, comprises an E3 ubiquitin ligase domain, preferably a Novel E3 ubiquitin ligase, optionally comprises at least one leucine-rich repeat, is a cell-penetrating protein, which translocates into eukaryotic cells without the requirement of a bacterial T3SS, or the use of a variant or fragment of said effector protein for delivering at least one cargo molecule across the membrane of a eukaryotic cell, wherein the fusion construct of cargo molecule and said effector protein or variant or fragment thereof is a cell-penetrating construct, which translocates into eukaryotic cells without the requirement of a bacterial T3SS.

In another embodiment the invention relates to the use of an isolated effector protein of a type III secretion system (T3SS)-containing bacterium of the genus *Salmonella* or *Shigella*, wherein the effector protein is characterized in that it is recombinantly produced or chemically synthesized, optionally comprises an E3 ubiquitin ligase domain, optionally comprises at least one leucine-rich repeat, is a cell-penetrating protein, which translocates into eukaryotic cells without the requirement of a bacterial T3SS, and is linked to at least one cargo molecule, for delivering the at least one cargo molecule across the membrane of a eukaryotic cell, wherein the fusion construct of cargo molecule(s) and said effector protein is a cell-penetrating construct, which translocates into eukaryotic cells without the requirement of a bacterial T3SS.

Optionally the present invention provides pharmaceutical compositions comprising an isolated effector protein of a type III secretion system (T3SS)-containing bacterium of the genus *Salmonella* or *Shigella*, wherein the effector protein is characterized in that it is recombinantly produced or chemically synthesized, comprises an E3 ubiquitin ligase domain, preferably a Novel E3 ubiquitin ligase, optionally comprises at least one leucine-rich repeat, is a cell-penetrating protein, which translocates into eukaryotic cells without the requirement of a bacterial T3SS, or the use of a variant or fragment of said effector protein for delivering at least one cargo molecule across the membrane of a eukaryotic cell, wherein the fusion construct of cargo molecule and said effector protein or variant or fragment thereof is a cell-penetrating construct, which translocates into eukaryotic cells without the requirement of a bacterial T3SS.

In another aspect, the present invention relates to an isolated effector protein of a type III secretion system (T3SS)-containing bacterium of the genus *Salmonella* or *Shigella* or a variant, fragment or immunomodulatory domain of said effector protein, wherein said effector protein, variant, fragment or immunomodulatory domain is linked to a cargo molecule and/or cell-specific targeting agent. In the context of the present application the following proteins are denoted as "compound(s) of the invention" or "polypeptide(s) of the invention":

i) isolated effector protein of a type III secretion system (T3SS)-containing bacterium, preferably of the genus *Salmonella* or *Shigella*, wherein the effector protein is characterized in that it a) is recombinantly produced or chemically synthesized,
b) comprises an E3 ubiquitin ligase domain,
c) optionally comprises at least one leucine-rich repeat, and
d) is a cell-penetrating protein, which translocates into eukaryotic cells without the requirement of a bacterial T3SS;

ii) variants, fragments or immunomodulatory domain of an effector protein as defined under point i);

and iii) SspH1, SspH2, IpaH1.4, IpaH2.5, IpaH3, IpaH4.5, IpaH7.8, IpaH9.8 and SlrP as well as variants, fragments or immunomodulatory domain of SspH1, SspH2, IpaH1.4, IpaH2.5, IpaH3, IpaH4.5, IpaH7.8, IpaH9.8 and SlrP.

The term "effector protein" as defined under point i), includes "variants", "fragments" or "immunomodulatory domains" as defined under point ii).

The terms "SspH1", "SspH2", "IpaH1.4", "IpaH2.5", "IpaH3", "IpaH4.5", "IpaH7.8", "IpaH9.8" and "SlrP", as disclosed herein, include "variants", "fragments" and "immunomodulatory domains" of these proteins, namely SspH1, SspH2, IpaH1.4, IpaH2.5, IpaH3, IpaH4.5, IpaH7.8, IpaH9.8 and SlrP.

The terms "effector protein" and "effector protein of the invention" and the like refer herein to effector proteins of bacteria which contain a type III secretion system (T3SS), as well as to fragments of said effector proteins, such as a immunomodulatory domain or protein transduction domain, and to variants of said effector proteins Preferably these effector proteins are secreted via the T3SS of a pathogenic gram-negative bacterium and promote infection and/or suppress host cell defenses. Hence the term "effector protein(s)" preferably refers herein to bacterial T3SS effector proteins. Effector proteins of the present invention preferably comprise an E3 ubiquitin ligase domain and interfere with the immune response of a subject. More preferably effector proteins of the present invention comprise an NEL E3 ubiquitin ligase domain and/or belong to effector proteins of the LPX subtype. Even more preferably effector proteins of the present invention are able to autonomously translocate in an isolated recombinant form into eukaryotic cells without the requirement of a bacterial T3SS. Preferably effector proteins of the present invention modulate cytokines and/or cytokine receptors of eukaryotic cells and/or eukaryotic genes which respond to cytokines of eukaryotic cells after said effector proteins have autonomously penetrated into said eukaryotic cells. "Modulate" as used herein refers to inducing, enhancing, and/or suppressing. The present invention includes, but is not limited to the following effector proteins: SspH1 (*Salmonella*-secreted protein), SspH2, IpaH1.4 (Invasion plasmid antigen), IpaH2.5, IpaH3, IpaH4.5, IpaH7.8, IpaH9.8 and SlrP.

The findings of the inventors strongly suggest that of effector protein of a type III secretion system (T3SS)-containing bacterium of the genus *Salmonella* or *Shigella* (beside the above listed), which are characterized in that they comprise an E3 ubiquitin ligase domain and optionally comprise at least one leucine-rich repeat are able to autonomously translocate into eukaryotic cells and modulate cytokines and/or cytokine receptors of eukaryotic cells and/or eukaryotic genes which respond to cytokines, after they have autonomously penetrated into eukaryotic cells. Hence said other effector proteins are also part of the invention, e.g. IpaH1, IpaH2, IpaH4, IpaH5, IpaH6, IpaH7, or SopA.

Moreover it is most likely that also effector proteins of other type III secretion system (T3SS)-containing bacteria than those of the genus *Salmonella* or *Shigella*, which are characterized in that they comprise an E3 ubiquitin ligase domain and optionally comprise at least one leucine-rich repeat are able to autonomously translocate into eukaryotic cells and modulate cytokines and/or cytokine receptors of eukaryotic cells and/or eukaryotic genes which respond to cytokines, after they have autonomously penetrated into eukaryotic cells.

Said other type III secretion system (T3SS)-containing bacteria include but are not limited to *Yersinia* spp., *Escherichia* spp., *Pseudomonas* spp. and *Chlamydia* spp. Hence effector proteins of the invention also include, e.g. YPA_3361, YPA_3364; PflO1_4099, PflO1_4565, PP_2212, PP_2394, PSPTO_1492, PSPTO_4093; EcoI5_01000486, EcoI5_01001536, EcoI5_01001967, EcoI5_01003958, EcoI5_01004202, EcoI5_01004539, EcoI5_01004764, EcoI5_01004830, and EcoI5_01004885 (Hicks and Galan, 2010).

The T3SS effector protein YopM as well as YopM variant and YopM fragment are not part of the present invention.

In particular embodiments the effector proteins of the invention have an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 9 and are preferably encoded by a polynucleotide with an nucleotide sequence selected from the group consisting of SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 18.

Preferably effector proteins of the present invention are effector proteins of type III secretion system (T3SS)-containing bacterium of the genus *Salmonella* or *Shigella*. More preferably effector proteins of the present invention are effector proteins of *Salmonella bongori*, *Salmonella enterica*, *Salmonella subterranean*, *Salmonella typhi*, *Salmonella typhimurium*, *Salmonella enterica* serovar *typhimurium*, *Salmonella enteritidis*, *Salmonella pullorum*, *Salmonella dublin*, *Salmonella arizonae*, *Salmonella choleraesius*, *Shigella flexneri*, *Shigella dysenteriae*, *Shigella sonnei*, or *Shigella boydii*.

Compounds of the invention preferably comprise an E3 ubiquitin ligase domain, optionally a NEL E3 ubiquitin ligase (NEL).

The NEL (Novel E3 Ligase) domain is a newly identified structure of ubiquitin E3 ligases that is distinct from HECT and RING domains commonly found in eukaryotic and prokaryotic E3 ligases. In contrast, the NEL domain has only been found in bacterial effector proteins of different pathogenic bacteria. These proteins functionally mimic eukaryotic E3 ligases but are structurally different from the eukaryotic HECT and RING domains. These proteins are furthermore characterised by a N-terminal LRR domain that is thought to determine the substrate specificity for the E3 ligase and has been suggested to be involved in autoinhibition of the ligase activity by covering the reserved catalytic Cys residue (Hicks and Galan 2010). Further characteristics of NELs are known to the skilled person.

Preferably compounds of the invention comprise an E3 ubiquitin ligase domain as marked in Example 7 and FIGS. 14 to 22. Alternatively compounds of the invention comprise an E3 ubiquitin ligase domain having an amino acid sequence selected from the group consisting of SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, or SEQ ID NO: 27.

In some embodiments compound(s) of the invention comprising a E3 ubiquitin ligase domain as described herein above may additionally comprise at least one leucine-rich repeat. The term "at least one leucine-rich repeat" relates to a leucine rich repeat as present in a polypeptide of a compound of the invention as described herein, as can be determined according to methods known in the art. Such leucine-rich repeats are described in Evdokimov et al. (*J. Mol. Biol.* 312: 807-821 (2001)). The leucine-rich repeat may be in any orientation or order with respect to a second or further leucine-rich repeat and/or with respect to an E3 ligase domain of a compound of the invention and/or with respect to other structural elements in the polypeptides of the invention. The leucine-rich repeat may be N-terminally located or C-terminally located or may be localized at any other suitable position within the polypeptide or molecule. Preferably the leucine-rich repeat is N-terminally located.

Preferably, such compound(s) of the invention has/have the capability of modulate cellular pathway of the innate immune system of eukaryotic cells in a subject. Optionally said compound(s) of the invention has/have the capability of autopenetrating the cell membrane and integrating into the cell cytosol without the requirement of additional factors. Both can be tested in accordance with an assay as described herein.

The leucine-rich repeat (LRR) motif is commonly found in eukaryotic proteins and is thought to be involved in protein-protein interaction. The LPX repeat is a subtype of the LRR motif that has exclusively been found in T3SS-secreted effector proteins of *Salmonella, Shigella, Yersinia, Edwardsiella, Rhizobium*, and *Bradyrhizobium* species. Most of the LRRs of SspH1 correspond exactly to the LPX structure (LTSLPxLPxxLxxLxaxxNx; SEQ ID NO:552). The LPX domain has been suggested to determine the specificity for binding of the LPX proteins to its ligand which may account for the multiple copies of these genes that have been identified in *Salmonella, Shigella* and *Yersinia* spec (Miao et al. (1999); Haraga et al. (2003). Further characteristics of LRRs and LPX repeats are known to the skilled person.

Compounds of the invention preferably comprise at least one leucine-rich repeat (LRR), i.e. one, two, three, four, five, six, seven, eight, nine, ten, eleven, twelve, thirteen, fourteen, fifteen LRRs. Optionally compounds of the invention belong to the LPX-family, a subtype of the LRR superfamily of protein binding domains (Symmons et al. 1997) of bacterial effector proteins that share the presence of an LRR motif as well as an N-terminal alpha-helical structure. Preferably compounds of the invention comprise at least one leucine-rich repeat, that either corresponds to a "LRR stretch" as marked in Example 7 and FIGS. 14 to 22 (marked in light grey;non-edged) or a segment of a "LRR stretch" as marked in Example 7 and FIGS. 14 to 22 (marked in light grey; non-edged). An "LRR stretch" as marked in Example 7 and FIGS. 14 to 22 corresponds to a predicted LRR domain. Alternatively compounds of the invention comprise at least one leucine-rich repeat that is comprised in an amino acid sequence selected from the group consisting of SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, or SEQ ID NO: 36.

Preferably compounds of the invention comprise at least one leucine-rich repeat that corresponds to at least one of the reference sequences LxxLPxxLPxxLxxLxaxxNx (SEQ ID NO:553), LTSLPxLPxxLxxLxaxxNx (SEQ ID NO:552) or $Lx_6Lx_2I/LPx_3P$ (SEQ ID NO:554) (Dean P.FEMS Microbiol Rev. 2011 November; 35(6):1100-25. doi: 10.1111/j.1574-6976.2011.00271.x. Epub 2011 May 18. Review).

The effector protein SspH1 of the present invention, or SspH1 variants, SspH1 fragments or immunomodulatory domains of SspH1 preferably comprise at least one leucine-rich repeats that correspond to at least one of the reference sequences LxxLPxxLPxxLxxLxaxxNx, LTSLPxLPxxLxxLxaxxNx or $Lx_6Lx_2I/LPx_3P$.

Compounds of the invention preferably comprise at least one of the leucine-rich repeats indicated in Example 14. Preferably compounds of the invention comprise at least one leucine-rich repeat selected from one of the groups of LRRs denoted in Example 14 as group 1, group 2, group 3, group 4, group 5, group 6, group 7, group 8, and group 9. Preferably said leucine-rich are orientated within a compound of the invention in a way that a leucine-rich repeat with a lower identification number is located n-terminally to a leucine-rich repeat with a higher identification number, e.g. N-terminus→LRR1→LRR2→LRR3→C-terminus.

Preferably the E3 ubiquitin ligase domain of a compound of the invention is closer to the C-terminus of the compound of the invention than to its N-terminus. Furthermore it is preferred that leucine-rich repeat(s) of a compound of the invention is/are closer to the N-terminus of the compound of the invention than to its C-terminus. More preferably leucine-rich repeat(s) of a compound of the invention are mainly located within the N-terminal half of the compound of the invention. Furthermore the E3 ubiquitin ligase domain of compounds of the invention is preferably located C-terminal in compared to leucine-rich repeat(s) of the compound.

Compound(s) of the invention are preferably cell-penetrating proteins (CPPs). That means that the compound(s) of the invention are able to cross eukaryotic cell membranes on its/their own. In other words compound(s) of the invention cross eukaryotic cell membranes autonomously. Preferably compound(s) of the invention translocate into eukaryotic cells without the requirement of a bacterial T3SS or any other auxiliary agent which can cause the penetration of a protein, e.g a compound of the invention, into a eukaryotic cell. "Auxiliary agent" refers to any molecule that is able to deliver a cargo molecule into a eukaryotic cell. Within the present invention auxiliary agents include but are not limited to non-bacterial cell-penetrating peptides, YopM, YopM fragment and YopM variants, and cell-penetrating nanoparticles. Within the present invention auxiliary agent also refers to functional bacterial secretion systems, preferably to functional T3SS. Hence compounds of the invention are preferably able to penetrate into eukaryotic cells in an isolated form and in the absence of T3SS-containing bacteria. Preferably compounds of the invention translocate into the eukaryotic cytosol, optionally also into the eukaryotic nucleus. Moreover cell-penetrating compounds of the invention are preferably able to facilitate cellular uptake of a molecular cargo.

"Isolated" means that the compound(s) of the invention is/are separated out of its/their natural environment, preferably separated from T3SS-containing bacteria which naturally comprise the compound of the invention or the effector protein the compound of the invention is derived from. Compound(s) of the invention may be produced by recombinant expression or chemical protein synthesis. Hence "isolated" refer to compound(s) of the invention which are separated from the genetically modified host organism used for the production of the compound(s) of the invention. However, as described below, the compound(s) of the invention may be administered as living therapeutics. In this case "isolated" does preferably not mean that compound(s) of the invention are separated from the genetically modified host organism.

The ability of compounds of the invention to autonomously penetrate into eukaryotic cells is preferably mediated by at least one protein transduction domain (PTD). The term "Protein transduction domain(s)" as used herein preferably refers to the domain(s) of a cell-penetrating protein that mediate(s) translocation of said protein across the cell membrane. (It cannot be excluded that the terms "protein transduction domain" and "cell-penetrating protein" are sometimes used herein interchangeable.) How potential PTDs can be predicted is described in the Examples of the invention. Whether predicted PTDs correspond to functional cell-penetrating entities can be tested experimentally, for instance as explained in the examples of these invention. Alternatively functional PTDs of compounds of the invention can be identified by deleting and/or mutating predicted PTDs and subsequently investigating whether the deletion-and/or mutation-construct penetrates autonomously into eukaryotic cells. "Mutating" means any amino acid substitution(s) or amino acid modification(s) that destroy the cell-penetrating ability of a PTD.

The terms "autopenetrating", "autonomously penetrating" and "penetrate/pass/cross the membrane of eukaryotic cells without the assistance of exogenous factors, such as a T3SS" are used herein interchangeably. The terms mean that the compounds of the invention are able to cross/pass a membrane which separates two different compartments. It is preferred that the mentioned two compartments refer to the exterior and interior of a cell. The "cell membrane" is therefore preferably a plasma membrane that separates the interior of a cell from the exterior. It will be understood that the compounds of the invention preferably cross the plasma membrane from the exterior of the cell towards the interior of the cell.

The compounds of the invention may enter eukaryotic cells, without the need to interact with a receptor, i.e. the compounds of the invention may enter eukaryotic cells irrespective of a receptor.

The capability to pass the cell membrane and to enter the cytosol of a cell without the assistance of exogenous factors can be tested and determined by methods known to a person skilled in the art. The autopenetration of compound(s) of the invention into the cell membrane and its integration into the cell cytosol can be tested by a method of cell fractionation as described e.g. by Kenny B, Finlay B B. Infect Immun. 1997 July; 65(7):2528-36 and/or by the methods described in the appended examples. For example, such a method comprises the incubation of cells to be tested, e.g. HeLa cells, with compound(s) of the invention, e.g. a recombinant compound(s) of the invention, for a time period of 10 to 60 min, preferably of 20 to 40 min, more preferably of 25 to 35 min and most preferably of 30 min. The compound(s) of the invention may be present in any suitable medium known to the skilled person. For example, the protein is provided in an infection medium comprising, e.g. DMEM, FCS, L-glutamine, HEPES and methyl-α-D-mannose. Preferably, the infection medium comprises 500 ml DMEM, 10% (v/v) FCS, 1 mM L-glutamine, 10 mM HEPES and 1% (w/v) methyl-α-D-mannose. For the assay cell culture dishes comprising the cells to be tested, e.g. as a confluently grown surface layer may be incubated with the compound(s) of the invention present in an infection medium as described herein above in any suitable concentration, e.g. a concentration of 1 to 100 μg per ml, preferably of 5 to 50 μg per ml, more preferably of 10 to 30 μg per ml and most preferably of 15 to 25 μg per ml. Subsequently, the cells may be washed with any suitable buffer known to the skilled person, e.g. with D-PBS/Mg$^{2+}$. Preferably, the washing is carried out in ice-cold buffer and repeated twice. This is optionally followed by an acid-wash with 0.2 M glycine, pH 2.0. Subsequently, the cells are permeabilised by any suitable means known to the skilled person. Preferably, the cells are suspended in a suitable sonication buffer and the suspension may then be permeabilised by sonication. Subsequently, the resulting suspension may be separated into cell fractions, for example by centrifugation, e.g. at 108.000×g for 15 min at 4° C. After the fractionation step, the supernatant comprising suspended cytoplasmic proteins may be recovered. A resulting pellet may optionally be washed with any suitable buffer known to the person skilled in the art, e.g. with a sonication buffer. The sonication buffer comprises exemplarily TrisHCl, NaCl, EDTA, EGTA, glycerol, NaVO$_4$ and NaF. Preferably, the sonication buffer comprises 50 mM TrisHCl pH 7.6, 150 mM NaCl, 1 mM EDTA, 1 mM EGTA, 30% glycerol, 0.4 mM NaVO$_4$ and 1 mM NaF Subsequently, the pellet may be resuspended in any suitable buffer known to the person skilled in the art, e.g. in a TRITON™ buffer, preferably in 1 ml of a TRITON™ buffer comprising 1% (v/v) TRITON™ in a sonication buffer as described herein above. The suspension may then be incubated in a shaker for a suitable period of time known to the skilled person, e.g. for 30 min at 4° C. at 15 U/min. Subsequently, the suspension may again be centrifuged, e.g. at 108.000×g for 15 min at 4° C. A resulting supernatant may be recovered as 'membrane fraction'. Subsequently, the resulting fractions may be precipitated by suitable means known to the skilled person, e.g. with trichloro acetic acid (TCA). For the detection of autopenetration and integration of compound(s) of the invention, a cytoplasmic and membrane fraction obtained by the method as described herein above may be analysed with any method known to the person skilled in the art, for example by way of immunostaining. Exemplarily, the fractions may be analysed by Western-blotting as known to the person skilled in the art and derivable, e.g., from Lottspeich and Zorbas, (Bioanalytik, 1998). The detection may be performed e.g. with an antiserum against the compound(s) of the invention.

A compound of the invention is regarded to be capable of autopenetrating the cell membrane and integrating into the cell cytosol without the requirement of additional factors if a tested molecule can be detected in the cytoplasmic fraction, either associated with vesicles as outlined above or already released in the cytosol, the latter being preferred. More preferably, a compound of the invention is regarded to be capable of autopenetrating the cell membrane and integrating into the cell cytosol without the requirement of additional factors if at least 10%, 20%, 30%, 40%, 50%, 60%, or 70%, 80%, 90%, 91%, 92%, 93%, 94%, 95%, 96%, 97%, 98%, 99% or 100% of the tested compound is detected in the cytoplasmic fraction, in comparison to the total amount of the compound of the invention added. Methods for quantification of the amount of protein uptake are known to the skilled artisan. It is envisaged that the compound of the invention, which is detected in the cytoplasmic fraction, is associated with vesicles as indicated above, and/or already released into the cytosol, the latter being preferred.

Alternatively, the autopenetration of compound(s) of the invention into the cell membrane and its integration into the cell cytosol can be tested by a translocation coefficient assay as known to the person skilled in the art, for example as described in Langel, Ü. (ed) (*Cell-penetrating peptides: Processes and Applications*, CRC Press, Boca Raton, Fla. 2002,) and references therein. Briefly, a compound of the invention is linked to a suitable label, for example a dye like for example Cy3 or Cy5 or to gold particles, GFP, RFP etc. Subsequently, a defined amount of the labelled protein is incubated with target cells, for example such as described herein. Afterwards, the cells are lysed and fractionated, for example such as described herein in the context of the method of cell fractionation. A translocation coefficient $K_T$=[protein of interest$_{intracellular}$]/[Protein of interest$_{extracellular}$] may be determined by measuring the amount of the label in the intracellular cell fractions [protein of interest$_{intracellular}$] and comparing it with the originally used amount for the incubation [protein of interest$_{extracellular}$], e.g. by determining the fluorescence of Cy3. Alternatively, ELISA methods may be used or further corresponding methods including e.g. radioactivity counting, biotinylation/cell-ELISA, fluorescence labelling/spectrophotometer/FACS, resonance energy transfer, HPLC detection, immunodetection, fluorescence correlation microscopy (FCM), cell activity by capillary electrophoresis (CACE), or MALDI-TOF MS, as known to the skilled person, for example such as described in Langel, Ü. (ed) (*Handbook of cell-penetrating peptides*, CRC Press, Boca Raton, Fla., 2007), and Langel, Ü. (ed) (*Cell-penetrating peptides: Processes and Applications*, CRC Press, Boca Raton, Fla. 2002).

The test for determining whether a molecule, in particular a compound of the invention, is capable of autopenetrating the cell membrane and integrating into the cell cytosol without the requirement of additional factors is preferably a test as described herein e.g. in the Examples.

Compounds of the invention preferably comprise at least one PTD of the PTDs marked in Example 7 and FIGS. 14 to 22 and designated as "maximal protein-transduction domain" and/or at least one PTD of the PTDs indicated in Example 9 and designated as "predicted PTD sequences". FIG. 12 illustrates the PTDs of maximal length as marked in Example 7 and FIGS. 14 to 22. The in-silico prediction of Example 5 determined several PTDs encompassed within the maximal PTDs. These shorter PTDs corresponds to C-terminally or N-terminally truncated segments of the depicted "maximal protein-transduction domains". Compounds of the invention preferably comprise at least one PTD of these C-terminally or N-terminally truncated segments of the "maximal protein-transduction domains". However, since the PTDs denoted "maximal protein-transduction domains" in FIGS. 14 to 22 refer to predicted PTDs, it is possible that the effector protein comprise further functional PTDs that C- or N-terminally overlap the PTDs depicted as "maximal protein-transduction domains". Such PTDs, which are one, two, three, four or five amino acids longer than the "maximal protein-transduction domains", either N-terminally or C-terminally, are therefore also encompassed by the present invention.

Example 9 indicates all protein transduction domains determined in Example 5, including the PTDs of maximal length and all shorter PTDs which correspond to C-terminally or N-terminally truncated segments of said PTDs of maximal length. Compounds of the invention preferably comprise at least one PTD denoted herein as "maximal protein-transduction domain" and/or at least one PTD described herein as "C-terminally or N-terminally truncated segments of a "maximal protein-transduction domain" and/or at least at least one PTD of the PTDs indicated in Example 9 and designated as "predicted PTD sequences".

Compounds of the invention preferably comprise at least one amino acid sequence selected from the group consisting of SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65 or SEQ ID NO: 550, and/or at least one amino acid sequence that corresponds to a C-terminally or N-terminally truncated fragment of an amino acid sequence selected from the group consisting of SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65 or SEQ ID NO: 550.

Other Compounds of the invention preferably comprise at least one amino acid sequence selected from the group consisting SEQ ID NOs: 66 to 529.

"Truncated fragment" as used above refers to the amino acid sequences that are denoted in Example 9 as "Predicted PTD sequences".

In a second embodiment the present invention provides a pharmaceutical composition, comprising an isolated variant, fragment, or immunomodulatory domain of an effector protein effector protein of a type III secretion system (T3SS)-containing bacterium of the genus *Salmonella* or *Shigella*, wherein said effector protein is characterized in that it a) is recombinantly produced or chemically synthesized,
b) comprises an E3 ubiquitin ligase domain,
c) optionally comprises at least one leucine-rich repeat, and
d) is a cell-penetrating protein, which translocates into eukaryotic cells without the requirement of a bacterial T3SS.

The term "effector protein", as used herein, includes fragments of the effector proteins of the invention. A "fragment" of an effector protein of the invention is characterized as follows.

The term "fragment" relates to a sub-portion of the "effector protein" polypeptides according to the present invention. In particular, the term "fragment" refers to a short amino acid sequence contained in an effector protein according to the invention as described herein. Preferably "fragment" refers to a polypeptide that is characterized in that it a) is recombinantly produced or chemically synthesized,
b) comprises an E3 ubiquitin ligase domain,
c) optionally comprises at least one leucine-rich repeat, and
d) is a cell-penetrating protein, which translocates into eukaryotic cells without the requirement of a bacterial T3SS.

Furthermore, a "fragment" of an effector protein of the invention may correspond to a immunomodulatory domain of a effector protein of the invention. Likewise, a "fragment" of an effector protein of the invention may correspond to a protein transduction domain of an effector protein of the invention.

Protein fragments may be "free-standing", i.e. separated out of their natural environment (which is the effector protein, the fragment is derived from), or they may be attached to a polypeptide or comprised within a polypeptide of which the fragment forms a part or region, for example as a single continuous region. "Attached to" includes that the fragment and the polypeptide are expressed/expressable on/from a single nucleic acid as a single continuous region or that both entities are linked/coupled otherwise (for example by way of chemical linkage like biotin/streptavidin etc.). Methods to "attach" two entities, in particular two proteins, are well-known to the skilled person. It is preferred that the polypeptide, to which the fragment of the invention is "attached to" or "comprised within", is heterologous to said fragment or the effector protein, the fragment is derived from respectively, i.e. it is preferably but not exclusively not derived from bacteria of the genus *Salmonella* or *Shigella*. Further characteristics of fragments of the invention are described below.

Polynucleotides encoding fragments of the invention are also contemplated.

The term "effector protein", as used herein, includes variants of the effector proteins of the invention. A "variant" of an effector protein of the invention is characterized as follows.

In the context of the present invention a "variant" encompasses compounds of the, which comprise, or alternatively consist of, an amino acid sequence which is at least 40%, 50%, 60%, 70%, 80%, 90%, 91%, 92%, 93%, 94%, 95%, 96%, 97%, 98%, or 99% identical to the polypeptide sequence or an effector protein of the invention, preferably SlrP, SspH1, SspH2, IpaH1.4, IpaH2.5, IpaH3, IpaH4.5, IpaH7.8, or IpaH9.8, more preferably to the SlrP, SspH1, SspH2, IpaH1.4, IpaH2.5, IpaH3, IpaH4.5, IpaH7.8, or IpaH9.8 polypeptide identified as SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 9 and/or polypeptide fragments of any effector protein of the invention. Moreover, polynucleotides encoding these variants are also contemplated. Preferably "variant" refers to a polypeptide that is characterized in that it a) is recombinantly produced or chemically synthesized,
b) comprises an E3 ubiquitin ligase domain,
c) optionally comprises at least one leucine-rich repeat, and
d) is a cell-penetrating protein, which translocates into eukaryotic cells without the requirement of a bacterial T3SS.

Preferably "variants" of the invention are generated by deleting, inserting, inversing, repeating, modifying or substituting amino acids of effector proteins of the invention.

Further characteristics of fragments of the invention are described below.

The term "effector protein", as used herein, includes fragments of the effector proteins of the invention, such as the immunomodulatory domain of an effector protein of the invention. The term "immunomodulatory domain" or "immunomodulatory domain of the invention" refers to a domain of an effector protein of the invention that mediates modulation of pathway(s) of the innate immune system of eukaryotic cells. Preferably immunomodulatory domains of the invention modulates cytokines and/or cytokine receptors and/or genes which respond to cytokines of eukaryotic cells after said immunomodulatory domains have autonomously penetrated into said eukaryotic cells. More preferably immunomodulatory domains of the invention downregulate cytokines and/or cytokine receptors and/or genes which respond to cytokines of eukaryotic cells after said immunomodulatory domains have autonomously penetrated into said eukaryotic cells.

Preferably immunomodulatory domains of the invention comprise an E3 ubiquitin ligase domain, preferably a Novel E3 ubiquitin (NEL) ligase domain. Optionally immunomodulatory domains comprise at least one leucine-rich repeat. Preferably immunomodulatory domains of the invention comprise a Novel E3 ubiquitin ligase domain and at least one leucine-rich repeat (LRR). Preferably an "immunomodulatory domain" polypeptide of the invention comprises an amino acid sequence selected from the group consisting of NELs and LRRs.

Preferably an immunomodulatory domain of the invention is characterized in that it a) is recombinantly produced or chemically synthesized,
b) comprises an E3 ubiquitin ligase domain,
c) optionally comprises at least one leucine-rich repeat, and
d) is a cell-penetrating protein, which translocates into eukaryotic cells without the requirement of a bacterial T3SS.

An effector protein, variant, fragment, or immunomodulatory domain according to present invention is preferably a cell-penetrating protein, which translocates into eukaryotic cells without the requirement of a bacterial T3SS.

Hence pharmaceutical compositions of the invention preferably comprise an effector protein, variant, fragment, or immunomodulatory domain of the present invention that is preferably a cell-penetrating protein, which translocates into eukaryotic cells without the requirement of a bacterial T3SS.

An effector protein, variant, fragment, or immunomodulatory domain according to present invention preferably comprises an E3 ubiquitin ligase domain and optionally at least one leucine-rich domain.

Hence pharmaceutical compositions of the invention preferably comprise an effector protein, variant, fragment, or immunomodulatory domain that comprises an E3 ubiquitin ligase domain and optionally at least one leucine-rich domain.

An effector protein, variant, fragment, or immunomodulatory domain according to present invention preferably comprises an E3 ubiquitin ligase domain that is classified as Novel E3 Ligase.

Hence pharmaceutical compositions of the invention preferably comprise an effector protein, variant, fragment, or immunomodulatory domain of the present invention that preferably comprises a Novel E3 ubiquitin ligase domain.

Pharmaceutical compositions of the invention preferably comprise an effector protein, variant, fragment, or immunomodulatory domain of the invention, which comprises a E3 ubiquitin ligase domain that is closer to the C-terminus of effector protein, variant, fragment, or immunomodulatory domain than to its N-terminus.

Pharmaceutical compositions of the invention preferably comprise an effector protein, variant, fragment, or immunomodulatory domain of the invention which comprises at least one leucine-rich repeat of the LPX-subtype. Preferably said leucine-rich repeat(s) is/are closer to the N-terminus of the effector protein, variant, fragment, or immunomodulatory domain of the invention than to its C-terminus. More preferably said leucine-rich repeat(s) is/are mainly located within the N-terminal half of the compound of the invention.

Effector proteins according to present invention are preferably T3SS effector proteins of the LPX-subtype. Pharmaceutical compositions of the invention preferably comprise effector proteins according to the invention that belong to effector proteins of the LPX-subtype.

Effector proteins according to the present invention are preferably is SspH1, SspH2, SlrP, IpaH1.4, IpaH2.5, IpaH3, IpaH4.5, IpaH7.8, and IpaH9.8. Pharmaceutical compositions of the invention preferably comprise SspH1, SspH2, SlrP, IpaH1.4, IpaH2.5, IpaH3, IpaH4.5, IpaH7.8, and IpaH9.8.

Preferably an effector protein according to present invention has an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 9. Hence pharmaceutical compositions of the invention preferably comprise an effector protein that has an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 9. Moreover pharmaceutical compositions of the invention preferably comprise an effector protein that is encoded by a polynucleotide selected from the group consisting of SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 18.

In the context of the present invention the terms "fragment", "variant" or "immunomodulatory domain" includes that the fragment, variant or immunomodulatory domain is biologically active. The term "biologically active" means that the fragment, variant or immunomodulatory domain has biological activities of the effector protein of the invention from which it is derived. Preferably a fragment, variant or immunomodulatory domain of the invention has a biological activity of SspH1, SspH2, SlrP, IpaH1.4, IpaH2.5, IpaH3, IpaH4.5, IpaH7.8, and IpaH9.8.

Preferably "biologically active" means that the fragment, variant or immunomodulatory domain of the invention is capability of autopenetrating the cell membrane and integrating into the cell cytosol without the requirement of additional factors and is able to modulates cytokines and/or cytokine receptors and/or genes which respond to cytokines.

An effector protein, variant, fragment, or immunomodulatory domain according to present invention preferably comprises an amino acid sequence selected from the group consisting of SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, or SEQ ID NO: 27.

An effector protein, variant, fragment, or immunomodulatory domain according to present invention preferably comprises at least one Leucine-rich repeat, preferably at least one Leucine-rich repeat that is comprised in an amino acid sequence selected from the group consisting of SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, or SEQ ID NO: 36.

An effector protein, variant, fragment, or immunomodulatory domain according to present invention preferably comprises at least one amino acid sequence selected from the group consisting of SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, or SEQ ID NO: 550, or are C-terminally or N-terminally truncated fragment thereof.

Alternatively, an effector protein, variant, fragment, or immunomodulatory domain according to present invention preferably comprises at least one amino acid sequence selected from the group consisting of SEQ ID NOs: 66 to 529.

Pharmaceutical compositions of the invention preferably comprise an effector protein, variant, fragment, or immunomodulatory domain as defined above.

Optionally effector proteins, variants, fragments, or immunomodulatory domains according to present invention are linked to a cell-specific targeting agent.

The compounds of the invention may enter eukaryotic cells without the need to interact with a receptor. Thus, in a further embodiment, the compound(s) of the invention is/are additionally linked to a specific, for example a cell-specific, targeting agent. Such a linkage may be any linkage as described herein above, preferably a peptide linkage.

The term "specific targeting agent" or "cell-specific targeting agent" means a molecule, which allows a (cell) specific interaction with structures on the surface of a cell and thereby facilitates the recognition of different cell types or tissue types in the animal body, preferably in the human body. Molecules which allow such (cell-) specific interaction may, for example, be ligands which specifically interact with receptors or receptor fragments which are located on the surface of a cell (e.g. tumor cells) and which are differentially expressed in specific cell types or tissue types. The term includes any suitable CD antigen as known to the person skilled in the art, for example from www.pathology-outlines.com, more preferably to CD1d, which may be used for the targeting of, e.g., dendritic cells, intestinal epithelial cells, B cell subset, NK T cell subset; CD 11a,b,c,d; CD14 and CD16/18, which may be used for the targeting of, e.g., macrophages; CD23, which may be used for the targeting of e.g., activated mature B cells expressing IgM or IgD (particularly mantle cells), activated monocytes/macrophages, T cell subsets, platelets, eosinophils, Langerhans cells, follicular dendritic cells, or intestinal epithelium; CD54 (also known as ICAM-1), which may be used for the targeting of, e.g., B and T cells and B cell precursors, monocytes, osteoclasts, endothelial cells, and various epithelial cells; CD57, which may be used for the targeting of, e.g., cells of the NK subset, T cell subset, neuroectodermal tissue, retina, brain, prostate, renal proximal tubules;

CD64 (also called Fc gamma RI), which may be used for the targeting of antigen presenting cells including macrophages/monocytes, activated granulocytes, dendritic cells or early myeloid cells; CD91 (also known as Low density lipoprotein receptor-related protein 1 (LRP1); also called alpha-2-macroglobulin receptor), which may be used for the targeting of fibroblasts, dendritic cells, macrophages, liver, brain or lung tissue as well as CD-20, CD-45. Furthermore, the term relates to anti-CD antibodies, to molecular danger signals, TLRs, bacterial toxins, e.g. 'trapo' for nerve cells as described in WO 2006/114308 or DEC-205, which is typically present on dendritic cells. In addition, the term relates to a vascular-homing peptide, which may be specific for certain organs or tissues, like e.g. brain, kidney, lung, skin, or heart. More preferably, the term relates to such peptides as mentioned in Arap, W. et al. *Proc. Nati Acad Sci. U.S.A.*, 99:1527-1531 (2002); Rajotte, D. et al., *J. Clin Invest.*, 102:430-437 (1998); Pasqualini, R., and Ruoslahti, E. (2002) *Nat. Rev.* Cancer 2:83; Rajotte, D. and Ruoshlati, E., *J. Biol. Chem.* 274:11593-11598 (1999); Essler, M., and Ruoshlati, E., *Proc. Nati Acad. Sci. U.S.A.*, 99:2252-2257 (2002). Tumour homing peptide are also envisaged. The term "tumour homing peptide" means a protein, which comprises an RGD- and/or a NGR motif. Typically, proteins with a RGD motif bind to αvβ3 and αvβ5 integrins, which in turn are considered to be specific markers for angiogenic blood vessels (Eliceiri, B. P. and Cheresh, D. A., *Cancer J.* 6:S245-S249 (2000)). Furthermore, proteins with an NGR-Motif may bind to an aminopeptidase N, which in turn is specific for angiogenic, endothelia cells (Pasqualini, R. et al., Cancer Res. 60:722-727 (2000)). In a preferred embodiment, a tumour homing peptide comprising an RGD- and/or a NGR motif may be used for the general targeting of angiogenic cells independently of the tumour type involved, as the person skilled in the art would know, e.g. from Arap, W. et al., Science, 279:377-380 (1998); Pasqualini, R. et al., *Nat. Biotech.* 15:542-546 (1997)).

In a further preferred embodiment compound of the invention may be fused in frame with the carboxyl terminus of the heavy chain of the αDEC-205 as described in Boscardin et al. (*J. Exp. Med.*, 203: 599-606 (2006)).

In a further embodiment the term "cell-specific targeting agent" includes agents which bind to (a) cell-marker which allow(s) the, preferably specific, targeting of osteoclasts. A particularly preferred cell-marker for osteoclasts is the calcitonin-receptor, alpha-V-beta3-integrine and/or vitronectine (Marta Monjo, Sébastien F. Lamolle, S. Petter Lyngstadaas, H. Jacob Rønold and Jan Eirik Ellingsen 2008 Biomaterials 29(28): 3771-3780; Susanne Granholm, Pernilla Lundberg, and Ulf H. J. Cell. Biochem. 104(3): 920-933; Davies J, Warwick J, Totty N, Philp R, Helfrich M, and Horton M 1989 J. Cell Biol. 109: 1817-1826; Clove J, Dodds R A, and Gowen M 1992. J. Cell Sci. 103: 267-271). Agents which may bind to this cell-marker are described herein and include for example antibodies etc.

In another embodiment the term "cell-specific targeting agent" relates to a virus, preferably an attenuated virus, which is linked to a compound of the invention. Such a combination may convey a cell or tissue tropism depending on the host cell spectrum of the virus used. The term "cell-specific targeting agent" also includes retroviridae, adenoviridae etc.

The term "cell-specific targeting agent" also includes an "antibody and functional fragments thereof" and refers to a monoclonal or a polyclonal antibody (see Harlow and Lane, "*Antibodies, A Laboratory Manual*", CSH Press, Cold Spring Harbor, USA, 1988) or a derivative of said antibody which retains or essentially retains its binding specificity. Preferred derivatives of such antibodies are chimeric antibodies comprising, for example, a mouse or rat variable region and a human constant region. The term "functional fragment" as used herein refers to fragments of the antibodies as specified herein which retain or essentially retain the binding specificity of the antibodies like, separated light and heavy chains, Fab, Fab/c, Fv, Fab', F(ab')2. The term "antibody" also comprises bifunctional (bispecific) antibodies and antibody constructs, like single-chain Fvs (scFv) or antibody-fusion proteins. The term "scFv fragment" (single-chain Fv fragment) is well understood in the art and preferred due to its small size and the possibility to produce such fragments recombinantly. Said antibody or antibody binding portion is a human antibody or a humanized antibody. The term "humanized antibody" means, in accordance with the present invention, an antibody of non-human origin, where at least one complementarity determining region (CDR) in the variable regions such as the CDR3 and preferably all 6 CDRs have been replaced by CDRs of an antibody of human origin having a desired specificity. Optionally, the non-human constant region(s) of the antibody has/have been replaced by (a) constant region(s) of a human antibody. Methods for the production of humanized antibodies are described in, e.g., EP-A1 0 239 400 and WO90/07861.

Optionally effector proteins, variants, fragments, or immunomodulatory domains according to present invention are linked to a linked to a cargo molecule.

The term "linked to a cargo molecule" means that the cargo molecule may be connected by any means known to the person skilled in the art to the compounds of the invention (for example covalently, non-covalently etc.). It is envisaged that structures on the surface of the cargo molecule like functional or reactive chemical groups are used to establish a linkage or binding between a compound of the invention and a cargo molecule. "Linked to" also includes that the compounds of the invention and the cargo molecules are expressed/expressable on/from a single nucleic acid as a single continuous region. Fusion proteins consisting of a proteinaceous cargo (polypeptides, antibodies etc.) and the compound(s) of the invention are likewise contemplated. Nucleic acids encoding these fusion proteins, vectors comprising these nucleic acids and pharmaceutical compositions comprising these vectors or nucleic acids are likewise contemplated.

The compounds of the present invention may be linked to a cargo by any method known to the person skilled in the art, e.g. by chemical cross-linking, an avidin bridge, a glutation-S-transferase bridge, a linkage comprising at least one, at least two or at least three disulfide bonds or at least one peptide bond or at least two peptide bonds.

Various functional groups, such as hydroxyl, amino or halogen groups present on the cargo may be used as a handle to attach a suitable complexing group. For example, a hydroxyl group may be modified to include an acidic phosphate group. It is also envisaged that the linkage includes a disulfide bond. The linkage may also include a streptavidin-biotin complex. It is envisaged that the delivery peptide, i.e. a compound of the invention is biotinylated and the cargo molecule is avidin labeled. Thus, "linked to" also includes a non-covalent linkage/association of cargo molecules with the compounds of the invention.

The linkage between the delivery peptide and the cargo may also be achieved by a peptide bond. Examples including those peptide bonds or linkers are described for example in U.S. Pat. No. 5,073,627.

In a preferred embodiment, the cargo is linked via a peptide bond in the form of a protein-protein fusion. In such a protein-protein fusion, the cargo may be separated from the compounds of the invention by an amino acid linker (spacer). Such a linker is preferably of the size of 1, 2, 3, 4, 5, 6, 7, 8, 9, 10, 11, 12, 13, 14, 15 or 16 to 50 amino acids or of any other suitable size known to the person skilled in the art. The linker may consist of any suitable amino acid known to the person skilled in the art. Preferably, a linker comprising the amino acid glycine is used. The linker is not restricted to amino acids but may also comprise other entities/molecules, for example such as poly ('hydroxy'methylene) groups.

In a further preferred embodiment, the protein-protein fusion may be in the form of a transcriptional fusion. Suitable transcriptional fusions, as well as suitable methods to generate corresponding constructs, are known to the person skilled in the art.

Furthermore, the compounds of the invention may be linked to a cargo by a cleavable linker.

It is envisaged that the cargo is modified using a number of methods known in the art, either directly, e.g. with a carbodiimide, or via at least one linking moiety. In particular, carbamate, ester, thioether, disulfide, and hydrazone linkages may be formed. Ester and disulfide linkages are envisaged, if the linkage is to be readily degraded in the cytosol, after transport of the cargo across the cell membrane.

In a further embodiment a compound of the invention as described herein above is linked to a cargo via a linkage at the C-terminus or the N-terminus of the compounds of the invention. Preferably, such a linkage at the C-terminus or the N-terminus is a peptide bond, more preferably said linkage is a protein-protein fusion including, for instance, the presence of a spacer or linker of the size of 1, 2, 3, 4, 5, 6, 7, 8, 9, 10, 11, 12, 13, 14, 15 or 16 to 50 amino acids or of any other suitable size known to the person skilled in the art. The linker may consist of any suitable amino acid known to the person skilled in the art. Preferably, a linker comprising the amino acid glycine is used.

In a further embodiment, the compound of the invention is biotinylated and the cargo molecule is avidin labeled or vice versa.

The term "cargo" or "cargo molecule", as used herein, refers to any entity (e.g. a small molecule, macromolecule or macromolecular complex), which may be delivered/transferred/is transferable across the membrane of a cell or into the cytosol of a target cell. It is envisaged that a "cargo" or "cargo molecule" is transferable/transferred or delivered across the membrane of a cell or into the cytosol of a target cell, if it is detected/detectable in the cytoplasmic fraction—either associated with vesicles and/or already released into the cytosol, the latter being preferred. The cytoplasmic fraction denotes the interior of a cell.

It is preferred but not exclusive that the "cargo" is heterologous to a compound of the invention. By the term "heterologous" as used herein is meant that it does not come from, is not normally/naturally produced by and/or required for viability of Salmonella or Shigella. It is also preferred that the cargo is not a a component of a type III secretion system.

It is particularly preferred that the cargo exerts a beneficial effect in a medical context, i.e. the cargo displays therapeutical and/or diagnostic activity/capabilities, following delivery into the cells, ex vivo and/or in vivo. "Therapeutic activity" includes treatment, amelioration and/or prophylaxis of a disease. "Diagnostic activity" includes visualizing, detecting, distinguishing and/or identifying a pathological/medical condition and attributing the deviation to a clinical picture.

Preferably, the term "cargo" includes, but is in no way limited to, a nucleic acid, a polypeptide, an antibody or a functional fragment thereof, an organic molecule, a small organic molecule, a metal, a nanoparticle, a virus, a modified virus, a viral vector, and/or a plasmid.

This invention is generally applicable for therapeutic, prophylactic, or diagnostic intracellular delivery of small molecules and of macromolecules, such as proteins, nucleic acids, and/or polysaccharides, that are not inherently capable of entering target cells at a useful rate. It should be appreciated, however, that alternate embodiments of this invention are not limited to clinical applications. This invention may be advantageously applied in medical and biological research. In research applications of this invention, the cargo may be e. g. a drug or a reporter molecule.

Pharmaceutical compositions of the invention preferably comprise an effector protein, variant, fragment, or immunomodulatory domain as defined above.

Preferably effector proteins, variants, fragments, or immunomodulatory domains according to present invention are functional ubiquitin ligases. That means that an effector protein, variant, fragment, or immunomodulatory domain of the invention is able to ubiquitinate itself and/or eukaryotic proteins after it has autonomously penetrated into a eukaryotic cell in an isolated form and in the absence a T3SS-containing bacterium of the genus Salmonella or Shigella. "Ubiquitinate" as used herein includes monoubiquitination, oligoubiquitination and polyubiquitination. Preferably effector proteins, variants, fragments, or immunomodulatory domains according to present invention polyubiquitinate themself and/or eukaryotic proteins. Said eukaryotic proteins that are ubiquitinylated are preferably involved in pathways of the innate immune system. More preferably said eukaryotic proteins are involved in the regulation or modulation of cytokines and/or cytokine receptors and/or genes which respond to cytokines of eukaryotic. Even more preferred said eukaryotic proteins are involved in the regulation of the expression of cytokines and/or cytokine receptors. In one preferred embodiment the compound of the invention is SspH1, or a variant, fragment or immunomodulatory domain thereof, wherein SspH1, or a variant, fragment or immunomodulatory domain thereof ubiquitinate itself and mammalian PKN1.

Ubiquitin has seven lysine residues and an N-terminus that may serve as points of ubiquitination, they are K6, K11, K27, K29, K33, K48 and K63.

Effector proteins, variants, fragments, or immunomodulatory domains according to present invention are preferably able to ubiquitinate by forming K63-linked-ubiquitin-chains and/or K48-linked-ubiquitin chains.

An effector proteins, variant, fragment, or immunomodulatory domain according to present invention preferably modulates pathway(s) of the innate immune system of eukaryotic cells after said effector proteins, variant, fragment, or immunomodulatory domain has autonomously penetrated into said eukaryotic cells.

Preferably an effector proteins, variant, fragment, or immunomodulatory domain according to present invention modulates cytokines and/or cytokine receptors and/or genes which respond to cytokines of a eukaryotic cell after said effector proteins, variant, fragment, or immunomodulatory domain has autonomously penetrated into said eukaryotic cell.

Optionally an effector proteins, variant, fragment, or immunomodulatory domain according to present invention downregulates the expression of cytokines and/or cytokine receptors of a eukaryotic cell after it has autonomously penetrated into said eukaryotic cell.

Pharmaceutical compositions of the invention preferably comprise an effector protein, variant, fragment, or immunomodulatory domain as defined above.

"Modulate" includes inducing, enhancing, or suppressing cellular pathway of the innate immune system.

As described above, the present inventors surprisingly found that recombinant SspH1, which so far has not been characterized as a potential immunosuppressive therapeutic, is, once it has integrated into the cell cytosol, capable of effectively downregulating cytokines.

Cytokines are an essential class of mediators in physiology and pathology. In the context of inflammation and disease cytokines and particularly pro-inflammatory cytokines play a key role in the acceleration and regulation of inflammatory reactions either by direct interactions or by their ability to induce the synthesis of cellular adhesion molecules or of other cytokines in various cell types involved in the immunological defense network. Many cytokines have beneficial as well as deleterious effects for the organism. Thus, a delicate balance between different cytokine groups, in particular between pro-inflammatory, anti-inflammatory and regulatory cytokines has to be maintained and is vital for health. If this balance is disturbed, diseases like inflammatory bowel disease, rheumatoid arthritis, vascular disease or autoimmunity may develop. The unexpected downregulation of cytokines, in particular of pro-inflammatory cytokines, by recombinant SspH1 that has autonomously penetrated the eukaryotic cell membrane and entered the cytosol, as shown by the present inventors and illustrated in the Examples, converts SspH1 and its derivatives into efficient medical tools for the regulation of inflammatory reactions, for immunomodulation or especially for immunosuppression.

The term "cytokines" relates to soluble proteins and peptides that act as humoral regulators, which, either under normal or pathological conditions, modulate the functional activities of individual cells and tissues and also mediate interactions between cells directly and regulate processes taking place in the extracellular environment. The term encompasses type 1 cytokines produced by Th1 T-helper, type 2 cytokines produced by Th2 T-helper cells, interleukins, chemokines or interferons, e.g. IL-1ra (antagonist), CNTF, LIF, OSM, Epo, G-CSF, GH, PRL, IP10, I309, IFN-alpha, IFN-beta, IFN-gamma, IL2, IL3, IL4, IL5, IL6, IL7, IL8, IL9, IL10, IL11, 1L12 (p35+p40), 1L13, 1L14, IL15, 1L16, 1L17 A-F, 1L18, 1L19, IL20, IL21, IL22, IL23 (p19+p40), IL24, IL25, IL26, IL27 (p28–EBI3), IL28A, IL28B, IL29, IL30, IL31, IL32, IL33, IL35 (p35–EBI3), LT-alpha, LT-beta, LIGHT, TWEAK, APRIL, BAFF, TL1A, GITRL, OX40L, CD40L, FASL, CD27L, CD30L, 4-1BBL, TRAIL, RANK, GM-CSF, M-CSF, SCF, IL1-alpha, IL1-beta, aFGF, bFGF, int-2, KGF, EGF, TGF-alpha, TGF-beta, TNF-alpha, TNF-beta, betacellulin, SCDGF, amphiregulin or HB-EGF, as is known to the person skilled in the art and can be derived, for example, from Tato, C. M. & Cua, D. J. (*Cell* 132: 900; *Cell* 132: 500, *Cell* 132: 324, (2008)) or from Cytokines & Cells Online Pathfinder Encyclopaedia www.copewith-cytokines.de. "Pro-inflammatory cytokines" are also contemplated. The term "pro-inflammatory cytokine" means an immunoregulatory cytokines that favours inflammation. Typically, pro-inflammatory cytokines comprise IL-1-alpha, IL-1-beta, IL-6, and TNF-alpha. These pro-inflammatory cytokines are largely responsible for early responses. Other pro-inflammatory mediators include LIF, IFN-gamma, IFN-alpha, OSM, CNTF, TGF-beta, GM-CSF, TWEAK, IL-11, IL-12, IL-15, IL-17, IL-18, IL-19, IL-20, IL-8, IL-16, IL-22, IL-23, IL-31, and IL-32 (Tato, C. M. & Cua, D. J. *Cell* 132:900; *Cell* 132:500, *Cell* 132, 324 (2008)). These pro-inflammatory cytokines may act as endogenous pyrogens (IL-1, IL-6, TNF-alpha), up-regulate the synthesis of secondary mediators and pro-inflammatory cytokines by both macrophages and mesenchymal cells (including fibroblasts, epithelial and endothelial cells), stimulate the production of acute phase proteins, or attract inflammatory cells. Preferably, the term "pro-inflammatory cytokine" relates to TNF-alpha, IL-15, IFN-gamma, IFN-alpha, IL-1-beta, IL-8, IL-16 and IL-22.

The term "downregulates" means that the mRNA levels of an expressed gene, e.g. of a cytokine gene, and/or the protein levels expressed by such mRNAs is reduced in the presence of compound(s) of the invention. The downregulation of mRNA and/or protein expressed by that mRNA in the context of the compounds of the invention can be tested and determined by methods known to a person skilled in the art or by methods exemplified in the appended examples. "Downregulating" encompasses that the expression (either on mRNA or protein level) is reduced by at least 5%, 10%, 15%, 20%, 25%, 30%, 35%, 40%, 45%, 50%, 55%, 60%, 65%, 70%, 75%, 80%, 85%, 90%, 95% or 99% in comparison to a control, in which the incubation has been carried out without compound(s) of the invention, e.g. solely in the presence of medium. It can be tested by a method of quantitive RNA analysis, as described in Myers, T. W. and Gelfand, D. H., *Biochem.* 30:7661-7667 (1991); Krug, M. S. and Berger, S. L., *Methods Enzymol.* 152:316-325 (1987); Bustin, S. A., *J. Mol. Endocrinol.* 29:169-193 (2000); Bustin, S. A., *J. Mol. Endocrinol.* 25:23-39 (2002); Ståhlberg, A. et al., Clin. Chem. 50:509-515 (2004)).

A compound of the invention is preferably capable of downregulating pro-inflammatory cytokines.

More preferably, it is capable of downregulating any one of pro-inflammatory cytokines described above, preferably TNF-alpha, IL-15, IFN-alpha, IL-1-beta, IL-8, IL-16 and/or IL-22. The term "downregulating" has been described herein above. The downregulation may be tested in a RNA quantification assay or a test known to the person skilled in the art, for example a test as described in the Examples.

The term "cytokine receptor" refers to any receptor molecule, which is able to bind a cytokine as a ligand. In the context of the present invention, the term preferably relates to any receptor of the cytokines mentioned herein above, more preferably of the pro-inflammatory cytokines described herein above. The term "downregulates" has been described herein above. The downregulation may be tested in a RNA quantification assay or test known to the person skilled in the art and/or by a method as described in the Examples.

In a further preferred embodiment the compounds of the invention are capable of downregulating cytokines, cytokine receptors and/or genes which respond to cytokines i.e. the compounds of the invention comprise in this embodiment the immunomodulatory domain(s) of compounds of the invention, particularly E3 ligase domain(s) and optionally also at least one leucine-rich repeat (LRR), i.e. one, two, three, four, five, six, seven or eight LRRs. The addition of further LRRs is also envisaged. It is likewise envisaged that these compounds of the invention are linked to/attached to a cargo molecule.

The term "genes which respond to cytokines" refers to any gene, which is regulated, i.e. can be activated or inactivated, or whose transcription can be initiated or stopped by any of the cytokines mentioned herein above. More preferably, it relates to genes that are regulated by TNF-alpha or IFN. Most preferably, the term relates to genes that are induced by TNF-alpha or induced by IFN. The term "downregulates" has been described herein above. The downregulation may be tested in a RNA quantification assay or test known to the person skilled in the art.

Pharmaceutical compositions of the invention preferably comprise an effector protein, variant, fragment, or immunomodulatory domain as defined above.

For modulation of cellular pathway of the innate immune system of a eukaryotic cell of a subject compounds of the invention preferably penetrate into the nucleus of a eukaryotic cell after autopenetration.

Hence an effector proteins, variant, fragment, or immunomodulatory domain according to present invention optionally penetrates into the nucleus of a eukaryotic cell after said effector protein, variant, fragment, or immunomodulatory domain has autonomously entered said eukaryotic cell.

Moreover pharmaceutical compositions of the invention optionally comprise an effector proteins, variant, fragment, or immunomodulatory domain of the invention that penetrates into the nucleus of a eukaryotic cell after said effector protein, variant, fragment, or immunomodulatory domain has autonomously entered said eukaryotic cell.

The term "penetrating the nucleus of a eukaryotic cell" or "entering the cell nucleus" means that a compound of the invention passes across the nuclear membrane of a cell. The capability of a compound of the invention to enter the cell nucleus can be tested by any suitable methods and assays known to the person skilled in the art, preferably by nuclear localization assays as described in Hällbrink M., et al., (2004) (*Biochem. Biophys*. Acta 1667:222) and Nare B., et al., (1999) (Anal. Biol. 267:390).

Preferably, the capability of a compound of the invention to enter the cell nucleus is linked to the presence of a nuclear localization sequence (NLS). More preferably, a compound of the invention comprises the NLS of said compound of the invention as known to the person skilled in the art. In a preferred embodiment compound(s) of the invention used in the context of pharmaceutical compositions comprise a NLS sequence.

Preferably pharmaceutical compositions of the invention lack any auxiliary agent which can cause the penetration of said effector protein into a eukaryotic cell. "Auxiliary agent" refers to any molecule that is able to deliver a cargo molecule into a eukaryotic cell. "Auxiliary agent" does not refer to compounds of the invention. Within the present invention auxiliary agents include but are not limited to non-bacterial cell-penetrating peptides, YopM, YopM fragment and YopM variants, and cell-penetrating nanoparticles. Within the present invention auxiliary agent also refers to functional bacterial secretion systems, preferably to functional T3SS.

More preferably pharmaceutical compositions of the invention lack any auxiliary agent selected from the group consisting of T3SS-containing bacterium, bacterium of the genus *Salmonella* or *Shigella*, and cell-penetrating molecule, including cell-penetrating protein that is different from an effector protein of the invention and cell-penetrating nanoparticle.

Pharmaceutical compositions of the invention preferably comprise an effector protein, variant, fragment, or immunomodulatory domain as defined above.

In one embodiment pharmaceutical compositions of the invention are for use in immunomodulatory therapy of animals or humans. Immunomodulatory therapy thereby refers to the treatment of disease by inducing, enhancing, or suppressing an immune response.

In another embodiment pharmaceutical compositions of the invention are for use in immunosuppressive therapy of animals or humans.

In another embodiment pharmaceutical compositions of the invention are for use in the regulation of inflammatory reactions of the immune system, treatment of diseases caused by autoimmunity, acute inflammation or chronic inflammation, treatment of inflammatory disorders, and/or for suppressing the immune system.

In one aspect the present invention relates to a pharmaceutical composition as defined herein above for immunomodulation, preferably for immunomodulation of inflammatory reactions. The term "immunomodulation" means regulation of reactions of the immune system. The term "immunomodulation of inflammatory reactions" refers to the regulation of inflammatory reactions of the immune system. Such inflammatory reactions are known to the skilled person and can be derived, for example, from Schmidt-Schönbein (*Annu. Rev. Biomed. Eng.* 8: 93-151 (2006)).

In a preferred embodiment the pharmaceutical composition as defined herein above is for the treatment of diseases caused by autoimmunity of the host. The term "diseases caused by autoimmunity of the host" means a disease, which is caused by an immune reaction of the host's immune system. Such diseases are known to the person skilled in the art and can be derived, for example, from www.sbi.uni-rostock.de. Preferably, the term relates to acute disseminated encephalomyelitis (ADEM), Addison's disease, ankylosing spondylitis, antiphospholipid antibody syndrome (APS), aplastic anemia, autoimmune hepatitis, autoimmune Oophoritis, celiac disease, Crohn's disease (Morbus Crohn), diabetes mellitus type 1, gestational pemphigoid, goodpasture's syndrome, Graves' disease, Guillain-Barré syndrome (GBS), Hashimoto's disease, idiopathic thrombocytopenic purpura, Kawasaki's disease, lupus erythematosus, Mixed Connective Tissue Disease, multiple sclerosis, myasthenia gravis, opsoclonus myoclonus syndrome (OMS), optic neuritis, Ord's thyroiditis, pemphigus, pernicious anaemia, primary biliary cirrhosis, rheumatoid arthritis, Reiter's syndrome, Sjögren's syndrome, Takayasu's arteritis, temporal arteritis, Warm autoimmune hemolytic anemia and Wegener's granulomatosis.

In a further preferred embodiment the pharmaceutical composition as defined herein above is for the treatment of "inflammation". The term "inflammation" means a biological response of tissues, e.g. vascular tissues, to harmful stimuli, such as pathogens, damaged cells, or irritants. Such a pathological condition is known to the person skilled in the art and can be derived, for example, from Schmidt-Schönbein (*Annu. Rev. Biomed. Eng.* 8: 93-151 (2006)). Preferably, the term relates to acute inflammation or chronic inflammation. Furthermore, it encompasses inflammatory disorders like asthma, chronic prostatitis, glomerulonephritis, hypersensitivities, inflammatory bowel diseases, pelvic inflammatory disease, reperfusion injury, arthritis, osteoarthritis, (juvenile) chronic arthritis, rheumatoid arthritis, psoriatic arthritis, *A. mutilans*, septic arthritis, infectious arthritis and/or reactive arthritis, transplant rejection or vasculitis. It also encompasses allergic reactions, inflammatory myopathies, atherosclerosis, ischaemic heart disease, gastroenteritis, chronic gastritis, colitis ulcerose and psoriasis or psoriasis arthritis.

More preferably, the pharmaceutical composition is for the regulation of inflammatory reactions of the immune system, the treatment of diseases caused by autoimmunity of the host, the treatment of inflammation, chronic inflammation, gastroenteritis, chronic gastritis, inflammatory bowel diseases (IBD), colitis ulcerosa, psoriasis, allergic reactions, Morbus Crohn, arthritis, osteoarthritis, (juvenile) chronic arthritis, rheumatoid arthritis, psoriatic arthritis, *A. mutilans*, septic arthritis, infectious arthritis and/or reactive arthritis or for suppressing the immune system.

In another aspect, the present invention relates to the use of compounds of the invention for the preparation of a pharmaceutical composition for immunomodulation of inflammatory reactions, the regulation of inflammatory reactions of the immune system, the treatment of diseases caused by autoimmunity of the host, and/or the treatment of inflammation, chronic inflammation, gastroenteritis, chronic gastritis, inflammatory bowel diseases (IBD), colitis ulcerosa, psoriasis, allergic reactions, Morbus Crohn, arthritis, osteoarthritis, (juvenile) chronic arthritis, rheumatoid arthritis, psoriatic arthritis, *A. mutilans*, septic arthritis, infectious arthritis, and/or reactive arthritis, or for suppressing the immune system.

In another embodiment the present invention relates to a method of treatment of any of the diseases and medical conditions mentioned herein, in particular in the context of the pharmaceutical composition as defined herein, comprising administering at least one compound of the invention, including all modifications as indicated herein (e.g linked cargo; linked cell specific targeting) to a subject. Preferably, the present invention relates to a method of preventing, ameliorating and/or treating diseases which were exemplified herein elsewhere. Preferably, the subject to be treated is an animal and more preferably, the subject to be treated is a human being.

Preferably the present invention provides a method of treatment of diseases caused by autoimmunity, treatment of acute inflammation, chronic inflammation, inflammatory disorders, pathogenic inflammatory reactions of the immune system, and/or a method of suppressing the immune system in a subject, comprising administering a therapeutically effective amount of a pharmaceutical composition of the invention to said subject. The term "therapeutical amount" is described elsewhere herein.

The present invention also provides kits or pharmaceutical packages that can be used in the context of the present invention, for example in the context of administration of the pharmaceutical composition. In one embodiment, a kit/package comprises at least one compound of the invention as defined herein, in one or more containers. Optionally, the kit/package further comprises a documentation indicating the treatment regimen, use and/or employment of the kits/package components or the pharmaceutical composition.

In one aspect, the present invention relates to the use of an isolated effector protein of a type III secretion system (T3SS)-containing bacterium of the genus *Salmonella* or *Shigella*, wherein the effector protein is characterized in that it
a) is recombinantly produced or chemically synthesized
b) comprises an E3 ubiquitin ligase domain, preferably an Novel E3 ubiquitin ligase
c) optionally comprises at least one leucine-rich repeat;
d) is a cell-penetrating protein, which translocates into eukaryotic cells without the requirement of a bacterial T3SS;
or use of a variant, fragment or immunomodulatory domain of said effector protein, for the preparation of a pharmaceutical composition for regulating inflammatory reactions of the immune system, treating diseases caused by autoimmunity, treating acute inflammation or chronic inflammation, treating of inflammatory disorders, and/or suppressing the immune system.

In another aspect, the present invention relates to the use of an isolated effector protein of a type III secretion system (T3SS)-containing bacterium of the genus *Salmonella* or *Shigella*, wherein the effector protein is characterized in that it
a) is recombinantly produced or chemically synthesized
b) comprises an E3 ubiquitin ligase domain, preferably an Novel E3 ubiquitin ligase
c) optionally comprises at least one leucine-rich repeat;
d) is a cell-penetrating protein, which translocates into eukaryotic cells without the requirement of a bacterial T3SS;
or use of a variant, fragment of said effector protein for the preparation of a pharmaceutical composition for delivering at least one cargo molecule across the membrane of a eukaryotic cell, wherein the fusion construct of cargo molecule and said effector protein or variant or fragment thereof is a cell-penetrating construct, which translocates into eukaryotic cells without the requirement of a bacterial T3SS.

"Cargo molecule" is described above.

The term "delivering a cargo molecule" means that said isolated compound of the invention is capable of transporting and delivering a cargo molecule as defined herein, e.g. peptides or proteins, DNA, RNA, carbohydrates, lipids or chemically devised molecules of natural or non-natural origin without accessory factors into higher cells.

Compounds of the invention also include polypeptides which comprise non-classical amino acids including D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoroamino acids, designer amino acids such as β-methyl amino acids, Cα-methyl amino acids, Nα-methyl amino acids, and amino acid analogs in general. Furthermore, the amino acid can be D (dextrorotary) or L (levorotary).

In the context of the present invention the term "compounds of the invention" also includes polypeptides which are differentially modified during or after translation, e. g. by glycosylation, acetylation, phosphorylation, amidation, derivatization by known protecting/blocking groups, or proteolytic cleavage etc. Any of numerous chemical modifications may be carried out by known techniques, including but not limited, to specific chemical cleavage by cyanogen bromide, trypsin, chymotrypsin, papain, V8 protease, acetylation, formylation, oxidation, reduction; or metabolic synthesis in the presence of tunicamycin; etc.

Additional post-translational modifications encompassed by the invention include, for example N-linked or O-linked carbohydrate chains, processing of N-terminal or C-terminal ends, attachment of chemical moieties to the amino acid backbone, chemical modifications of N-linked or O-linked carbohydrate chains, and addition or deletion of an N-terminal methionine residue as a result of prokaryotic host cell expression.

The present invention also relates to polypeptides of the invention (compounds of the invention). In one aspect the invention provides an isolated effector protein of a type III secretion system (T3SS)-containing bacterium of the genus *Salmonella* or *Shigella* or a variant, fragment or immunomodulatory domain of said effector protein, wherein the compound of the invention is artificially modified. "Artificially modified" refers to man-made modifications, such as labeling, chemical modification or derivatization as described below. By way of example, the invention relates to an isolated effector protein of a type III secretion system (T3SS)-containing bacterium of the genus *Salmonella* or *Shigella* or a variant, fragment or immunomodulatory domain of said effector protein, wherein said effector protein, variant, fragment or immunomodulatory domain is linked to a cargo molecule and/or cell-specific targeting agent.

Compounds of the invention may also be modified with a detectable label, such as an enzymatic, fluorescent, isotopic or affinity label to allow for detection and isolation of the protein, the addition of epitope tagged peptide fragments (e. g., His, FLAG, HA, GST, thioredoxin, maltose binding protein, etc.), attachment of affinity tags such as biotin and/or streptavidin, the covalent attachment of chemical moieties to the amino acid backbone, N-or C-terminal processing of the polypeptides ends (e. g., proteolytic processing), deletion of the N-terminal methionine residue, etc.

Compounds of the invention encompass chemically modified derivatives that may provide additional advantages such as increased solubility, stability, and circulating time of the polypeptide altogether increasing its half-life, or decreased immunogenicity (see U.S. Pat. No. 4,179,337). The chemical moieties for derivatization may be selected from water soluble polymers such as polyethylene glycol, ethylene glycol/propylene glycol copolymers, carboxymethyl cellulose, dextran, polyvinyl alcohol and the like. The polypeptides may be modified at random positions within the molecule, or at predetermined positions within the molecule and may include one, two, three or more attached chemical moieties. Preferably, a chemical derivatization is contemplated wherein the chemical is a hydrophilic polymer residue. Exemplary hydrophilic polymers, including derivatives, may be those that include polymers in which the repeating units contain one or more hydroxy groups (polyhydroxy polymers), including, for example, poly (vinyl alcohol); polymers in which the repeating units contain one or more amino groups (polyamine polymers), including, for example, peptides, polypeptides, proteins and lipoproteins, such as albumin and natural lipoproteins; polymers in which the repeating units contain one or more carboxy groups (polycarboxy polymers), including, for example, carboxymethyl cellulose, alginic acid and salts thereof, such as sodium and calcium alginate, glycosaminoglycans and salts thereof, including salts of hyaluronic acid, phosphorylated and sulfonate derivatives of carbohydrates, genetic material, such as interleukin-2 and interferon, and phosphorothioate oligomers; and polymers in which the repeating units contain one or more saccharide moieties (polysaccharide polymers), including, for example, carbohydrates.

The molecular weight of the hydrophilic polymers may vary, and is generally about 50 to about 5,000,000, with polymers having a molecular weight of about 100 to about 50,000 being preferred. The polymers may be branched or unbranched. More preferred polymers have a molecular weight of about 150 to about 10,000, with molecular weights of 200 to about 8,000 being even more preferred.

For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e. g., the duration of sustained release desired, the effects, if any on biological activity, the ease in handling, the degree or lack of antigenicity and other known effects of the polyethylene glycol to a therapeutic protein or analog). Additional preferred polymers, which may be used to derivatize the compounds of the invention, include, for example, poly(ethylene glycol) (PEG), poly(vinylpyrrolidine), polyoxomers, polysorbate and poly(vinyl alcohol), with PEG polymers being particularly preferred. Preferred among the PEG polymers are PEG polymers having a molecular weight from about 100 to about 10,000. More preferably, the PEG polymers have a molecular weight of from about 200 to about 8,000, with PEG 2,000, PEG 5,000 and PEG 8,000, which have molecular weights of 2,000, 5,000 and 8,000, respectively, being even more preferred. Other suitable hydrophilic polymers, in addition to those exemplified above, are known to the person skilled in the art. Generally, the polymers used may include polymers that can be attached to the polypeptides of the invention via alkylation or acylation reactions.

The polyethylene glycol molecules (or other chemical moieties) should be attached to the compounds of the invention with consideration of effects on functional or antigenic domains of the protein. There are a number of attachment methods available to those skilled in the art, e.g derivable from EP 0 401 384. For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group. One may specifically desire proteins chemically modified at the N-terminus.

Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein.

The method of obtaining the N-terminally pegylated preparation (i. e., separating this moiety from other monopegylated moieties if necessary) may be by purification of the N-terminally pegylated material from a population of pegylated protein molecules.

Selective proteins chemically modified at the N-terminus modification may be accomplished by reductive alkylation that exploits differential reactivity of different types of primary amino groups (lysine versus the N-terminus) available for derivatization in a particular protein. Under the appropriate reaction conditions, substantially selective derivatization of the protein at the N-terminus with a carbonyl group containing polymer is achieved.

As with the various polymers exemplified above, it is contemplated that the polymeric residues may contain functional groups in addition, for example, to those typically involved in linking the polymeric residues to the compound of the invention in accordance with the present invention. Such functionalities include, for example, carboxyl, amine, hydroxy and thiol groups.

In addition to residues of hydrophilic polymers, the chemical used to derivatize the polypeptides of the present invention can be a saccharide residue. Exemplary saccharides which can be derived include, for example, monosaccharides or sugar alcohols, such as erythrose, threose, ribose, arabinose, xylose, lyxose, fructose, sorbitol, mannitol and sedoheptulose, with preferred monosaccharides being fructose, mannose, xylose, arabinose, mannitol and sorbitol; and disaccharides, such as lactose, sucrose, maltose and cellobiose. Other saccharides include, for example, inositol and ganglioside head groups. Other suitable saccharides, in addition to those exemplified above, will be readily apparent to one skilled in the art based on the present disclosure. Generally, saccharides that may be used for derivatization include saccharides that can be attached to the polypeptides of the invention via alkylation or acylation reactions.

Moreover, the invention also encompasses derivatization of the compounds of the invention, for example, with lipids (including cationic, anionic, polymerized, charged, synthetic, saturated, unsaturated, and any combination of the above, etc.) or stabilizing agents. Preferably, the present invention encompasses derivatization of compound of the invention with compounds that may serve a stabilizing function (e.g., to increase the polypeptides half-life in solution, to make the polypeptides more water soluble, to increase the polypeptides hydrophilic or hydrophobic character, etc.). Polymers useful as stabilizing materials may be of natural, semi-synthetic (modified natural) or synthetic origin. Exemplary natural polymers include naturally occurring polysaccharides, such as, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dermatan, hyaluronic acid, alginic acid, xanthin gum, starch and various other natural homopolymer or heteropolymers, such as those containing one or more of the following aldoses, ketoses, acids or amines: erythose, threose, ribose, arabinose, xylose, lyxose, allose, altrose, glucose, dextrose, mannose, gulose, idose, galactose, talose, erythrulose, ribose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Accordingly, suitable polymers include, for example, proteins, such as albumin, polyalginates, and polylactide-coglycolide polymers. Exemplary semi-synthetic polymers include carboxymethylcellulose, hydroxymethyl-cellulose, hydroxypropylmethylcellulose, methylcellulose, and methoxycellulose. Exemplary synthetic polymers include polyphosphazenes, hydroxyapatites, fluoro-apatite polymers, polyethylenes (such as, for example, polyethylene glycol, polyoxyethylene, and polyethylene terephthlate), polypropylenes (such as, for example, polypropylene glycol), polyurethanes (such as, for example, polyvinyl alcohol (PVA), polyvinyl chloride and polyvinylpyrrolidone), polyamides including nylon, polystyrene, polylactic acids, fluorinated hydrocarbon polymers, fluorinated carbon polymers (such as, for example, polytetrafluoroethylene), acrylate, methacrylate, and polymethylmethacrylate, and derivatives thereof. Methods for the preparation of derivatized polypeptides of the invention which employ polymers as stabilizing compounds will be readily apparent to one skilled in the art, in view of the present disclosure, when coupled with information known in the art, such as that described and referred to in U.S. Pat. No. 5,205,290.

The "type III secretion system" (T3SS) is a complex molecular injection machine of many pathogenic gram-negative bacteria (see e.g. Cornelis G R et al., 2006; Büttner D et al., 2006). According to phylogenetic differences in amino acid sequences, T3S systems from animal- and plant-pathogenic or symbiotic bacteria have been classified into different families, including flagellar T3SS, Ysc, Inv-Mxi-Spa, Ssa-Esc, Hrp1, and Hrp2 T3S systems as well as T3SS of the Chlamydiales and Rhizobiales families (Büttner D et al., 2006). Within the present invention the term "T3SS" encompasses all classes of type III secretion systems.

Pathogenic bacteria use the needle-like structure of the T3SS as a sensory probe to detect the presence of eukaryotic organisms and to secrete proteins, called effector proteins directly from the bacterial cell into the eukaryotic host cell. Within the present invention T3SS-containing bacteria include *Salmonella* spp., *Shigella* spp., *Yersinia* spp., *Escherichia* spp., *Pseudomonas* spp. and *Chlamydia* spp. These species include *Salmonella bongori, Salmonella enterica, Salmonella subterranean, Salmonella typhi, Salmonella typhimurium, Salmonella enterica* serovar *typhimurium, Salmonella enteritidis, Salmonella pullorum, Salmonella dublin, Salmonella arizonae, Salmonella choleraesius, Shigella flexneri, Shigella dysenteriae, Shigella sonnei, Shigella Yersinia pestis, Yersinia enterocolitica, Yersinia pseudotuberculosis*, Enteropathogenic *Escherichia coli* strains (EPEC), *Pseudomonas aeruginosa, Pseudomonas syringae*. Subspecies of species above listed are also encompassed within the present invention.

Salmonellae are described to contain two type III secretion systems, which are encoded by two distinct gene clusters termed SPI-1 and SPI-2 (for Salmonella pathogenicity island) (Hueck C J, 1998). T3SS-containing *Salmonella* spp. refer herein to *Salmonella* spp. containing a T3SS encoded by SPI-1 and to *Salmonella* spp. containing a T3SS encoded SPI-2.

The term "cell" or "eukaryotic cell" means any type of isolated eukaryotic cell, cells in the context of a living organism or in tissue as well as isolated cells/tissues in cell cultures (for example HeLa cells, T84 cells, HL60 cells or XS52 cells etc.). Preferably, the term relates to higher eukaryotic cells, more preferably to animal cells, even more preferably to mammalian cells and most preferred to human cells. Epithelial cells, fibroblasts (for example synovial fibroblasts—see Example 9), primary cells, endothelial cells (for example human intestinal microvascular endothelial cells HIMEC—see Example 8), cells of the immune system like monocytes, dendritic cells, macrophages and/or NK cells are also envisaged.

Whether any particular polypeptide is at least 40%, 50%, 60%, 70%, 80%, 90%, 91%, 92%, 93%, 94%, 95%, 96%, 97%, 98%, or 99% identical to the sequence of a compound of the invention as described herein can be determined by any means known to the person skilled in the art, e.g. by using conventionally known computer programs. A preferred method for determining the best overall match between a query sequence (a sequence of the present invention) and a subject sequence, also referred to as a global sequence alignment, can be determined using the CLUSTALW computer program (Thompson, J. D., et al., *Nucleic Acids Research*, 2 (22): 4673-4680, (1994)), which is based on the algorithm of Higgins, D. G., et al., *Computer Applications in the Biosciences* (CABIOS), 8 (2): 189-191, (1992). The result of said global sequence alignment is in percent identity. Preferred parameters used in a CLUSTALW alignment of protein sequences to calculate percent identity via pairwise alignments are: Matrix=Gonnet, k-tuple=1, Number of Top Diagonals=5, Gap Penalty=3, Gap Open Penalty 10, Gap Extension Penalty=0. 1, Scoring Method=Percentage, Window Size=5 or the length of the subject polypeptide sequence, whichever is shorter. The pairwise and multiple alignment parameters provided for CLUSTALW above represent the default parameters as provided with the AlignX software program (Vector NTI suite of programs).

The present invention encompasses the application of a manual correction to the percent identity results, in the instance where the subject sequence is shorter than the query sequence because of N-terminal or C-terminal deletions, not because of internal deletions. If only the local pairwise percent identity is required, no manual correction is needed.

However, a manual correction may be applied to determine the global percent identity from a global polypeptide alignment. Percent identity calculations based upon global polypeptide alignments are often preferred since they reflect the percent identity between the polypeptide molecules as a whole (i. e., including any overhangs, not just overlapping regions), as opposed to, only local matching polypeptides. Manual corrections for global percent identity determinations are required since the CLUSTALW program does not account for N-terminal or C-terminal truncations of the subject sequence when calculating percent identity. For subject sequences truncated at the N-terminal or C-terminal ends, relative to the query sequence, the percent identity is corrected by calculating the number of amino acids of the query sequence that are N-terminal or C-terminal of the subject sequence, which are not matched/aligned, as a percent of the total amino acids of the query sequence. Whether an amino acid is matched/aligned is determined by results of the CLUSTALW sequence alignment. This percentage is then subtracted from the percent identity, calculated by the above CLUSTALW program using the specified parameters, to arrive at a final percent identity score. This corrected score may be used for the purposes of the present invention. In addition to the above method of aligning two or more polypeptide sequences to arrive at a percent identity value for the aligned sequences, it may be desirable in some circumstances to use a modified version of the CLUSTALW algorithm which takes into account known structural features of the sequences to be aligned, such as for example, the SWISS-PROT designations for each sequence. The result of such a modified CLUSTALW algorithm may provide a more accurate value of the percent identity for two polypeptide sequences. Support for such a modified version of CLUSTALW is provided within the CLUSTALW algorithm and would be readily appreciated to a person skilled in the art.

Polynucleotides encoding compound(s) of the invention may contain alterations in the coding regions, non-coding regions, or both. For example, the polynucleotides encoding compound(s) of the invention may contain alterations, which produce silent substitutions, additions, or deletions, but do not alter the properties or activities of the encoded polypeptide. Nucleotide variants produced by silent substitutions due to the degeneracy of the genetic code are preferred.

Compounds of the invention are preferably produced recombinantly, for example, by any suitable method known to the person skilled in the art. The present invention, thus, also encompasses methods for the production of polypeptides of the invention. Accordingly, the present invention contemplates polynucleotides encoding polypeptides of the invention and vectors containing said polynucleotides, host cells comprising those polynucleotides and/or vectors, and the production of polypeptides of the invention by recombinant techniques. A suitable vector may be, for example, a phage, plasmid, viral, or retroviral vector. Retroviral vectors may be replication-competent or replication-defective. In the latter case, viral propagation generally will occur only in complementing host cells.

Polynucleotides encoding polypeptides of the invention may be joined to a vector containing a selectable marker for propagation in a host.

As indicated, the expression vectors will preferably include at least one selectable marker. Such markers include, for instance, dihydrofolate reductase, G418, or neomycin resistance for eukaryotic cell culture and tetracycline, kanamycin, or ampicillin resistance genes for culturing in *E. coli* and other bacteria.

Representative examples of appropriate hosts include, but are not limited to, bacterial cells, such as *E. coli, Streptomyces* and *Salmonella typhimurium* cells; fungal cells, such as yeast cells (e.g., *Saccharomyces cerevisiae* or *Pichia pastoris*); insect cells such as *Drosophila melanogaster* S2 and *Spodoptera frugiperda* Sf9 cells; animal cells such as CHO, COS, HEK 293, and Bowes melanoma cells; and plant cells. Appropriate culture mediums and conditions for the above described host cells are known in the art.

Vectors preferred for use in bacteria are known to the person skilled in the art.

Introduction of the construct into the host cell can be effected by methods described in many standard laboratory manuals, such as Davis et al., (*Basic Methods In Molecular Biology* (1986)).

Polypeptides of the invention can be recovered and purified from recombinant cell cultures by any suitable method known to the person skilled in the art.

Polypeptides of the invention can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells.

In addition, polypeptides of the invention can be chemically synthesized using techniques known in the art (Creighton, 1983, *Proteins: Structures and Molecular Principles*, W. H. Freeman & Co., N. Y., and Hunkapiller et al., *Nature,* 310: 105-111 (1984)). For example, a polypeptide corresponding to a fragment of a polypeptide sequence of the invention can be synthesized by use of a peptide synthesizer.

It is envisaged that pharmaceutical compositions of the invention comprise one or more compounds of the invention which are further modified as explained herein, for example which are linked to a cargo molecule and/or linked to a cell-specific targeting agent. It is likewise envisaged that the pharmaceutical compositions of the present invention comprise the nucleic acids and/or polynucleotides of the present invention. The pharmaceutical composition may optionally comprise a pharmaceutically acceptable carrier.

A pharmaceutical composition according to the present invention may be administered with the help of various delivery systems known to the person skilled in the art, e. g., encapsulation in liposomes, microparticles, microcapsules, recombinant cells capable of expressing the compound, receptor-mediated endocytosis (see, e. g., Wu and Wu, J. Biol. Chem. 262: 4429-4432 (1987)), construction of a nucleic acid as part of a retroviral or other vector, etc. Methods of introduction include intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e. g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e. g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein of the invention, care must be taken to use materials to which the protein does not absorb.

A preferred method of local administration is by direct injection. Preferably, the compounds of the present invention as well as the nucleic acids/vectors of the present invention is/are complexed with a delivery vehicle to be administered by direct injection into or locally within the area of arteries.

For systemic administration, compounds of the invention can be complexed to a targeted delivery vehicle.

In another embodiment the pharmaceutical composition may be delivered directly to disease sites in internal organs, body cavities and the like by use of imaging devices used to guide an injecting needle directly to the disease site. The pharmaceutical composition may also be administered to disease sites at the time of surgical intervention.

In another embodiment, the pharmaceutical composition can be delivered in a vesicle, in particular a liposome (Langer, R., Science 249:1527-1533 (1990); Treat et al., in Liposomes in the Therapy of Infectious Disease and Cancer, Lopez-Berestein and Fidler (eds.), Liss, N.Y., pp. 353-365 (1989); Lopez-Berestein, ibid., pp. 317-327).

In yet another embodiment, the composition can be delivered in a controlled release system. In one embodiment, a pump may be used (Sefton, CRC Crit. Ref. Biomed. Eng. 14: 201 (1987); Buchwald et al., Surgery 88: 507 (1980); Saudek et al., N. Engl. J. Med. 321: 574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23: 61 (1983); see also Levy et al., Science 228: 190 (1985); During et al., Ann. Neurol. 25: 351 (1989); Howard et al., J. Neurosurg. 71: 105 (1989)). In yet another embodiment, a controlled release system can be placed in proximity of the therapeutic target, i. e., the brain, thus requiring only a fraction of the systemic dose (see, e. g., Goodson, in Medical Applications of Controlled Release, supra, vol. 2, pp. 115-138 (1984)).

Preferably the pharmaceutical composition is in a form, which is suitable for oral, local or systemic administration. In a preferred embodiment the pharmaceutical composition is administered locally, orally or systemically.

The term "pharmaceutically acceptable" means approved by a regulatory agency or other generally recognized pharmacopeia for use in animals, and more particularly in humans. The term "carrier" refers to a diluent, adjuvant, excipient, or vehicle with which the therapeutic is administered. Such a carrier is pharmaceutically acceptable, i.e. is non-toxic to a recipient at the dosage and concentration employed. It is preferably isotonic, hypotonic or weakly hypertonic and has a relatively low ionic strength, such as provided by a sucrose solution. Examples of suitable pharmaceutical carriers are described in "Remington's Pharmaceutical Sciences" by E. W. Martin.

Generally, the ingredients are supplied either separately or mixed together in unit dosage form, for example, as a dry lyophilised powder or water free concentrate in a hermetically sealed container such as an ampoule or sachette indicating the quantity of active agent.

Assays, e.g. those described in the Examples, may optionally be employed to help identify optimal dosage ranges. The precise dose to be employed in the formulation will also depend on the route of administration, and the seriousness of the disease or disorder, and should be decided according to the judgment of the practitioner and each patient's circumstances.

It is envisaged that pharmaceutical compositions of the invention comprise the compounds of the invention in a therapeutically effective amount.

The term "administered" means administration of a therapeutically effective dose of the aforementioned composition. By "therapeutically effective amount" is meant a dose that produces the effects for which it is administered, preferably this effect is the downregulation of cytokines, and/or cytokine receptors and/or genes which respond to cytokines. The exact dose will depend on the purpose of the treatment, and will be ascertainable by one skilled in the art using known techniques. As is known in the art and described above, adjustments for systemic versus localized delivery, age, body weight, general health, sex, diet, time of administration, drug interaction and the severity of the condition may be necessary, and will be ascertainable with routine experimentation by those skilled in the art.

The pharmaceutical composition may be used in both human therapy and veterinary therapy. The compounds described herein having the desired therapeutic activity may be administered in a physiologically acceptable carrier to a patient, as described herein. The concentration of the therapeutically active compound in the formulation may vary from about 0.01-100 wt %. The agent may be administered alone or in combination with other treatments.

A typical dose can be, for example, in the range of 0.001 to 1000 µg; however, doses below or above this exemplary range are envisioned, especially considering the aforementioned factors.

It is also envisaged that the pharmaceutical compositions are employed in co-therapy approaches, i.e. in co-administration with other medicaments or drugs, for example other immunosuppressive drugs.

Topical administration of the pharmaceutical composition of the present invention is useful when the desired treatment involves areas or organs readily accessible by topical administration. For a topically application, e.g. to the skin, the pharmaceutical composition is preferably formulated with a suitable paste, ointment, lotion, cream, gel or transdermal patches.

In a further embodiment compound(s) of the invention provided in the form of a living therapeutic. The term "living therapeutic" means that said compound(s) of the invention, for example as defined in the context of the pharmaceutical composition, is/are expressed in a live carrier. Accordingly, the present invention relates to polynucleotides encoding compounds of the invention as defined herein above which are suitable for expression in a living cell or carrier. The term "live carrier" relates to any appropriate living host cell or virus known to the person skilled in the art. Representative examples of appropriate hosts include, but are not limited to, bacterial cells such as *Escherichia coli* or *Lactobacillus*, fungal cells, such as yeast cells, protozoa, insect cells, or animal cells. Preferably, the term relates to attenuated bacteria, attenuated fungal cells or attenuated protozoa.

The present invention also relates to the use of a compound of the invention for the manufacture of a pharmaceutical composition. It is envisaged that compound(s) of the invention are linked/attached to a cargo molecule and/or a cell-specific targeting molecule as described herein. The mentioned pharmaceutical composition is for use in any of the diseases described herein.

The terms "leucine-rich repeat(s)" and "leucine-rich domain(s)" are used herein interchangeably.

The terms "cell-penetrating peptide", "CPP", "cell-penetrating protein", "cell-permeable peptide", "cell-penetrating protein" and are used herein interchangeably.

The terms "protein transduction domain" (PTD) and "cell-penetrating entity" are used herein interchangeably.

"Autopenetration" or "cell-penetration" as used herein describes the capability of compounds of the invention to penetrate the cell membrane and to enter the cytosol of a cell without the assistance of exogenous factors, such as a T3SS.

The terms "autopenetrating", "autonomously penetrating" and "penetrate/pass/cross the membrane of eukaryotic cells without the assistance of exogenous factors, such as a T3SS" are used herein interchangeably.

The terms "amino acid sequence" and "polypeptide sequence" are used herein interchangeably.

It is to be understood that this invention is not limited to the particular methodology, protocols, proteins, bacteria, vectors, reagents etc. described herein as these may vary. It is also to be understood that the terminology used herein is for the purpose of describing particular embodiments only, and is not intended to limit the scope of the present invention that will be limited only by the appended claims.

Several documents are cited throughout the text of this specification. Each of the documents cited herein (including all patents, patent applications, scientific publications, manufacturer's specifications, instructions, etc.), whether supra or infra, is hereby incorporated by reference in their entirety. Nothing herein is to be construed as an admission that the invention is not entitled to antedate such disclosure by virtue of prior invention.

It must be noted that as used herein and in the appended claims, the singular forms "a", "an", and "the", include plural referents unless the context clearly indicates otherwise. Thus, for example, reference to "a polypeptide" includes one or more of such polypeptides, and reference to "the method" includes reference to equivalent steps and methods known to those of ordinary skill in the art that could be modified or substituted for the methods described herein.

DESCRIPTION OF THE DRAWINGS

FIG. 3 shows an immunofluorescence microscopy of HeLa cells incubated with SspH1-Cy3 and SspH1-Nter-Cy3 1 h. DNA was stained with DAPI. Both fluorescence images were merged.

FIGS. 1 to 4 show that SspH1 and SspH1-Nter translocate into the host cell cytoplasm independently of Salmonella's T3SS.

FIGS. 6 to 10 show that recombinant SspH1 possesses E3 ubiquitin ligase activity.

FIG. 13.

FIGS. 14 to 22 shows amino acid sequences of SlrP, SspH1, SspH2, IpaH1.4, IpaH2.5, IpaH3, IpaH4.5, IpaH7.8 and IpaH9.8. leucine-rich repeats (called "LRR stretch") are marked in light grey and are non-edged. E3 Ubiquitin ligase domains are marked in dark grey and are edged. Sequence sections within which the protein transduction domains (PTDs) are predicted are bold and underlined. Marked are the maximal sequence sections within the PTD is predicted. PTDs can correspond to the marked sequence sections or to C-terminally and/or N-terminally truncated fragments of the marked sequence sections.

Western blot analysis after cell fractionation of HeLa cells which were incubated with the indicated LPX effector protein (25 µg/ml) for 3 h. Proteins were separated by 12.5% SDS-PAGE and immobilized on a nitrocellulose membrane by Western blotting. Proteins were detected using an a FLAG-antibody and corresponding PO-conjugated secondary antibody. Purity of both the cytoplasmic (CF) and membrane fraction (MF) were assesses using an α-GAPDH-antibody and a TF-R-antibody and corresponding PO-conjugated secondary antibodies.

Figure 24:
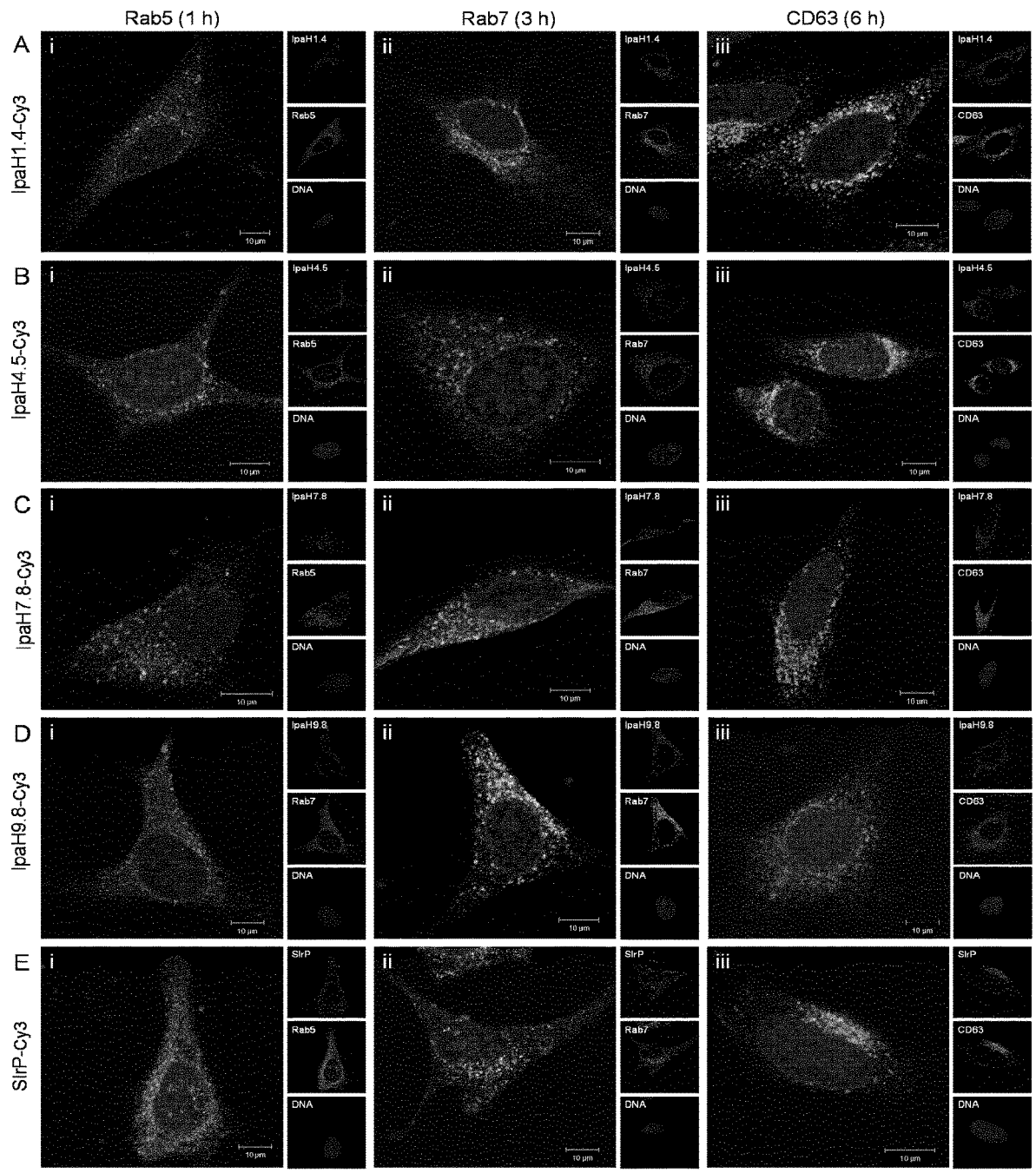

FIG. 24 shows a confocal fluorescence microscopy of HeLa cells incubated with recombinant IpaH1.4, IpaH4.5, IpaH7.8, IpaH9.8, or SlrP, concerning co-localization with the endocytic markers Rab5, Rab7, and CD63. HeLa cells were incubated with the indicated recombinant, Cy3-labeled (red) LPX effector proteins (25 µg/ml) for 1 h (i), 3 h (ii), and 6 h (iii), respectively (A)-(F). The endocytic markers Rab5, Rab7, and CD63 were detected using appropriate primary antibodies and stained via incubation with Cy2-labelled (green) secondary antibodies. DNA was stained using Draq5 (blue). Overlays of all three channels are shown in large squares; pictures of the individual channels are shown on the right. Magnification 63×.

Figure 25:
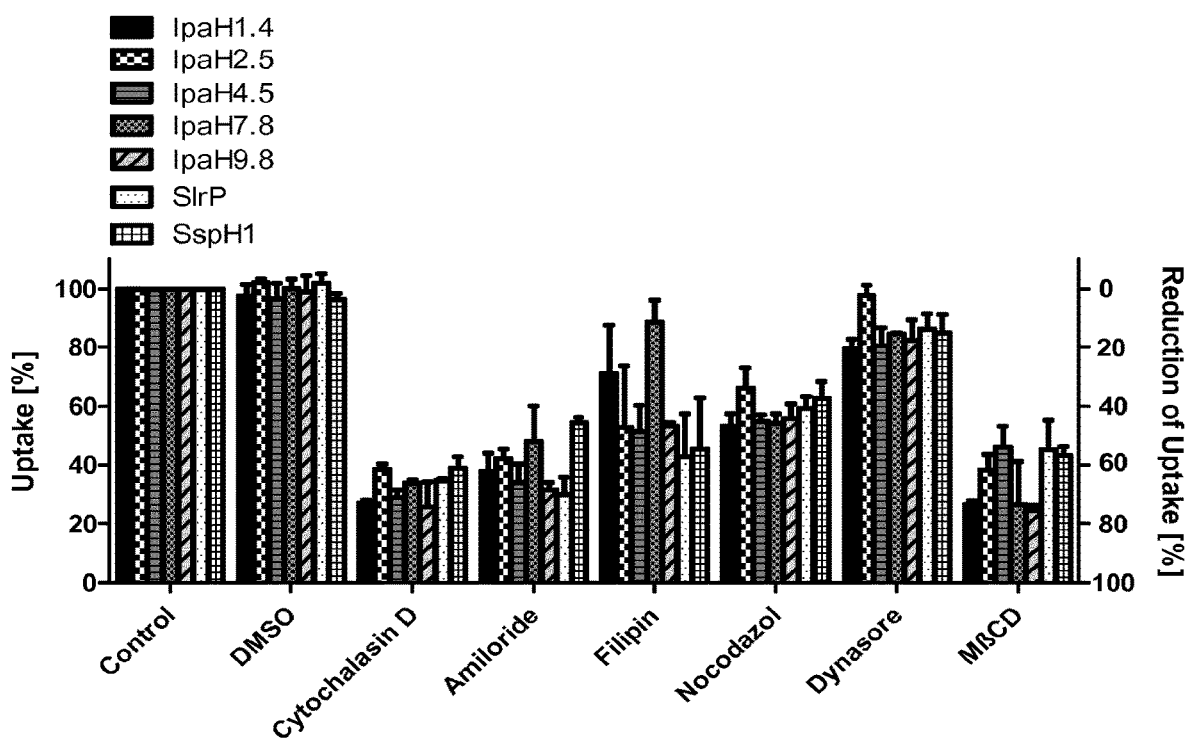
Figure 26:
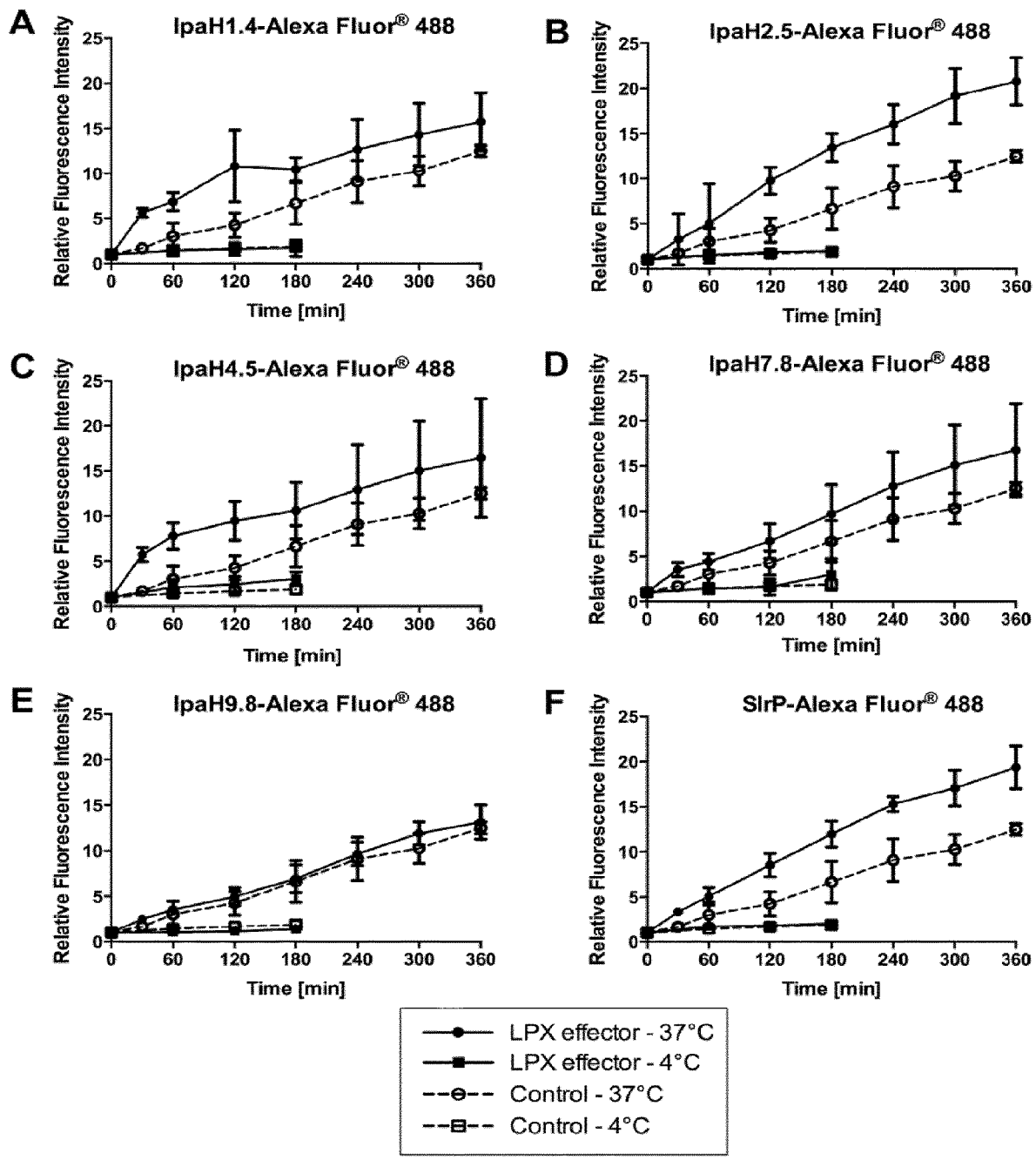

FIG. 25 shows a flow cytometry analysis of effector proteins of the LPX family. HeLa cells were with endocytic inhibitors cytochalasin D (2.5 µM), amiloride (3 mM), filipin (7.5 µM), nocodazole (20 µM), dynasore (80 µM), methyl-β-cyclodextrin (5 mM) for 1 h prior to the addition of recombinant LPX effectors. Three hours later the cells were washed with D-PBS (with $Ca^{2+}/Mg^{2+}$), trypsinized, resuspended in D-PBS (without $Ca^{2+}/Mg^{2+}$), diluted with trypan blue (final concentration 0.2%) and analyzed by flow cytometry FIG. 26 shows a membrane integrity assay of HeLa cells incubated with recombinant IpaH1.4, IpaH2.5, IpaH4.5, IpaH7.8, IpaH9.8, or SlrP. HeLa cells were co-incubated with both the indicated LPX effector protein (25 µg/ml) and propidium iodide (PI) (1 µg/ml) at 37° C. or 4° C. for a total duration of 6 h and 3 h, respectively, (A)-(F). Samples were taken from the ongoing incubation at given time points and subjected to FACS analysis. Fluorescence of PI was detected at 617 nm. All samples were measured twice and three independent experiments were carried out for each protein. (A)-(F): Diagrams show the fluorescence intensity of HeLa cells co-incubated with the indicated ALEXA FLUOR® 488-labeled LPX effector protein and PI at different incubation times both at 37° C. and 4° C. in comparison to HeLa cells which were solely incubated with PI (dashed lines). The geometric mean fluorescence [arbitrary units] (normalized to negative/untreated control cells) is plotted against the incubation time [minutes].

Figure 27:
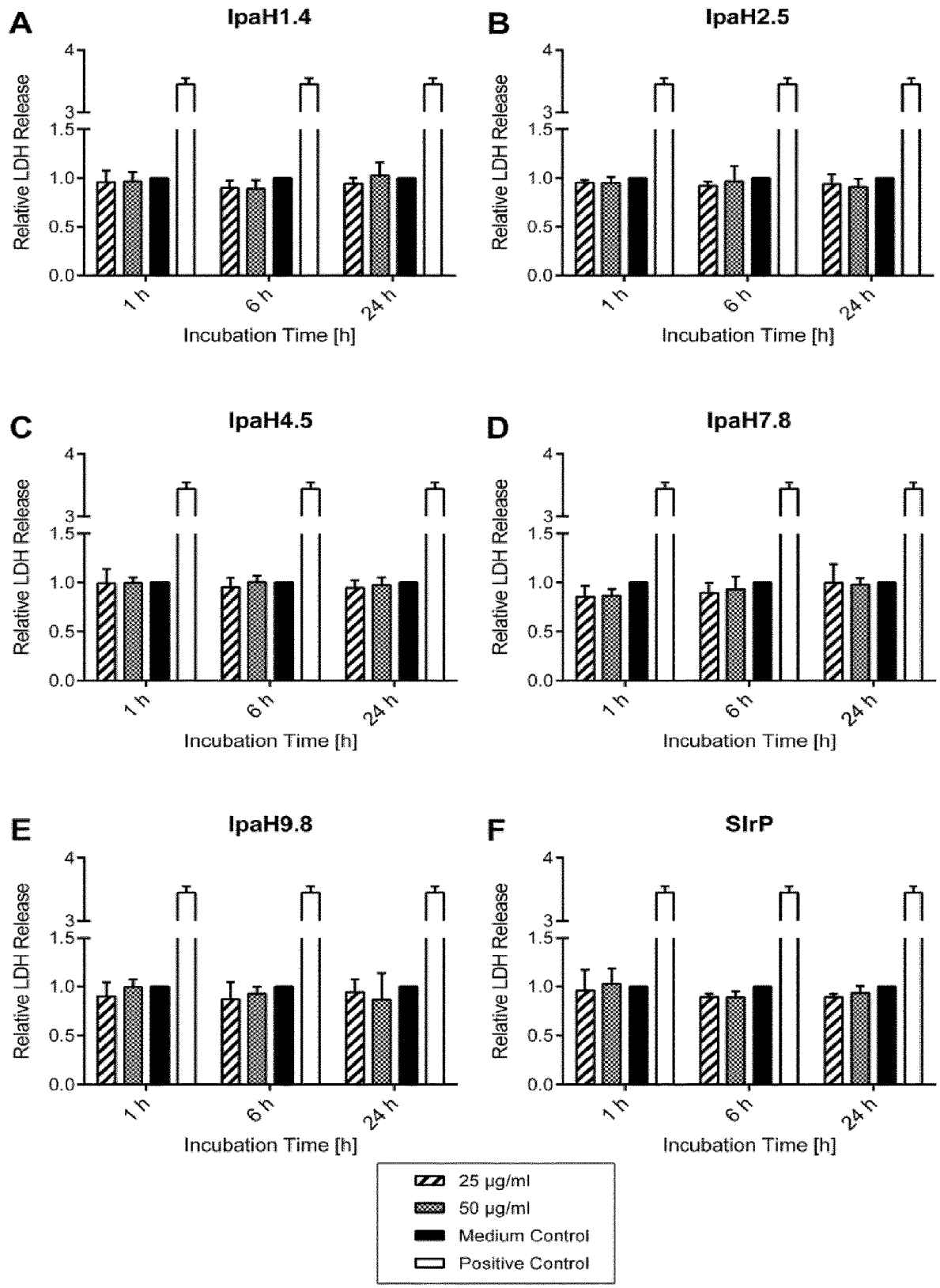

FIG. 27 shows the relative release of LDH of HeLa cells upon incubation with recombinant IpaH1.4, IpaH2.5, IpaH4.5, IpaH7.8, IpaH9.8, or SlrP. HeLa cells were incubated with the indicated LPX effector protein (25 µg/ml) for a total duration of 24 h, 6 h, and 1 h, respectively, (A)-(F). The release of LDH was measured using the CYTOTOX® 96 Non-Radioactive Cytotoxicity Assay. Diagrams show the relative amount of released LDH normalized to the amount releases by non-treated (Medium control) which was set equal to 1. Additionally, a LDH positive control was measured. LDH: Lactate dehydrogenase.

Figure 28:
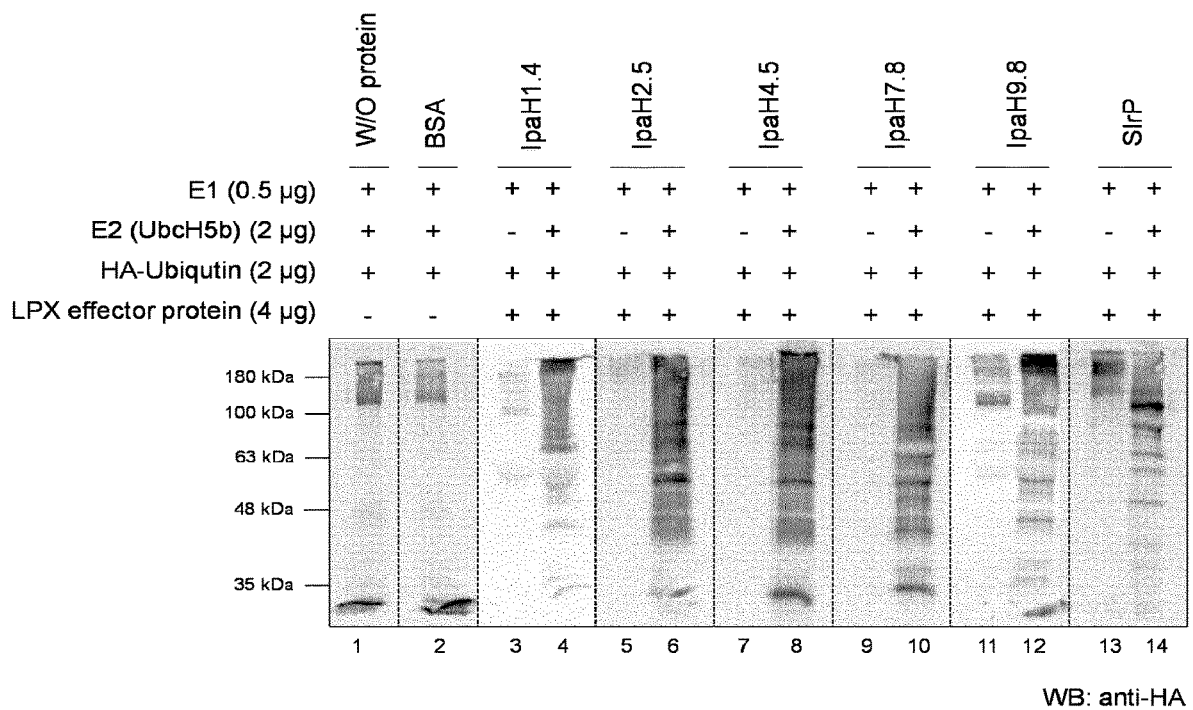

FIG. 28 shows an in vitro ubiquitination assay using either recombinant IpaH1.4, IpaH2.5, IpaH4.5, IpaH7.8, IpaH9.8, or SlrP. Western blot analysis of in vitro ubiquitination assays which were performed in 40 µl reaction mixtures containing (+) or not containing (−) the indicated protein (4 µg), HA-tagged ubiquitin (2 µg), E2 (UbcH5b)(2 µg), and E1 (0.5 µg). Reactions were stopped by the addition of 4× SDS sample buffer without DTT. Samples were subjected to 10% SDS-PAGE and immobilized on a Nitrocellulose membrane by Western blotting. Ubiquitin was detected using an α-HA antibody and a corresponding PO-conjugated secondary antibody. Different Western blots are separated by dashed lines.

DESCRIPTION OF THE SEQUENCE LISTING

SEQ ID NO: 1: Amino acid sequence of SlrP from *Salmonella enterica* subsp. *enterica* serovar *Typhimurium* str. 14028S SEQ ID NO: 2: Amino acid sequence of SspH1 from *Salmonella enterica* subsp. *enterica* serovar *Typhimurium* str. 14028S SEQ ID NO: 3: Amino acid sequence of SspH2 from *Salmonella enterica* subsp. *enterica* serovar *Typhimurium* str. 14028S SEQ ID NO: 4: Amino acid sequence of IpaH1.4 from *Shigella flexneri*

SEQ ID NO: 5: Amino acid sequence of IpaH2.5 from *Shigella flexneri*

SEQ ID NO: 6: Amino acid sequence of IpaH3 from *Shigella flexneri*

SEQ ID NO: 7: Amino acid sequence of IpaH4.5 from *Shigella flexneri*

SEQ ID NO: 8: Amino acid sequence of IpaH7.8 from *Shigella flexneri*

SEQ ID NO: 9: Amino acid sequence of IpaH9.8 from *Shigella flexneri*

SEQ ID NO: 10: Nucleotide sequence encoding the amino acid sequence shown in SEQ ID NO: 1

SEQ ID NO: 11: Nucleotide sequence encoding the amino acid sequence shown in SEQ ID NO: 2

SEQ ID NO: 12: Nucleotide sequence encoding the amino acid sequence shown in SEQ ID NO: 3

SEQ ID NO: 13: Nucleotide sequence encoding the amino acid sequence shown in SEQ ID NO: 4

SEQ ID NO: 14: Nucleotide sequence encoding the amino acid sequence shown in SEQ ID NO: 5

SEQ ID NO: 15: Nucleotide sequence encoding the amino acid sequence shown in SEQ ID NO: 6

SEQ ID NO: 16: Nucleotide sequence encoding the amino acid sequence shown in SEQ ID NO: 7

SEQ ID NO: 17: Nucleotide sequence encoding the amino acid sequence shown in SEQ ID NO: 8

SEQ ID NO: 18: Nucleotide sequence encoding the amino acid sequence shown in SEQ ID NO: 9

SEQ ID NOs: 19 to 27: Ubiquitin ligase domains of SEQ ID NOs: 1 to 9 as indicated in FIGS. 14-22

SEQ ID NOs: 28 to 36: Leucine rich repeat stretches or areas of comprising Leucine rich repeat stretches SEQ ID NOs: 1 to 9 as indicated in FIGS. 14-22

SEQ ID NOs: 37 to 65 and 550: Maximal protein-transduction domains of SEQ ID NOs: 1 to 9 as indicated in FIGS. 14-22

SEQ ID NOs: 66 to 529: Protein-transduction domains of SEQ ID NOs: 1 to 9 as determined in Example 5 and indicated in Example 9

SEQ ID NOs: 530 to 549: Oligonucleotide sequences as indicated in Table 3.3

EXAMPLES

The following examples are for illustrative purposes only and are not intended to limit the scope of the claims.

Example 1

SspH1 can Translocate into the Host Cell Cytoplasm Independently of *Salmonella*'s T3SS The present inventors constructed and recombinantly expressed SspH1, an LPX effector protein of *Salmonella enterica* serovar *typhimurium*. Potential T3SS-independent translocation of this effector protein was analyzed by cell fractionation of HeLa cells, immunofluorescence microscopy, and FACS.

Figure 1:
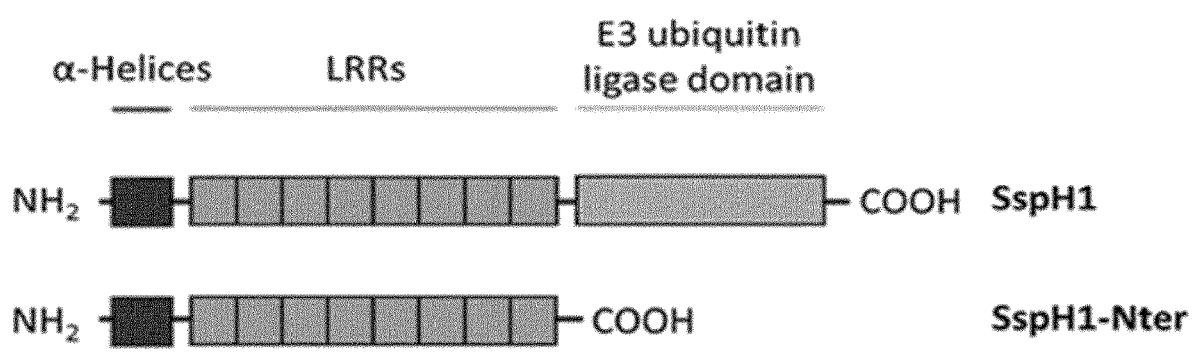
FIG. 1 shows a schematic overview of the recombinant SspH1 and its derivative SspH1-Nter. SspH1-Nter lacks the C-terminal domain of SspH1 which encodes an ubiquitin ligase. Proteins were tagged with a C-terminal 6× His-tag (not shown) for purification.

To enable the expression and purification of SspH1, recombinant proteins tagged with a C-terminal 6× His-tag were constructed. The C-terminal region of SspH1 encodes an ubiquitin ligase that might interfere with potential T3SS-independent uptake of SspH1 due to size and structure. Therefore, a truncated derivative of SspH1 was constructed in addition to the full length SspH1 protein. The N-terminal construct SspH1-Nter comprises the N-terminal α-helical domain as well as the Leucine-rich repeats (LRRs), lacking the enzymatic domain (FIG. 1). In order to initially analyse whether the recombinant proteins SspH1 and SspH1-Nter are able to translocate into the cytoplasm of eukaryotic host cells, cell fractionation of HeLa cells was performed.

Figure 2:
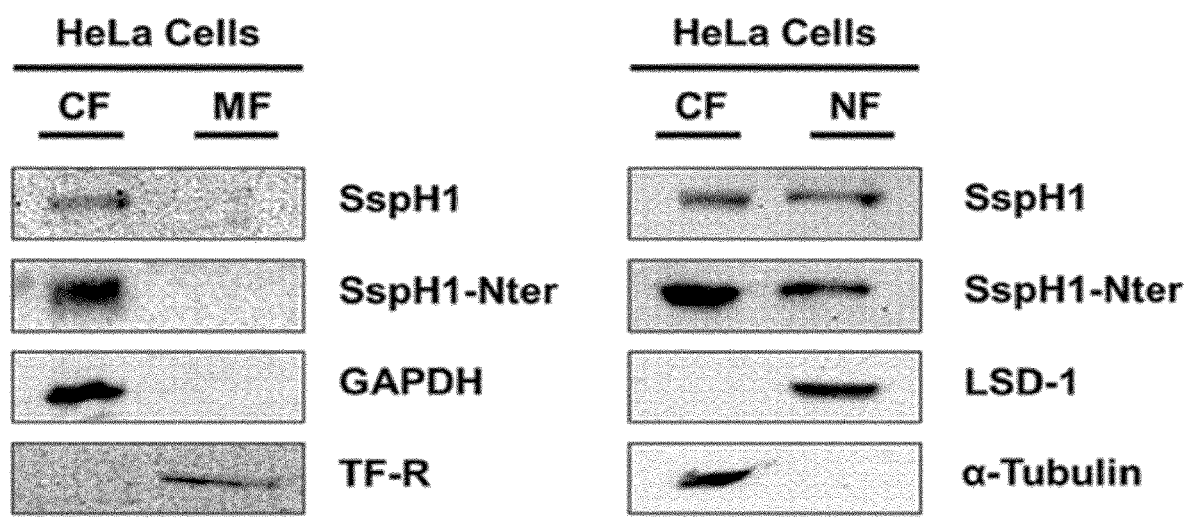
FIG. 2 shows an immunoblot analysis of subcellular fractionations of HeLa cells incubated with 25 µg/ml SspH1 and SspH1-Nter, respectively. In order to assess their purity, membrane and cytosolic fractions were analyzed using antibodies against transferrin receptor (TF-R) and glyceraldehyde 3-phosphate dehydrogenase (GAPDH), respectively (left panel). Purity of cytoplasmic and nuclear fractions was determined using antibodies against tubulin and Lysine-specific demethylase 1 (LSD-1), respectively (right panel). SspH1 and SspH1-Nter partition was assessed using anti-FLAG antibody. CF: cytoplasmic fraction MF: membrane fraction NF: nuclear fraction.

The results of the cell fractionation indicate that recombinant SspH1 is able to translocate across eukaryotic plasma membranes in a T3SS-independent manner and is taken up into the host cell cytoplasm. Furthermore, the N-terminal construct of SspH1 (SspH1-Nter), comprising the N-terminal α-helical domain and the LRRs, was also detected in the cytoplasmic fraction after 1 h of incubation of HeLa cells with the recombinant protein (FIG. 2). Internalization of the N-terminal construct indicates that T3SS-independent uptake of recombinant SspH1 depends on the N-terminal domain of the protein. The enzymatic C-terminal domain of SspH1 does not seem to interfere with membrane penetration. During infection, T3SS-translocated SspH1 has been shown to localize to the host cell nucleus (Haraga & Miller, 2003). In order to analyze localization of recombinant SspH1 to the nucleus, nuclear fractionation was performed. SspH1 as well as SspH1-Nter were detected in the nuclear fraction of HeLa cells after 1 h of incubation (FIG. 2), indicating that recombinant SspH1 is able to translocate to the nucleus following internalization by a yet unknown mechanism.

The uptake of recombinant SspH1 was further characterized by immunofluorescence microscopy of HeLa cells incubated with the recombinant protein. In order to allow detection of SspH1 and SspH1-Nter by immunofluorescence microscopy, the proteins were labeled with the fluorescent dye Cy3 (GE Healthcare, Braunschweig). Both proteins, Cy3-labeled SspH1 and SspH1-Nter are clearly detected in the HeLa cell cytoplasm indicating uptake of SspH1 (FIG. 3). The proteins show no obvious difference in their intracellular localization. Both proteins are equally distributed throughout the cytoplasm following internalization (FIG. 3).

Figure 4:
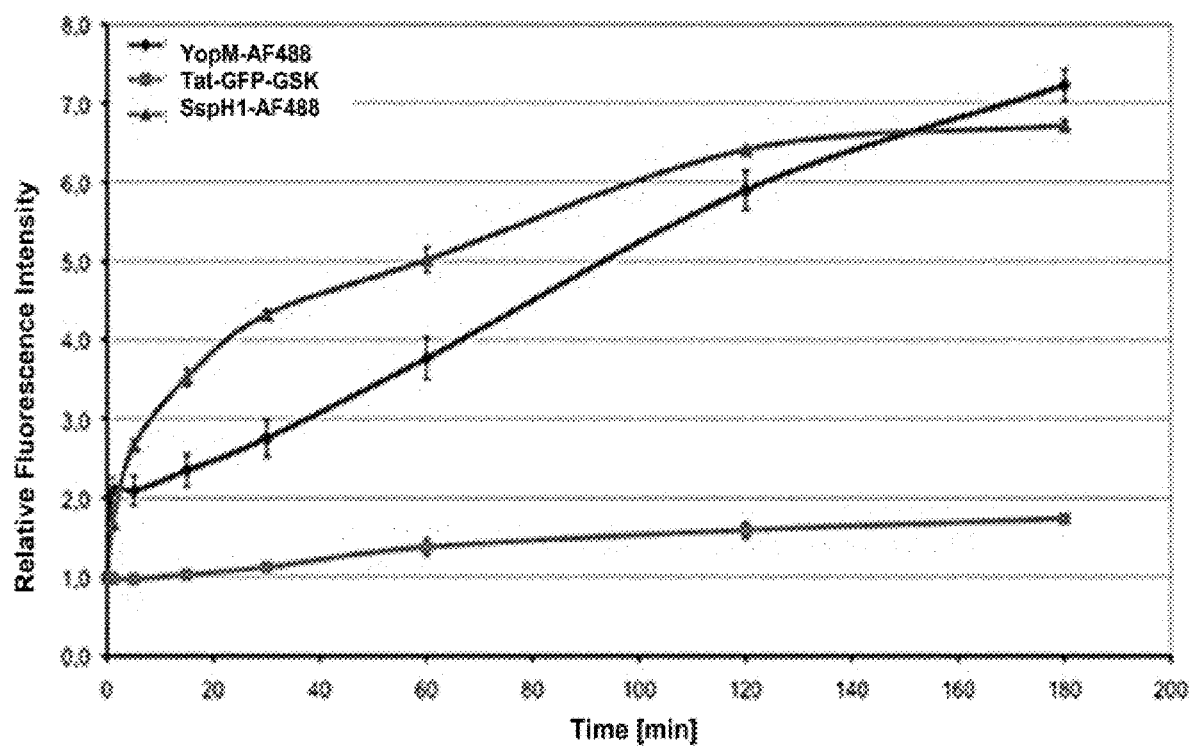
FIG. 4 shows a quenched time lapse assay of HeLa cells incubated with YopM-ALEXA FLUOR® 488, SspH1-ALEXA FLUOR® 488 or Tat-GFP-GSK. HeLa cells were incubated with 20 µg/ml protein. Samples were taken from the incubation at different time points. Extracellular fluorescence was quenched with trypan blue (final concentration: 0.2%) and intracellular fluorescence was measured using a flow cytometer. Data are expressed as geometric means of fluorescence intensities from at least 10,000 cells relative to background fluorescence of untreated cells, and are presented as means±standard deviations from three independent experiments.

For quantitative analysis of cell-penetration by SspH1, a flow cytometry-based quenched time-lapse assay was performed and compared to uptake efficiencies of YopM and the Tat-GFP-GSK fusion protein (FIG. 4). The results indicate a significantly higher uptake of the bacterial proteins YopM and SspH1 compared to the Tat-GFP-GSK fusion protein. After 3 h of incubation, the relative fluorescence intensity of cells incubated with AF488-labeled SspH1 and YopM, respectively is about 3.5 to 4 times higher than of cells incubated with Tat-GFP-GSK. These results correlate with the data obtained from fluorescence microscopy, where less Tat-GFP-GSK was detected within the cells compared to YopM.

Taken together, these experiments show that both bacterial effector proteins YopM and SspH1 are efficient cell-penetrating effector proteins (CPE), which share the ability to enter host cells independently of T3SS.

Example 2

Recombinant SspH1 Affects Membrane Integrity but is Not Cytotoxic

Figure 5:
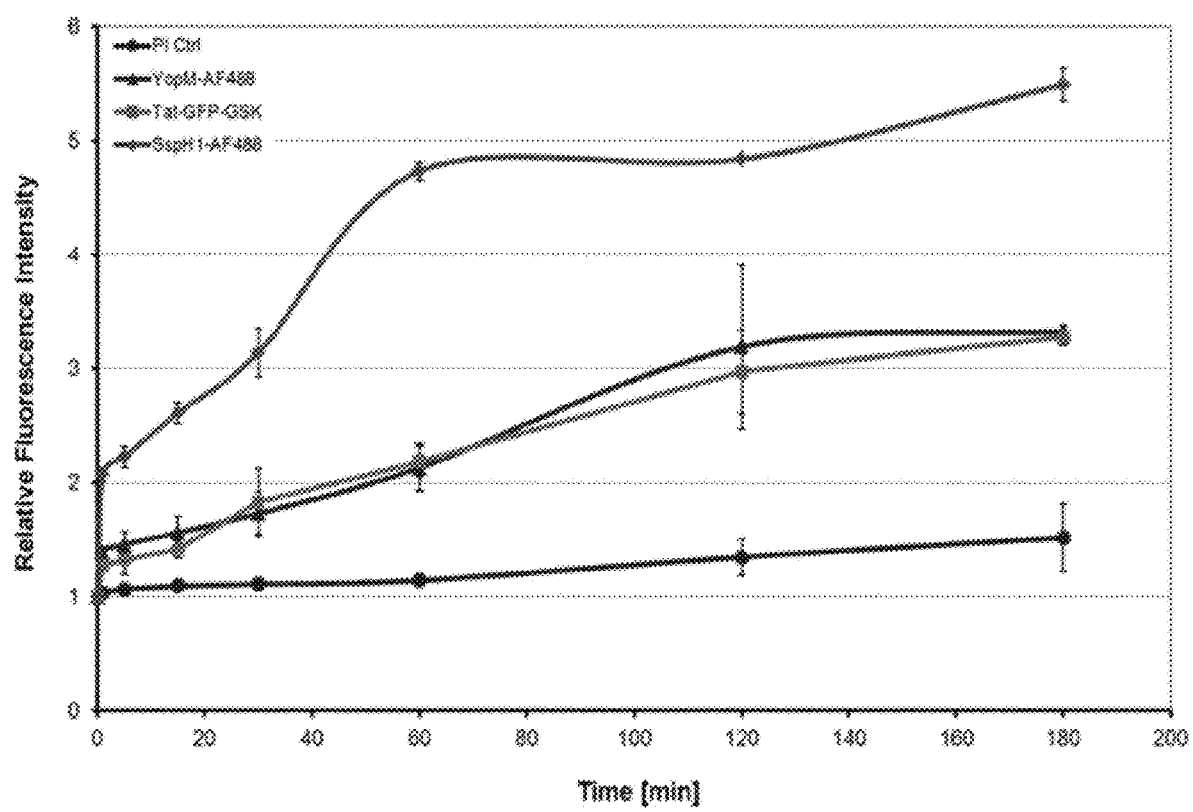
FIG. 5 shows a Membrane integrity assay of HeLa cells incubated with SspH1, YopM and Tat, respectively. Cells were incubated with 20 µg/ml protein and co-incubated with 1 µg/ml propidium iodide (P1).

HeLa cells were incubated with the recombinant proteins SspH1-AF488, YopM-AF488 and Tat-GFP-GSK and co-incubated with 1 μg/ml PI during the ongoing incubation (FIG. 5). Samples were taken from the culture at defined time points and directly subjected to FACS analysis. In addition to fluorescence of PI, the fluorescence of the recombinant proteins was measured to monitor uptake of the peptides. As a negative control, HeLa cells were incubated with PI but without addition of recombinant proteins. Untreated control cells were used to select viable cells for data acquisition before the samples were measured in triplicate with 10,000 events per measurement.

In order to monitor potential peptide-induced membrane lysis, the fluorescence intensity of PI of cells incubated with the recombinant proteins YopM-AF488, SspH1-AF488 and Tat-GFP-GSK, respectively, was measured. Membrane disruption is indicated by an increase of PI fluorescence due to increasing permeability of the plasma membrane for PI. Cells incubated with the recombinant proteins were compared to control cells which were also incubated with PI but not with the proteins.

Incubation of HeLa cells with SspH1 results in the highest increase of PI fluorescence indicating massive membrane disruption by the recombinant protein. The PI fluorescence intensity of cells incubated with SspH1 is 4 to 5 times higher during the course of incubation compared to the control cells. However, SspH1-induced membrane disruption does not seem to lead to cell lysis since only viable cells were detected for data acquisition. Cells incubated with the bacterial CPP YopM and the well described Tat peptide show an approximately 2-fold increase in PI fluorescence intensity compared to the control cells. These data indicate some effect on the membrane integrity by YopM and Tat though compared to SspH1, the effects are much lower. However, both proteins have been suggested to be internalised by endocytic uptake mechanisms which per se do not imply disruption of the plasma membrane. Thus, the present results indicate that accumulation of both proteins at the plasma membrane might cause destabilisation of the plasma membrane. Whether the observed membrane disruption leads to a potentially direct uptake of the peptides cannot be concluded from the present results. As for cells incubated with SspH1, effects of YopM and Tat-GFP-GSK do not lead to complete cell lysis as cells were still detected as viable.

Figure 6:
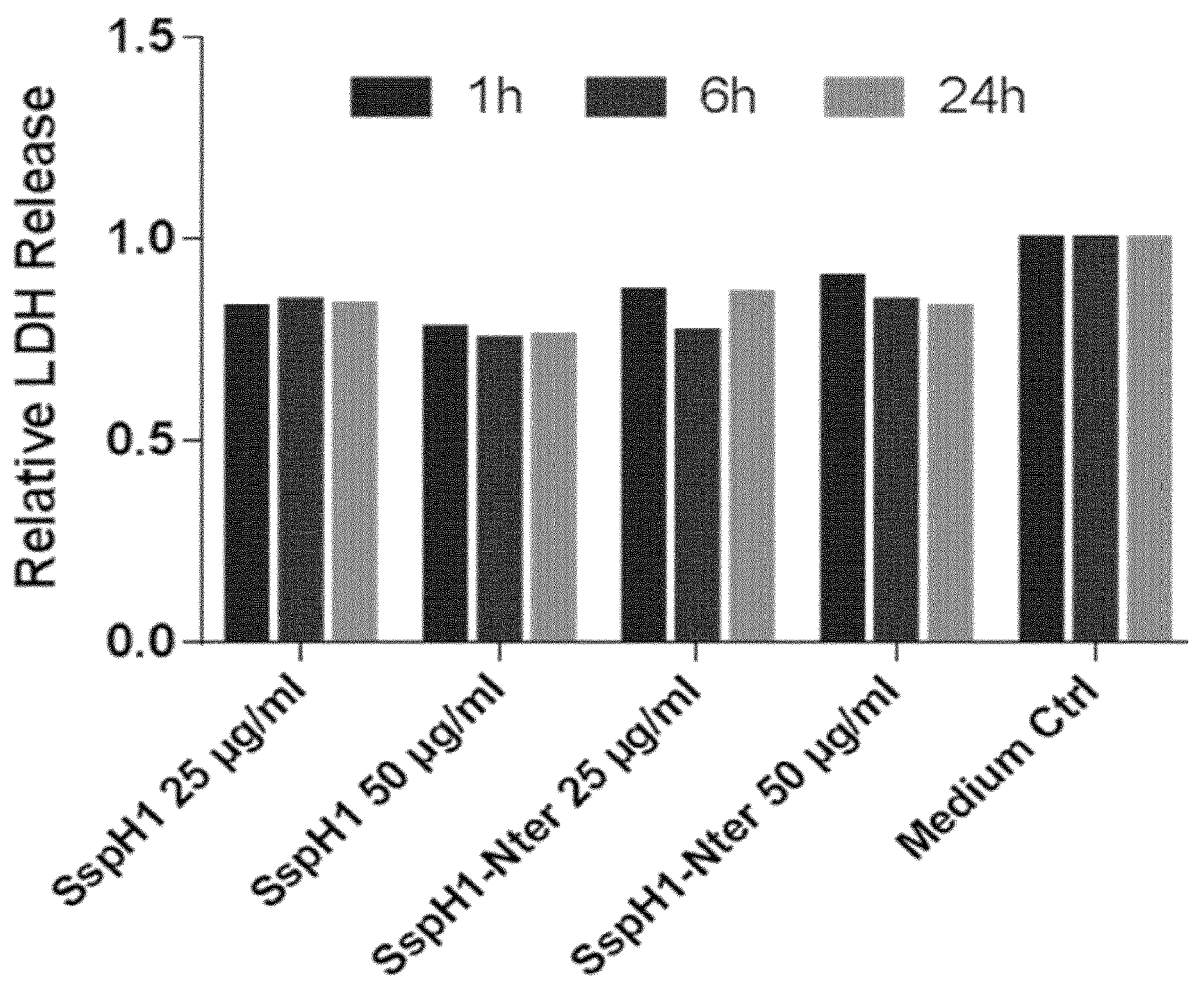
FIG. 6 shows Recombinant SspH1 and SspH1-Nter do not have cytotoxic effects on Hela cells. Cells were incubated with SspH1 and SspH1-Nter, respectively, for 1, 6, and 24 h and analysed using the CYTOTOX 96® Non-Radioactive Cytotoxicity Assay. LDH: lactate dehydrogensase.

In order to further exclude that the observed effect of SspH1 on membrane integrity result from cell lysis, a cytotoxicity assay was performed (FIG. 6). Therefore, HeLa cells were incubated with 25-50 µg/ml SspH1 and SspH1-Nter, respectively for 1, 6 and 24 h. Cytotoxicity was measured using the CYTOTOX 96® Non-Radioactive Cytotoxicity Assay (Promega). In this assay, the amount of lactate dehydrogenase (LDH) released by the cells into the supernatant is measured. An increase in LDH release indicates cytotoxic effects of the proteins. Following incubation with SspH1 and SspH1-Nter, no increase in LDH release was observed when compared to untreated control cells even after 24 h of incubation, indicating that the proteins do not have any cytotoxic effects on the HeLa cells.

The strong effects of SspH1 on the membrane integrity of HeLa cells with no effects on cell viability, suggest a potential direct uptake mechanism by the formation of a transient membrane pore.

Example 3

Functionality of the Bacterial Effector Protein SspH1

SspH1 belongs to the family of proteins containing the LRR motif and comprises 8 LRRs. The C-terminal domain of the protein resembles that of the type III secreted IpaH proteins from *Shigella flexneri which possess* E3 ubiquitin ligase activity. Ubiquitin ligases mediate the transfer of ubiquitin to target proteins. Ubiquitination is a process generally occurring in all eukaryotic cells that is involved in protein degradation, signal transduction as well as cell cycle regulation. It has been shown that the C-terminal domain of SspH1 is indeed an E3 ubiquitin ligase domain (Quezada et al, 2009) that uses ubiquitin as well as protein kinase 1 (PKN1) as substrates for ubiquitination (Rohde et al, 2007). Furthermore, it has been suggested that this interaction is involved in downregulation of expression of pro-inflammatory cytokines by SspH1.

To test if recombinant SspH1 is also functional and could polyubiquitinate proteins, in vitro ubiquitination assays were carried out in a 40 µl reaction mixture containing ubiquitination buffer (25 mM Tris.HCl [pH 7.5], 50 mM NaCl, 5 mM ATP, 10 mM MgCl2, 0.1 mM DTT), 2 µg Ha-ubiquitin, 0.5 µg E1, and 2 µg E2 (UbcH5B) in the presence or absence of 1 µg recombinant SspH1 Ubiquitination analysis of PKN1 was performed in the presence or absence of additional 0.4 µg GST-tagged PKN1. Reactions were incubated at 37° C. for 1 h and stopped by the addition of Laemmli sample buffer with or without 100 mM DTT.

Figure 7:
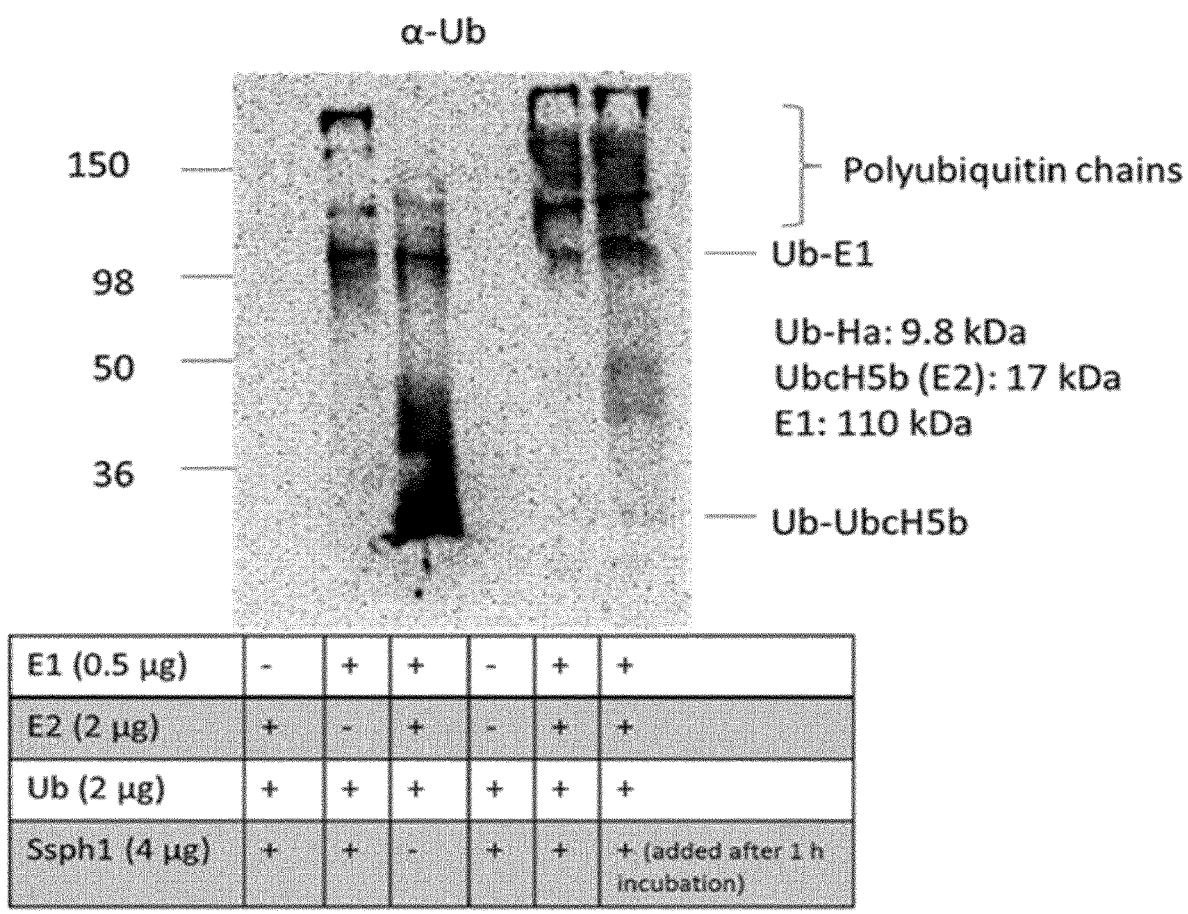
FIG. 7 shows in vitro ubiquitination assays which were performed in the presence of UbcH5c. Shown are synthesized unanchored polyubiquitin chains detected by anti-ubiquitin western blot. Upon incubation with E1, E2 and ubiquitin, SspH1 was able to remove ubiquitin from the E2 enzyme and perform self-ubiquitination
Figure 8:
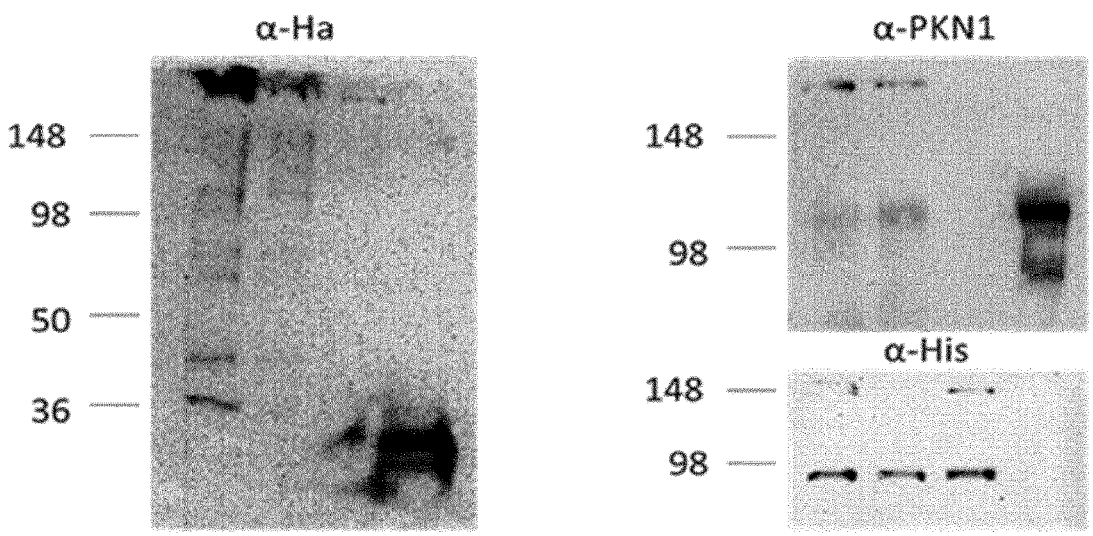
FIG. 8 shows that recombinant SspH1 ubiquitinates PKN1 in vitro. Shown are immunoblot analysis using anti-HA, anti-PKN1, and anti-His antibodies of reactions performed in the presence of Ub-Ha, E1, E2, Ub-Ha, SspH1, and PKN1. Upon incubation with E1, E2 and ubiquitin, SspH1 was able to remove ubiquitin from the E2 enzyme and ubiquitinate PKN1.
Figure 9:
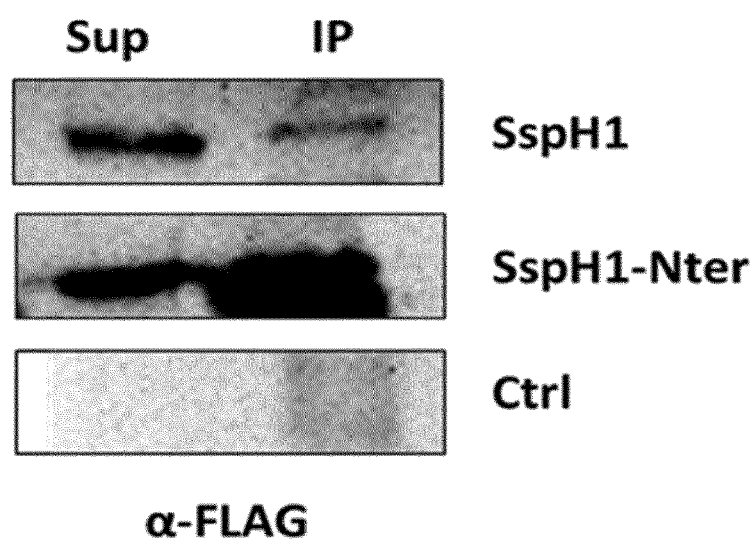
FIG. 9 shows that recombinant SspH1 co-immunoprecipitates with PKN1 from transfected cells and self-ubiquitinates. HeLa cells were transiently transfected with PKN1-Myc. 24 h later, cells were incubated with FLAG-tagged SspH1 for 3 h. Following SspH1 incubation, PKN1 was immunoprecipitated and the immunoprecipitates and supernatants were immunoblotted using anti-FLAG and anti-Ubiquitin antibodies.

Western blot analysis showed that also recombinant SspH1 has the ability to remove ubiquitin from ubiquitinated UbcH5B, to autoubiquitinate, and to polyubiquitinate Ha-tagged ubiquitin (FIG. 7). Additionally, the inventors also tested ubiquitination of PKN1 by SspH1. When the reaction was performed in the presence of SspH1 and PKN1 in vitro, anti-PKN1 antibodies detected an additional species migrating at a size >148 kDa (FIG. 8). Furthermore, the inventors wanted to confirm interaction of SspH1 with PKN1 and its Ubiquitination also in vivo (FIG. 9). Therefore, HeLa cells were transiently transfected with a PKN1 expression vector and subsequently incubated with recombinant FLAG-tagged SspH1 and Ssph1-Nter, respectively. The proteins were then immunoprecipitated with anti-PKN1-agarose antibody conjugate. As shown in FIG. 9, Ssph1-FLAG co-immunoprecipitated with PKN1. Furthermore, using anti-ubiquitin antibodies, the inventors could confirm self-ubiquitination of SspH1 in HeLa cells.

Figure 10:
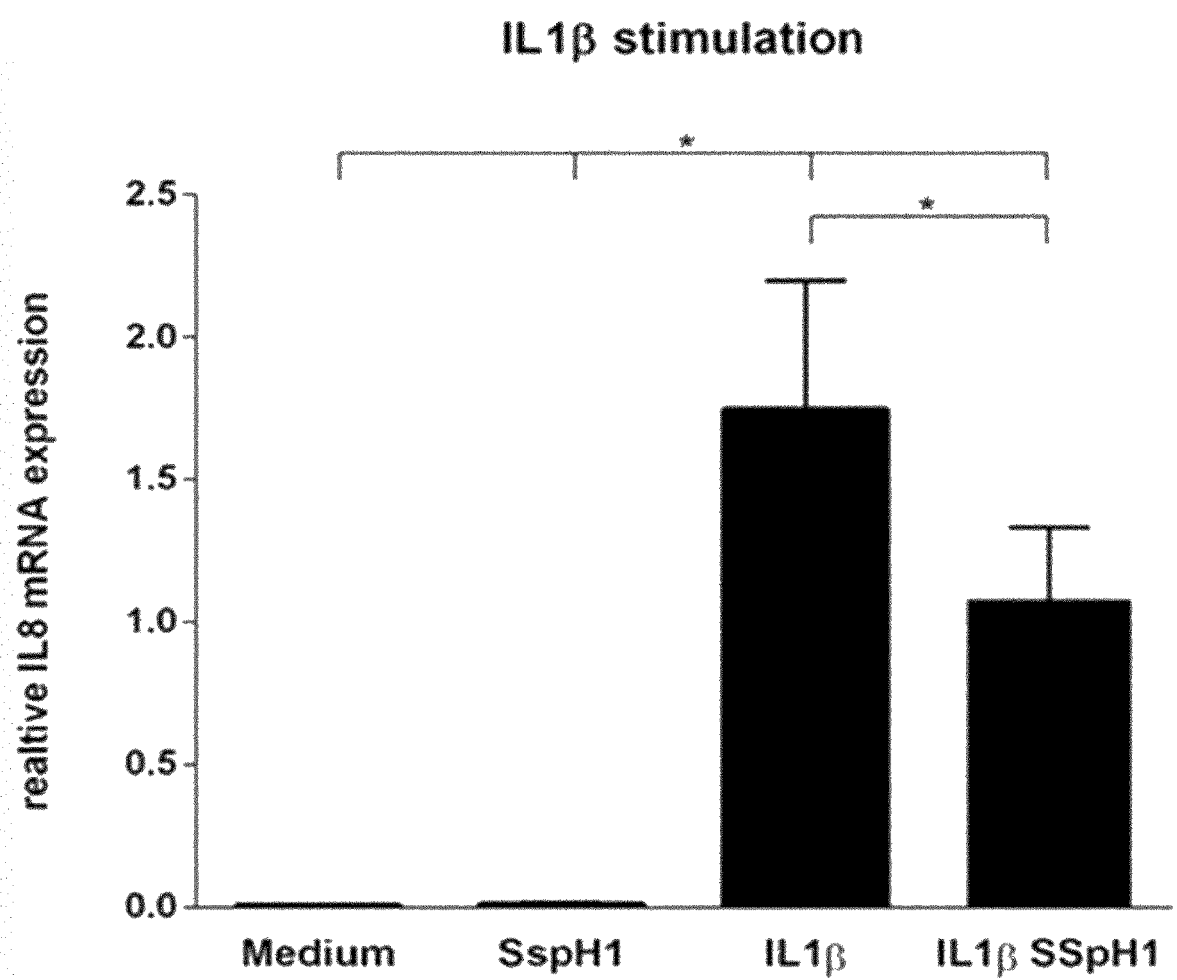
FIG. 10 shows the effect of SspH1 on IL-8 mRNA in A549 cells stimulated with IL1β. A549 cells were incubated with SspH1 for 3 h and subsequently stimulated with 20 ng/ml IL1β. After RNA isolation and cDNA synthesis, all qRT-PCR data were obtained using SYBR green and IL8-specific primers. The HPRT1 gene (hypoxanthine phosphoribosyl-transferase I), a low abundance housekeeping gene, was used as reference. Data represent means and standard deviations of at least three independent experiments each performed in duplicate * p<0.05.
Figure 11A:
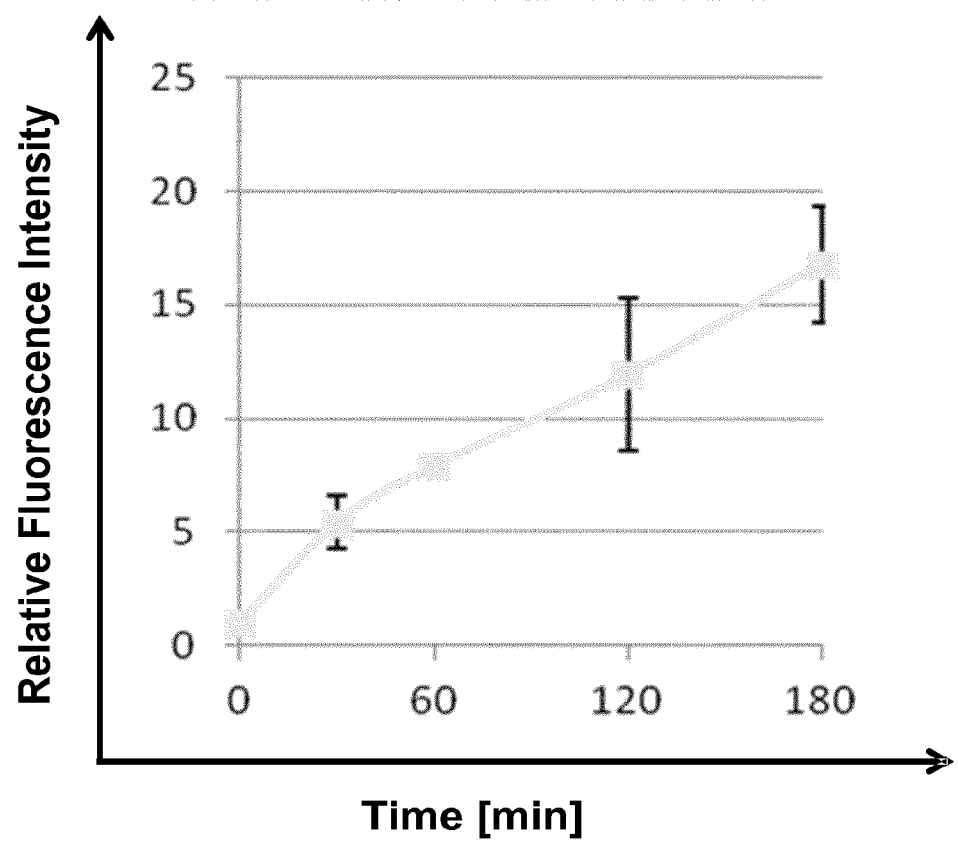
FIGS. 11a to 11e shows an uptake analysis of effector proteins of the LPX family. Upper panel: Confocal laser scanning immunofluorescence microscopy of HeLa cells incubated with IpaH1.4-Cy3, IpaH4.5-Cy3, IpaH7.8-Cy3, IpaH9.8-Cy3, and SlrP-cy3 for 1 h. Actin was counterstained with phalloidin ALEXA FLUOR® 488 and nuclei with DRAQ5. All three fluorescence images were merged and confocal Z-stack projections are included in all images. The cross hairs show the position of the xy and yz planes. Scale bars: 10 µm. Lower panel: Quenched time-lapse assay of HeLa cells incubated with different ALEXA FLUOR® 488 labeled effector proteins (20 µg/ml). Samples were taken from the incubation at different time points. Extracellular fluorescence was quenched with trypan blue (final concentration: 0.2%) and intracellular fluorescence was measured using a flow cytometer. Data are expressed as geometric means of fluorescence intensities from at least 10,000 cells relative to fluorescence of untreated cells, and are presented as means±standard deviations from three independent experiments.
Figure 11B:
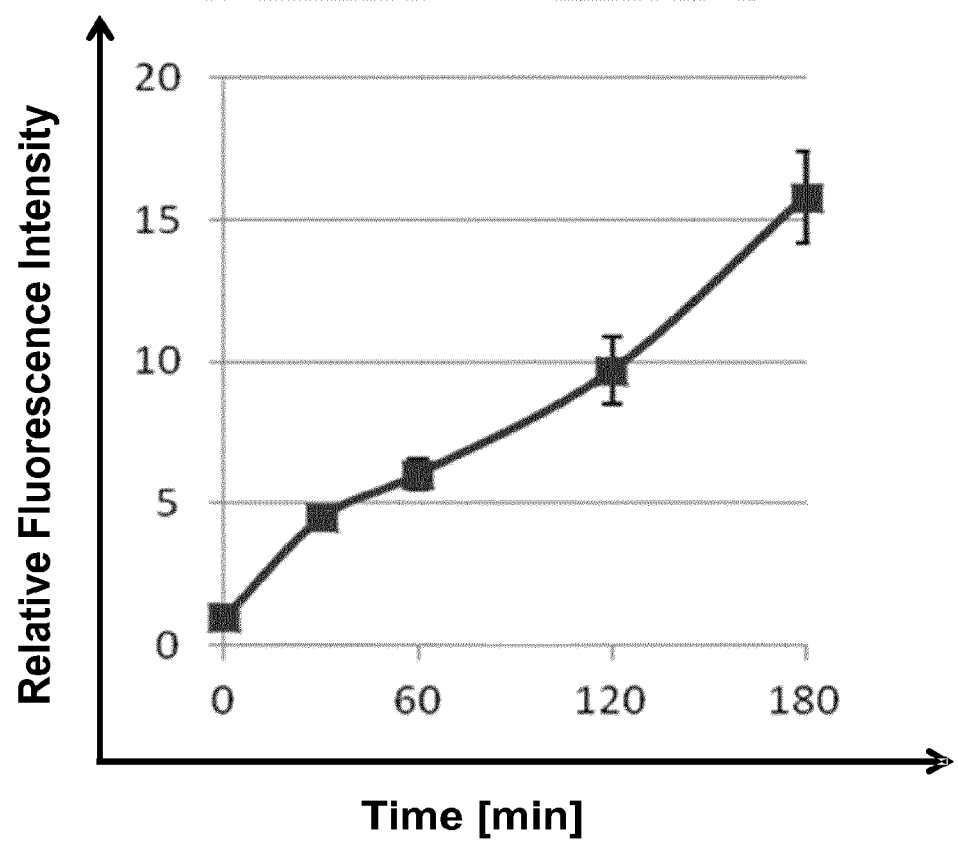
Figure 11C:
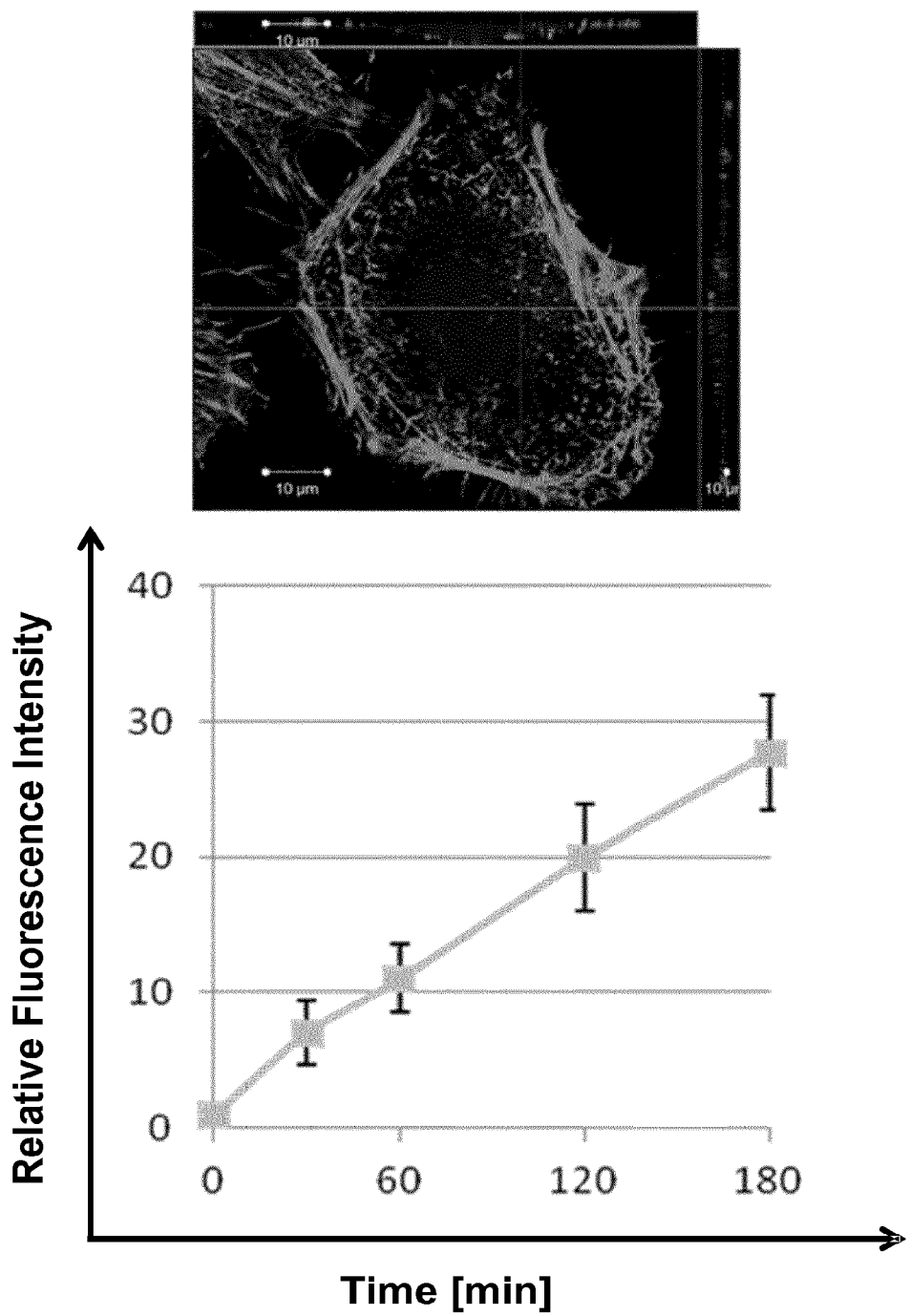
Figure 11D:
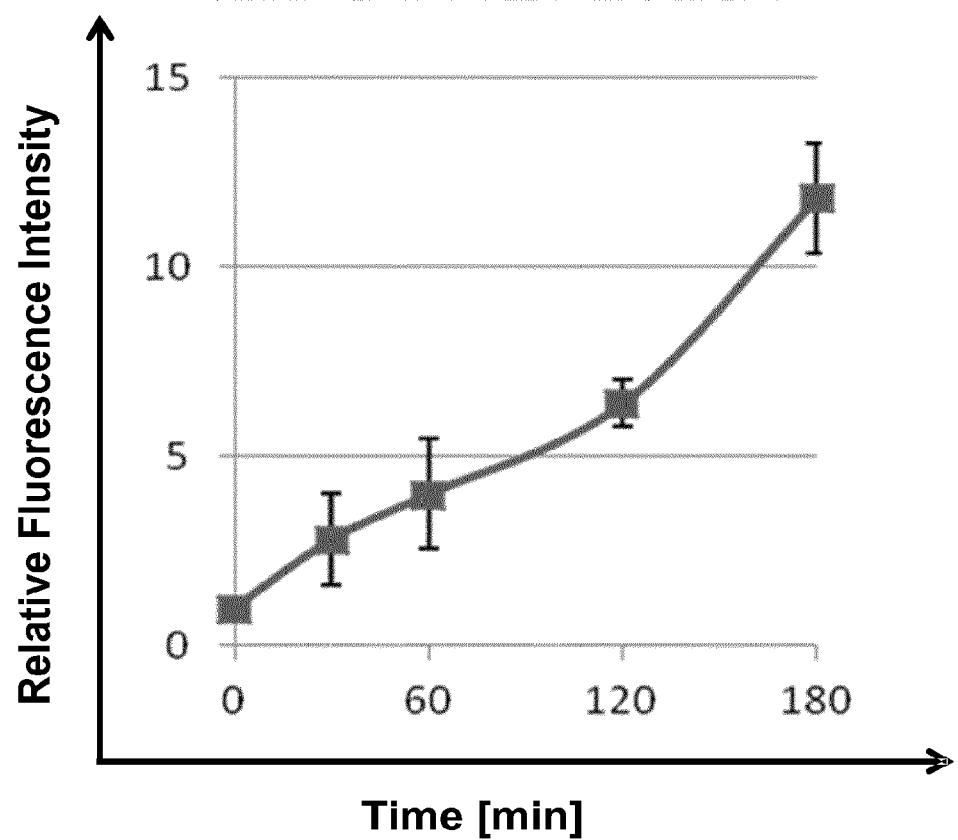
Figure 11E:
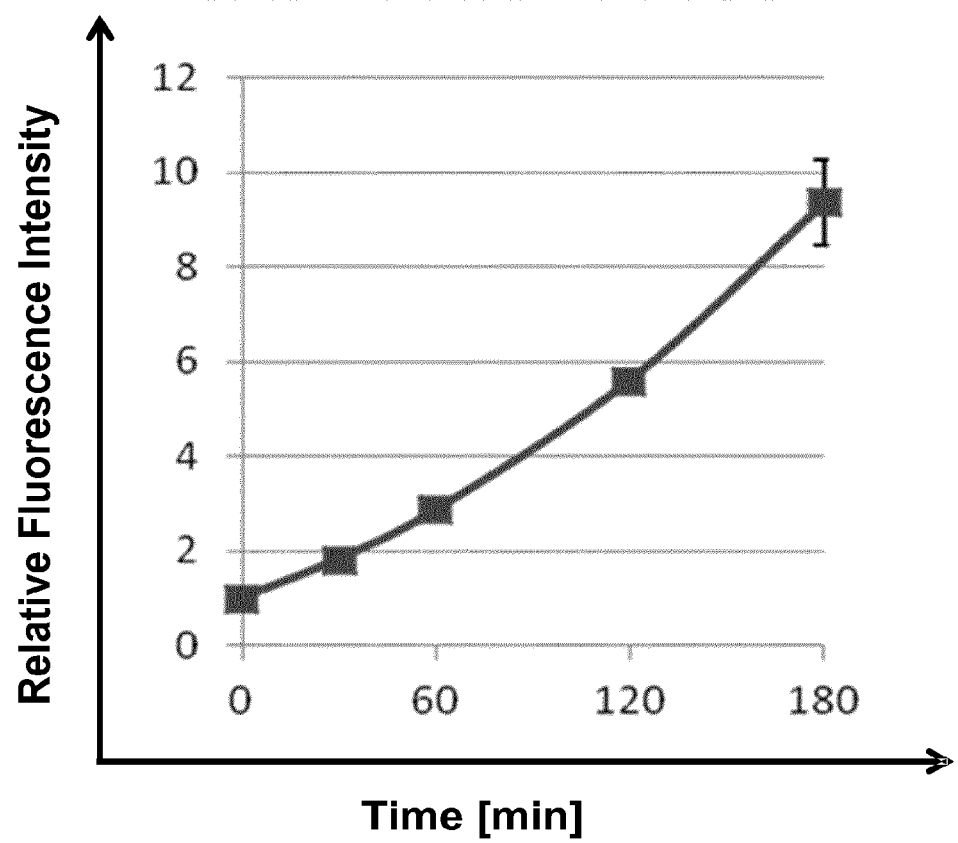

To determine whether cytokine production is also downregulated by recombinant SspH1, the levels of IL-8 mRNA of A549 cells after stimulation with IL1β in the presence or absence of SspH1 were analyzed. As shown in FIG. 10, cells which have been pre-incubated with SspH1 for 3 h produced significantly less IL-8 mRNA upon IL-1β stimulation than untreated cells.

Figure 13A:
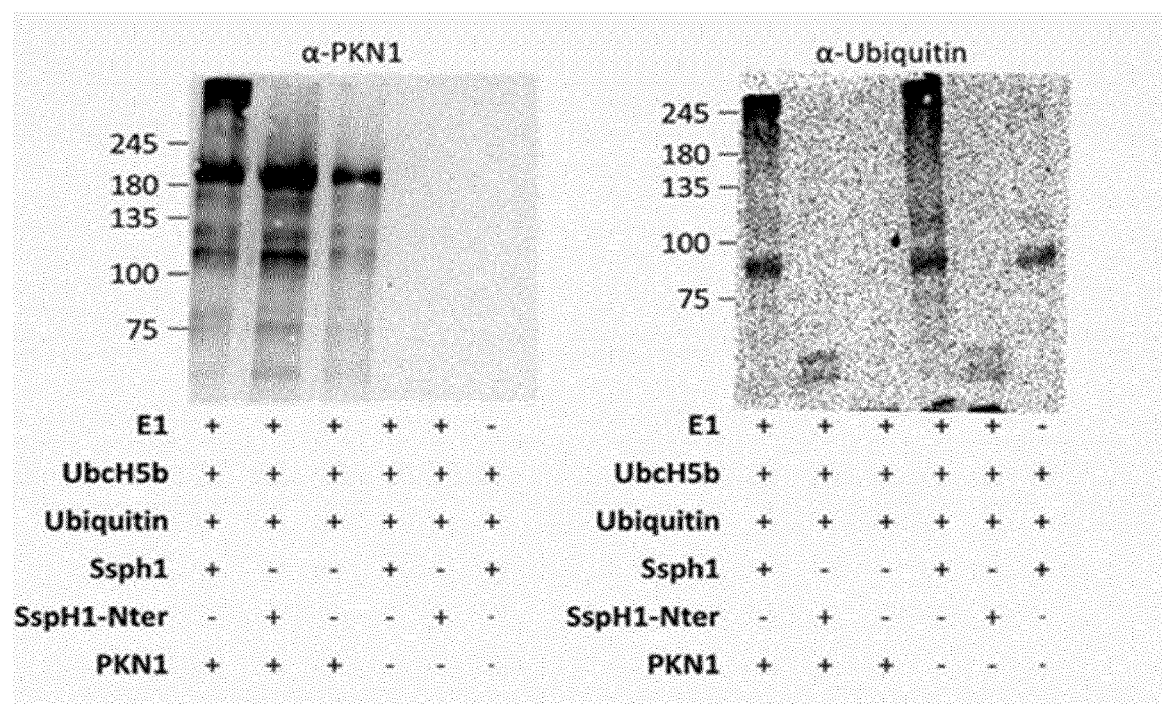
FIG. 13a shows an in vitro ubiquitination assay of recombinant SspH1. Upon incubation with E1, E2 and ubiquitin, SspH1 is able to remove ubiquitin from the E2 enzyme and to self-ubiquitinate (see also FIG. 7). In the presence of PKN1, SspH1, but not SspH1-Nter, polyubiquitinates the kinase (FIG. 13a).
Figure 13B:
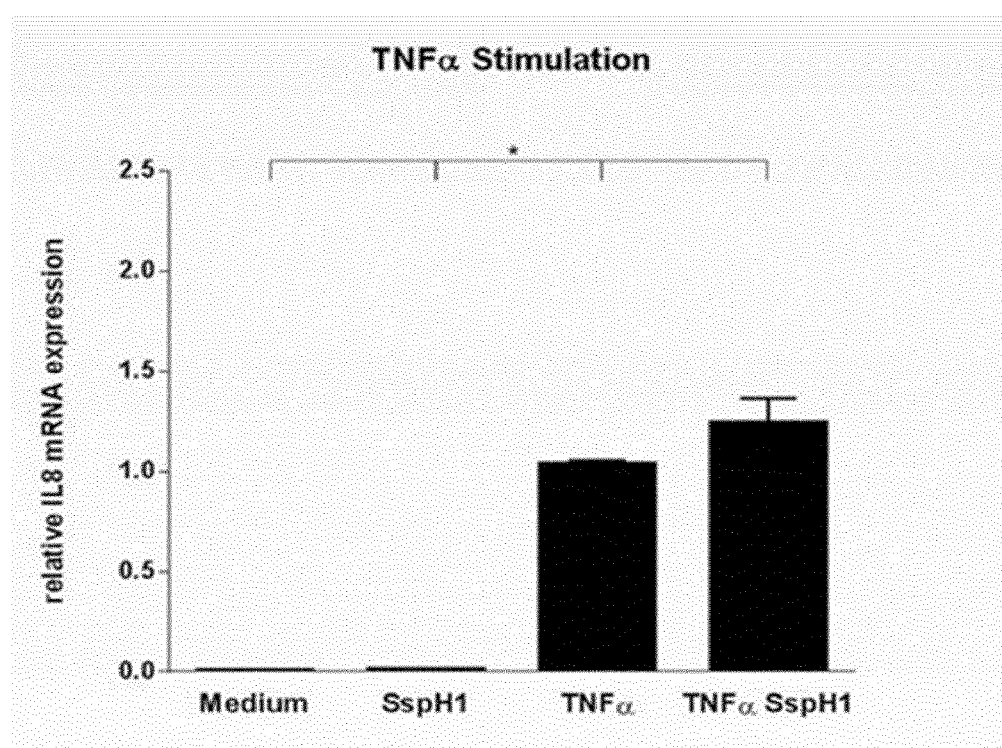
FIG. 13b shows Il8 mRNA expression in A549 cells following incubation with SspH1 and subsequent stimulation with TNFα.

Taken together, the present inventors showed that the SspH1 effector protein of *Salmonella enterica* serovar *typhimurium* is able to translocate into eukaryotic cells without a requirement for additional factors. Furthermore, the inventors demonstrated that recombinant SspH1 is functional as an E3 ubiquitin ligase that uses PKN1 as substrate after penetrating the host cells and that is able to reduce the expression of Interleukin 8 in IL1β stimulated cells, but not in TNFα-stimulated cells (FIG. 13b)

Example 4

Analysis of Further Effector Proteins of the LPX Family

The inventors identified SspH1 as a bacterial cell-penetrating protein. Subsequently the inventors investigated whether there is a general concept of T3SS-independent translocation by LPX effector proteins. For this, the effector proteins of the IpaH subset from *Shigella flexneri* as well as SlrP from *Salmonella enterica* serovar typhimurium have been cloned with a C-terminal 6× His-tag for purification. After purification, the different effector proteins were labelled with the fluorescent dyes Cy3 (IF) or ALEXA FLUOR® 488 (FACS) for subsequent uptake analysis by immunofluorescence microscopy and FACS (FIG. 11a-e).

Fluorescence microscopy analysis revealed that the effector proteins of the IpaH subset (IpaH1.4-Cy3, IpaH4.5-Cy3, IpaH7.8-Cy3, IpaH9.8-Cy3), as well as Cy3-labeled SlrP have entered cells after 1 h incubation (FIG. 11a-e, upper panel). Although the intracellular amount of the different effector proteins appeared to differ, all proteins are distributed throughout the cytoplasm and show only little difference in their intracellular localization (FIG. 11a-e, upper panel). Additionally, after the proteins have been conjugated to an ALEXA FLUOR® 488 fluorescent dye, a flow cytometry based quenched time lapse assay was performed for quantitative analysis of uptake efficiency (FIG. 11a-e, lower panel). In all cases, an increase of relative fluorescence intensity was monitored for HeLa cells after incubation with the recombinant proteins, indicating efficient internalization. The increase of fluorescence intensities appeared different for the shown effector proteins. However, comparison of the curves over the entire time course shows a considerable increase of intracellular fluorescence intensity for incubation times of up to 180 min for IpaH1.4, IpaH4.5, IpaH7.8, IpaH9.8, and SlrP respectively, indicating an efficient internalization (FIG. 11a-e, lower panel).

In summary, the experiments of the inventors demonstrate that the LPX-family from *S. flexneri* and *S. enterica* serovar *typhimurium* share the ability of YopM and SspH1 to enter the cytosol independently of the T3SS. These results strengthen the hypothesis of a new general concept for internalization of these effector proteins.

Example 5

In-Silico Prediction of Cell-Penetrating Properties of LPX Family Members

To identify putative protein transduction domains (PTD) within the amino acid sequences of the LPX family members, the inventors used in-silico prediction of cell-penetrating properties based on a method developed by Stephen White's laboratory shareware (blanco.biomol.uci.edu; Jaysinghe S., 2009). This approach utilizes the Wimley-White hydrophobicity scales (White & Wimley, 1999), reflecting the ability of binding and insertion into lipid bilayers. Hence, available amino acid sequences of SspH1, SspH2, IpaH1.4, IpaH2.5, IpaH3, IpaH4.5, IpaH7.8, IpaH9.8, SlrP, YopM were screened for putative PTD with the help of CEPEP company (Ülo Langel, Schweden). The results of this screen are described in Example 5 and summarized in FIG. 12.

Figure 12:
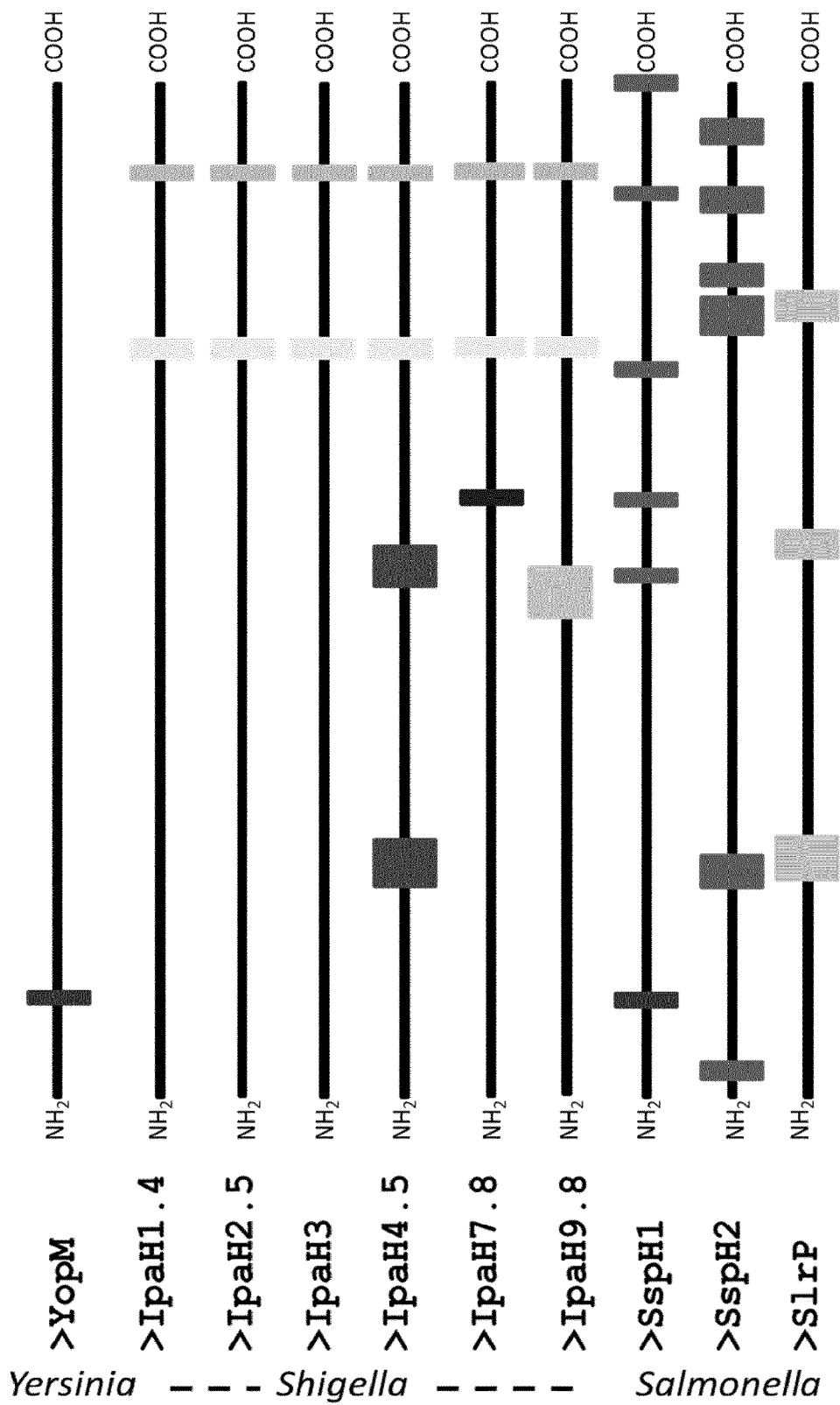
FIG. 12 shows a schematic overview of an in-silico prediction analysis YopM, SspH1, SspH2, SlrP, IpaH1.4, IpaH2.5, IpaH3, IpaH4.5, IpaH7.8, and IpaH9.8. Boxes indicate sequence segments containing predicted PTD sequences (PTDs of maximal length).

The computational analysis of the YopM amino acid sequence from *Y. enterocolitica* (pYV8081) identified a PTD within the N-terminal domain of the protein (FIG. 12). This sequence overlaps with the previous experimentally identified transport domain of YopM (Rüter et al., 2010), indicating that the in-silico prediction of cell-penetrating properties is a usable tool to identify potential PTDs within the amino acid sequences of CPEs. Several unknown PTDs have been predicted for the rest of the family members. Obviously, all effector proteins of the IpaH subset share two potential PTDs in their C-terminal region (FIG. 12). Furthermore, IpaH4.5 harbors two additional PTDs and IpaH7.8 as well as IpaH9.8 only one additional transport domain. Similarly to the IpaH proteins of *Shigella*, several PTDs were also identified within the sequence of the effector proteins from *Salmonella*. While three unknown PTDs were identified within the sequence of SlrP, both SspH effector proteins (SspH1&2) showed in total twelve PTDs (six each) with different sequences to the previously reported.

Taken together, the in-silico PTD-prediction analysis of SspH1, SspH2, SlrP, IpaH1.4, IpaH2.5, IpaH3, IpaH4.5, IpaH7.8, and IpaH9.8 in compare to YopM revealed that they harbor several unknown PTDs, which might be responsible for T3SS-independent uptake of the effector proteins into eukaryotic cells.

Example 6

Methods and Materials of Experiments 1 to 5 and FIGS. 1 to 22

Construction of 6× His-Tagged Recombinant Proteins
1.1 Restriction Free (RF) Cloning by Linear Amplification Restriction Free (RF) cloning is an alternative method to insert a DNA fragment into a desired location within the vector (Chen et al. 2000, van den Ent & Löwe, 2006) Using primers that contain a 3' target-specific sequence and a 5' extension that is complementary to the desired insertion site within the vector, a double-stranded PCR product is generated, containing the target sequence and the sequence of the insertion site at both the 3' and 5' end. This PCR product is then used as a pair of mega-primers in a second amplification reaction. Both strands of the PCR product anneal to the insertion site of the vector and are extended in a linear amplification reaction resulting in a nicked double-stranded plasmid.

The PCR reaction for target DNA amplification was carried out as listed in Tables 1 & 2.

TABLE 1

| PCR reaction RF cloning | |
| --- | --- |
| Template DNA | ~1-200 ng |
| dNTP mix (10 mM each) | 1 µl (final concentration 100 µM) |
| Oligonucleotide primers | 0.1 µg (each) |
| Phusion Polymerase buffer | 1 x |
| Phusion Polymerase | 1 unit |
| | Add H$_2$0 to 50 µl |

TABLE 2

| PCR cycling conditions | | | |
| --- | --- | --- | --- |
| Reaction step | Temperature | Duration | Cycles |
| I Initial denaturation | 98° C. | 1 min | 1x |
| II Denaturation | 98° C. | 30 s | |
| III Annealing | T$_m$ | 30 s | 35x |
| IV Elongation | 72° C. | 15-30 s/kb | |
| V Final elongation | 72° C. | 10 min | 1x |

Linear amplification of vector and insert using the double-stranded PCR product from the first PCR as megaprimers was performed according to Unger et al. (2010) using the reaction mixture listed in Table 3 and carried out in a PCR thermal cycler with the cycling conditions listed in Table 4.

TABLE 3

| PCR reaction linear amplification | |
| --- | --- |
| Template DNA | 20 ng |
| dNTP mix (10 mM each) | 1 µl (final concentration 200 µM) |
| PCR product (mega-primers) | 100 ng |
| Phusion Polymerase buffer | 1 x |
| Phusion Polymerase | 1 unit |
| | Add H$_2$0 to 50 µl |

TABLE 4

| PCR cycling conditions for linear amplification | | | |
| --- | --- | --- | --- |
| Reaction step | Temperature | Duration | Cycles |
| I Initial denaturation | 98° C. | 30 s | 1x |
| II Denaturation | 98° C. | 30 s | |
| III Annealing | 60° C. | 1 min | 30x |
| IV Elongation | 72° C. | 5 min | |
| V Final elongation | 72° C. | 7 min | 1x |

Following the amplification reaction, 0.2 U/µl DpnI were added for 2 h at 37° C. to eliminate parental plasmid DNA. 10 µl of the DpnI treated reaction mixture were then used for transformation of competent *E. coli* DH5α cells.

2. Expression and Purification of Recombinant Protein

2.1 Expression of Recombinant Protein in E. Coli

For expression of recombinant proteins, the pET24b(+) expression vector was chosen which provides the coding sequence for a C-terminal 6× His-tag. All plasmids used in this study are derivatives of pET24b(+).

For protein expression, the recombinant plasmids carrying the respective coding sequences were transformed into *E. coli* BL21(DE3) cells. Expression of the target proteins was carried out in 500 ml of Standard I medium containing 50 µg/µl kanamycin. The culture was inoculated 1:100 with an overnight culture and incubated at 37° C. and 180 rpm until an $OD_{600}$ of 0.6-0.8 was reached. Then expression of the recombinant proteins was induced by adding IPTG to a final concentration of 1 mM before the culture was incubated for an additional 4 h. Cells were harvested by centrifugation at 3,000×g and 4° C. for 15 min and the cell pellet was stored at −20° C. until further usage.

2.2 Preparation of Cleared E. Coli Lysates

The bacterial pellets were thawed on ice and resuspended in 10 ml of lysis buffer. Cleared lysates were prepared by sonication (Branson Sonifier 250; 4×30 s, level 4, 50% cycle, on ice). Bursts were followed by 15 s breaks. The cellular debris was removed by centrifugation (7,200×g, 15 min, 4° C.) and the supernatant containing the recombinant protein was subjected to affinity chromatography.

Heterologous expression of recombinant proteins can lead to formation of inclusion bodies; aggregates of the overexpressed protein that remain insoluble. These can be solubilised by addition of anionic detergents such as N-lauroylsarcosine sodium salt. Where the desired protein was detected in the insoluble fraction, 2% (w/v) N-lauroylsarcosine sodium salt were added following sonication and incubated on a rotary shaker (15 rpm, 4° C.) for 1 h before centrifugation as mentioned above.

| Lysis buffer | |
|---|---|
| Tris-HCl, pH 8.0 | 50 mM |
| NaCl | 500 mM |
| Imidazole | 10 mM |
| Glycerol | 10% (v/v) |
| TRITON ™X-100 | 0.1% (v/v) |
| N-Lauroylsarcosine sodium salt | |
| | |
| Tris-HCl, pH 8.0 | 25 mM |
| NaCl | 100 mM |
| N-Lauroylsarcosine sodium salt | 10% (w/v) |

2.3 Purification of Recombinant Protein

Protein purification was performed by nickel-nitrilotriacetic acid (Ni-NTA) metal-affinity chromatography (Qiagen, Hilden) under native conditions according to "The QIAexpressionist" handbook (Qiagen, Hilden).

To enable binding of the 6× His-tagged recombinant protein to the Ni-NTA resin, 1 ml of Ni-NTA Agarose was added to the cleared lysate and mixed by shaking an a rotary shaker (15 rpm, 4° C.) for 1 h. The mixture was centrifuged (800×g, 2 min, 4° C.) and the supernatant was discarded. Three wash steps were carried out (800×g, 2 min, 4° C.) using 10 ml of wash buffer each before the mixture was loaded into a column. Generally, wash buffer I was used for purification. Wash buffer II was employed for purification of proteins that have previously been solubilised using N-lauroylsarcosine sodium salt. The protein was eluted in 500 µl aliquots using 5 ml of elution buffer. All fractions were stored at 4° C. for SDS-PAGE analysis.

| Wash buffer I | |
|---|---|
| Tris-HCl, pH 8.0 | 50 mM |
| NaCl | 300 mM |
| Imidazole | 20 mM |
| Glycerol | 10% (v/v) |
| TRITON ™X-100 | 0.1% (v/v) |
| Wash buffer II | |
| Tris-HCl, pH 8.0 | 50 mM |
| NaCl | 300 mM |
| Imidazole | 20 mM |
| Glycerol | 10% (v/v) |
| TRITON ™X-100 | 2% (v/v) |
| Elution buffer | |
| Tris-HCl, pH 8-0 | 50 mM |
| NaCl | 300 mM |
| Imidazole | 200 mM |
| Glycerol | 10% (v/v) |
| TRITON ™X-100 | 0.1% (v/v) |

2.4 Protein Dialysis and Concentration

After purification, fractions of highest purity were pooled and dialysed in PBS. The protein solution was applied to a dialysis tube (pore size: 6-10 kDa, Roth, Karlsruhe) and dialysed overnight in 2 l PBS at 4° C. with gentle stirring. After dialysis, the protein was concentrated to a final volume of 2 ml using AMICON® centrifugal filters (Millipore, Eschborn) at 500×g and 4° C.

2.5 Protein Labelling with Fluorescent Dyes

In order to detect the recombinant proteins used in this study by fluorescence microscopy and FACS analysis, the proteins were labelled using fluorescent dyes.

Protein Labelling with ALEXA FLUOR® 488

For FACS analysis, the recombinant proteins YopM and SspHI were labelled with the green fluorescent dye ALEXA FLUOR® 488 using the ALEXA FLUOR® 488 Protein labelling kit (Invitrogen, Karlsruhe). Fluorescence of proteins labelled with ALEXA FLUOR® 488 can be excited at 494 nm and emission is detected at 519 nm.

Labelling of recombinant YopM and SspHI with ALEXA FLUOR® 488 was performed according to the manufacturer's recommendations.

Protein Labelling with Cy3

For subsequent fluorescence microscopy, recombinant proteins were labelled with the orange fluorescent cyanine dye Cy3 using the Cy3 Ab labelling kit (Amersham Biosciences, Freiburg). Fluorescence of Cy3-labelled proteins can be excited at 550 nm and emission is detected at 570 nm.

3 Cell Fractionation of Eukaryotic Cells

Cell fractionation of eukaryotic cells allows separation of soluble cytoplasmic proteins from insoluble membrane proteins (Behrens, 1938). In this study, cell fractionation was used to check for autointegration of the recombinant proteins into the cytoplasm (Kenny and Finlay, 1997; Gauthier et al., 2000).

The cells were cultured to confluency in a 10 cm culture dish and subsequently incubated with recombinant protein (25 µg/ml) in 10 ml culture medium for 1 h. Cells were washed with ice cold D-PBS (with $Ca^{2+}$ and $Mg^{2+}$) 3× for 15 min before the cells were quenched with acid buffer wash for 5 min. After an additional wash step with D-PBS (with $Ca^{2+}$ and $Mg^{2+}$), the cells were scraped from the surface and resuspended in 1 ml sonication buffer (supplemented with Complete EDTA-free Protease Inhibitor Cocktail (Roche Biochemicals, Mannheim) prior to use). The cells were permeabilised by sonication (ultrasound water bath, 4×1 s, level 4, 4° C.) followed by centrifugation (108,000×g, 15 min, 4° C.). The supernatant containing the cytoplasmic proteins was collected and saved as cytoplasmic fraction (CF) until further usage. The insoluble pellet was washed once in 1 ml sonication buffer before it was resuspended in 1 ml TRITON™ buffer (supplemented with Complete EDTA-free Protease Inhibitor Cocktail (Roche Biochemicals, Mannheim) prior to use) and incubated on a rotary shaker (15 rpm, 4° C.) for 30 min. The cell lysate was centrifuged (108,000×g, 15 min, 4° C.) again and the supernatant containing membrane proteins soluble in TRITON™ X-100 was collected as the membrane fraction (MF). Cytoplasmic and membrane fraction were precipitated using trichloroacetic acid and subsequently analysed by Western blotting.

| Sonication Buffer | |
|---|---|
| Tris-HCl | 50 mM |
| NaCl | 150 mM |
| EDTA | 1 mM |
| EGTA | 1 mM |
| Glycerol | 30% (v/v) |
| NaVO$_4$ | 0.4 mM |
| NaF | 1 mM |
| TRITON ™ Buffer | |
| Sonication Buffer | 1 l |
| TRITON ™ X-100 | 1% (v/v) |
| Acid Buffer Wash | |
| Glycine | 0.2 g |
| D-PBS | Add to 100 ml |
| pH 2.0 | |

4 Nuclear Fractionation of Eukaryotic Cells

Nuclear fractionation allows separation of cytoplasmic and nuclear protein fractions. In this study nuclear fractionation was performed to verify cell penetration by recombinant proteins and to check for a potential nuclear localisation of these recombinant proteins. Therefore, the NE-PER Nuclear and Cytoplasmic Extraction Kit (Thermo Scientific, Rockford, USA) was used which is based on stepwise cell lysis and centrifugal separation of cytoplasmic and nuclear protein fractions.

Cells grown to confluency in a 10 cm culture dish were incubated with recombinant protein (25 µg/ml) for 1 h. Following incubation, the cells were washed with D-PBS (without Ca$^{2+}$ and Mg$^{2+}$) and subsequently detached with trypsin and centrifuged at 500×g for 5 min. The cells were washed with D-PBS, transferred to a microcentrifuge tube and centrifuged again (500×g, 3 min). All buffers were included in the NE-PER Nuclear and Cytoplasmic Extraction Kit (Thermo Scientific, Rockford, USA) and used at the recommended volumes. Buffers CER I and NER were supplemented with Complete EDTA-free Protease Inhibitor Cocktail (Roche Biochemicals, Mannheim) prior to use.

Immunofluorescence Microscopy

Recombinant proteins used for immunofluorescence analyses in this study were either GFP fusion proteins or labelled with the fluorescent dye Cy3.

In order to detect proteins by immunofluorescence analysis, cells were cultured on cover slips in 24-well plates and subsequently incubated with recombinant protein (25 µg/ml). Cells were washed with D-PBS (with Ca$^{2+}$ and Mg$^{2+}$) three times to remove non-integrated proteins. A different experimental setup included trypsinization after HeLa cells were incubated with the proteins. This procedure is supposed to be even more efficient in removing cell-surface bound proteins (Richard et al., 2003). After trypsinization, HeLa cells were seeded on cover slips in 24-well plates and incubated overnight to allow cell recovery. Afterwards cells were fixed using 500 µl 4% PFA (w/v) per well and washed with D-PBS for 5 min. Subsequently, the cells were quenched with 0.2% glycine for 20 min and washed again. Cells were permeabilised using 0.2% TRITON™ X-100 for 4 min followed by an additional wash step. DNA was selectively stained using Hoechst 33 258 (DAPI) diluted 1:1000 in D-PBS for 7.5 min followed by three wash steps with D-PBS for 5 min each. The preparations were embedded in Moviol/DABCO and analyzed by fluorescence microscopy using appropriate filters.

| 0.2% TRITON ™ X-100 | |
|---|---|
| TRITON ™ X-100 | 200 µl |
| D-PBS | Add to 100 ml |
| 0.2% Glycine | |
| Glycine | 0.2 g |
| D-PBS | Add to 100 ml |
| 4% PFA | |
| Paraformaldehyde | 4 g |
| D-PBS | Add to 100 ml |

6 Fluorescence Activated Cell Sorting (FACS)

Internalisation of YopM, SspHI and Tat-GFP-GSK into HeLa cells was monitored by fluorescence activated cell sorting (FACS). FACS is a specialised type of flow cytometry which allows separation of cells labelled with fluorescent markers and measurement of fluorescence intensity (Bonner et al., 1972).

In this study, FACS analyses were performed to confirm and further investigate uptake of YopM and SspH1 in comparison to the Tat-GFP-GSK construct, a derivative of the well characterised CPP Tat. Uptake of the recombinant proteins was examined by determining the fluorescence intensity of HeLa cells. Therefore recombinant YopM and SspH1 were labelled with the fluorescent dye ALEXA FLUOR® 488.

HeLa cells were grown to confluency in 175 cm$^2$ culture flasks and subsequently detached from the surface by adding trypsin. The cells were centrifuged and resuspended in D-PBS (without Ca$^{2+}$ and Mg$^{2+}$) and preheated to 37° C. prior to incubation with the recombinant proteins (20 µg/ml). To assure that only viable cells are detected, the FACS cytometer was adjusted using control cells that were not incubated with protein. Dead cells and cellular debris can be excluded from acquisition by measuring forward and side scatter which display cell size and granularity, respectively. Dead cells have lower forward scatter and higher side scatter which allows distinction from living cells. First, the control cells were applied to the cytometer and viable cells were gated due to side and forward scatter and thus selected for acquisition. The cytometer (BD Biosciences, Heidelberg) was set to acquire 10,000 events from the gated cell population per run, every event being a single cell. In case of internalisation of the proteins tagged with the fluorescent markers GFP and ALEXA FLUOR® 488, respectively, fluorescence of the cells can be measured. However, even cells without labelling show fluorescence, so-called autofluorescence which is caused by components of the cell like pyridinic (NADPH) and flavin coenzymes (Monici, 2005). To subtract the autofluorescence from the total fluorescence intensity, the fluorescence intensity of HeLa cells which were not incubated with the fluorescent labelled proteins was measured.

6.1 Quenched Time-Lapse Uptake and CPP-induced Membranolysis Assay

In this study, the uptake kinetics of the recombinant proteins YopM, SspHI and Tat-GFP-GSK were monitored in two parallel experiments that are based on an ongoing incubation and allow measurements from the same incubation at different time points (Florén et al., 2011).

The first approach is based on addition of trypan blue (TB) to the samples prior to FACS analysis to measure the protein uptake rate. TB is a quencher that is not able to enter the cells and efficiently eliminates fluorescence (Sahlin et al., 1983, Hed et al., 1987). Thus extracellular fluorescence can be excluded from the measurement, ensuring that only intracellularly located proteins are detected which are inaccessible to TB.

The second assay allows monitoring of potential lytic effects of the recombinant proteins on membrane integrity. Protein-induced membranolysis can be assessed by the addition of propidium iodide (PI). PI is a fluorescent DNA intercalating agent that is not able to cross membranes of intact cells. PI can only enter cells with disrupted membranes and hence accumulates in dead cells. Thus, protein-induced membrane lysis can be monitored by the detection of PI fluorescence (Radosevic et al., 1990).

In order to measure the fluorescence intensity of the samples, the detectors were tuned to the appropriate wavelength of emission of the used fluorescent marker. As mentioned above, YopM and SspHI were labelled with ALEXA FLUOR® 488 which can be excited at 494 nm and emits light at 519 nm. Fluorescence intensity of cells incubated with Tat-GFP-GSK depends on fluorescence of GFP which is excited at 488 nm and emission was detected at 510 nm. For monitoring membranolytic effects of the proteins, 1 µg/ml PI was added to the medium.

Fluorescence of PI is excited at 536 nm and can be detected at 617 nm. Samples for measuring intracellular accumulation of the proteins were diluted 1:1 with TB (0.4% (w/v)) prior to FACS analysis. The samples were applied to the cytometer and fluorescence emitted by the cells was measured. In addition, side and forward scatter were measured for each cell crossing the laser beam. The obtained data were analysed using CellQuest™ Pro (BD Biosciences, Heidelberg).

7 In Vitro Ubiquitination Assay

In vitro ubiquitination experiments were performed in 40 µl reaction buffer (50 mM Tris-HCl, pH7.4, 10 mM $MgCl_2$, 0.1 mM DTT and 2 mM ATP) containing 0.5 µg E1, 2 µg UbcH5b (E2), 2 µg HA-ubiquitin, 2 µg SspH1/SspH1-Nter in the presence or absence of 0.4 µg PKN1. Reactions were incubated at 37° C. for 1 h and stopped by addition of SDS sample buffer, with or without 100 mM DTT. Samples were separated by SDS-PAGE and subjected to western blotting using anti-ubiquitin, anti-His and anti-PKN1 antibodies.

8 Immunoprecipitation (IP)

HeLa cells were grown to 80% confluency in 10 cm dishes and subsequently transfected with pCMVEntry-PKN1-Myc. 24 h post transfection, cells were incubated with 25 µg/ml FLAG-tagged SspH1 and SspH1-Nter, respectively for 3 h. Cells were washed with D-PBS (with $Ca^{2+}$ and $Mg^{2+}$) (3×5 min), before they were scraped from the surface and resuspended in 800 µl IP lysis buffer (supplemented with Complete EDTA-free Protease Inhibitor Cocktail (Roche Biochemicals, Mannheim) prior to use). The cells were permeabilised by sonication (3×20 s, 4° C.) and subsequently incubated on a rotary shaker for 30 min at 4° C. Lysates were cleared by centrifugation (16,000×g, 30 min, 4° C.) and a sample of the lysate was taken and stored at −20° C. until further usage. 30 µl protein A/G agarose beads (Santa Cruz, sc-2003) were incubated with 5 µg α-PKN1 antibody (BD Biosciences) on ice for 5 min before the lysate was added to the mix and incubated on a rotary shaker overnight at 4° C. The beads were pelleted by centrifugation (1000×g, 3 min, 4° C.) and a sample of the supernatant was collected and stored until further usage. The beads were washed with 600 µl IP lysis buffer three times and centrifuged as mentioned above. The supernatant was discarded and 30 µl 4× SDS sample buffer were added to the beads, heated at 95° C. for 5 min and subsequently centrifuged at 16,000×g for 5 min. The supernatant along with the samples of the lysate and the unbound protein were subjected to immuno blot analysis.

| IP lysis Buffer | | |
|---|---|---|
| Tris-HCl pH 7.4 | 50 | mM |
| NaCl | 150 | mM |
| EDTA | 2 | mM |

9 Non-Radioactive Cytotoxicity Assay

In order to analyse a potential cytotoxic effect of the recombinant proteins on the eukaryotic cells, the CYTOTOX 96® Non-Radioactive Cytotoxicity Assay (Promega) was used. HeLa cells were grown in 96 well plates and incubated with 25-50 µg/ml SspH1 and SspH1-Nter, respectively for different time points (1, 6 & 24 h). Following incubation, the assay was performed according to the manufacturer's recommendations.

10 Analysis of Eukaryotic Gene Expression

In order to analyse the effect of recombinant SspH1 on cytokine and chemokine expression, qRT-PCR was performed. Therefore, A459 cells were grown in 6 well plates to confluency and incubated with SspH1 for 3 h. The cells were subsequently stimulated with 20 ng/ml II1β, before RNA was isolated according to the manufacturer's recommendations using the RNeasy Mini Kit (Qiagen, Hilden).

10.1 cDNA Synthesis

The RNA was then used for cDNA synthesis using the Transcriptor Reverse Transcriptase-Kit (Roche, Mannheim) according to the manufacturer's recommendations. First, primers were annealed to the RNA, before the cDNA synthesis was initiated by addition of the RT mix.

| Step | Reaction mixture | Concentration | Program |
|---|---|---|---|
| I. | RNA | 3-5 µg | 10 min, |
| | T7 Oligo $(dT)_{24}$ Primer | 10 pmol | 65° C. |
| | DNA/RNA free $H_2O$ | ad 13 µl | −>4° C. |
| II. | 5 x RT-Puffer | 4 µl | |
| | dNTPS | 2 µl | 30 min, |
| | RNase Inhibitor (40 U/µl) | 0.5 µl | 55° C. |
| | Reverse Transcriptase (20 U/µl) | 0.5 µl | 5 min, |
| | | | 85° C. |
| | | | −>4° C. | cDNA was synthesised in a PCR thermo cycler and stored at −20° C. until further usage.

10.2 Quantitative Real Time PCR

The qRT-PCR enables quantification of PCR products by measuring the fluorescent intensities of a DNA-intercalating fluorescent dye. In this study, qRT-PCR was performed using the LightCycler1.5 (Roche, Mannheim). Data was analysed using the LIGHTCYCLER® Data Analysis 5.3.2 software (Roche, Mannheim). Values for each sample were normalised for a low abundance Housekeeping gene (here HPRT: Hypoxanthin-Phosphoribosyl-Transferase I) (Vandesompele et al., 2002).

qRT-PCR was performed using the LIGHTCYCLER® Fast Start DNA Master$^{PLUS}$ SYBR Green I kit (Roche, Mannheim) which contains the reaction buffer, the dNTP mix, the SYBR Green I dye and $MgCl_2$. The hot start Taq polymerase is added to the mix and heat-activated at 95° C. for 15 min before the PCR reaction. Different dilutions of the cDNA were prepared (1:10, 1:100, 1:1000) in sterile $dH_2O$ and used as a template for the qRT-PCR.

| | |
|---|---|
| 2 µl | cDNA |
| 2 µl | LightCycler ® Fast Start DNA Master$^{PLUS}$ SYBR Green I |
| 2 µl | Primer Mix |
| 4 µl | Sterile $dH_2O$ | qRT-PCR was performed using the following cycling conditions.

| | Reaction Step | Temperature | Time | Cycles |
|---|---|---|---|---|
| I. | Denaturation and DNA Polymerase Activation | 95° C. | 15 min | 1 x |
| II. | 1. Denaturation | 95° C. | 12 s | |
| | 2. Annealing | 60° C. | 10 s | 35-55 x |
| | 3. Elongation | 72° C. | 12 s | |
| III. | Melting | 60-95° C. | stepwise | 1 x |

Statistical analysis of the obtained data was performed using Prism 4 (GraphPad Software). The statistical significance of differences in gene expression was analysed using the unpaired student t-test and values $p<0.05$ were regarded as significant.

3 Material 3.1 Bacterial Strains

Bacterial strains used in this study are listed in Table 3.1.

TABLE 3.1

Bacterial strains

| Strain | Relevant Characteristics | Reference |
|---|---|---|
| E. coli DH5α | F$^-$, endA1, recA1, hsdR17($r_K^-$ $M_K^+$) deoR, thi-1, supE44, gyrA96, Δ(lacZYA-argF) U169 (Φ80dlacZΔM15) | Hanahan et al., 1991 |
| E. coli BL21 (DE3) | F$^-$, hsdS$_B$ ($r_B^-m_B^-$), dcm, gal, ompT, (λDE3) | Studier & Moffatt, 1986 |

3.4 Plasmids and Oligonucleotides

Plasmids used in this study are listed in Table 3.3.

TABLE 3.2

Plasmids

| Plasmid | Relevant Characteristics | Reference |
|---|---|---|
| pET24b(+) | Expression vector, Kan$^R$ | Novagen |
| pET-YopM | Nucleotides 1-1101 of yopM from Y. enterocolitica O:8 JB580v (NheI/XhoI) in pET24b(+) | Heusipp et al., 2006 |
| pET-SspHI | Nucleotides 1-2103 of sspHI of S. enterica subspec. enterica serovar Typhimurium 14928S (NheI/XhoI) in pET24b(+) | Lubos, M.-L. |
| pET-SspHI-Nter | Nucleotides 1-1161 of sspHI of S. enterica subspec. enterica serovar Typhimurium 14928S (NheI/XhoI) in pET24b(+) | Lubos, M.-L. |
| pET:Tat-GFP-GSK | Coding sequence of the Tat CPP with 3' GFP coding sequence and GSK-3β tag coding sequence in pET24b(+) | Lubos, M.-L. |
| pET:IpaH1.4 | ipaH1.4 of S. flexneri in pET24b+ | S. Norkowski |
| pET:IpaH2.5 | ipaH2.5 of S. flexneri in pET24b+ | S. Norkowski |
| pET:IpaH3 | ipaH3 of S. flexneri in pET24b+ | S. Norkowski |
| pET:IpaH4.5 | ipaH4.5 of S. flexneri in pET24b+ | S. Norkowski |
| pET:IpaH7.8 | ipaH7.8 of S. flexneri in pET24b+ | S. Norkowski |
| pET:IpaH9.8 | ipaH9.8 of S. flexneri in pET24b+ | S. Norkowski |
| pET:SspH2 | SspH2 of S. typhimurium in pET24b+ | S. Norkowski |
| pET:SlrP | slrP of S. typhimurium in pET24b+ | S. Norkowski |
| pCMVEntry-PKN1 | Myc-DDK-tagged Human pkn1 transcript variant 1 in pCMV6-Entry, RC215735 | Origene |

Synthetic oligonucleotides used for DNA amplification are listed in Table 3.4. All primers were purchased from MWG Biotech AG (Ebersberg).

TABLE 3.3

Oligonucleotide sequences for DNA amplification by PCR (restriction sites are underlined)

| Oligonucleotide | Sequence (5'→3') |
| --- | --- |
| F-SspHI (NheI) SEQ ID NO: 530 | CTA GCT AGC GTT ACC GAT AAA TAA TAA CTT |
| R-SspHI (XhoI) SEQ ID NO: 531 | CCC CTC GAG TGA ATG GTG CAG TTG TGA GCC |
| R-SspHI-Nter (XhoI) SEQ ID NO: 532 | CCG CTC GAG CCG TGG GCC GTG GTA GTC CGG |
| F-Tat (NdeI) SEQ ID NO: 533 | TAT GAT GTG CGG CCG TAA GAA ACG TCG CCA GCG TCG CCG TCC GCC GCA ATG CG |
| R-Tat (NheI) SEQ ID NO: 534 | CTA GCG CAT TGC GGC GGA CGG CGA CGC TGG CGA CGT TTC TTA CGG CCG CAC AGC A |
| F-IpaH1.4 SEQ ID NO: 535 | GTT TAA CTT TAA GAA GGA GAT ATA CAT ATG ATT AAA TCA ACC AAT ATA CAG |
| R-IpaH1.4 SEQ ID NO: 536 | CTT ATC GTC GTC ATC CTT GTA ATC GCT AGC TGC GAT ATG ATT TGA GCC GTT TTC AGA CAA |
| F-IpaH2.5/IpaH4.5 SEQ ID NO: 537 | GTT TAA CTT TAA GAA GGA GAT ATA CAT ATG ATT AAA TCA ACA AAT ATA CAG GTA ATC GGT |
| R-IpaH2.5 SEQ ID NO: 538 | CTT ATC GTC GTC ATC CTT GTA ATC GCT AGC GGC CAG TAC CTC GTC AGT CAA CTG ACG GTA |
| F-IpaH3 SEQ ID NO: 539 | GTT TAA CTT TAA GAA GGA GAT ATA CAT ATG TTA CCG ATA AAT AAT AAC TTT TCA TTG TCC |
| R-IpaH3 SEQ ID NO: 540 | CTT ATC GTC GTC ATC CTT GTA ATC GCT AGC GTC AGC TGA CGG TAA ATC TGC TGT TAC AGT |
| F-IpaH4.5 SEQ ID NO: 541 | GTT TAA CTT TAA GAA GGA GAT ATA CAT ATG AAA CCG ATC AAC AAT CAT TCT TTT TTT CGT |
| F-IpaH7.8 SEQ ID NO: 542 | GTT TAA CTT TAA GAA GGA GAT ATA CAT ATG TTC TCT GTA AAT AAT ACA CAC TCA TCA GTT |
| R-IpaH7.8 SEQ ID NO: 543 | CTT ATC GTC GTC ATC CTT GTA ATC GCT AGC TGA ATG GTG CAG TCG TGA GCC GTT TTC AGA |
| F-IpaH9.8 SEQ ID NO: 544 | GTT TAA CTT TAA GAA GGA GAT ATA CAT ATG TTA CCG ATA AAT AAT AAC TTT TCA TTG CCC |
| R-IpaH9.8 SEQ ID NO: 545 | CTT ATC GTC GTC ATC CTT GTA ATC GCT AGC TGA ATG GTG CAG TTG TGA GCC GTT TTC AAA |
| F-SspH2 SEQ ID NO: 546 | GTT TAA CTT TAA GAA GGA GAT ATA CAT ATG CCC TTT CAT ATT GGA AGC GGA TGT CTT CCC |
| R-SspH2 SEQ ID NO: 547 | CTT ATC GTC GTC ATC CTT GTA ATC GCT AGC GTT ACG ACG CCA CTG AAC GTT CAG ATA GCT |
| F-SlrP SEQ ID NO: 548 | GTT TAA CTT TAA GAA GGA GAT ATA CAT ATG TTT AAT ATT ACT AAT ATA CAA TCT ACG GCA |
| R-SlrP SEQ ID NO: 549 | CTT ATC GTC GTC ATC CTT GTA ATC GCT AGC TCG CCA GTA GGC GCT CAT GAG CGA GCT CAC |

3.6 Antibodies

Primary and secondary antibodies used for Western blot analysis and fluorescent dyes for immunofluorescence studies are listed in Tables 3.6 and 3.7.

TABLE 3.4

Primary antibodies used for Western blot analyses

| Antibody | Dilution | Characteristics | Reference |
|---|---|---|---|
| α-Penta-His | 1:1000 | Mouse monoclonal antibody against His$_6$-epitope (SEQ ID NO: 555), isotype IgG | Quiagen (Hilden) |
| Anti-α-Tubulin | 1:5000 | Mouse monoclonal antiserum against human α-tubulin | Sigma-Aldrich (München) |
| α-LSD1 (C69G12) | 1:1000 | Rabbit monoclonal antibody against human lysine-specific demethylase 1 (LSD1) | Cell Signaling (Danvers, USA) |
| α-GAPDH | 1:200 | Rabbit polyclonal antibody against glyceraldehyde 3-phosphate dehydrogenase (GAPDH) | Santa Cruz Biotechnology (Heidelberg) |
| α-Transferrin receptor | 1:500 | Mouse monoclonal antibody against human transferrin receptor | Invitrogen (Karlsruhe) |
| α-FLAG | 1:1000 | Mouse monoclonal antibody against DYKDDDDK -tag epitope (SEQ ID NO: 556), Clone M2 | Sigma-Aldrich (München) |
| α-PKN1 | 1:1000 | Monoclonal mouse antibody against human protein kinase N1 | BD Bioscience (Heidelberg) |

TABLE 3.5

Secondary antibodies used for Western blot (WB) analyses and fluorescent dyes for immunofluorescence (IF) analyses

| Antibody | Dilution | Characteristics | Reference |
|---|---|---|---|
| GAM-PO | (WB) 1:10000 | Peroxidase (PO) conjugated goat monoclonal antibody against mouse-IgG | Dianova (Hamburg) |
| GAR-PO | (WB) 1:10000 | Peroxidase (PO) conjugated goat monoclonal antibody against rabbit-IgG | Dianova (Hamburg) |
| Hoechst 33258 (DAPI) | (IF) 1:1000 | Selective DNA dye | Sigma Aldrich (Taufkirchen) |

3.7 Kits

Kits used in this study are listed in Table 3.6.

TABLE 3.6

Kits

| Kit | Supplier |
|---|---|
| ZYPPY ™ Plasmid Miniprep Kit | Zymo Research (Irvine, USA) |
| ZYMOCLEAN ™ Gel DNA Recovery Kit | Zymo Research (Irvine, USA) |
| Cy3 Ab Labelling Kit PA 33000 | GE Healthcare (Braunschweig) |
| ALEXA FLUOR ® 488 Protein Labelling Kit | Invitrogen (Karlsruhe) |
| NE-PER Nuclear and Cytoplasmic Extraction Reagents | Thermo Scientific (Rockford, USA) |
| CYTOTOX 96 ® Non-Radioactive Cytotoxicity Assay | Promega |

References (Materials and Methods of Examples 1 to 5)

Behrens, M. (1938), Hoppe-Seylers Z, 253, *Pflügers Archly—European Journal of Physiology*, 185.

Bonner, W. A., Hulett, H. R., Sweet, R. G. and Herzenberg, L. A. (1972), Fluorescence activated cell sorting. *Rev. Sci. Instrum.*, 43(3), 404-409.

Chen, G. J., Qiu, N., Karrer, C., Caspers, P. and Page, M. G. (2000), Restriction site-free insertion of PCR products directionally into vectors. *BioTechniques*, 28(3), 498-500, 504-5.

Gauthier, A., de Grado, M. and Finlay, B. B. (2000), Mechanical fractionation reveals structural requirements for enteropathogenic *Escherichia coli* Tir insertion into host membranes. *Infect. Immun.*, 68(7), 4344-4348.

Hed, J., Hallden, G., Johansson, S. G. and Larsson, P. (1987), The use of fluorescence quenching in flow cytofluorometry to measure the attachment and ingestion phases in phagocytosis in peripheral blood without prior cell separation. *J. Immunol. Methods*, 101(1), 119-125.

Kenny, B. and Finlay, B. B. (1997), Intimin-dependent binding of enteropathogenic *Escherichia coli* to host cells triggers novel signaling events, including tyrosine phosphorylation of phospholipase C-gamma1. *Infect. Immun.*, 65(7), 2528-2536.

Radosevic, K., Garritsen, H. S., Van Graft, M., De Grooth, B. G. and Greve, J. (1990), A simple and sensitive flow cytometric assay for the determination of the cytotoxic activity of human natural killer cells. *J. Immunol. Methods*, 135(1-2), 81-89.

Sahlin, S., Hed, J. and Rundquist, I. (1983), Differentiation between attached and ingested immune complexes by a fluorescence quenching cytofluorometric assay. *J. Immunol. Methods*, 60(1-2), 115-124.

Unger, T., Jacobovitch, Y., Dantes, A., Bernheim, R. and Peleg, Y. (2010), Applications of the Restriction Free (RF) cloning procedure for molecular manipulations and protein expression. *J. Struct. Biol.*, 172(1), 34-44.

van den Ent, F. and Lowe, J. (2006), RF cloning: a restriction-free method for inserting target genes into plasmids. *J. Biochem. Biophys. Methods*, 67(1), 67-74.

Methods of Examples 7 to 20

The experiments described in Examples 7 to 20 and shown in FIGS. 23 to 28 may be carried out in various ways well-known to one skilled in the art. For example, according to the methods indicated above or described in Examples 7 to 20.

Selected methods are described below in more detail. Methods well-known to one skilled in the art have not been described in detail in order to not unnecessarily obscure the present invention.

Cell Fractionation of Eukaryotic Cells

Cellular uptake of proteins was assessed by cell fractionation of eukaryotic cells. This method allows separation of soluble cytoplasmic proteins from insoluble membrane proteins (Behrens, 1938).

Therefore, HeLa cells were seeded in 10 cm cell-culture dishes and grown to 80% confluence. Upon protein treatment, the dishes were transferred to ice and the cells were washed twice with ice-cold D-PBS (with Ca2+/Mg2+). An additional wash step with acid buffer for 5 min was used to remove any residual surface-bound proteins (Langel, Ü. (ed) (2005). Handbook of cell-penetrating peptides. CRC Press, Taylor and Francis Group). After washing the cells again with D-PBS (with Ca2+/Mg2+), cells were collected using a cell scraper, transferred to a reaction tube on ice and resuspended in 1 ml sonication buffer (supplemented with Complete EDTA-free Protease Inhibitor Cocktail). The suspension was applied to sonication (ultrasound water bath, 4×1 sec, level 4, 4° C.) in order to permeabilize the cells. Subsequently, the suspension was centrifuged (108,000×g, 15 min, 4° C.) and the supernatant was taken as the cytoplasmic fraction (CF). After the insoluble pellet was washed once with 1 ml sonication buffer (108,000×g, 15 min, 4° C.), it was resuspended in 1 ml TRITON™ buffer (supplemented with Complete EDTA-free Protease Inhibitor Cocktail) and incubated on a rotary shaker at 15 rpm and 4° C. for 1 h or overnight. Subsequently, the cell lysate was centrifuged (108,000×g, 30 min, 4° C.) and the supernatant was taken as the membrane fraction (MF).

Both the cytoplasmic and the membrane fraction were precipitated using trichloracetic acid.

Subsequently, the samples were subjected to SDS-PAGE and analyzed by Western blotting.

| Acid Buffer | |
|---|---|
| Glycine in PBS, pH 2.0 | 62.5 mM |
| TRITON™ buffer | |
| TRITON™ X-100 in Sonication buffer | 1% (v/v) |
| Sonication buffer | |
| 1 mM Tris-HCl, pH 7.8 | |
| NaCl | 50 mM |
| EDTA | 150 mM |
| EGTA | 1 mM |
| Glycerol | 1 mM |
| NaVO4 | 30% (v/v) |
| NaF | 0.4 mM |
| | 1 mM |

Membranolysis Assay

For analysis of effects on membrane integrity induced by LPX effector proteins, a FACS-based membranolysis assay following the 'CPP-induced Membranolysis Assay' (Florén et al., 2011) was performed.

HeLa cells were cultured and prepared as described above. For monitoring membranolytic effects of the proteins, HeLa cells were incubated with the respective protein and co-incubated with 1 µg/ml PI. After defined time points samples were taken and applied to the FACS analysis. Each sample was measured in duplicates. Fluorescence of PI is excited at 536 nm and can be detected at 617 nm. The obtained data were analyzed using the CELLQUEST™ Pro software.

Lactate Dehydrogenase Assay

In order to assess cytotoxicity and potential lytic effects of recombinant proteins, the release of lactate dehydrogenase (LDH) can be measured and used as a parameter for membrane integrity. Cytotoxicity and potential lytic effects of recombinant proteins were measured using CYTOTOX® 96 Non-Radioactive Cytotoxicity Assay according to the manufacturer's instructions.

HeLa cells were seeded in 96-well plates and grown to 80% confluence. Upon incubation with recombinant proteins for 24, 6, and 1 h in 100 µl culture medium, the plate was centrifuged (400×g, 4 min, RT) and 50 µl of the supernatant from each well of the assay plate were transferred to the corresponding well of a new 96-well plate. In addition, 50 µl of a LDH positive control were added to separate wells in order to verify that the assay is functioning properly. HeLa cells contained in the remaining 50 µl were lysed by adding 5.5 µl Lysis Solutions (10×) for 30 min. Afterwards, 50 µl of the reconstituted Substrate Mix were added to each well of the two plates and both plates were incubated for 30 min at RT, protected from light. Finally, 50 µl of the Stop Solution were added to each well of the plates and the absorbance at 490 nm was recorded. All buffers used for this procedure were provided by the CYTOTOX® 96 Non-Radioactive Cytotoxicity Assay-Kit.

In Vitro Ubiquitination Assay

In order to verify the functionality of recombinant LPX effectors as proposed E3 ubiquitin ligases, in vitro ubiquitination assays were performed. Upon incubation with ubiquitin-activating enzymes E1, ubiquitin-conjugating enzymes E2, and ubiquitin, LPX effector proteins were tested whether they were able to remove ubiquitin from the E2 enzyme and catalyze the formation of poly-ubiquitin chains.

In vitro ubiquitination assays were performed in a volume of 40 µl at 37° C. for 1 h. The reaction mixture was composed as shown below. The reaction was stopped by adding of 10 µl of 4× SDS sample buffer without dithiothreitol (DTT). The samples were prepared for subsequent SDS-PAGE analysis by incubation at 95° C. for 10 min Reaction Mixture of In Vitro Ubiquitination Assay:

| Component | Amount |
|---|---|
| E1 | 0.5 µg |
| E2 (UbcH5b) | 2 µg |
| Ubiquitin-HA | 2 µg |
| Putative E3 | 4 µg |
| Ubiquitin reaction buffer | ad to 40 µl |

| Ubiquitination reaction buffer | |
|---|---|
| Tris-HCl, pH 7.5 | 25 mM |
| NaCl | 50 mM |
| ATP | 5 mM |
| MgCl2 | 10 mM |

-continued

| 4 x SDS sample buffer without DTT | |
|---|---|
| Tris-HCl, pH 6.8 | 30 mM |
| Glycerol | 10% (v/v) |
| SDS | 1.5% (v/v) |
| Bromophenol blue | Spatula tip |
| DTT | 0.1 mM |

Example 7

Functional Domains of LPX Family Members

Functional domains of SlrP, SspH1, SspH2, IpaH1.4, IpaH2.5, IpaH3, IpaH4.5, IpaH7.8 and IpaH9.8 are shown in FIGS. 14 to 22.

Sequence segment comprising leucine-rich repeats (called "LRR stretch") are marked in light grey and are non-edged. E3 Ubiquitin ligase domains are marked in dark grey and are edged.

Sequence sections within which the protein transduction domains (PTDs) are predicted are bold and underlined. Marked are the maximal sequence sections within the PTD is predicted. PTDs can correspond to the marked sequence sections or to c-terminally and/or N-terminally truncated fragments of the marked sequence sections.

Example 8

Corresponding DNA Sequences of the Proteins of the Invention Analyzed in the Examples Above SlrP
SEQ ID NO: 10
>gb|CP001363.1|:867285-869582 *Salmonella enterica* subsp. *enterica* serovar *Typhimurium* str. 14028S, complete genome
SspH1
SEQ ID NO: 11
>gb|CP001363.1|:1332051-1334153 *Salmonella enterica* subsp. *enterica* serovar *Typhimurium* str. 14028S
SspH2
SEQ ID NO: 12
>gb|CP001363.1|:2392438-2394804 *Salmonella enterica* subsp. *enterica* serovar *Typhimurium* str. 14028S, complete genome
IpaH1.4
SEQ ID NO: 13
>gi|12329037:206811-208538 *Shigella flexneri* virulence plasmid pWR100: from 1 to 213494
IpaH2.5
SEQ ID NO: 14
>gi|12329037:43257-44948 *Shigella flexneri* virulence plasmid pWR100: from 1 to 213494
IpaH3
SEQ ID NO: 15
>ENA|EID62303|EID62303.1 *Shigella flexneri* 5a str. M90T invasion plasmid antigen: Location: 1..1752
IpaH4.5
SEQ ID NO: 16
>gi|12329037:66187-67911 *Shigella flexneri* virulence plasmid pWR100: from 1 to 213494
IpaH7.8
SEQ ID NO: 17
>gi|12329037:64062-65759 *Shigella flexneri* virulence plasmid pWR100: from 1 to 213494
IpaH9.8
SEQ ID NO: 18
>gi|12329037:174343-175980 *Shigella flexneri* virulence plasmid pWR100: from 1 to 213494

Example 9

Protein Transduction Domains Determined in Example 5

IpaH1.4
SEQ ID NO: 4
>tr|Q9AJU5|Q9AJU5_SHIFL Putative uncharacterized protein ipaH1.4 OS=*Shigella flexneri* GN=ipaH1.4 PE=4 SV=1
Predicted PTD Sequences:

| 519 | SQRVADRLKA | SEQ ID NO: 361 | 371 | RVALTWNNLRKTL | SEQ ID NO: 367 |
|---|---|---|---|---|---|
| 520 | QRVADRLKAS | SEQ ID NO: 362 | 371 | RVALTWNNLRKTLL | SEQ ID NO: 368 |
| 521 | RVADRLKASG | SEQ ID NO: 363 | 370 | DRVALTWNNLRKTLL | SEQ ID NO: 369 |
| 520 | QRVADRLKASG | SEQ ID NO: 364 | 371 | RVALTWNNLRKTLLV | SEQ ID NO: 370 |
| 521 | RVADRLKASGL | SEQ ID NO: 365 | | | |
| 520 | QRVADRLKASGL | SEQ ID NO: 366 | | | |

IpaH2.5
SEQ ID NO: 5
>gi|12329051|emb|CAC05782.1| IpaH2.5, member of the IpaH family, probably secreted by the Mxi-Spa machinery, function unknown [*Shigella flexneri* 5a str. M90T]
Predicted PTD Sequences:

| 519 | SQRVADRLKA | SEQ ID NO: 371 | 371 | RVALTWNNLRKTL | SEQ ID NO: 377 |
|---|---|---|---|---|---|
| 520 | QRVADRLKAS | SEQ ID NO: 372 | 371 | RVALTWNNLRKTLL | SEQ ID NO: 378 |
| 521 | RVADRLKASG | SEQ ID NO: 373 | 370 | DRVALTWNNLRKTLL | SEQ ID NO: 379 |

| | | | | | |
|---|---|---|---|---|---|
| 520 | QRVADRLKASG | SEQ ID NO: 374 | 371 | RVALTWNNLRKTLLV | SEQ ID NO: 380 |
| 521 | RVADRLKASGL | SEQ ID NO: 375 | | | |
| 520 | QRVADRLKASGL | SEQ ID NO: 376 | | | |

IpaH3
SEQ ID NO: 6
>tr|I0VDT7|I0VDT7_SHIFL Invasion plasmid antigen OS=*Shigella flexneri* 5a str. M90T GN=ipaH_3 PE=4 SV=1
Predicted PTD Sequences:

| | | | | | |
|---|---|---|---|---|---|
| 511 | PQRVADRLKA | SEQ ID NO: 381 | 513 | RVADRLKASGL | SEQ ID NO: 386 |
| 512 | QRVADRLKAS | SEQ ID NO: 382 | 363 | RVALTWNNLRKTL | SEQ ID NO: 387 |
| 513 | RVADRLKASG | SEQ ID NO: 383 | 511 | PQRVADRLKASGL | SEQ ID NO: 388 |
| 511 | PQRVADRLKAS | SEQ ID NO: 384 | 363 | RVALTWNNLRKTLL | SEQ ID NO: 389 |
| 512 | QRVADRLKASG | SEQ ID NO: 385 | 362 | DRVALTWNNLRKTLL | SEQ ID NO: 390 |
| 363 | RVALTWNNLRKTLLV | SEQ ID NO: 391 | | | |

IpaH4.5
SEQ ID NO: 7
>gi|12329057|emb|CAC05788.1| IpaH4.5, member of the IpaH family, probably secreted by the Mxi-Spa secretion machinery, function unknown [*Shigella flexneri* 5a str. M90T]
Predicted PTD Sequences:

| | | | | | |
|---|---|---|---|---|---|
| 48 | NRIQAVRLLK | SEQ ID NO: 392 | 204 | SLKYLKVGENQLRRL | SEQ ID NO: 437 |
| 49 | RIQAVRLLKI | SEQ ID NO: 393 | 205 | LKYLKVGENQLRRLS | SEQ ID NO: 438 |
| 50 | IQAVRLLKIC | SEQ ID NO: 394 | 208 | LKVGENQLRRLSRLP | SEQ ID NO: 439 |
| 51 | QAVRLLKICL | SEQ ID NO: 395 | 204 | SLKYLKVGENQLRRL | SEQ ID NO: 440 |
| 54 | RLLKICLDTR | SEQ ID NO: 396 | 205 | LKYLKVGENQLRRLS | SEQ ID NO: 441 |
| 208 | LKVGENQLRR | SEQ ID NO: 397 | 208 | LKVGENQLRRLSRLP | SEQ ID NO: 442 |
| 209 | KVGENQLRRL | SEQ ID NO: 398 | 214 | QLRRLSRLPQELLAL | SEQ ID NO: 443 |
| 530 | SQRVADRLKA | SEQ ID NO: 399 | 381 | DRVALTWNNLRKTLL | SEQ ID NO: 444 |
| 531 | QRVADRLKAS | SEQ ID NO: 400 | 382 | RVALTWNNLRKTLLV | SEQ ID NO: 445 |
| 532 | RVADRLKASG | SEQ ID NO: 401 | 48 | NRIQAVRLLKICLDTR | SEQ ID NO: 446 |
| 47 | ENRIQAVRLLK | SEQ ID NO: 402 | 49 | RIQAVRLLKICLDTRE | SEQ ID NO: 447 |
| 48 | NRIQAVRLLKI | SEQ ID NO: 403 | 203 | QSLKYLKVGENQLRRL | SEQ ID NO: 448 |
| 49 | RIQAVRLLKIC | SEQ ID NO: 404 | 208 | LKVGENQLRRLSRLPQ | SEQ ID NO: 449 |
| 208 | LKVGENQLRRL | SEQ ID NO: 405 | 213 | NQLRRLSRLPQELLAL | SEQ ID NO: 450 |
| 531 | QRVADRLKASG | SEQ ID NO: 406 | 47 | ENRIQAVRLLKICLDTR | SEQ ID NO: 451 |
| 532 | RVADRLKASGL | SEQ ID NO: 407 | 48 | NRIQAVRLLKICLDTRE | SEQ ID NO: 452 |
| 46 | TENRIQAVRLLK | SEQ ID NO: 408 | 205 | LKYLKVGENQLRRLSRL | SEQ ID NO: 453 |
| 47 | ENRIQAVRLLKI | SEQ ID NO: 409 | 204 | SLKYLKVGENQLRRLSRL | SEQ ID NO: 454 |
| 48 | NRIQAVRLLKIC | SEQ ID NO: 410 | 39 | WAREGTTTENRIQAVRLLK | SEQ ID NO: 455 |

-continued

| Pos | Sequence | SEQ ID | Pos | Sequence | SEQ ID |
|---|---|---|---|---|---|
| 49 | RIQAVRLLKICL | SEQ ID NO: 411 | 203 | QSLKYLKVGENQLRRLSRL | SEQ ID NO: 456 |
| 52 | AVRLLKICLDTR | SEQ ID NO: 412 | 208 | LKVGENQLRRLSRLPQELL | SEQ ID NO: 457 |
| 216 | RRLSRLPQELLA | SEQ ID NO: 413 | 209 | KVGENQLRRLSRLPQELLA | SEQ ID NO: 458 |
| 531 | QRVADRLKASGL | SEQ ID NO: 414 | 39 | WAREGTTTENRIQAVRLLKI | SEQ ID NO: 459 |
| 46 | TENRIQAVRLLKI | SEQ ID NO: 415 | 208 | LKVGENQLRRLSRLPQELLA | SEQ ID NO: 460 |
| 47 | ENRIQAVRLLKIC | SEQ ID NO: 416 | 209 | KVGENQLRRLSRLPQELLAL | SEQ ID NO: 461 |
| 48 | NRIQAVRLLKICL | SEQ ID NO: 417 | 205 | LKYLKVGENQLRRLSRLPQEL | SEQ ID NO: 462 |
| 49 | RIQAVRLLKICLD | SEQ ID NO: 418 | 206 | KYLKVGENQLRRLSRLPQELL | SEQ ID NO: 463 |
| 51 | QAVRLLKICLDTR | SEQ ID NO: 419 | 208 | LKVGENQLRRLSRLPQELLAL | SEQ ID NO: 464 |
| 208 | LKVGENQLRRLSR | SEQ ID NO: 420 | 54 | RLLKICLDTREPVLNLSLLKLR | SEQ ID NO: 465 |
| 209 | KVGENQLRRLSRL | SEQ ID NO: 421 | 205 | LKYLKVGENQLRRLSRLPQELL | SEQ ID NO: 466 |
| 215 | LRRLSRLPQELLA | SEQ ID NO: 422 | 206 | KYLKVGENQLRRLSRLPQELLA | SEQ ID NO: 467 |
| 216 | RRLSRLPQELLAL | SEQ ID NO: 423 | 207 | YLKVGENQLRRLSRLPQELLAL | SEQ ID NO: 468 |
| 382 | RVALTWNNLRKTL | SEQ ID NO: 424 | 205 | LKYLKVGENQLRRLSRLPQELLA | SEQ ID NO: 469 |
| 47 | ENRIQAVRLLKICL | SEQ ID NO: 425 | 206 | KYLKVGENQLRRLSRLPQELLAL | SEQ ID NO: 470 |
| 48 | NRIQAVRLLKICLD | SEQ ID NO: 426 | 204 | SLKYLKVGENQLRRLSRLPQELLA | SEQ ID NO: 471 |
| 49 | RIQAVRLLKICLDT | SEQ ID NO: 427 | 205 | LKYLKVGENQLRRLSRLPQELLAL | SEQ ID NO: 472 |
| 50 | IQAVRLLKICLDTR | SEQ ID NO: 428 | 206 | KYLKVGENQLRRLSRLPQELLALD | SEQ ID NO: 473 |
| 205 | LKYLKVGENQLRRL | SEQ ID NO: 429 | 51 | QAVRLLKICLDTREPVLNLSLLKLR | SEQ ID NO: 474 |
| 208 | LKVGENQLRRLSRL | SEQ ID NO: 430 | 203 | QSLKYLKVGENQLRRLSRLPQELLA | SEQ ID NO: 475 |
| 214 | QLRRLSRLPQELLA | SEQ ID NO: 431 | 204 | SLKYLKVGENQLRRLSRLPQELLAL | SEQ ID NO: 476 |
| 215 | LRRLSRLPQELLAL | SEQ ID NO: 432 | 205 | LKYLKVGENQLRRLSRLPQELLALD | SEQ ID NO: 477 |
| 382 | RVALTWNNLRKTLL | SEQ ID NO: 433 | 49 | RIQAVRLLKICLDTREPVLNLSLLKL | SEQ ID NO: 478 |
| 46 | TENRIQAVRLLKICL | SEQ ID NO: 434 | 50 | IQAVRLLKICLDTREPVLNLSLLKLR | SEQ ID NO: 479 |
| 48 | NRIQAVRLLKICLDT | SEQ ID NO: 435 | 203 | QSLKYLKVGENQLRRLSRLPQELLAL | SEQ ID NO: 480 |
| 49 | RIQAVRLLKICLDTR | SEQ ID NO: 436 | 49 | RIQAVRLLKICLDTREPVLNLSLLKLR | SEQ ID NO: 481 |
| | | | 48 | NRIQAVRLLKICLDTREPVLNLSLLKLR | SEQ ID NO: 482 |
| | | | 49 | RIQAVRLLKICLDTREPVLNLSLLKLRS | SEQ ID NO: 483 |
| | | | 47 | ENRIQAVRLLKICLDTREPVLNLSLLKLR | SEQ ID NO: 484 |
| | | | 49 | RIQAVRLLKICLDTREPVLNLSLLKLRSL | SEQ ID NO: 485 |
| | | | 48 | NRIQAVRLLKICLDTREPVLNLSLLKLRSL | SEQ ID NO: 486 |

IpaH7.8
SEQ ID NO: 8 55
>gi|12329056|emb|CAC05787.1| IpaH7.8, member of the IpaH family, secreted by the Mxi-Spa secretion machinery, function unknown [*Shigella flexneri* 5a str. M90T]
Predicted PTD Sequences:

| Pos | Sequence | SEQ ID | Pos | Sequence | SEQ ID |
|---|---|---|---|---|---|
| 238 | TRVLQSLQRL | SEQ ID NO: 487 | 510 | RVADRLKASGL | SEQ ID NO: 493 |
| 239 | RVLQSLQRLT | SEQ ID NO: 488 | 509 | QRVADRLKASGL | SEQ ID NO: 494 |
| 508 | SQRVADRLKA | SEQ ID NO: 489 | 360 | RVALTWNNLRKTL | SEQ ID NO: 495 |

| | | | | | |
|---|---|---|---|---|---|
| 509 | QRVADRLKAS | SEQ ID NO: 490 | 360 | RVALTWNNLRKTLL | SEQ ID NO: 496 |
| 510 | RVADRLKASG | SEQ ID NO: 491 | 359 | DRVALTWNNLRKTLL | SEQ ID NO: 497 |
| 509 | QRVADRLKASG | SEQ ID NO: 492 | 360 | RVALTWNNLRKTLLV | SEQ ID NO: 498 |

IpaH9.8
SEQ ID NO: 9
>gi|12329122|emb|CAC05853.1| IpaH9.8, secreted by the Mxi-Spa secretion machinery, function unknown [*Shigella flexneri* 5a str. M90T]
Predicted PTD Sequences:

| | | | | | |
|---|---|---|---|---|---|
| 155 | LPQALKNLRA | SEQ ID NO: 499 | 154 | SLPQALKNLRATR | SEQ ID NO: 515 |
| 157 | QALKNLRATR | SEQ ID NO: 500 | 155 | LPQALKNLRATRN | SEQ ID NO: 516 |
| 158 | ALKNLRATRN | SEQ ID NO: 501 | 158 | ALKNLRATRNFLT | SEQ ID NO: 517 |
| 488 | PQRVADRLKA | SEQ ID NO: 502 | 340 | RVALTWNNLRKTL | SEQ ID NO: 518 |
| 489 | QRVADRLKAS | SEQ ID NO: 503 | 488 | PQRVADRLKASGL | SEQ ID NO: 519 |
| 490 | RVADRLKASG | SEQ ID NO: 504 | 153 | PSLPQALKNLRATR | SEQ ID NO: 520 |
| 156 | PQALKNLRATR | SEQ ID NO: 505 | 154 | SLPQALKNLRATRN | SEQ ID NO: 521 |
| 488 | PQRVADRLKAS | SEQ ID NO: 506 | 157 | QALKNLRATRNFLT | SEQ ID NO: 522 |
| 489 | QRVADRLKASG | SEQ ID NO: 507 | 340 | RVALTWNNLRKTLL | SEQ ID NO: 523 |
| 490 | RVADRLKASGL | SEQ ID NO: 508 | 152 | LPSLPQALKNLRATR | SEQ ID NO: 524 |
| 155 | LPQALKNLRATR | SEQ ID NO: 509 | 153 | PSLPQALKNLRATRN | SEQ ID NO: 525 |
| 489 | QRVADRLKASGL | SEQ ID NO: 510 | 155 | LPQALKNLRATRNFL | SEQ ID NO: 526 |
| 151 | SLPSLPQALKNLRATR | SEQ ID NO: 511 | 156 | PQALKNLRATRNFLT | SEQ ID NO: 527 |
| 152 | LPSLPQALKNLRATRN | SEQ ID NO: 512 | 339 | DRVALTWNNLRKTLL | SEQ ID NO: 528 |
| 154 | SLPQALKNLRATRNFL | SEQ ID NO: 513 | 340 | RVALTWNNLRKTLLV | SEQ ID NO: 529 |
| 155 | LPQALKNLRATRNFLT | SEQ ID NO: 514 | | | |

SspH1
SEQ ID NO: 2
>gi|267993082|gb|ACY87967.1| SspH1 [*Salmonella enterica* subsp. *enterica* serovar *Typhimurium* str. 14028S]
Predicted PTD Sequences:

| | | | | | |
|---|---|---|---|---|---|
| 372 | LSVRTLQALR | SEQ ID NO: 152 | 693 | LTARWRLN | SEQ ID NO: 155 |
| 70 | ARLKALTFPA | SEQ ID NO: 153 | 319 | LQKLWAYNNRL | SEQ ID NO: 156 |
| 626 | RFNALREKQI | SEQ ID NO: 154 | 476 | ALRAKTFAMAT | SEQ ID NO: 157 |

SspH2
SEQ ID NO: 3
>gi|267994325|gb|ACY89210.1| leucine-rich repeat-containing protein [*Salmonella enterica* subsp. *enterica* serovar *Typhimurium* str. 14028S]
Predicted PTD Sequences:

| | | | | | |
|---|---|---|---|---|---|
| 185 | SRGRAAVVQK | SEQ ID NO: 158 | 627 | QIAREKVRTL | SEQ ID NO: 260 |
| 186 | RGRAAVVQKM | SEQ ID NO: 159 | 628 | IAREKVRTLA | SEQ ID NO: 261 |

-continued

| | | | | | |
|---|---|---|---|---|---|
| 187 | GRAAVVQKMR | SEQ ID NO: 160 | 629 | AREKVRTLAL | SEQ ID NO: 262 |
| 188 | RAAVVQKMRA | SEQ ID NO: 161 | 630 | REKVRTLALV | SEQ ID NO: 263 |
| 187 | GRAAVVQKMRA | SEQ ID NO: 162 | 648 | YQNKLKKSLG | SEQ ID NO: 264 |
| 188 | RAAVVQKMRAC | SEQ ID NO: 163 | 649 | QNKLKKSLGL | SEQ ID NO: 265 |
| 620 | FRLGKLEQIAR | SEQ ID NO: 164 | 709 | RKAPERVNAL | SEQ ID NO: 266 |
| 624 | KLEQIAREKVR | SEQ ID NO: 165 | 710 | KAPERVNALR | SEQ ID NO: 267 |
| 627 | QIAREKVRTLA | SEQ ID NO: 166 | 646 | LAYQNKLKKSL | SEQ ID NO: 268 |
| 628 | IAREKVRTLAL | SEQ ID NO: 167 | 647 | AYQNKLKKSLG | SEQ ID NO: 269 |
| 629 | AREKVRTLALV | SEQ ID NO: 168 | 714 | RVNALREKQIS | SEQ ID NO: 270 |
| 185 | SRGRAAVVQKMR | SEQ ID NO: 169 | 12 | ATISNRRIYRIA | SEQ ID NO: 271 |
| 186 | RGRAAVVQKMRA | SEQ ID NO: 170 | 619 | MFRLGKLEQIAR | SEQ ID NO: 272 |
| 188 | RAAVVQKMRACL | SEQ ID NO: 171 | 621 | RLGKLEQIAREK | SEQ ID NO: 273 |
| 177 | RRAAPAEESRGRA | SEQ ID NO: 172 | 623 | GKLEQIAREKVR | SEQ ID NO: 274 |
| 185 | SRGRAAVVQKMRA | SEQ ID NO: 173 | 627 | QIAREKVRTLAL | SEQ ID NO: 275 |
| 186 | RGRAAVVQKMRAC | SEQ ID NO: 174 | 628 | IAREKVRTLALV | SEQ ID NO: 276 |
| 188 | RAAVVQKMRACLN | SEQ ID NO: 175 | 646 | LAYQNKLKKSLG | SEQ ID NO: 277 |
| 620 | FRLGKLEQIAREK | SEQ ID NO: 176 | 647 | AYQNKLKKSLGL | SEQ ID NO: 278 |
| 621 | RLGKLEQIAREKV | SEQ ID NO: 177 | 751 | RTIGARAMESAKK | SEQ ID NO: 279 |
| 622 | LGKLEQIAREKVR | SEQ ID NO: 178 | 177 | RRAAPAEESRGRAA | SEQ ID NO: 280 |
| 627 | QIAREKVRTLALV | SEQ ID NO: 179 | 184 | ESRGRAAVVQKMRA | SEQ ID NO: 281 |
| 645 | WLAYQNKLKKSLG | SEQ ID NO: 180 | 186 | RGRAAVVQKMRACL | SEQ ID NO: 282 |
| 646 | LAYQNKLKKSLGL | SEQ ID NO: 181 | 619 | MFRLGKLEQIAREK | SEQ ID NO: 283 |
| 705 | RVLERKAPERVNAL | SEQ ID NO: 182 | 620 | FRLGKLEQIAREKV | SEQ ID NO: 284 |
| 706 | VLERKAPERVNALR | SEQ ID NO: 183 | 621 | RLGKLEQIAREKVR | SEQ ID NO: 285 |
| 710 | KAPERVNALREKQI | SEQ ID NO: 184 | 644 | VWLAYQNKLKKSLG | SEQ ID NO: 286 |
| 751 | RTIGARAMESAKKT | SEQ ID NO: 185 | 645 | WLAYQNKLKKSLGL | SEQ ID NO: 287 |
| 616 | GREMFRLGKLEQIAR | SEQ ID NO: 186 | 177 | RRAAPAEESRGRAAV | SEQ ID NO: 288 |
| 619 | MFRLGKLEQIAREKV | SEQ ID NO: 187 | 185 | SRGRAAVVQKMRACL | SEQ ID NO: 289 |
| 620 | FRLGKLEQIAREKVR | SEQ ID NO: 188 | 186 | RGRAAVVQKMRACLN | SEQ ID NO: 290 |
| 751 | RTIGARAMESAKKTF | SEQ ID NO: 189 | 176 | WRRAAPAEESRGRAAV | SEQ ID NO: 291 |
| 621 | RLGKLEQIAREKVRT | SEQ ID NO: 190 | 177 | RRAAPAEESRGRAAVV | SEQ ID NO: 292 |
| 644 | VWLAYQNKLKKSLGL | SEQ ID NO: 191 | 182 | AEESRGRAAVVQKMRA | SEQ ID NO: 293 |
| 645 | WLAYQNKLKKSLGLT | SEQ ID NO: 192 | 186 | RGRAAVVQKMRACLNN | SEQ ID NO: 294 |
| 706 | VLERKAPERVNALREK | SEQ ID NO: 193 | 619 | MFRLGKLEQIAREKVR | SEQ ID NO: 295 |
| 751 | RTIGARAMESAKKTFL | SEQ ID NO: 194 | 620 | FRLGKLEQIAREKVRT | SEQ ID NO: 296 |
| 176 | WRRAAPAEESRGRAAVV | SEQ ID NO: 195 | 621 | RLGKLEQIAREKVRTL | SEQ ID NO: 297 |
| 177 | RRAAPAEESRGRAAVVQ | SEQ ID NO: 196 | 609 | LAALVATGREMFRLGKL | SEQ ID NO: 298 |
| 178 | RAAPAEESRGRAAVVQK | SEQ ID NO: 197 | 614 | ATGREMFRLGKLEQIAR | SEQ ID NO: 299 |
| 706 | VLERKAPERVNALREKQ | SEQ ID NO: 198 | 616 | GREMFRLGKLEQIAREK | SEQ ID NO: 300 |

| | | | | | |
|---|---|---|---|---|---|
| 176 | WRRAAPAEESRGRAAVVQ | SEQ ID NO: 199 | 617 | REMFRLGKLEQIAREKV | SEQ ID NO: 301 |
| 177 | RRAAPAEESRGRAAVVQK | SEQ ID NO: 200 | 618 | EMFRLGKLEQIAREKVR | SEQ ID NO: 302 |
| 615 | TGREMFRLGKLEQIAREK | SEQ ID NO: 201 | 619 | MFRLGKLEQIAREKVRT | SEQ ID NO: 303 |
| 619 | MFRLGKLEQIAREKVRTL | SEQ ID NO: 202 | 620 | FRLGKLEQIAREKVRTL | SEQ ID NO: 304 |
| 620 | FRLGKLEQIAREKVRTLA | SEQ ID NO: 203 | 621 | RLGKLEQIAREKVRTLA | SEQ ID NO: 305 |
| 621 | RLGKLEQIAREKVRTLAL | SEQ ID NO: 204 | 706 | VLERKAPERVNALREKQI | SEQ ID NO: 306 |
| 175 | AWRRAAPAEESRGRAAVVQ | SEQ ID NO: 205 | 707 | LERKAPERVNALREKQIS | SEQ ID NO: 307 |
| 176 | WRRAAPAEESRGRAAVVQK | SEQ ID NO: 206 | 617 | REMFRLGKLEQIAREKVRT | SEQ ID NO: 308 |
| 177 | RRAAPAEESRGRAAVVQKM | SEQ ID NO: 207 | 618 | EMFRLGKLEQIAREKVRTL | SEQ ID NO: 309 |
| 178 | RAAPAEESRGRAAVVQKMR | SEQ ID NO: 208 | 619 | MFRLGKLEQIAREKVRTLA | SEQ ID NO: 310 |
| 175 | AWRRAAPAEESRGRAAVVQK | SEQ ID NO: 209 | 620 | FRLGKLEQIAREKVRTLAL | SEQ ID NO: 311 |
| 176 | WRRAAPAEESRGRAAVVQKM | SEQ ID NO: 210 | 621 | RLGKLEQIAREKVRTLALV | SEQ ID NO: 312 |
| 177 | RRAAPAEESRGRAAVVQKMR | SEQ ID NO: 211 | 611 | ALVATGREMFRLGKLEQIAR | SEQ ID NO: 313 |
| 178 | RAAPAEESRGRAAVVQKMRA | SEQ ID NO: 212 | 615 | TGREMFRLGKLEQIAREKVR | SEQ ID NO: 314 |
| 705 | RVLERKAPERVNALREKQIS | SEQ ID NO: 213 | 616 | GREMFRLGKLEQIAREKVRT | SEQ ID NO: 315 |
| 751 | RTIGARAMESAKKTFLDGLR | SEQ ID NO: 214 | 617 | REMFRLGKLEQIAREKVRTL | SEQ ID NO: 316 |
| 174 | SAWRRAAPAEESRGRAAVVQK | SEQ ID NO: 215 | 618 | EMFRLGKLEQIAREKVRTLA | SEQ ID NO: 317 |
| 175 | AWRRAAPAEESRGRAAVVQKM | SEQ ID NO: 216 | 619 | MFRLGKLEQIAREKVRTLAL | SEQ ID NO: 318 |
| 176 | WRRAAPAEESRGRAAVVQKMR | SEQ ID NO: 217 | 620 | FRLGKLEQIAREKVRTLALV | SEQ ID NO: 319 |
| 177 | RRAAPAEESRGRAAVVQKMRA | SEQ ID NO: 218 | 621 | RLGKLEQIAREKVRTLALVD | SEQ ID NO: 320 |
| 610 | AALVATGREMFRLGKLEQIAR | SEQ ID NO: 219 | 705 | RVLERKAPERVNALREKQIS | SEQ ID NO: 321 |
| 612 | LVATGREMFRLGKLEQIAREK | SEQ ID NO: 220 | 751 | RTIGARAMESAKKTFLDGLR | SEQ ID NO: 322 |
| 614 | ATGREMFRLGKLEQIAREKVR | SEQ ID NO: 221 | 174 | SAWRRAAPAEESRGRAAVVQK | SEQ ID NO: 323 |
| 616 | GREMFRLGKLEQIAREKVRTL | SEQ ID NO: 222 | 175 | AWRRAAPAEESRGRAAVVQKM | SEQ ID NO: 324 |
| 617 | REMFRLGKLEQIAREKVRTLA | SEQ ID NO: 223 | 176 | WRRAAPAEESRGRAAVVQKMR | SEQ ID NO: 325 |
| 618 | EMFRLGKLEQIAREKVRTLAL | SEQ ID NO: 224 | 177 | RRAAPAEESRGRAAVVQKMRA | SEQ ID NO: 326 |
| 619 | MFRLGKLEQIAREKVRTLALV | SEQ ID NO: 225 | 610 | AALVATGREMFRLGKLEQIAR | SEQ ID NO: 327 |
| 620 | FRLGKLEQIAREKVRTLALVD | SEQ ID NO: 226 | 612 | LVATGREMFRLGKLEQIAREK | SEQ ID NO: 328 |
| 621 | RLGKLEQIAREKVRTLALVD | SEQ ID NO: 227 | 614 | ATGREMFRLGKLEQIAREKVR | SEQ ID NO: 329 |
| 175 | AWRRAAPAEESRGRAAVVQKMR | SEQ ID NO: 228 | 614 | ATGREMFRLGKLEQIAREKVR | SEQ ID NO: 330 |
| 176 | WRRAAPAEESRGRAAVVQKMRA | SEQ ID NO: 229 | 616 | GREMFRLGKLEQIAREKVRTL | SEQ ID NO: 331 |
| 177 | RRAAPAEESRGRAAVVQKMRAC | SEQ ID NO: 230 | 617 | REMFRLGKLEQIAREKVRTLA | SEQ ID NO: 332 |
| 609 | LAALVATGREMFRLGKLEQIAR | SEQ ID NO: 231 | 618 | EMFRLGKLEQIAREKVRTLAL | SEQ ID NO: 333 |
| 611 | ALVATGREMFRLGKLEQIAREK | SEQ ID NO: 232 | 619 | MFRLGKLEQIAREKVRTLALV | SEQ ID NO: 334 |
| 614 | ATGREMFRLGKLEQIAREKVRT | SEQ ID NO: 233 | 620 | FRLGKLEQIAREKVRTLALVD | SEQ ID NO: 335 |
| 615 | TGREMFRLGKLEQIAREKVRTL | SEQ ID NO: 234 | 172 | VWSAWRRAAPAEESRGRAAVVQK | SEQ ID NO: 336 |
| 616 | GREMFRLGKLEQIAREKVRTLA | SEQ ID NO: 235 | 174 | SAWRRAAPAEESRGRAAVVQKMR | SEQ ID NO: 337 |
| 617 | REMFRLGKLEQIAREKVRTLAL | SEQ ID NO: 236 | 175 | AWRRAAPAEESRGRAAVVQKMRA | SEQ ID NO: 338 |
| 618 | EMFRLGKLEQIAREKVRTLALV | SEQ ID NO: 237 | 176 | WRRAAPAEESRGRAAVVQKMRAC | SEQ ID NO: 339 |
| 619 | MFRLGKLEQIAREKVRTLALVD | SEQ ID NO: 238 | 177 | RRAAPAEESRGRAAVVQKMRACL | SEQ ID NO: 340 |

| | | | | | |
|---|---|---|---|---|---|
| 173 | WSAWRRAAPAEESRGRAAVVQKMR | SEQ ID NO: 239 | 610 | AALVATGREMFRLGKLEQIAREK | SEQ ID NO: 341 |
| 174 | SAWRRAAPAEESRGRAAVVQKMRA | SEQ ID NO: 240 | 612 | LVATGREMFRLGKLEQIAREKVR | SEQ ID NO: 342 |
| 176 | WRRAAPAEESRGRAAVVQKMRACL | SEQ ID NO: 241 | 614 | ATGREMFRLGKLEQIAREKVRTL | SEQ ID NO: 343 |
| 177 | RRAAPAEESRGRAAVVQKMRACLN | SEQ ID NO: 242 | 615 | TGREMFRLGKLEQIAREKVRTLA | SEQ ID NO: 344 |
| 609 | LAALVATGREMFRLGKLEQIAREK | SEQ ID NO: 243 | 616 | GREMFRLGKLEQIAREKVRTLAL | SEQ ID NO: 345 |
| 610 | AALVATGREMFRLGKLEQIAREKV | SEQ ID NO: 244 | 617 | REMFRLGKLEQIAREKVRTLALV | SEQ ID NO: 346 |
| 611 | ALVATGREMFRLGKLEQIAREKVR | SEQ ID NO: 245 | 171 | AVWSAWRRAAPAEESRGRAAVVQKMR | SEQ ID NO: 347 |
| 614 | ATGREMFRLGKLEQIAREKVRTLA | SEQ ID NO: 246 | 172 | VWSAWRRAAPAEESRGRAAVVQKMRA | SEQ ID NO: 348 |
| 615 | TGREMFRLGKLEQIAREKVRTLAL | SEQ ID NO: 247 | 609 | LAALVATGREMFRLGKLEQIAREKVR | SEQ ID NO: 349 |
| 616 | GREMFRLGKLEQIAREKVRTLALV | SEQ ID NO: 248 | 610 | AALVATGREMFRLGKLEQIAREKVRT | SEQ ID NO: 350 |
| 617 | REMFRLGKLEQIAREKVRTLALVD | SEQ ID NO: 249 | 611 | ALVATGREMFRLGKLEQIAREKVRTL | SEQ ID NO: 351 |
| 608 | DLAALVATGREMFRLGKLEQIAREKVR | SEQ ID NO: 250 | 612 | LVATGREMFRLGKLEQIAREKVRTLA | SEQ ID NO: 352 |
| 609 | LAALVATGREMFRLGKLEQIAREKVRT | SEQ ID NO: 251 | 613 | VATGREMFRLGKLEQIAREKVRTLAL | SEQ ID NO: 353 |
| 610 | AALVATGREMFRLGKLEQIAREKVRTL | SEQ ID NO: 252 | 614 | ATGREMFRLGKLEQIAREKVRTLALV | SEQ ID NO: 354 |
| 611 | ALVATGREMFRLGKLEQIAREKVRTLA | SEQ ID NO: 253 | 171 | AVWSAWRRAAPAEESRGRAAVVQKMRA | SEQ ID NO: 355 |
| 612 | LVATGREMFRLGKLEQIAREKVRTLAL | SEQ ID NO: 254 | 607 | NDLAALVATGREMFRLGKLEQIAREKVR | SEQ ID NO: 356 |
| 614 | ATGREMFRLGKLEQIAREKVRTLALVD | SEQ ID NO: 255 | 608 | DLAALVATGREMFRLGKLEQIAREKVRT | SEQ ID NO: 357 |
| 607 | NDLAALVATGREMFRLGKLEQIAREKVRTL | SEQ ID NO: 256 | 609 | LAALVATGREMFRLGKLEQIAREKVRTL | SEQ ID NO: 358 |
| 608 | DLAALVATGREMFRLGKLEQIAREKVRTLA | SEQ ID NO: 257 | 610 | AALVATGREMFRLGKLEQIAREKVRTLA | SEQ ID NO: 359 |
| 609 | LAALVATGREMFRLGKLEQIAREKVRTLAL | SEQ ID NO: 258 | 611 | ALVATGREMFRLGKLEQIAREKVRTLAL | SEQ ID NO: 360 |
| 610 | AALVATGREMFRLGKLEQIAREKVRTLALV | SEQ ID NO: 259 | | | |

SlrP
SEQ ID NO: 1      40
>gi|267992540|gb|ACY87425.1| leucine-rich repeat-containing protein [*Salmonella enterica* subsp. *enterica* serovar *Typhimurium* str. 14028S]
Predicted PTD Sequences:

| | | | | | |
|---|---|---|---|---|---|
| 593 | SLAREKVKRL | SEQ ID NO: 66 | 173 | RDCLKNNKTELRLKILG | SEQ ID NO: 110 |
| 175 | CLKNNKTELRLKI | SEQ ID NO: 67 | 175 | CLKNNKTELRLKILGLT | SEQ ID NO: 111 |
| 176 | LKNNKTELRLKIL | SEQ ID NO: 68 | 172 | MRDCLKNNKTELRLKILG | SEQ ID NO: 112 |
| 177 | KNNKTELRLKILG | SEQ ID NO: 69 | 173 | RDCLKNNKTELRLKILGL | SEQ ID NO: 113 |
| 175 | CLKNNKTELRLKIL | SEQ ID NO: 70 | 386 | LPAALQIMQASRNNLVRL | SEQ ID NO: 114 |
| 176 | LKNNKTELRLKILG | SEQ ID NO: 71 | 585 | IFRLEQIESLAREKVKRL | SEQ ID NO: 115 |
| 177 | KNNKTELRLKILGL | SEQ ID NO: 72 | 171 | RMRDCLKNNKTELRLKILG | SEQ ID NO: 116 |
| 389 | ALQIMQASRNNLVR | SEQ ID NO: 73 | 172 | MRDCLKNNKTELRLKILGL | SEQ ID NO: 117 |
| 388 | AALQIMQASRNNLVR | SEQ ID NO: 74 | 173 | RDCLKNNKTELRLKILGLT | SEQ ID NO: 118 |
| 389 | ALQIMQASRNNLVRL | SEQ ID NO: 75 | 171 | RMRDCLKNNKTELRLKILGL | SEQ ID NO: 119 |
| 175 | CLKNNKTELRLKILGL | SEQ ID NO: 76 | 172 | MRDCLKNNKTELRLKILGLT | SEQ ID NO: 120 |
| 176 | LKNNKTELRLKILGLT | SEQ ID NO: 77 | 173 | RDCLKNNKTELRLKILGLTT | SEQ ID NO: 121 |
| 388 | AALQIMQASRNNLVRL | SEQ ID NO: 78 | 168 | AVQRMRDCLKNNKTELRLKIL | SEQ ID NO: 122 |

| | | | | | |
|---|---|---|---|---|---|
| 587 | RLEQIESLAREKVKRL | SEQ ID NO: 79 | 169 | VQRMRDCLKNNKTELRLKILG | SEQ ID NO: 123 |
| 581 | AGREIFRLEQIESLAREKVKR | SEQ ID NO: 80 | 170 | QRMRDCLKNNKTELRLKILGL | SEQ ID NO: 124 |
| 582 | GREIFRLEQIESLAREKVKRL | SEQ ID NO: 81 | 171 | RMRDCLKNNKTELRLKILGLT | SEQ ID NO: 125 |
| 167 | EAVQRMRDCLKNNKTELRLKIL | SEQ ID NO: 82 | 173 | RDCLKNNKTELRLKILGLTTI | SEQ ID NO: 126 |
| 168 | AVQRMRDCLKNNKTELRLKILG | SEQ ID NO: 83 | 167 | EAVQRMRDCLKNNKTELRLKILG | SEQ ID NO: 127 |
| 169 | VQRMRDCLKNNKTELRLKILGL | SEQ ID NO: 84 | 168 | AVQRMRDCLKNNKTELRLKILGL | SEQ ID NO: 128 |
| 170 | QRMRDCLKNNKTELRLKILGLT | SEQ ID NO: 85 | 169 | VQRMRDCLKNNKTELRLKILGLT | SEQ ID NO: 129 |
| 171 | RMRDCLKNNKTELRLKILGLTT | SEQ ID NO: 86 | 170 | QRMRDCLKNNKTELRLKILGLTT | SEQ ID NO: 130 |
| 580 | MAGREIFRLEQIESLAREKVKR | SEQ ID NO: 87 | 171 | RMRDCLKNNKTELRLKILGLTTI | SEQ ID NO: 131 |
| 581 | AGREIFRLEQIESLAREKVKRL | SEQ ID NO: 88 | 579 | IMAGREIFRLEQIESLAREKVKR | SEQ ID NO: 132 |
| 167 | EAVQRMRDCLKNNKTELRLKILGL | SEQ ID NO: 89 | 580 | MAGREIFRLEQIESLAREKVKRL | SEQ ID NO: 133 |
| 168 | AVQRMRDCLKNNKTELRLKILGLT | SEQ ID NO: 90 | 581 | AGREIFRLEQIESLAREKVKRLF | SEQ ID NO: 134 |
| 170 | QRMRDCLKNNKTELRLKILGLTTI | SEQ ID NO: 91 | 167 | EAVQRMRDCLKNNKTELRLKILGL | SEQ ID NO: 135 |
| 578 | LIMAGREIFRLEQIESLAREKVKR | SEQ ID NO: 92 | 168 | AVQRMRDCLKNNKTELRLKILGLT | SEQ ID NO: 136 |
| 579 | IMAGREIFRLEQIESLAREKVKRL | SEQ ID NO: 93 | 165 | REEAVQRMRDCLKNNKTELRLKILG | SEQ ID NO: 137 |
| 578 | LIMAGREIFRLEQIESLAREKVKRL | SEQ ID NO: 94 | 167 | EAVQRMRDCLKNNKTELRLKILGLT | SEQ ID NO: 138 |
| 164 | NREEAVQRMRDCLKNNKTELRLKILG | SEQ ID NO: 95 | 168 | AVQRMRDCLKNNKTELRLKILGLTT | SEQ ID NO: 139 |
| 165 | REEAVQRMRDCLKNNKTELRLKILGL | SEQ ID NO: 96 | 171 | RMRDCLKNNKTELRLKILGLTTIPA | SEQ ID NO: 140 |
| 168 | AVQRMRDCLKNNKTELRLKILGLTTI | SEQ ID NO: 97 | 162 | AANREEAVQRMRDCLKNNKTELRLKIL | SEQ ID NO: 141 |
| 161 | EAANREEAVQRMRDCLKNNKTELRLKIL | SEQ ID NO: 98 | 163 | ANREEAVQRMRDCLKNNKTELRLKILG | SEQ ID NO: 142 |
| 162 | AANREEAVQRMRDCLKNNKTELRLKILG | SEQ ID NO: 99 | 164 | NREEAVQRMRDCLKNNKTELRLKILGL | SEQ ID NO: 143 |
| 163 | ANREEAVQRMRDCLKNNKTELRLKILGL | SEQ ID NO: 100 | 165 | REEAVQRMRDCLKNNKTELRLKILGLT | SEQ ID NO: 144 |
| 164 | NREEAVQRMRDCLKNNKTELRLKILGLT | SEQ ID NO: 101 | 157 | APAKEAANREEAVQRMRDCLKNNKTELRLK | SEQ ID NO: 145 |
| 165 | REEAVQRMRDCLKNNKTELRLKILGLTT | SEQ ID NO: 102 | 158 | PAKEAANREEAVQRMRDCLKNNKTELRLKI | SEQ ID NO: 146 |
| 168 | AVQRMRDCLKNNKTELRLKILGLTTIPA | SEQ ID NO: 103 | 159 | AKEAANREEAVQRMRDCLKNNKTELRLKIL | SEQ ID NO: 147 |
| 157 | APAKEAANREEAVQRMRDCLKNNKTELRL | SEQ ID NO: 104 | 160 | KEAANREEAVQRMRDCLKNNKTELRLKILG | SEQ ID NO: 148 |
| 159 | AKEAANREEAVQRMRDCLKNNKTELRLKI | SEQ ID NO: 105 | 161 | EAANREEAVQRMRDCLKNNKTELRLKILGL | SEQ ID NO: 149 |
| 161 | EAANREEAVQRMRDCLKNNKTELRLKILG | SEQ ID NO: 106 | 162 | AANREEAVQRMRDCLKNNKTELRLKILGLT | SEQ ID NO: 150 |
| 162 | AANREEAVQRMRDCLKNNKTELRLKILGL | SEQ ID NO: 107 | 163 | ANREEAVQRMRDCLKNNKTELRLKILGLTT | SEQ ID NO: 151 |
| 163 | ANREEAVQRMRDCLKNNKTELRLKILGLT | SEQ ID NO: 108 | | | |
| 165 | REEAVQRMRDCLKNNKTELRLKILGLTTI | SEQ ID NO: 109 | | | |

Example 13

Analysis of T3SS-Independent Internalisation of Bacterial Effector Proteins of the LPX Subtype Bacterial pathogens including *Salmonella*, *Yersinia* and *Shigella* spp. express effector proteins of the LPX subtype of leucine-rich repeat (LRR) proteins that are translocated into the host cell via a type three secretion system (T3SS) during infection.

Previous studies identified the LPX effector protein YopM of *Yersinia enterocolitica* as a novel bacterial cell-penetrating protein. YopM's ability to translocate across the host cell plasma membrane independently of *Yersinia's* T3SS is mediated by it's two N-terminal α-Helices.

The inventors therefore constructed and recombinantly expressed LPX effector proteins of *Shigella flexneri* and *Salmonella typhimurium*. Potential T3SS-independent translocation of these proteins was analysed by cell fractionation of HeLa cells, immunofluorescence microscopy and FACS analyses. Functionality of the recombinant proteins was assessed by in vitro ubiquitination assays. Additionally, an effect of the recombinant proteins on the expression of pro-inflammatory cytokines was analysed by quantitative real time PCR.

The inventors could show that the SspH1 effector protein of *Salmonella typhimurium* is able to translocate into eukaryotic cells without a requirement for additional factors. Furthermore the inventors could show that recombinant SspH1 is a functional E3 ubiquitin ligase that is able to reduce the expression of Interleukin 8 in IL1β stimulated cells.

These results show that SspH1 is a novel bacterial cell-penetrating protein and, together with YopM, a hint for a general concept of T3SS-independent translocation by LPX effector proteins.

Example 14

Group 1:
Leucine-rich repeats of SspH1, wherein SspH1 has the amino acid sequence indicated as SEQ ID NO: 2.
LRR1 (identification number 1): AA217-238 of SEQ ID NO: 2.
LRR2 (identification number 2): AA239-257 of SEQ ID NO: 2.
LRR3 (identification number 3): AA258-279 of SEQ ID NO: 2.
LRR4 (identification number 4): AA280-297 of SEQ ID NO: 2.
LRR5 (identification number 5): AA 298-319 of SEQ ID NO: 2.
LRR6 (identification number 6): AA320-337 of SEQ ID NO: 2.
LRR7 (identification number 7): AA338-360 of SEQ ID NO: 2.
LRR8 (identification number 8): AA361-381 of SEQ ID NO: 2.

Group 2:
Leucine-rich repeats of SspH2, wherein SspH2 has the amino acid sequence indicated as SEQ ID NO: 3.
LRR1 (identification number 1): AA223-242 of SEQ ID NO: 3.
LRR2 (identification number 2): AA243-264 of SEQ ID NO: 3.
LRR3 (identification number 3): AA265-282 of SEQ ID NO: 3.
LRR4 (identification number 4): AA283-302 of SEQ ID NO: 3.
LRR5 (identification number 5): AA303-324 of SEQ ID NO: 3.
LRR6 (identification number 6): AA325-342 of SEQ ID NO: 3.
LRR7 (identification number 7): AA343-364 of SEQ ID NO: 3.
LRR8 (identification number 8): AA365-382 of SEQ ID NO: 3.
LRR9 (identification number 9): AA383-404 of SEQ ID NO: 3.
LRR10 (identification number 10): AA405-422 of SEQ ID NO: 3.
LRR11 (identification number 11): AA423-445 of SEQ ID NO: 3.
LRR12 (identification number 12): AA446-466 of SEQ ID NO: 3.

Group 3:
Leucine-rich repeats of Slrp, wherein Slrp has the amino acid sequence indicated as SEQ ID NO: 1.
LRR1 (identification number 1): AA200-219 of SEQ ID NO: 1.
LRR2 (identification number 2): AA221-242 SEQ ID NO: 1.
LRR3 (identification number 3): AA243-262 SEQ ID NO: 1.
LRR4 (identification number 4): AA263-284 SEQ ID NO: 1.
LRR5 (identification number 5): AA285-305 SEQ ID NO: 1.
LRR6 (identification number 6): AA306-325 SEQ ID NO: 1.
LRR7 (identification number 7): AA326-346 SEQ ID NO: 1.
LRR8 (identification number 8): AA347-368 SEQ ID NO: 1.
LRR9 (identification number 9): AA369-389 SEQ ID NO: 1.
LRR10 (identification number 10): AA390-410 SEQ ID NO: 1.

Group 4:
Predicted leucine-rich repeats of IpaH1.4, wherein IpaH1.4 has the amino acid sequence indicated as SEQ ID NO: 4.
LRR1 (identification number 1): AA92-113 of SEQ ID NO: 4.
LRR2 (identification number 2): AA132-153 of SEQ ID NO: 4.
LRR3 (identification number 3): AA172-191 of SEQ ID NO: 4.
LRR4 (identification number 4): AA192-213 of SEQ ID NO: 4.

Group 5:
Predicted leucine-rich repeats of IpaH2.5, wherein IpaH2.5 has the amino acid sequence indicated as SEQ ID NO: 5.
LRR1 (identification number 1): AA92-113 of SEQ ID NO: 5
LRR2 (identification number 2): AA132-153 of SEQ ID NO: 5
LRR3 (identification number 3): AA172-191 of SEQ ID NO: 5
LRR4 (identification number 4): AA192-213 of SEQ ID NO: 5

Group 6:
Predicted leucine-rich repeats of IpaH3, wherein IpaH3 has the amino acid sequence indicated as SEQ ID NO: 6.
LRR1 (identification number 1): AA80-99 of SEQ ID NO: 6
LRR2 (identification number 2): AA100-121 of SEQ ID NO: 6
LRR3 (identification number 3): AA140-161 of SEQ ID NO: 6
LRR4 (identification number 4): AA162-179 of SEQ ID NO: 6
LRR5 (identification number 5): AA180-201 of SEQ ID NO: 6
LRR6 (identification number 6): AA220-241 of SEQ ID NO: 6

Group 7:
Leucine-rich repeats of IpaH4.5, wherein IpaH4.5 has the amino acid sequence indicated as SEQ ID NO: 7.
LRR1 (identification number 1): AA63-82 of SEQ ID NO: 7.
LRR2 (identification number 2): AA83-104 of SEQ ID NO: 7.
LRR3 (identification number 3): AA105-122 of SEQ ID NO: 7.
LRR4 (identification number 4): AA123-143 of SEQ ID NO: 7.

LRR5 (identification number 5): AA144-165 of SEQ ID NO: 7.
LRR6 (identification number 6): AA 166-183 of SEQ ID NO: 7.
LRR7 (identification number 7): AA 184-205 of SEQ ID NO: 7.
LRR8 (identification number 8): AA206-223 of SEQ ID NO: 7.
LRR9 (identification number 9): AA224-246 of SEQ ID NO: 7.
LRR10 (identification number 10): AA247-270 of SEQ ID NO: 7.

Group 8:
Leucine-rich repeats of IpaH7.8, wherein IpaH7.8 has the amino acid sequence indicated as SEQ ID NO: 8.
LRR1 (identification number 1): AA58-79 of SEQ ID NO: 8.
LRR2 (identification number 2): AA80-97 of SEQ ID NO: 8.
LRR3 (identification number 3): AA98-119 of SEQ ID NO: 8.
LRR4 (identification number 4): AA120-137 of SEQ ID NO: 8.
LRR5 (identification number 5): AA138-157 of SEQ ID NO: 8.
LRR6 (identification number 6): AA158-179 of SEQ ID NO: 8.
LRR7 (identification number 7): AA180-199 of SEQ ID NO: 8.
LRR8 (identification number 8): AA202-223 of SEQ ID NO: 8.
LRR9 (identification number 9): AA225-248 of SEQ ID NO: 8.

Group 9:
Leucine-rich repeats of IpaH9.8, wherein IpaH9.8 has the amino acid sequence indicated as SEQ ID NO: 9.
LRR1 (identification number 1): AA57-77 of SEQ ID NO: 9.
LRR2 (identification number 1): 78-99 of SEQ ID NO: 9.
LRR3 (identification number 1): 100-117 of SEQ ID NO: 9.
LRR4 (identification number 1): 118-139 of SEQ ID NO: 9.
LRR5 (identification number 1): 140-157 of SEQ ID NO: 9.
LRR6 (identification number 1): 158-179 of SEQ ID NO: 9.
LRR7 (identification number 1): 182-203 of SEQ ID NO: 9.
LRR8 (identification number 1): 205-228 of SEQ ID NO: 9.

Example 15

The uptake of recombinant LPX effector proteins was further analyzed by sub-cellular fractionation of eukaryotic HeLa cells. By this method, the internalization of putative CPPs can be assessed due to the separation of soluble cytoplasmic and insoluble membrane proteins (Behrens, 1938; Rüter et al., 2010). HeLa cells which were grown to 80% confluence were incubated with the recombinant proteins (25 µg/ml) for 3 h. After isolation of cytoplasmic and membrane fractions, proteins were separated by SDS-PAGE and subsequently immobilized on a nitrocellulose membrane by Western blotting. For detection of the recombinant protein, an α-FLAG-antibody was used as a primary antibody. In case of internalization, proteins were expected to be detected in the cytoplasmic fraction. Since recombinant LPX effector proteins harboring only a single FLAG-tag were not detectable in the HeLa cell background at all (data not shown), constructs with 3× FLAG-tags were chosen for this assay due to their improved detectability (Terpe, 2003).

Figure 23:
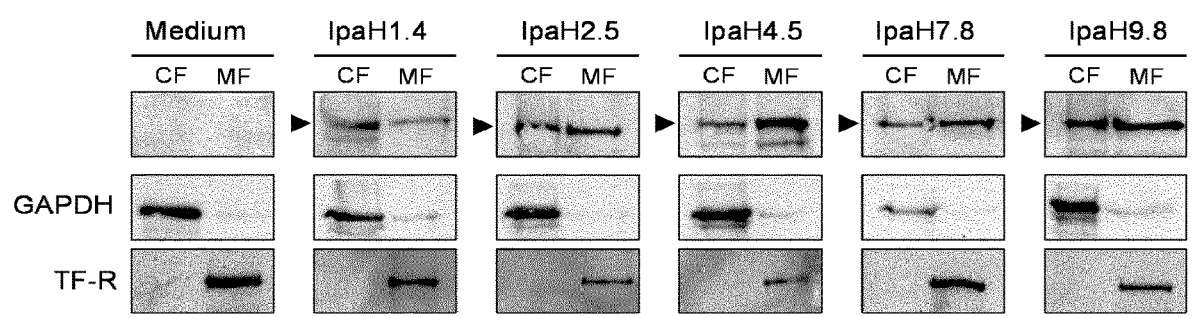
FIG. 23 shows a cell fractionation of HeLa cells incubated with recombinant IpaH1.4, IpaH2.5, IpaH4.5, IpaH7.8, and IpaH9.8, respectively.

Recombinant IpaH1.4, IpaH2.5, IpaH4.5, IpaH7.8, and IpaH9.8 could be detected in the cytoplasmic fraction after 3 h incubation of HeLa cells, indicating successful internalization in a T3SS-independent manner (FIG. 23). However, all proteins were also detected in the membrane fraction in comparable amounts. Upon incubation with IpaH4.5 and IpaH7.8 the amounts found in the membrane fraction appear to be even slightly higher. Both the cytoplasmic and the membrane fraction appear to be free of contamination since the membrane marker transferring receptor (TF-R) is solely detectable in the membrane fraction, whereas a prominent band for GAPDH can be observed in all cytoplasmic but not in the membrane fractions.

Example 16

Analysis of Intracellular Trafficking of Recombinant LPX Effector Proteins by Co-Localization with Endocytic Markers For investigations of possible endocytic uptake mechanisms of recombinant LPX effector proteins, co-localization studies with endocytic markers were performed. Appropriate markers for this purpose are regulatory proteins which are involved in intracellular membrane trafficking between different sub-cellular compartments. These include both vesicle formation and movements as well as membrane fusion. Rab5 served as marker for early endosomes, whereas Rab7 was used as an indicator for maturation into late endosomes. In addition, CD63 served as marker for trafficking from late endosomes to lysosomes.

HeLa cells were incubated with recombinant Cy3-labeled LPX effector proteins for 1 h, 3 h, and 6 h. Following incubation, cells were washed, fixed and permeabilized. Cell-compartment specific markers including Rab5, Rab7, and CD63 were stained using specific fluorescent antibodies. In addition, the nucleus was stained using Draq5. Finally, the co-localization with the Cy3-labeled LPX effector proteins was analyzed by confocal fluorescence microscopy. As depicted in FIG. 24 all tested LPX effector proteins were found to be partially co-localized with endosomal compartments. For each marker protein, representative pictures which revealed the highest amount of co-localization are shown; in case of Rab5, pictures taken after 1 h incubation of HeLa cells with labeled proteins show on average the highest degrees of co localization, whereas for Rab7 and CD63 maximal co-localizations were observed only after longer incubation times of 3 h and 6 h.

All tested LPX effector proteins were found to be partially associated with early endosomes (i) since co-localization with the early endosomal marker Rab5 can be detected to some extent. After internalization, the proteins seem to remain in the endosomal compartments; so all shown LPX effector proteins co-localize with the late endosomal marker protein Rab7 (ii) after 3 h incubation. In addition, the overlay images reveal co-localization with CD63 (iii) after 6 h incubation.

In summary, fluorescence microcopy studies reveal partial co-localization with the endosomal markers Rab5, Rab7, and CD63 indicating that endocytic mechanisms seem to be involved in the T3SS-independent uptake of the recombinant LPX effectors IpaH1.4, IpaH2.5, IpaH4.5, IpaH7.8, IpaH9.8, and SlrP into HeLa cells.

Example 16

Role of Different Endocytic Pathways in HeLa Cell Uptake of Recombinant LPX Effector Proteins HeLa cells were with endocytic inhibitors cytochalasin D (2.5 µM), amiloride (3 mM), filipin (7.5 µM), nocodazole (20 µM), dynasore (80 µM), methyl-β-cyclodextrin (MβCD) (5 mM) for 1 h prior to the addition of recombinant LPX effectors. Three hours later the cells were washed with D-PBS (with $Ca^{2+}/Mg^{2+}$), trypsinized, resuspended in D-PBS (without $Ca^{2+}/Mg^{2+}$), diluted with trypan blue (final concentration 0.2%) and analyzed by flow cytometry. Fluorescence of ALEXA FLUOR® 488 was detected at 510 nm. For exclusion of dead cells and cellular debris, forward and side scatter were set up appropriately and scaled to the living cell population before starting the incubation. Each sample was measured in duplicate counting 10,000 cells in every run. Three independent assays were performed for each protein.

FIG. 25 summarizes the results of FACS-based uptake analysis of recombinant LPX effectors in the presence of different endocytic inhibitors. It can be recognized that the different LPX effectors act similar in response to a certain inhibitor. Especially the presence of cytochalasin D which effectively blocks actin-mediated endocytosis, of amiloride which inhibits macropinocytotic events as well as of methyl-β-cyclodextrin which serves as in inhibitor of "lipid-raft"-mediated endocytosis, leads to an enormous reduction of cellular internalization of all tested recombinant LPX effectors. These results indicate that especially the aforementioned endocytic pathways might act synergistically in the cellular transduction of LPX effectors.

Example 18

For investigation of possible membranolytic effects of recombinant LPX effectors, the FACS-based membranolysis assay was performed (Florén et al., 2011).

HeLa cells were co-incubated with 1 µg/ml PI and different ALEXA FLUOR® 488-labeled proteins. At given time points, samples were taken from the ongoing incubation and subjected to FACS analysis. Fluorescence of PI was detected at 617 nm. For exclusion of dead cells and cellular debris, forward and side scatter were set up appropriately and scaled to the living cell population before starting the incubation. Each sample was measured in duplicate counting 10,000 cells in every run. Three independent assays were performed for each protein. As a control, HeLa cells were incubated solely with PI under equal conditions.

FIG. 26 summarizes the results of the membranolysis assays of HeLa cells which were incubated with recombinant LPX effector proteins. Disruption of the membrane leads to increased fluorescence intensities of PI due to increased permeability. Indeed, for all tested LPX effector proteins an increase of PI fluorescence intensity over the entire time is visible when HeLa cells were incubated at 37° C. However, this increase appears to slightly differ for the tested LPX effectors. In direct comparison to non-treated control cells (represented by dashed-lined curves), the strongest increase of PI fluorescence is induced by incubation with IpaH2.5, whereas upon incubation with IpaH9.8 almost no difference to non-treated cells is detectable. In contrast, co-incubation of HeLa cells with LPX effectors and PI at 4° C. does not result in increased levels of PI fluorescence intensity and is almost comparable to non-treated control cells.

Example 19

Quantification of Lactate Dehydrogenase (LDH) Release Induced by Recombinant LPX Effector Proteins For the evaluation of putative cytotoxic effects of recombinant LPX effector proteins on HeLa cells, the amount of released lactate dehydrogenase (LDH) was taken as a parameter for membrane integrity and measured colorimetrically using the CYTOTOX® 96 Non-Radioactive Cytotoxicity Assay. For that, HeLa cells were cultured in 96-well plates and incubated with different recombinant LPX effector proteins (25 or 50 µg/ml) for 24 h, 6 h, and 1 h. The amounts of released LDH of both culture supernatants and lysates were determined by measuring the absorbance at 490 nm. The quotient of both was calculated and normalized to non-treated cells.

FIG. 27 shows the relative LDH release of HeLa cells upon incubation with recombinant IpaH1.4, IpaH2.5, IpaH4.5, IpaH7.8, IpaH9.8, or SlrP in comparison to non-treated cells and a LDH positive control. The measured amounts of LDH released upon incubation with the specific LPX effector proteins are comparable to basal LDH release displayed by HeLa cells incubated in culture medium (Medium Control). This appears to be independent of the protein concentration (25 µg/ml or 50 µg/ml) or the incubation time (24 h, 6 h, or 1 h). The large amounts of LDH measured for the positive control ensure that the assay was functional.

Based on the amounts of LDH released by HeLa cells upon incubation with recombinant IpaH1.4, IpaH2.5, IpaH4.5, IpaH7.8, IpaH9.8, or SlrP potential cytotoxic effects of these LPX effector proteins can be excluded.

Example 20

The proteins of the IpaH subset as well as the LPX effector SlrP and the SspH proteins of *Salmonella* harbor an enzymatic domain that was shown to possess an E3 ubiquitin ligase activity (Rohde et al., 2007; Singer et al., 2008; Zhu et al., 2008). In order to test whether recombinant LPX effector proteins are enzymatically functional as ubiquitin E3 ligases an in vitro ubiquitination assay was carried out. The assay was performed in a 40 µl reaction mixture containing ubiquitin reaction buffer, 2 µg of HA-tagged ubiquitin, 0.5 µg of E1 and 2 mg of E2 (UbcH5b) in the presence or absence of 4 µg of recombinant IpaH1.4, IpaH2.5, IpaH4.5, IpaH7.8, IpaH9.8, SlrP, or BSA as a negative control. As further controls, the mixtures were prepared without the E2 (UbcH5b) enzyme. Reactions were incubated for 1 h at 37° C. before they were stopped by the addition of 4× SDS sample buffer without DTT.

The results of Western blot analysis which are depicted in FIG. 28 reveal a ladder of ubiquitin chains from ~40 to 200 kDa in reactions performed in the presence of LPX effectors. In reactions performed in the absence of E2 (UbcH5b), if anything, only ubiquitinated E1 at a size of >110 kDa was detected. In the presence of E2 (UbcH5b) but in the absence of any LPX effector proteins (see lane 1+2) both E1 (>110 kDa) and E2 (~30 kDa) were found to be ubiquitinated.

The results of the in vitro ubiquitination assay show that recombinant IpaH1.4, IpaH2.5, IpaH4.5, IpaH7.8, IpaH9.8, and SlrP have the ability to remove ubiquitin from ubiquitinated UbcH5b in order to form poly-ubiquitin chains of the HA-tagged ubiquitin. These findings confirm that the indicated LPX effector proteins are indeed enzymatically functional in vitro.

REFERENCES

Angot A (2007) Exploitation of Eukaryotic Ubiquitin Signaling Pathways by Effectors Translocated by Bacterial Type III and Type IV Secretion Systems. *PLOS Pathog.* 3:1-13

Behrens, M. (1938) Hoppe-Seylers Z, 253. In Pfluügers Archiv: Eur. J. Phiol. pp. 185.

Büttner D et al. (2006) Who comes first? How plant pathogenic bacteria orchestrate type III secretion. *Curr Opin Microbiol.* 2:193-200.

Cornelis G R (2006) The type III secretion injectisome. *Nature Reviews Microbiology* 4: 811-825

Cornelis G R (2002a) The *Yersinia* Ysc-Yop 'type III' weaponry. *Nat Rev Mol Cell Biol* 3: 742-752

Cornelis G R (2002b) The *Yersinia* Ysc-Yop virulence apparatus. *Int J Med Microbiol* 291: 455-462

Cornelis G R, Wolf-Watz H (1997) The *Yersinia* Yop virulon: a bacterial system for subverting eukaryotic cells. *Mol Microbiol* 23: 861-867

Florén, A., Mäger, I., and Langel, Ü. (2011) Uptake kinetics of cell-penetrating peptides. In Humana Press. pp. 117-128

Frankel A D, Pabo C O (1988) Cellular uptake of the tat protein from human immunodeficiency virus. *Cell* 55: 1189-1193

Ghosh S, Karin M (2002) Missing pieces in the NF-kappaB puzzle. *Cell* 109 Suppl: S81-96

Green M, Loewenstein P M (1988) Autonomous functional domains of chemically synthesized human immunodeficiency virus tat trans-activator protein. *Cell* 55: 1179-1188

Haraga A, Miller S I (2003) A *Salmonella enterica* serovar *typhimurium* translocated leucine-rich repeat effector protein inhibits NF-kappa B-dependent gene expression. *Infect Immun* 71: 4052-4058

Hicks S W and Galán J E (2010) Hijacking the host ubiquitin pathway: structural strategies of bacterial E3 ubiquitin ligases. *Curr Opin Microbiol.* 13:41-46

Hueck C J (1998) Type III Protein Secretion Systems in Bacterial Pathogens of Animals and Plants. *Microbiol. Mol. Biol. Rev.* 62:2 379-433

Jaysinghe S. H K, Wimley W., Snider C., and S. H. White. (2009) Membrane Protein Explorer (MPEx). http://blanco-.biomol.uci.edu/MPEx.

Keshet Y, Seger R (2010) The MAP kinase signaling cascades: a system of hundreds of components regulates a diverse array of physiological functions. Methods Mol Biol 661: 3-38

Langel Ü (2010). Cell-Penetrating Peptides: Methods and Protocols: (Methods in Molecular Biology). Springer, Berlin, 1st Edition.

Li S, Wilkinson M F (1997) Site-directed mutagenesis: a two-step method using PCR and DpnI. *Biotechniques* 23: 588-590

Matsumoto H, Young G M (2009) Translocated effectors of *Yersinia*. *Curr Opin Microbiol* 12: 94-100

Miao E A, Scherer C A, Tsolis R M, Kingsley R A, Adams L G, Baumler A J, Miller S I (1999) *Salmonella typhimurium* leucine-rich repeat proteins are targeted to the SPI1 and SPI2 type III secretion systems. *Mol Microbiol* 34: 850-864

Okuda J, Toyotome T, Kataoka N, Ohno M, Abe H, Shimura Y, Seyedarabi A, Pickersgill R, Sasakawa C (2005) *Shigella* effector IpaH9.8 binds to a splicing factor U2AF (35) to modulate host immune responses. *Biochem Biophys Res Commun* 333: 531-539

Quezada C M, Hicks S W, Galán J E, Stebbins C E (2009) A family of *Salmonella* virulence factors functions as a distinct class of autoregulated E3 ubiquitin ligases. *Proc Natl Acad Sci USA* 106: 4864-4869

Rohde J R, Breitkreutz A, Chenal A, Sansonetti P J, Parsot C (2007) Type III secretion effectors of the IpaH family are E3 ubiquitin ligases. *Cell Host Microbe* 1: 77-83

Rüter C, Buss C, Scharnert J, Heusipp G, Schmidt M A (2010) A newly identified bacterial cell-penetrating peptide that reduces the transcription of pro-inflammatory cytokines. *J Cell Sci* 123: 2190-2198

Sansonetti P J (2004) War and peace at mucosal surfaces. *Nat Rev Immunol* 4: 953-964

Scharnert J, Greune L, Zeuschner D, Lubos M L, Alexander Schmidt M, Rüter C (2013) Autonomous translocation and intracellular trafficking of the cell-penetrating and immune-suppressive effector protein YopM. *Cell Mol Life Sci.* 2013 Jul. 9. [Epub ahead of print]. DOI: 10.1007/s00018-013-1413-2

Singer, A. U., Rohde, J. R., Lam, R., Skarina, T., Kagan, O., Dileo, R., Chirgadze, N. Y., Cuff, M. E., Joachimiak, A., Tyers, M., Sansonetti, P. J., Parsot, C., and Savchenko, A. (2008) Structure of the *Shigella* T3SS effector IpaH defines a new class of E3 ubiquitin ligases. Nat Struct Mol Biol 15: 1293-301.

Symmons M F, Buchanan S G, Clarke D T, Jones G, Gay N J (1997) X-ray diffraction and far-UV CD studies of filaments formed by a leucine-rich repeat peptide: structural similarity to the amyloid fibrils of prions and Alzheimer's disease beta-protein. *FEBS Lett* 412: 397-403

Trabulo S, Resina S, Simões S, Lebleu B, Pedroso de Lima M C (2010) A non-covalent strategy combining cationic lipids and CPPs to enhance the delivery of splice correcting oligonucleotides. *J Control Release* 145: 149-158

White S H, Wimley W C (1999) Membrane protein folding and stability: physical principles. *Annu Rev Biophys Biomol Struct* 28: 319-365

Zhu Y, Li H, Hu L, Wang J, Zhou Y, Pang Z, Liu L, Shao F (2008) Structure of a *Shigella* effector reveals a new class of ubiquitin ligases. *Nat Struct Mol Biol* 15: 1302-1308

The invention claimed is:

1. A method of treatment of disease caused by autoimmunity, and/or treatment of acute inflammation, chronic inflammation, inflammatory disorder, or pathogenic inflammatory reaction of the immune system, and/or a method of suppressing the immune system in a subject, comprising administering a therapeutically effective amount of a pharmaceutical composition to said subject, wherein the pharmaceutical composition comprises an isolated effector protein of a type III secretion system (T3SS)-containing bacterium of the genus *Salmonella* or *Shigella*, or a variant, fragment, or immunomodulatory domain of the effector protein, wherein the effector protein or the variant, fragment, or immunomodulatory domain of the effector protein is covalently linked via a linker comprising a glycine-containing amino acid sequence to a cargo molecule selected from the group consisting of viruses, modified viruses, viral vectors, and antibodies wherein the effector protein or variant, fragment, or immunomodulatory domain of the effector protein:

a) is recombinantly produced or chemically synthesized,
b) comprises an E3 ubiquitin ligase domain,
c) is a cell-penetrating protein which translocates into eukaryotic cells without the requirement of a bacterial T3SS, and
d) optionally comprises at least one leucine-rich repeat.

2. The method of claim 1, wherein said type III secretion system (T3SS)-containing bacterium is classified as *Salmonella bongori, Salmonella enterica, Salmonella subterranean, Salmonella typhi, Salmonella typhimurium, Salmonella enterica* serovar *typhimurium, Salmonella enteritidis, Salmonella pullorum, Salmonella dublin, Salmonella arizonae, Salmonella choleraesius, Shigella flexneri, Shigella dysenteriae, Shigella sonnei*, or *Shigella boydi*.

3. The method of claim 1, wherein the E3 ubiquitin ligase domain is (a) classified as Novel E3 Ligase, (b) closer to the C-terminus of said effector protein than to the N-terminus of said effector protein, or both (a) and (b).

4. The method of claim 1, wherein the leucine-rich repeat(s) is/are (a) a leucine-rich repeat of the LPX-subtype, (b) closer to the N-terminus of said effector protein than to the C-terminus of said effector protein, or both (a) and (b).

5. The method of claim 1, wherein said effector protein is a bacterial effector protein of the LPX-Subtype, or is selected from the group consisting of SspH1, SspH2, SlrP, IpaH1.4, IpaH2.5, IpaH3, IpaH4.5, IpaH7.8, and IpaH9.8.

6. The method of claim 1, wherein said effector protein has (a) an amino acid sequence as set forth in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 9, and (b) is encoded by a polynucleotide sequence as set forth in SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 18.

7. The method of claim 1, wherein said effector protein, variant, fragment or immunomodulatory domain comprises an amino acid sequence as set forth in SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, or SEQ ID NO: 27.

8. The method of claim 1, wherein said effector protein comprises at least one Leucine-rich repeat, or at least one Leucine-rich repeat that is comprised in an amino acid sequence as set forth in SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, or SEQ ID NO: 36.

9. The method of claim 1, wherein said effector protein, or a variant, fragment or immunomodulatory domain thereof comprises at least one amino acid sequence as set forth in SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, or SEQ ID NO: 550; and/or at least one C-terminally or N-terminally truncated fragment of an amino acid sequence as set forth in SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, or SEQ ID NO: 550.

10. The method of claim 1, wherein the composition does not include: (a) an auxiliary agent which can cause the penetration of said effector protein into a eukaryotic cell, (b)

an auxiliary agent selected from the group consisting of T3 SS-containing bacterium, and bacterium of the genus *Salmonella* or *Shigella*, (c) a cell-penetrating molecule, that is different from an effector protein according to claim 1, or (d) a cell-penetrating nanoparticle, or (e) any combination of (a)-(d).

11. The method of claim 1, wherein said cargo molecule has therapeutic activity in a subject and/or is useful in a diagnostic method.

12. The method of claim 1, wherein said effector protein or a variant, fragment or immunomodulatory domain thereof is capable of (a) ubiquinating itself and/or eukaryotic proteins after it has autonomously penetrated into a eukaryotic cell, (b) modulating cellular pathway(s) of the innate immune system of eukaryotic cells after it has autonomously penetrated into said eukaryotic cells, (c) modulating cytokines and/or cytokine receptors of eukaryotic cells and/or eukaryotic genes which respond to cytokines of eukaryotic cells after said effector protein or variant, fragment or immunomodulatory domain has autonomously penetrated into said eukaryotic cells, (d) downregulating the expression of cytokines and/or cytokine receptors of eukaryotic cells after it has autonomously penetrated into said eukaryotic cells, or any combination of (a)-(d).

13. The method of claim 1, wherein the pharmaceutical composition is in the form of a kit, prior to the administering.

14. The method of claim 1, wherein the disease caused by autoimmunity comprises acute disseminated encephalomyelitis (ADEM), Addison's disease, ankylosing spondylitis, antiphospholipid antibody syndrome (APS), aplastic anemia, autoimmune hepatitis, autoimmune Oophoritis, celiac disease, Crohn's disease (Morbus Crohn), diabetes mellitus type 1, gestational pemphigoid, goodpasture's syndrome, Graves' disease, Guillain-Barré syndrome (GBS), Hashimoto's disease, idiopathic thrombocytopenic purpura, Kawasaki's disease, lupus erythematosus, Mixed Connective Tissue Disease, multiple sclerosis, myasthenia gravis, opsoclonus myoclonus syndrome (OMS), optic neuritis, Ord's thyroiditis, pemphigus, pernicious anaemia, primary biliary cirrhosis, rheumatoid arthritis, Reiter's syndrome, Sjögren's syndrome, Takayasu's arteritis, temporal arteritis, Warm autoimmune hemolytic anemia or Wegener's granulomatosis.

15. The method of claim 1 wherein acute inflammation or chronic inflammation comprises asthma, chronic prostatitis, glomerulonephritis, hypersensitivities, inflammatory bowel disease, pelvic inflammatory disease, reperfusion injury, arthritis, osteoarthritis, (juvenile) chronic arthritis, rheumatoid arthritis, psoriatic arthritis, arthritis mutilans, septic arthritis, infectious arthritis and/or reactive arthritis, transplant rejection, vasculitis, inflammatory myopathy, atherosclerosis, ischaemic heart disease, gastroenteritis, chronic gastritis, colitis ulcerose, or psoriasis or psoriasis arthritis.

16. The method of claim 1, wherein treatment of diseases caused by autoimmunity, and/or treatment of acute inflammation, chronic inflammation, inflammatory disorders, or pathogenic inflammatory reaction of the immune system, and/or suppressing the immune system comprises treatment of gastroenteritis, chronic gastritis, inflammatory bowel diseases (IBD), colitis ulcerosa, psoriasis, allergic reaction, Morbus Crohn, arthritis, osteoarthritis, (juvenile) chronic arthritis, rheumatoid arthritis, psoriatic arthritis, arthritis mutilans, septic arthritis, infectious arthritis or reactive arthritis.

* * * * *